(12) United States Patent
Rashidian et al.

(10) Patent No.: US 12,048,753 B2
(45) Date of Patent: Jul. 30, 2024

(54) LABELING OF ANTIBODIES

(71) Applicant: Whitehead Institute for Biomedical Research, Cambridge, MA (US)

(72) Inventors: Mohammad Rashidian, Cambridge, MA (US); Hidde L. Ploegh, Jamaica Plain, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 0 days.

(21) Appl. No.: 15/764,087

(22) PCT Filed: Oct. 1, 2016

(86) PCT No.: PCT/US2016/055074
§ 371 (c)(1),
(2) Date: Mar. 28, 2018

(87) PCT Pub. No.: WO2017/059397
PCT Pub. Date: Apr. 6, 2017

(65) Prior Publication Data
US 2018/0280551 A1    Oct. 4, 2018

Related U.S. Application Data

(60) Provisional application No. 62/236,117, filed on Oct. 1, 2015.

(51) Int. Cl.
| | |
|---|---|
| A61K 51/00 | (2006.01) |
| A61K 51/10 | (2006.01) |
| A61M 36/14 | (2006.01) |
| A61P 35/00 | (2006.01) |
| C07K 16/24 | (2006.01) |
| C07K 16/28 | (2006.01) |
| C12P 21/00 | (2006.01) |
| G01N 33/58 | (2006.01) |
| A61K 39/00 | (2006.01) |

(52) U.S. Cl.
CPC ...... *A61K 51/1093* (2013.01); *A61K 51/1021* (2013.01); *A61K 51/1027* (2013.01); *A61P 35/00* (2018.01); *C07K 16/247* (2013.01); *C07K 16/2833* (2013.01); *C07K 16/2845* (2013.01); *C12P 21/00* (2013.01); *C12Y 304/22* (2013.01); *G01N 33/58* (2013.01); *A61K 2039/505* (2013.01); *C07K 2317/22* (2013.01); *C07K 2317/35* (2013.01); *C07K 2317/569* (2013.01)

(58) Field of Classification Search
CPC ............ A61K 51/1093; A61K 51/1021; A61K 51/1027; A61K 2039/505; A61P 35/00; C07K 16/247; C07K 16/2833; C07K 16/2845; C07K 2317/22; C07K 2317/35; C07K 2317/569; C12P 21/00; C12Y 304/22; G01N 33/58
See application file for complete search history.

(56) References Cited

U.S. PATENT DOCUMENTS

| | | |
|---|---|---|
| 4,469,863 A | 9/1984 | Ts'o et al. |
| 5,096,815 A | 3/1992 | Ladner et al. |
| 5,198,346 A | 3/1993 | Ladner et al. |
| 5,223,409 A | 6/1993 | Ladner et al. |
| 5,283,433 A | 2/1994 | Tsien |
| 5,296,703 A | 3/1994 | Tsien |
| 5,403,484 A | 4/1995 | Ladner et al. |
| 5,530,101 A | 6/1996 | Queen et al. |
| 5,536,821 A | 7/1996 | Agrawal et al. |
| 5,541,306 A | 7/1996 | Agrawal et al. |
| 5,571,698 A | 11/1996 | Ladner et al. |
| 5,614,622 A | 3/1997 | Iyer et al. |
| 5,637,683 A | 6/1997 | Usher et al. |
| 5,637,684 A | 6/1997 | Cook et al. |
| 5,670,132 A | 9/1997 | Griffiths et al. |
| 5,700,922 A | 12/1997 | Cook |
| 5,707,622 A | 1/1998 | Fong et al. |
| 5,717,083 A | 2/1998 | Cook et al. |
| 5,719,262 A | 2/1998 | Buchardt et al. |
| 5,728,369 A | 3/1998 | Griffiths et al. |
| 5,739,308 A | 4/1998 | Kandimalla et al. |
| 5,739,314 A | 4/1998 | Roy et al. |
| 5,766,905 A | 6/1998 | Studier et al. |
| 5,773,601 A | 6/1998 | Agrawal |
| 5,886,165 A | 3/1999 | Kandimalla et al. |

(Continued)

FOREIGN PATENT DOCUMENTS

| | | |
|---|---|---|
| CN | 102559600 A | 7/2012 |
| JP | 2010115136 A | 5/2010 |

(Continued)

OTHER PUBLICATIONS

Vosjan et al. (Eur. J. Nucl. Med. 2011, 38, 753-763).*
Jokerst et al. (Nanomedicine 2011, 6, 715-728).*
ThermoFisher Scientific 2019.*
De Marco A. (2012) User-Friendly Expression Plasmids Enable the Fusion of VHHs to Application-Specific Tags. In: Saerens D., Muyldermans S. (eds) Single Domain Antibodies. Methods in Molecular Biology (Methods and Protocols), vol. 911. Humana Press, Totowa, NJ.*

(Continued)

*Primary Examiner* — Michael G. Hartley
*Assistant Examiner* — Melissa J Perreira
(74) *Attorney, Agent, or Firm* — Wolf, Greenfield & Sacks, P.C.

(57) ABSTRACT

Provided herein are methods for producing site specific PEG modifications to single domain antibodies (e.g., VHHs). Methods for producing site-specifically conjugated bivalent single domain antibodies (e.g., VHHs) are also provided. Methods for labeling (e.g., with a fluorophore or radionuclide) site-specifically PEGylated single domain antibodies and site-specifically conjugated bivalent single domain antibodies are also provided.

16 Claims, 26 Drawing Sheets

Specification includes a Sequence Listing.

(56) References Cited

U.S. PATENT DOCUMENTS

| | | | |
|---|---|---|---|
| 5,900,481 A | 5/1999 | Lough et al. |
| 5,929,226 A | 7/1999 | Padmapriya et al. |
| 5,955,599 A | 9/1999 | Iyer et al. |
| 5,962,674 A | 10/1999 | Iyer et al. |
| 5,977,296 A | 11/1999 | Nielsen et al. |
| 5,990,296 A | 11/1999 | Pastan et al. |
| 5,994,524 A | 11/1999 | Matsushima et al. |
| 6,022,688 A | 2/2000 | Jurinke et al. |
| 6,090,919 A | 7/2000 | Cormack et al. |
| 6,099,842 A | 8/2000 | Pastan et al. |
| 6,117,992 A | 9/2000 | Iyer |
| 6,133,436 A | 10/2000 | Koster et al. |
| 6,140,482 A | 10/2000 | Iyer et al. |
| 6,245,894 B1 | 6/2001 | Matsushima et al. |
| 6,261,776 B1 | 7/2001 | Pirrung et al. |
| 6,316,003 B1 | 11/2001 | Frankel et al. |
| 6,316,781 B1 | 11/2001 | Nagle et al. |
| 6,342,221 B1 | 1/2002 | Thorpe et al. |
| 6,379,974 B1 | 4/2002 | Parce et al. |
| 6,429,025 B1 | 8/2002 | Parce et al. |
| 6,440,722 B1 | 8/2002 | Knapp et al. |
| 6,451,538 B1 | 9/2002 | Cowsert |
| 6,451,602 B1 | 9/2002 | Popoff et al. |
| 6,455,263 B2 | 9/2002 | Payan |
| 6,455,307 B1 | 9/2002 | McKay et al. |
| 6,455,308 B1 | 9/2002 | Freier |
| 6,461,813 B2 | 10/2002 | Lorens |
| 6,593,292 B1 | 7/2003 | Rothbard et al. |
| 6,960,473 B2 | 11/2005 | Migliaccio et al. |
| 8,206,979 B2 | 6/2012 | Giarratana et al. |
| 8,211,656 B2 | 7/2012 | Hyde et al. |
| 8,496,912 B2 * | 7/2013 | McBride | A61K 47/6897 424/9.4 |
| 8,865,875 B2 * | 10/2014 | Liu | A61K 47/6819 530/391.5 |
| 8,940,501 B2 | 1/2015 | Ploegh et al. |
| 9,267,127 B2 | 2/2016 | Liu et al. |
| 9,751,945 B2 | 9/2017 | Ploegh et al. |
| 9,878,045 B2 | 1/2018 | DiStefano |
| 10,053,683 B2 | 8/2018 | Pasqual et al. |
| 10,081,684 B2 | 9/2018 | Ploegh et al. |
| 10,260,038 B2 | 4/2019 | Swee et al. |
| 10,335,504 B2 * | 7/2019 | Sundaram | A61P 25/28 |
| 10,471,009 B2 | 11/2019 | Lodish et al. |
| 10,471,099 B2 | 11/2019 | Lodish et al. |
| 10,556,024 B2 | 2/2020 | Rashidian et al. |
| 11,028,185 B2 | 6/2021 | Ploegh et al. |
| 11,266,695 B2 | 3/2022 | Lodish et al. |
| 11,492,590 B2 | 11/2022 | Swee et al. |
| 2002/0122768 A1 * | 9/2002 | Liu | A61K 51/088 424/1.11 |
| 2002/0142297 A1 | 10/2002 | Bogdanov et al. |
| 2002/0192773 A1 | 12/2002 | Walsh et al. |
| 2003/0022178 A1 | 1/2003 | Schneewind et al. |
| 2003/0104622 A1 | 6/2003 | Robbins et al. |
| 2003/0224490 A1 | 12/2003 | Dessain et al. |
| 2004/0213795 A1 | 10/2004 | Collins et al. |
| 2007/0178112 A1 | 8/2007 | Wang et al. |
| 2007/0218552 A1 | 9/2007 | Giarratana et al. |
| 2009/0088372 A1 | 4/2009 | Roy et al. |
| 2010/0092470 A1 * | 4/2010 | Bhatt | C07K 16/00 424/133.1 |
| 2011/0070154 A1 | 3/2011 | Hyde et al. |
| 2011/0195021 A1 | 8/2011 | Deckert et al. |
| 2011/0195068 A1 | 8/2011 | Langermann et al. |
| 2011/0321183 A1 | 12/2011 | Ploegh et al. |
| 2012/0039906 A1 | 2/2012 | Olive |
| 2012/0114649 A1 | 5/2012 | Langermann et al. |
| 2013/0095098 A1 | 4/2013 | Tyson |
| 2013/0108651 A1 | 5/2013 | Carven et al. |
| 2013/0109843 A1 | 5/2013 | Carven et al. |
| 2013/0122043 A1 | 5/2013 | Guimaraes et al. |
| 2013/0237580 A1 | 9/2013 | Sasikumar et al. |
| 2013/0266512 A1 | 10/2013 | Fox et al. |
| 2014/0030697 A1 | 1/2014 | Ploegh et al. |
| 2014/0057317 A1 | 2/2014 | Liu et al. |
| 2014/0249296 A1 | 9/2014 | Ploegh et al. |
| 2015/0086576 A1 | 3/2015 | Ploegh et al. |
| 2016/0082046 A1 | 3/2016 | Lodish et al. |
| 2016/0097773 A1 | 4/2016 | Pasqual et al. |
| 2016/0122707 A1 | 5/2016 | Ploegh et al. |
| 2016/0287734 A1 | 10/2016 | Rashidian et al. |
| 2018/0280440 A1 | 10/2018 | Lodish et al. |
| 2018/0346899 A1 | 12/2018 | Pasqual et al. |
| 2019/0112394 A1 | 4/2019 | Ploegh et al. |
| 2019/0256818 A1 | 8/2019 | Swee et al. |
| 2019/0359933 A1 | 11/2019 | Swee et al. |
| 2020/0069736 A1 | 3/2020 | Lodish et al. |
| 2020/0370016 A1 | 11/2020 | Lipsitz et al. |
| 2020/0384137 A1 | 12/2020 | Rashidian et al. |

FOREIGN PATENT DOCUMENTS

| | | |
|---|---|---|
| WO | WO 2000/62804 A2 | 10/2000 |
| WO | WO 2003/020885 A2 | 3/2003 |
| WO | WO 2005/012541 A1 | 2/2005 |
| WO | WO 2005/051976 A2 | 6/2005 |
| WO | WO 2005/086654 A2 | 9/2005 |
| WO | WO 2008/148143 A1 | 12/2008 |
| WO | WO 2010/078376 A2 | 7/2010 |
| WO | WO 2010/087994 A2 | 8/2010 |
| WO | WO 2011/101468 A1 | 8/2011 |
| WO | WO 2011/133704 A2 | 10/2011 |
| WO | WO 2012/142659 A1 | 10/2012 |
| WO | WO 2013/003555 A1 | 1/2013 |
| WO | WO 2013/155526 A2 | 10/2013 |
| WO | WO 2014/183006 A2 | 11/2014 |
| WO | WO 2015/073746 A2 | 5/2015 |
| WO | WO 2020/243006 A1 | 12/2020 |

OTHER PUBLICATIONS

De Groeve et al. (J. Nucl. Med. 2010, 51, 782-789).*
Kubetzko et al. (J. Biol. Chem. 2006, 281, 35186-35201).*
Xavier et al. (J. Nucl. Med. 2013, 54, 776-784).*
Kijanka et al. (Nanomedicine (Lond.) 2015, 10, 161-174.*
Li et al. (Mol. Cancer Ther. 2014, 13, 2607-2617).*
Wu et al. (J. Carbohydr. Chem. 2012, 31, 48-66; p. 1-5).*
Warden-Rothman et al. (Anal. Chem. 2013, 85, 11090-11097).*
Trilling et al. (Biosensor Bioelectronics 2014, 60, 130-136).*
Perez-Medina (J. Nucl. Med. 2014, 55, 1706-1711).*
Kolate et al. (J. Control. Release 2014, 192, 67-81).*
Pepinsky et al. (Bioconj. Chem. 2011, 22, 200-210).*
Leong et al. (Cytokine 2001, 16, 106-119).*
Extended European Search Report, mailed Jul. 26, 2019, in connection with EP 19171188.6.
Extended European Search Report, mailed Jul. 26, 2019, in connection with EP 19171190.2.
Extended European Search Report, mailed Apr. 29, 2019, in connection with EP 16852806.5.
[No Author Listed] Creative Biolabs. Single Domain Antibody Library. Retrieved from at www.creative-biolabs.com/single-domain-antibody-library-service.html?gclid=eaiaiqobchminozno5qo3givibczch3uhqhneaayaiaaegk-sfd_bwe on Oct. 17, 2018.
[No Author Listed], Fusion protein. Wikipedia. 7 pages Retrieved from https://en.wikipedia.org/Fusion_protein on Feb. 8, 2019.
Bentley et al., Engineering the substrate specificity of *Staphylococcus aureus* Sortase A. The beta6/beta7 loop from SrtB confers NPQTN recognition to SrtA. J Biol Chem. Mar. 2, 2007;282(9):6571-81. Epub Jan. 2, 2007.
Brotzel et al., Nucleophilicities of amino acids and peptides. Org Biomol Chem. Dec. 7, 2007;5(23):3814-20. Epub Oct. 16, 2007.
Bundy et al., Site-specific incorporation of p-propargyloxyphenylalanine in a cell-free ennvironment for direct protein-protein click conjugation. Bioconjug Chem. Feb. 17, 2010;21(2):255-63.
Cheung et al., A small-scale serum-free liquid cell culture model of erythropoiesis to assess the effects of exogenous factors. J Immunol Methods. Jan. 30, 2007;319(1-2):104-17. Epub Dec. 4, 2006.
Cooper et al., Comparison of (64)Cu-complexing bifunctional chelators for radioimmunoconjugation: labeling efficiency, specific activ-

(56) References Cited

OTHER PUBLICATIONS ity, and in vitro/in vivo stability. Bioconjug Chem. May 16, 2012;23(5):1029-39. doi: 10.1021/bc300037w. Epub Apr. 13, 2012.
David et al., Facile, efficient routes to diverse protected thiols and to their deprotection and addition to create functional polymers by thiol-ene coupling. Macromolec. 2008;41(4):1151-61.
Debets et al., Aza-dibenzocyclooctynes for fast and efficient enzyme PEGylation via copper-free (3+2) cycloaddition. Chem Commun (Camb). Jan. 7, 2010;46(1):97-9. doi: 10.1039/b917797c. Epub Nov. 6, 2009.
Delgado et al. Stabilities of divalent and trivalent metal ion complexes of macrocyclic triazatriacetic acids. Inorg. Chem. 1993; 32, 3320-3326.
Diamandis et al., The Biotin-(Strept) Avidin System: Principles and Applications in Biotechnology. Clin. Chem. 1991;37(5):625-36.
Fournier et al., Clicking polymers: a straightforward approach to novel macromolecular architectures. Chem Soc Rev. Aug. 2007;36(8):1369-80. Epub May 3, 2007.
Hess et al., M13 bacteriophage display framework that allows sortase-mediated modification of surface-accessible phage proteins. Bioconjug Chem. Jul. 18, 2012;23(7):1478-87. doi: 10.1021/bc300130z. Epub Jul. 3, 2012.
Hirakawa et al., Design of Ca2+-independent *Staphylococcus aureus* sortase A mutants. Biotechnol Bioeng. Dec. 2012;109(12):2955-61. doi: 10.1002/bit.24585. Epub Jul. 4, 2012. PubMed PMID: 22729808.
Idoyaga et al., Comparable T helper 1 (Th1) and CD8 T-cell immunity by targeting HIV gag p24 to CD8 dendritic cells within antibodies to Langerin, DEC205, and Clec9A. Proc Natl Acad Sci U S A. Feb. 8, 2011;108(6):2384-9. doi: 10.1073/pnas.1019547108. Epub Jan. 24, 2011.
Jevsevar et al., PEGylation of therapeutic proteins. Biotechnol J. Jan. 2010;5(1):113-28.
Keliher et al., High-yielding, two-step 18F labeling strategy for 18F-PARP1 inhibitors. ChemMedChem. Mar. 7, 2011;6(3):424-7. doi: 10.1002/cmdc.201000426. Epub Jan. 4, 2011.
Kolb et al., The growing impact of click chemistry on drug discovery. Drug Discov Today. Dec. 15, 2003;8(24):1128-37.
Li et al., Tetrazine-trans-cyclooctene ligation for the rapid construction of 18F labeled probes. Chem Commun (Camb). Nov. 14, 2010;46(42):8043-5. doi: 10.1039/c0cc03078c. Epub Sep. 22, 2010.
Lowrie et al., Chapter 20. EPO: Treating Anemia in Chronic Renal Failure. The National Kidney Foundation. 2011;1-6.
Miharada et al., Efficient enucleation of erythroblasts differentiated in vitro from hematopoietic stem and progenitor cells. Nat Biotechnol. Oct. 2006;24(10):1255-6. Epub Sep. 17, 2006.
Moreno et al., Immunohistochemical analysis of B3 integrin (CD61):expression in pig tissues and human tumors. Histol Histopathol. 2002;17:347-352.
Pritz et al., Synthesis of biologically active peptide nucleic acid-peptide conjugates by sortase-mediated ligation. J Org Chem. May 11, 2007;72(10):3909-12. Epub Apr. 14, 2007.
Race et al., Crystal structure of *Streptococcus pyogenes* sortase A: implications for sortase mechanism. J Biol Chem. Mar. 13, 2009;284(11):6924-33. Epub Jan. 6, 2009.
Selvaraj et al., trans-Cyclooctene—a stable, voracious dienophile for bioorthogonal labeling. Curr Opin Chem Biol. Oct. 2013;17(5):753-60. doi:10.1016/j.cbpa.2013.07.031. Epub Aug. 23, 2013.
Sharpless et al., Just click it: Undergraduate procedures for the copper(I)-catalyzed formation of 1,2,3-triazoles from azides and terminal acetylenes. J Chem Ed. 2005;82(12):1833-6.
Wu, F-18 Labeled Diabody-Luciferase Fusion Proteins for Optical-ImmunoPET. Department of Energy Final Scientific/Technical Report. Report No. DOE/SC0001220-1. University of California, Los Angeles. Jan. 18, 2013. doi: 10.2172/1060194. 11 pages.
Xiao et al., Synthesis of N-terminally linked protein dimers and trimers by a combined native chemical ligation-CuAAC click chemistry strategy. Org Lett. Sep. 17, 2009;11(18):4144-7. doi: 10.1021/ol9016468.

Zaslavskaia et al., Trophic conversion of an obligate photoautotrophic organism through metabolic engineering. Science. Jun. 15, 2001;292(5524):2073-5.
Zhao et al., an efficient on-column expressed protein ligation strategy: application to segmental triple labeling of human apolipoprotein E3. Protein Sci. Apr. 2008;17(4):736-47. Epub Feb. 27, 2008.
Extended European Search Report, mailed Nov. 30, 2012, in connection with EP 10736161.0.
Invitation to Pay Additional Fees, mailed Nov. 8, 2010, in connection with PCT/US2010/000274.
International Search Report and Written Opinion, mailed Dec. 22, 2010, in connection with PCT/US2010/000274.
International Preliminary Report on Patentability, mailed Aug. 11, 2011, in connection with PCT/US2010/000274.
Extended European Search Report, mailed Nov. 26, 2014, in connection with EP 12804570.5.
International Search Report and Written Opinion, mailed Nov. 15, 2012, in connection with PCT/US2012/044584.
International Preliminary Report on Patentability, mailed Jan. 16, 2014, in connection with PCT/US2012/044584.
Invitation to Pay Additional Fees, mailed Sep. 5, 2014, in connection with PCT/US2014/037554.
International Search Report and Written Opinion, mailed Nov. 6, 2014, in connection with PCT/US2014/037554.
International Preliminary Report on Patentability, mailed Nov. 19, 2015, in connection with PCT/US2014/037554.
International Search Report and Written Opinion, mailed Oct. 27, 2014, in connection with PCT/US2014/037545.
International Preliminary Report on Patentability, mailed Nov. 19, 2015, in connection with PCT/US2014/037545.
Invitation to Pay Additional Fees, mailed Mar. 20, 2015, in connection with PCT/US14/65574.
International Search Report and Written Opinion, mailed Jun. 4, 2015, in connection with PCT/US14/65574.
Extended European Search Report, mailed Nov. 9, 2016, in connection with EP 14795167.7.
Extended European Search Report, mailed Oct. 13, 2016, in connection with EP 14795120.6.
International Preliminary Report on Patentability, mailed Apr. 12, 2018, in connection with PCT/US2016/055074.
International Search Report and Written Opinion, mailed Feb. 6, 2017, in connection with PCT/US2016/055074.
Invitation to Pay Additional Fees, mailed Dec. 1, 2016, in connection with PCT/US2016/055074.
Ahlgren et al., Targeting of HER2-expressing tumors with a site-specifically 99mTc-labeled recombinant affibody molecule, ZHER2:2395, with C-terminally engineered cysteine. J Nucl Med. May 2009;50(5):781-9. doi: 10.2967/jnumed.108.056929. Epub Apr. 16, 2009.
Antos et al., A straight path to circular proteins. J Biol Chem. Jun. 5, 2009;284(23):16028-36. Epub Apr. 9, 2009.
Antos et al., Lipid modification of proteins through sortase-catalyzed transpeptidation. J Am Chem Soc. Dec. 3, 2008;130(48):16338-43.
Antos et al., Site-specific N- and C-terminal labeling of a single polypeptide using sortases of different specificity. J Am Chem Soc. Aug. 12, 2009;131(31):10800-1. doi: 10.1021/ja902681k.
Arnau et al., Current strategies for the use of affinity tags and tag removal for the purification of recombinant proteins. Protein Expr Purif. Jul. 2006;48(1):1-13. Epub Dec. 28, 2005.
Bader et al., Bioorganic synthesis of lipid-modified proteins for the study of signal transduction. Nature. Jan. 13, 2000;403(6766):223-6. doi: 10.1158/0008-5472.CAN-09-0547. Epub Jun. 9, 2009.
Barnett et al., Differential recognition of surface proteins in *Streptococcus pyogenes* by two sortase gene homologs. J Bacteriol. Apr. 2002;184(8):2181-91.
Baskin et al., Bioorthogonal click chemistry: Covalent labeling in living systems. QSAR Comb Sci. Dec. 2007;26(11-12):1211-9.
Becer et al., Click chemistry beyond metal-catalyzed cycloaddition. Angew Chem Int Ed Engl. 2009;48(27):4900-8.
Biagiotti et al., Drug delivery by red blood cells. IUBMB Life. Aug. 2011;63(8):621-31. doi: 10.1002/iub.478. Epub Jul. 15, 2011.

(56) References Cited

OTHER PUBLICATIONS

Binder et al., 'Click' Chemistry in Polymer and Materials Science. Macromol Rapid Commun. Jan. 5, 2007;28(1):15-54.

Blackman et al., Tetrazine ligation: fast bioconjugation based on inverse-electron-demand Diels-Alder reactivity. J Am Chem Soc. Oct. 15, 2008;130(41):13518-9. Epub Sep. 18, 2008.

Boellaard et al., FDG PET and PET/CT: EANM procedure guidelines for tumour PET imaging: version 1.0. Eur J Nucl Med Mol Imaging. Jan. 2010;37(1):181-200. doi: 10.1007/s00259-009-1297-4.

Boonyarattanakalin et al., Synthesis of an artificial cell surface receptor that enables oligohistidine affinity tags to func-tion as metal-dependent cell-penetrating peptides. J Am Chem Soc. Mar. 18, 2006;128(14):4917.

Borjesson et al., Radiation dosimetry of 89Zr-labeled chimeric monoclonal antibody U36 as used for immuno-PET in head and neck cancer patients. J Nucl Med. Nov. 2009;50(11):1828-36. doi: 10.2967/jnumed.109.065862. Epub Oct. 16, 2009.

Carrasquillo et al., (124)I-huA33 antibody PET of colorectal cancer. J Nucl Med. Aug. 2011;52(8):1173-80. doi: 10.2967/jnumed.110.086165. Epub Jul. 15, 2011.

Chan et al., Covalent attachment of proteins to solid supports and surfaces via Sortase-mediated ligation. PLoS One. Nov. 14, 2007;2(11):e1164. 5 pages.

Chang et al., Development and characterization of 89Zr-labeled panitumumab for immuno-positron emission tomographic imaging of the epidermal growth factor receptor. Mol Imaging. Jan.-Feb. 2013;12(1):17-27.

Chen et al., A general strategy for the evolution of bond-forming enzymes using yeast display. Proc Natl Acad Sci U S A. Jul. 12, 2011;108(28):11399-404. doi: 10.1073/pnas.1101046108. Epub Jun. 22, 2011.

Chudakov et al., Fluorescent proteins and their applications in imaging living cells and tissues.Physiol Rev. Jul. 2010;90(3):1103-63. doi: 10.1152/physrev.00038.2009.

Clow et al., Immobilization of proteins to biacore sensor chips using *Staphylococcus aureus* sortase A. Biotechnol Lett. Sep. 2008;30(9):1603-7. Epub Apr. 15, 2008.

Comfort et al., A comparative genome analysis identifies distinct sorting pathways in gram-positive bacteria. Infect Immun. May 2004;72(5):2710-22.

Cortez-Retamozo et al., Efficient tumor targeting by single-domain antibody fragments of camels. Int J Cancer. Mar. 20, 2002;98(3):456-62.

De Meyer et al., Nanobody-based products as research and diagnostic tools. Trends Biotechnol. May 2014;32(5):263-70. doi:10.1016/j.tibtech.2014.03.001. Epub Apr. 1, 2014.

Delgado, et al. "Stabilities of divalent and trivalent metal ion complexes of macrocyclic triazatriacetic acids.", Inorg. Chem. 1999; 32, 3320-3326.

Denk et al., Development of a (18) F-labeled tetrazine with favorable pharmacokinetics for bioorthogonal PET imaging. Angew Chem Int Ed Engl. Sep. 1, 2014;53(36):9655-9. doi:10.1002/anie.201404277. Epub Jul. 2, 2014.

Dijkers et al., Biodistribution of 89Zr-trastuzumab and PET imaging of HER2-positive lesions in patients with metastatic breast cancer. Clin Pharmacol Ther. May 2010;87(5):586-92. doi:10.1038/clpt.2010.12. Epub Mar. 31, 2010.

Divgi et al., Positron emission tomography/computed tomography identification of clear cell renal cell carcinoma: results from the REDECT trial.J Clin Oncol. Jan. 10, 2013;31(2):187-94. doi: 10.1200/JCO.2011.41.2445. Epub Dec. 3, 2012.

Dorr et al., Reprogramming the specificity of sortase enzymes. Proc Natl Acad Sci U S A. Sep. 16, 2014;111(37):13343-8. doi:10.1073/pnas.1411179111. Epub Sep. 3, 2014.

Dramsi et al., Sorting sortases: a nomenclature proposal for the various sortases of Gram-positive bacteria. Res Microbiol. Apr. 2005;156(3):289-97. Epub Jan. 28, 2005.

Engfeldt et al., Chemical synthesis of triple-labelled three-helix bundle binding proteins for specific fluorescent detection of unlabelled protein. Chembiochem. Jun. 2005;6(6):1043-50.

Evans et al., Bioorthogonal chemistry for (68) Ga radiolabelling of DOTA-containing compounds. J Labelled Comp Radiopharm. Apr. 2014;57(4):291-7. doi: 10.1002/jler.3153. Epub Dec. 5, 2013.

Evans, The rise of azide-alkyne 1,3-dipolar 'click' cycloaddition and its application to polymer science and surface modification. Australian J Chem. Jun. 18, 2007;60(6):384-95.

Gebauer et al., Engineered protein scaffolds as next-generation antibody therapeutics. Curr Opin Chem Biol. Jun. 2009;13(3):245-55. doi: 10.1016/j.cbpa.2009.04.627. Epub Jun. 6, 2009.

Genbank Submission; NIH/NCBI, Accession No. AAD48437; Mazmanian et al.; Aug. 11, 1999. Updated Nov. 30, 2009 and Mar. 10, 2010.

Genbank Submission; NIH/NCBI, Accession No. NP_375640. Jang et al., Aug. 26, 2013. 3 pages.

GenPept Accession No. YP 187332.1. Gill et al. Dec. 17, 2014.

Giarratana et al., Proof of principle for transfusion of in vitro-generated red blood cells. Blood. Nov. 10, 2011;118(19):5071-9. doi:10.1182/blood-2011-06-362038. Epub Sep. 1, 2011.

Godfrin et al., International seminar on the red blood cells as vehicles for drugs. Expert Opin Biol Ther. Jan. 2012;12(1):127-33. doi: 10.1517/14712598.2012.631909. Epub Oct. 25, 2011.

Goldenberg et al., Novel radiolabeled antibody conjugates. Oncogene. May 28, 2007;26(25):3734-44.

Groheux et al., Correlation of high 18F-FDG uptake to clinical, pathological and biological prognostic factors in breast cancer. Eur J Nucl Med Mol Imaging. Mar. 2011;38(3):426-35. doi:10.1007/s00259-010-1640-9. Epub Nov. 6, 2010.

Guimaraes et al., Site-specific C-terminal and internal loop labeling of proteins using sortase-mediated reactions. Nat Protoc. Sep. 2013;8(9):1787-99. doi:10.1038/nprot.2013.101. Epub Aug. 29, 2013.

Hackenberger et al., Chemoselective ligation and modification strategies for peptides and proteins. Angew Chem Int Ed Engl. 2008;47(52):10030-74. doi: 10.1002/anie.200801313.

Heal et al., Site-specific N-terminal labelling of proteins in vitro and in vivo using N-myristoyl transferase and bioorthogonal ligation chemistry. Chem Commun (Camb). Jan. 28, 2008;(4):480-2. Epub Nov. 13, 2007.

Hochuli et al., Genetic Approach to Facilitate Purification of Recombinant Proteins with a Novel Metal Chelate Adsorbent. Nature Biotechnology. 1988, 6, 1321-1325.

Holm et al., Electrophilic affibodies forming covalent bonds to protein targets. J Biol Chem. Nov. 20, 2009;284(47):32906-13. doi:10.1074/jbc.M109.034322. Epub Sep. 15, 2009.

Knowles et al., Advances in immuno-positron emission tomography: antibodies for molecular imaging in oncology. J Clin Oncol. Nov. 1, 2012;30(31):3884-92. doi: 10.1200/JCO.2012.42.4887. Epub Sep. 17, 2012.

Kolb et al., Click Chemistry: Diverse Chemical Function from a Few Good Reactions. Angew Chem Int Ed Engl. Jun. 1, 2001;40(11):2004-2021.

Kruger et al., Analysis of the substrate specificity of the *Staphylococcus aureus* sortase transpeptidase SrtA. Biochemistry. Feb. 17, 2004;43(6):1541-51.

Langenhan et al., "Recent Carbohydrate-Based Chemoselective Ligation Applications." Current Organic Synthesis. 2005; 2, 59-81.

Levary et al., Protein-protein fusion catalyzed by sortase A. PLoS One. Apr. 6, 2011;6(4):e18342. doi: 10.1371/journal.pone.0018342. 6 pages.

Liu et al., A Brief Review of Chelators for Radiolabeling Oligomers. Materials. 2010; 3(5): 3204-3217.

Lu et al. Biologic properties and enucleation of red blood cells from human embryonic stem cells. Blood. Dec. 1, 2008;112(12):4475-84. doi: 10.1182/blood-2008-05-157198. Epub Aug. 19, 2008.

Lundberg et al., Site-specifically conjugated anti-HER2 Affibody molecules as one-step reagents for target expression analyses on cells and xenograft samples. J Immunol Methods. Jan. 30, 2007;319(1-2):53-63. Epub Nov. 21, 2006.

Mao et al., Sortase-Mediated Protein Ligation: A New Method for Portein Engineering. J Am Chem Soc. Feb. 10, 2004;126:2670-1.

(56) References Cited

OTHER PUBLICATIONS

Mao, A self-cleavable sortase fusion for one-step purification of free recombinant proteins. Protein Expr Purif. Sep. 2004;37(1):253-63.
Maresso et al., Surface protein IsdC and Sortase B are required for heme-iron scavenging of Bacillus anthracis. J Bacteriol. Dec. 2006;188(23):8145-52. Epub Sep. 29, 2006.
Mariscotti et al., The Listeria monocytogenes sortase-B recognizes varied amino acids at position 2 of the sorting motif. J Biol Chem. Mar. 6, 2009;284(10):6140-6. Epub Jan. 7, 2009.
Marraffini et al., Sortase C-mediated anchoring of BasI to the cell wall envelope of Bacillus anthracis. J Bacteriol. Sep. 2007;189(17):6425-36. Epub Jun. 22, 2007.
Matsumoto et al., Site-specific tetrameric streptavidin-protein conjugation using sortase A. J Biotechnol. Mar. 10, 2011;152(1-2):37-42. doi: 10.1016/j.jbiotec.2011.01.008. Epub Jan. 22, 2011.
Matsumura et al., Emerging principles for the recognition of peptide antigens by MHC class 1 molecules, Sci. 1992;257:927-934.
Mazmanian et al., An iron-regulated sortase anchors a class of surface protein during *Staphylococcus aureus* pathogenesis. Proc Natl Acad Sci U S A. Feb. 19, 2002;99(4):2293-8. Epub Feb. 5, 2002.
Mazmanian et al., Sortase-catalysed anchoring of surface proteins to the cell wall of *Staphylococcus aureus*. Mol Microbiol. Jun. 2001;40(5):1049-57. Review.
Murciano et al., Prophylactic fibrinolysis through selective dissolution of nascent clots by tPA-carrying erythrocytes. Nat Biotechnol. Aug. 2003;21(8):891-6. Epub Jul. 6, 2003.
Muzykantov, Drug delivery by red blood cells: vascular carriers designed by mother nature. Expert Opin Drug Deliv. Apr. 2010;7(4):403-27. doi: 10.1517/17425241003610633.
Nair-Gill et al., Non-invasive imaging of adaptive immunity using positron emission tomography. Immunol Rev. Feb. 2008;221:214-28. doi: 10.1111/j.1600-065X.2008.00585.x.
Namavari et al., A novel method for direct site-specific radiolabeling of peptides using [18F]FDG. Bioconjug Chem. Mar. 18, 2009;20(3):432-6. doi: 10.1021/bc800422b.
Nayak et al., PET and MRI of metastatic peritoneal and pulmonary colorectal cancer in mice with human epidermal growth factor receptor 1-targeted 89Zr-labeled panitumumab. J Nucl Med. Jan. 2012;53(1):113-20. doi: 10.2967/jnumed.111.094169.
Ning et al., Visualizing metabolically labeled glycoconjugates of living cells by copper-free and fast huisgen cycloadditions. Angew Chem Int Ed Engl. 2008;47(12):2253-5.
Olafsen et al., ImmunoPET using engineered antibody fragments: fluorine-18 labeled diabodies for same-day imaging. Tumour Biol. Jun. 2012;33(3):669-77. doi: 10.1007/s13277-012-0365-8. Epub Mar. 6, 2012.
Orlova et al., Evaluation of [(111/114m)In]CHX-A-DTPA-ZHER2:342, an affibody ligand coniugate for targeting of HER2-expressing malignant tumors. Q J Nucl Med Mol Imaging. 2007;51:314-323.
Orlova et al., Tumor imaging using a picomolar affinity HER2 binding affibody molecule. Cancer Res. Apr. 15, 2006;66(8):4339-48.
Pallen et al., An embarrassment of sortases—a richness of substrates? Trends Microbiol. Mar. 2001;9(3):97-101.
Park et al., Anchoring foreign substances on live cell surfaces using Sortase A specific binding peptide. Chem Commun (Camb). Oct. 25, 2013;49(83):9585-7. doi: 10.1039/c3cc44753g.
Parthasarathy et al., Sortase A as a novel molecular "stapler" for sequence-specific protein conjugation. Bioconjug Chem. Mar.-Apr. 2007;18(2):469-76. Epub Feb. 16, 2007.
Paterson et al., Enzyme-mediated site-specific bioconjugation of metal complexes to proteins: sortase-mediated coupling of copper-64 to a single-chain antibody. Angew Chem Int Ed Engl. Jun. 10, 2014;53(24):6115-9. doi: 10.1002/anie.201402613. Epub Apr. 28, 2014.
Pellois et al., A ligation and photorelease strategy for the temporal and spatial control of protein function in living cells. Angew Chem Int Ed Engl. Sep. 5, 2005;44(35):5713-7.
Piotukh et al., D. Directed evolution of sortase A mutants with altered substrate selectivity profiles. J Am Chem Soc. Nov. 9, 2011;133(44):17536-9. doi: 10.1021/ja205630g. Epub Oct. 13, 2011.
Pishesha et al., Engineered erythrocytes covalently linked to antigenic peptides can protect against autoimmune disease. Proc Natl Acad Sci U S A. Mar. 21, 2017;114(12):3157-3162. doi:10.1073/pnas.1701746114. Epub Mar. 7, 2017.
Poli et al., Radretumab radioimmunotherapy in patients with brain metastasis: a 124I-L19SIP dosimetric PET study. Cancer Immunol Res. Aug. 2013;1(2):134-43. doi: 10.1158/2326-6066.CIR-13-0007. Epub May 20, 2013.
Popp et al., Making and breaking peptide bonds: protein engineering using sortase. Angew Chem Int Ed Engl. May 23, 2011;50(22):5024-32. doi: 10.1002/anie.201008267. Epub Apr. 27, 2011.
Popp et al., Site-specific protein labeling via sortase-mediated transpeptidation. Curr Protoc Protein Sci. Apr. 2009;Chapter 15:Unit 15.3. doi: 10.1002/0471140864.ps1503s56.
Popp et al., Sortagging: a versatile method for protein labeling. Nat Chem Biol. Nov. 2007;3(11):707-8. Epub Sep. 23, 2007.
Popp et al., Sortase-catalyzed transformations that improve the properties of cytokines. Proc Natl Acad Sci USA. Feb. 22, 2011;108(8):3169-74. doi: 10.1073/pnas.1016863108. Epub Feb. 4, 2011.
Popp et al., Substrate filtering by the active site crossover loop in UCHL3 revealed by sortagging and gain-of-function mutations. J Biol Chem. Feb. 6, 2009;284(6):3593-602. Epub Dec. 1, 2008.
Rashidian et al., A highly efficient catalyst for oxime ligation and hydrazone-oxime exchange suitable for bioconjugation. Bioconjug Chem. Mar. 20, 2013;24(3):333-42. doi: 10.1021/bc3004167.Epub Mar. 6, 2013.
Rashidian et al., Enzymatic labeling of proteins: techniques and approaches. Bioconjug Chem. Aug. 21, 2013;24(8):1277-94.
Rashidian et al., Noninvasive imaging of immune responses. Proc Natl Acad Sci U S A. May 12, 2015;112(19):6146-51. doi: 10.1073/pnas.1502609112. Epub Apr. 20, 2015.
Rashidian et al., The use of 18F-2-fluorodeoxyglucose (FDG) to label antibody fragments for immuno-PET of pancreatic cancer. ACS Cent Sci. Jun. 24, 2015;1(3):142-147. Epub Jun. 3, 2015.
Ronnmark et al., Construction and characterization of affibody-Fc chimeras produced in *Escherichia coli*. J Immunol Methods. Mar. 1, 2002;261(1-2):199-211.
Salsano et al., "PET imaging using radiolabeled antibodies: future direction in tumor diagnosis and correlate applications." Research and Reports in Nuclear Medicine. 2013: 3; 9-17.
Samantaray et al., Peptide-sugar ligation catalyzed by transpeptidase sortase: a facile approach to neoglycoconjugate synthesis. J Am Chem Soc. Feb. 20, 2008;130(7):2132-3. Epub Jan. 30, 2008.
Sankaran et al., Cyclin D3 coordinates the cell cycle during differentiation to regulate erythrocyte size and number. Genes Dev. Sep. 15, 2012;26(18):2075-87. doi: 10.1101/gad.197020.112. Epub Aug. 28, 2012.
Shi et al. Engineered red blood cells as carriers for systemic delivery of a wide array of functional probes. Proc Natl Acad Sci U S A. Jul. 15, 2014;111(28):10131-6. doi: 10.1073/pnas.1409861111. Epub Jun. 30, 2014.
Siontorou, Nanobodies as novel agents for disease diagnosis and therapy. Int J Nanomedicine. 2013;8:4215-27. doi: 10.2147/IJN.S39428. Epub Jan. 11, 2013.
Sletten et al., Bioorthogonal chemistry: fishing for selectivity in a sea of functionality. Angew Chem Int Ed Engl. 2009;48(38):6974-98. doi: 10.1002/anie.200900942.
Spicer et al., Selective chemical protein modification. Nat Commun. Sep. 5, 2014;5:4740. doi: 10.1038/ncomms5740.
Strijbis et al., Protein ligation in living cells using sortase. Traffic. Jun. 2012;13(6):780-9. doi: 10.1111/j.1600-0854.2012.01345.x. Epub Mar. 23, 2012.
Swee et al., One-step enzymatic modification of the cell surface redirects cellular cytotoxicity and parasite tropism. ACS Chem Biol. Feb. 20, 2015;10(2):460-5. doi: 10.1021/cb500462t.
Swee et al., Sortase-mediated modification of αDEC205 affords optimization of antigen presentation and immunization against a set of viral epitopes. Proc Natl Acad Sci USA. Jan. 22, 2013;110(4):1428-33. doi: 10.1073/pnas.1214994110. Epub Jan. 7, 2013.

(56) References Cited

OTHER PUBLICATIONS

Ta et al., Enzymatic single-chain antibody tagging: a universal approach to targeted molecular imaging and cell homing in cardiovascular disease. Circ Res. Aug. 5, 2011;109(4):365-73. doi: 10.1161/CIRCRESAHA.111.249375.
Tanaka et al., PET (positron emission tomography) imaging of biomolecules using metal-DOTA complexes: a new collaborative challenge by chemists, biologists, and physicians for future diagnostics and exploration of in vivo dynamics. Org Biomol Chem. Mar. 7, 2008;6(5):815-28. doi: 10.1039/b718157b. Epub Feb. 1, 2008.
Tanaka et al., Site-specific protein modification on living cells catalyzed by Sortase. Chembiochem. Mar. 25, 2008;9(5):802-7.
Tavare et al., Engineered antibody fragments for immuno-PET imaging of endogenous CD8+ T cells in vivo. Proc Natl Acad Sci U S A. Jan. 21, 2014;111(3):1108-13. doi: 10.1073/pnas.1316922111. Epub Jan. 3, 2014.
Theile et al., Site-specific N-terminal labeling of proteins using sortase-mediated reactions. Nat Protoc. Sep. 2013;8(9):1800-7. doi: 10.1038/nprot.2013.102. Epub Aug. 29, 2013.
Tolmachev et al., Radionuclide therapy of HER2-positive microxenografts using a 177Lu-labeled HER2-specific Affibody molecule. Cancer Res. Mar. 15, 2007;67(6):2773-82.
Ton-That et al., Anchoring of surface proteins to the cell wall of *Staphylococcus aureus*. Sortase catalyzed in vitro transpeptidation reaction using LPXTG peptide and NH(2)-Gly(3) substrates. J Biol Chem. Mar. 31, 2000;275(13):9876-81.
Ton-That et al., Protein sorting to the cell wall envelope of Gram-positive bacteria. Biochim Biophys Acta. Nov. 11, 2004;1694(1-3):269-78.
Ton-That et al., Purification and characterization of sortase, the transpeptidase that cleaves surface proteins of *Staphylococcus aureus* at the LPXTG motif. Proc Natl Acad Sci U S A. Oct. 26, 1999;96(22):12424-9.
Tornoe et al., Peptidotriazoles on solid phase: [1,2,3]-triazoles by regiospecific copper(i)-catalyzed 1,3-dipolar cycloadditions of terminal alkynes to azides. J Org Chem. May 3, 2002;67(9):3057-64.
Tran et al., (99m)Tc-maEEE-Z(HER2:342), an Affibody molecule-based tracer for the detection of HER2 expression in malignant tumors. Bioconjug Chem. Nov.-Dec. 2007;18(6):1956-64. Epub Oct. 19, 2007.
Truong et al., Copper-catalyzed, directing group-assisted fluorination of arene and heteroarene C—H bonds. J Am Chem Soc. Jun. 26, 2013;135(25):9342-5. doi: 10.1021/ja4047125. Epub Jun. 12, 2013.
Tsukiji et al., Sortase-mediated ligation: A Gift from Gram-Positive Bacteria to Protein Engineering, ChemBioChem 2009;10:787-798.
Vaidyanathan et al., Synthesis of N-succinimidyl 4-[18F]fluorobenzoate, an agent for labeling proteins and peptides with 18F. Nat Protoc. 2006;1(4):1655-61.
Vosjan et al., Conjugation and radiolabeling of monoclonal antibodies with zirconium-89 for PET imaging using the bifunctional chelate p-isothiocyanatobenzyl-desferrioxamine. Nat Protoc. Apr. 2010;5(4):739-43. doi: 10.1038/nprot.2010.13. Epub Mar. 25, 2010.
Waldherr et al., Monitoring antiproliferative responses to kinase inhibitor therapy in mice with 3'-deoxy-3'-18F-fluorothymidine Pet. J Nucl Med. Jan. 2005;46(1):114-20.
Witte et al., Preparation of unnatural N-to-N and C-to-C protein fusions. Proc Natl Acad Sci U S A. Jul. 24, 2012;109(30):11993-8. doi: 10.1073/pnas.1205427109. Epub Jul. 9, 2012.
Witte et al., Production of unnaturally linked chimeric proteins using a combination of sortase-catalyzed transpeptidation and click chemistry. Nat Protoc. Sep. 2013;8(9):1808-19. doi: 10.1038/nprot.2013.103. Epub Apr. 4, 2014. 16 pages.
Wriggers et al., Control of Protein Functional Dynamics by Peptide Linkers, Prat. Function. Dynam. 2005;80:736-746.
Wright et al., Designing the magic bullet? The advancement of immuno-PET into clinical use. J Nucl Med. Aug. 2013;54(8):1171-4. doi: 10.2967/jnumed.113.126086.
Wu et al., Sortase A-catalyzed transpeptidation of glycosylphosphatidylinositol derivatives for chemoenzymatic synthesis of GPI-anchored proteins. J Am Chem Soc. Feb. 10, 2010;132(5):1567-71. doi: 10.1021/ja906611x.
Wu et al., The use of sortase-mediated ligation for the immobilisation of bacterial adhesins onto fluorescence-labelled microspheres: a novel approach to analyse bacterial adhesion to host cells. Biotechnol Lett. Nov. 2010;32(11):1713-8. doi: 10.1007/s10529-010-0349-y.
Xiao et al., Protein N-terminal processing: substrate specificity of *Escherichia coli* and human methionine aminopeptidases. Biochemistry. Jul. 6, 2010;49(26):5588-99. doi: 10.1021/bi1005464.
Yamamoto et al., Expansion of the sortase-mediated labeling method for site-specific N-terminal labeling of cell surface proteins on living cells. Chem Commun (Camb). Mar. 7, 2009;(9):1022-4. doi: 10.1039/b818792d. Epub Jan. 7, 2009.
Yang et al., Metal-catalyzed one-pot synthesis of tetrazines directly from aliphatic nitriles and hydrazine. Angew Chem Int Ed Engl. May 21, 2012;51(21):5222-5. doi: 10.1002/anie.201201117. Epub Apr. 18, 2012.
Yoo et al.,Bio-inspired, bioengineered and biomimetic drug delivery carriers. Nat Rev Drug Discov. Jul. 1, 2011;10(7):521-35. doi: 10.1038/nrd3499.
Youssef et al., The use of 18F-FDG PET in the diagnosis of cardiac sarcoidosis: a systematic review and metaanalysis including the Ontario experience. J Nucl Med. Feb. 2012;53(2):241-8. doi:10.2967/jnumed.111.090662. Epub Jan. 6, 2012.
Zaitsev et al., Sustained thromboprophylaxis mediated by an RBC-targeted pro-urokinase zymogen activated at the site of clot formation. Blood. Jun. 24, 2010;115(25):5241-8. doi: 10.1182/blood-2010-01-261610. Epub Apr. 21, 2010.
Zhang et al., Positron emission tomography imaging of CD105 expression with a 64Cu-labeled monoclonal antibody: NOTA is superior to DOTA. PLoS One. 2011;6(12):e28005. doi: 10.1371/journal.pone.0028005. Epub Dec. 9, 2011.
Zong et al., Crystal structures of *Staphylococcus aureus* sortase A and its substrate complex. J Biol Chem. Jul. 23, 2004;279(30):31383-9. Epub Apr. 26, 2004.
Extended European Search Report, mailed Jun. 19, 2020, in connection with EP 19219550.1.
Debierre-Grockiego et al., Differential effect of dexamethasone on cell death and STAT5 activation during in vitro eosinopoiesis. *Br J Haematol.* Dec. 2003;123(5):933-41. doi: 10.1046/j.1365-2141.2003.04700.x.
Reese et al., Human mesenchymal stem cells provide stromal support for efficient CD34+ transduction. *J Hematother Stem Cell Res.* Oct. 1999;8(5):515-23. doi: 10.1089/152581699319966.
Dorn et al., In vitro proliferation and differentiation of human CD34+ cells from peripheral blood into mature red blood cells with two different cell culture systems. Transfusion. Jun. 2008;48(6):1122-32. doi: 10.1111/j.1537-2995.2008.01653.x. Epub Feb. 22, 2008.
Deshayes et al., Cell-penetrating peptides: tools for intracellular delivery of therapeutics. Cell Mol Life Sci. Aug. 2005;62(16):1839-49. doi: 10.1007/s00018-005-5109-0.
Marsden et al., Model systems for membrane fusion. Chem Soc Rev. Mar. 2011;40(3):1572-85. doi: 10.1039/c0cs00115e. Epub Dec. 13, 2010.
Wang et al., Efficient delivery of genome-editing proteins using bioreducible lipid nanoparticles. Proc Natl Acad Sci U S A. Mar. 15, 2016;113(11):2868-73. doi: 10.1073/pnas.1520244113. Epub Feb. 29, 2016.
Extended European Search Report, mailed Dec. 15, 2022, in connection with EP 22173120.1.
Fishburn, C.S., The pharmacology of PEGylation: balancing PD with PK to generate novel therapeutics. J Pharm Sci. Oct. 2008;97(10):4167-83. doi: 10.1002/jps.21278.
Extended European Search Report, mailed Jun. 26, 2023, in connection with EP 16852806.5.

\* cited by examiner

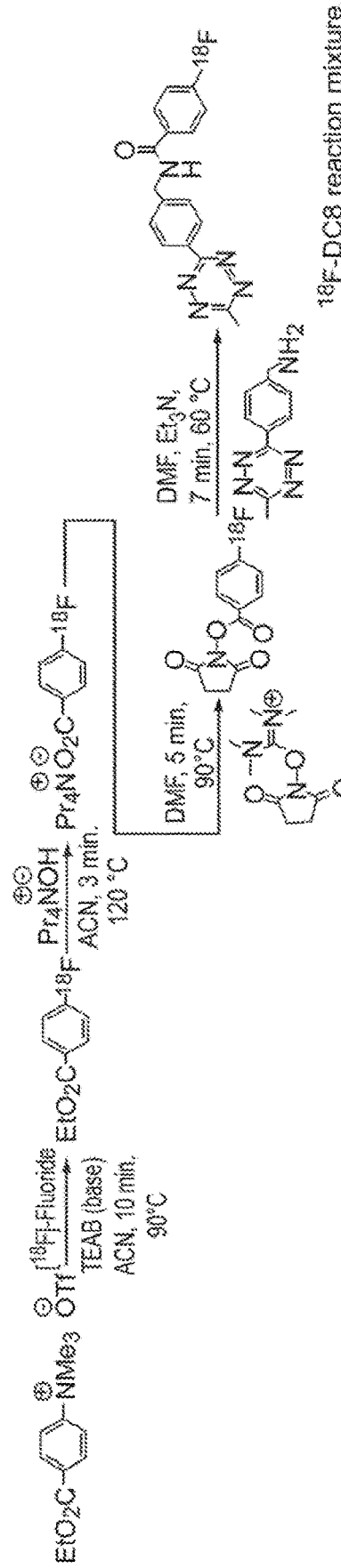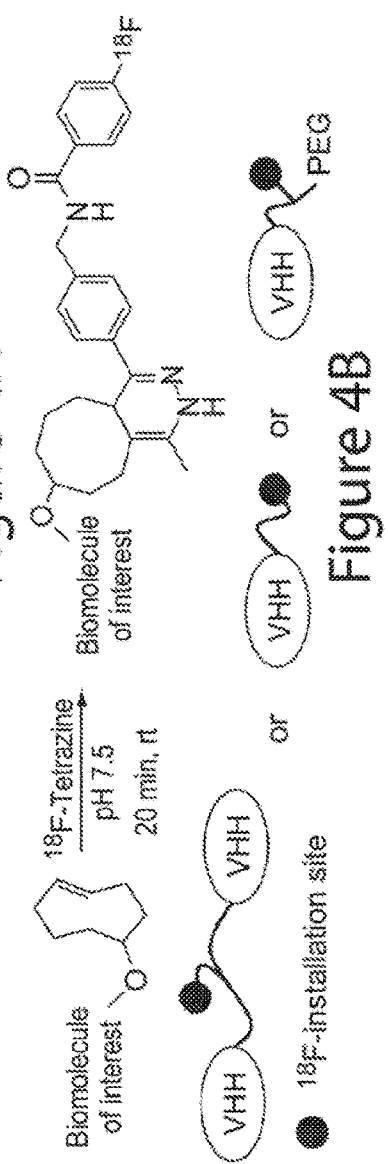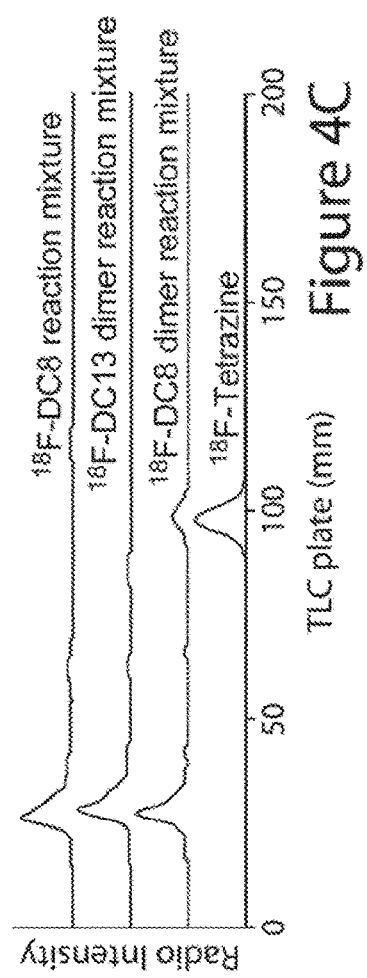
Figure 4A
Figure 4B
Figure 4C

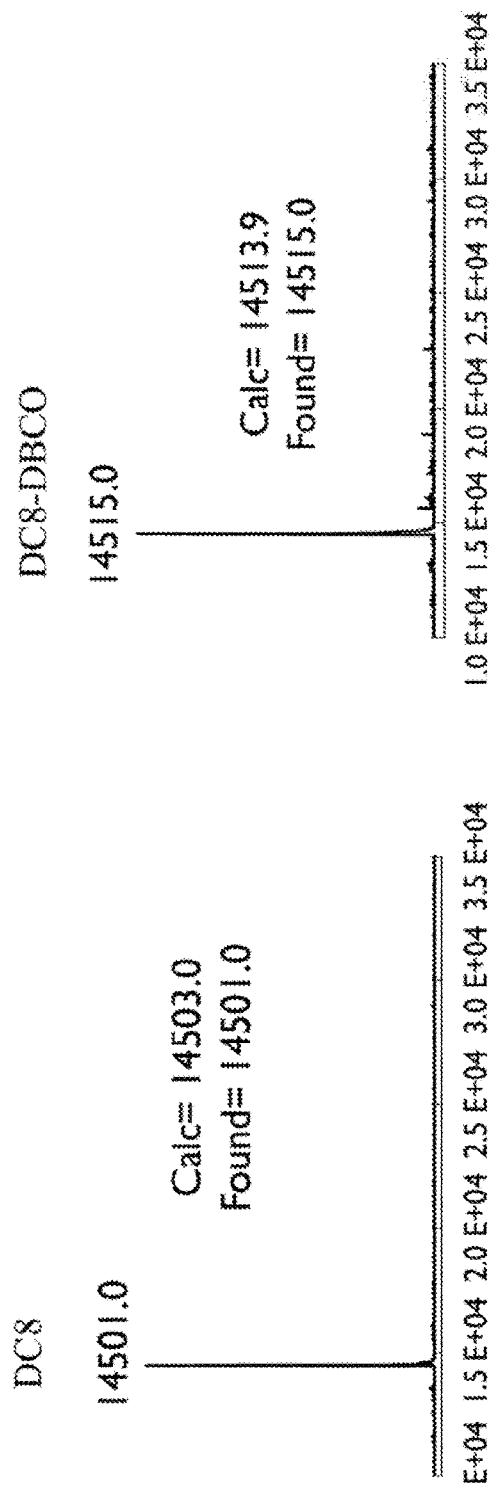
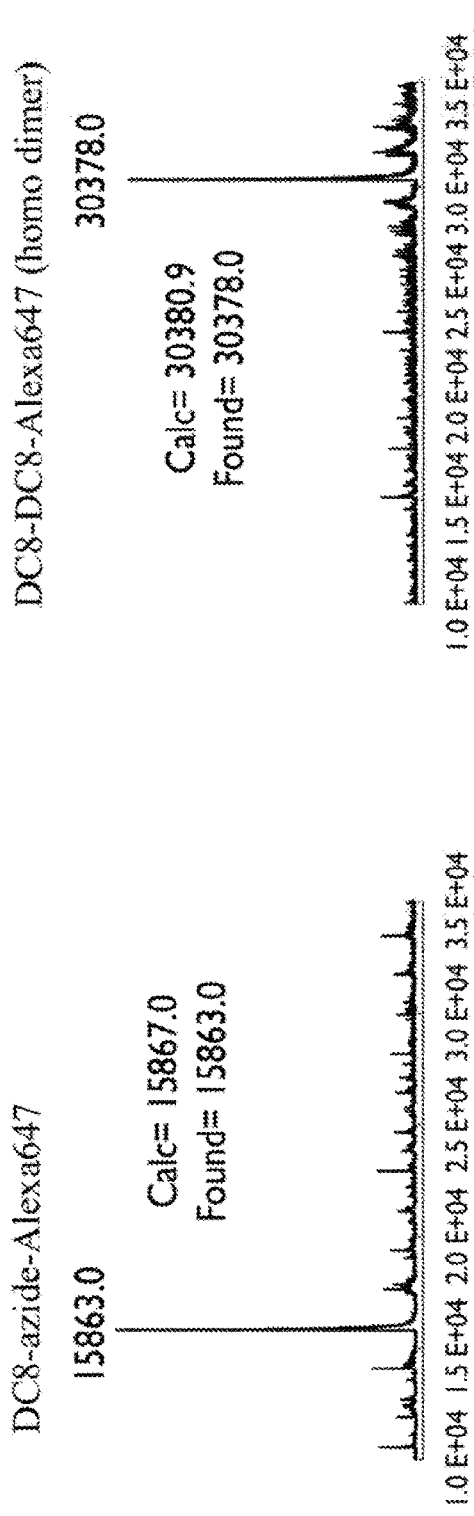

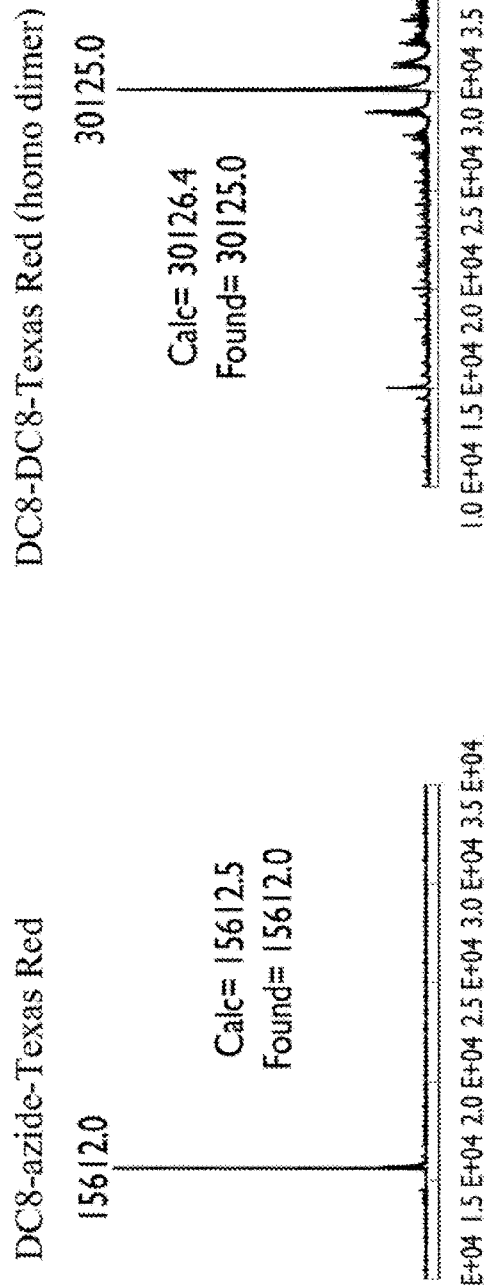
Figure 6E
Figure 6F
Figure 6G
Figure 6H

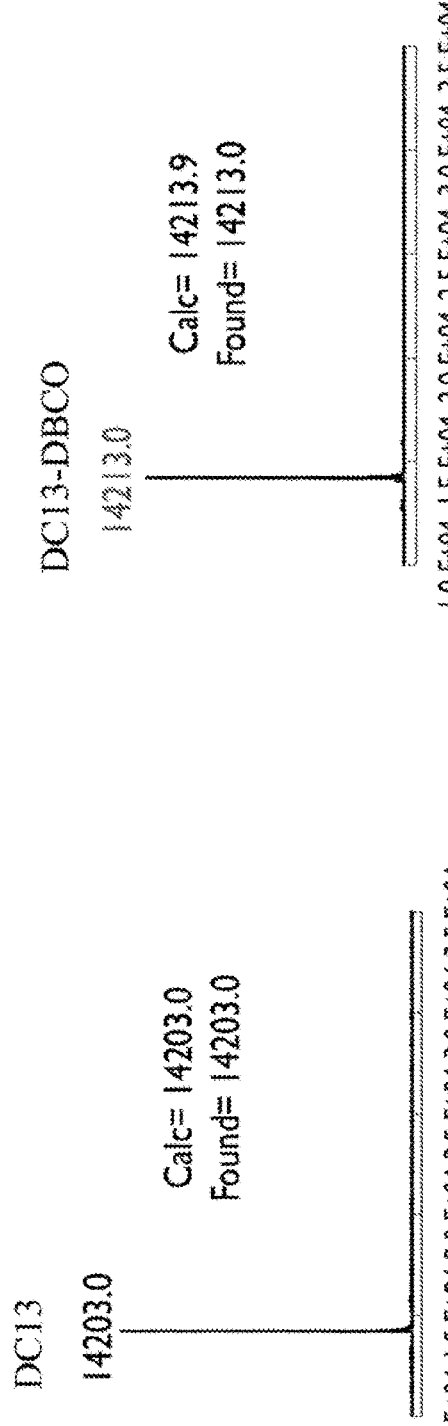
Figure 7A
Figure 7B
Figure 7C
Figure 7D

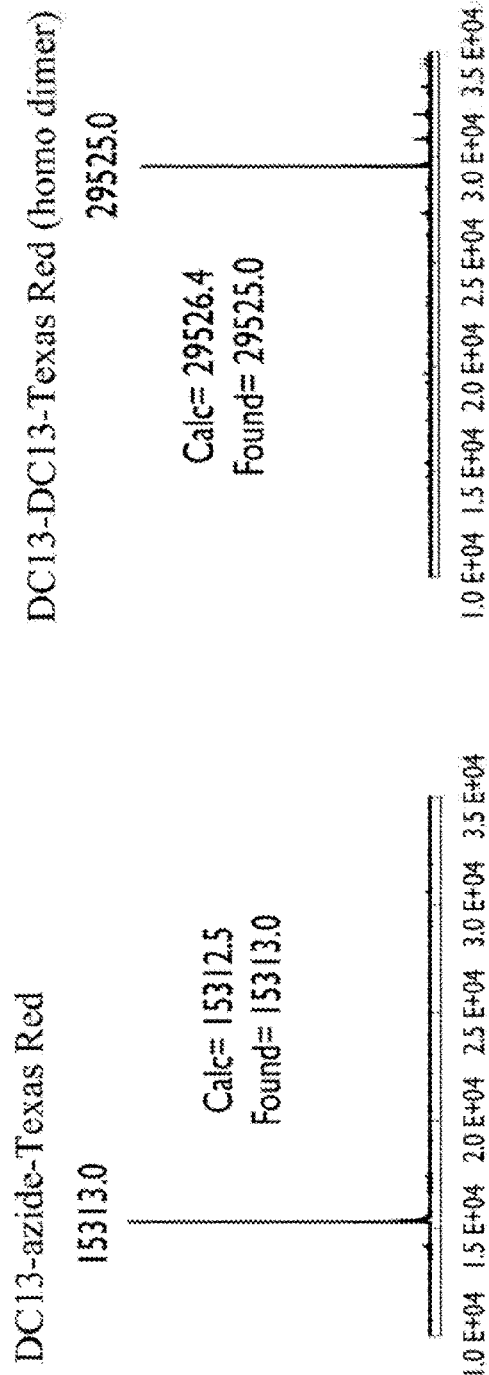
Figure 7E
Figure 7F
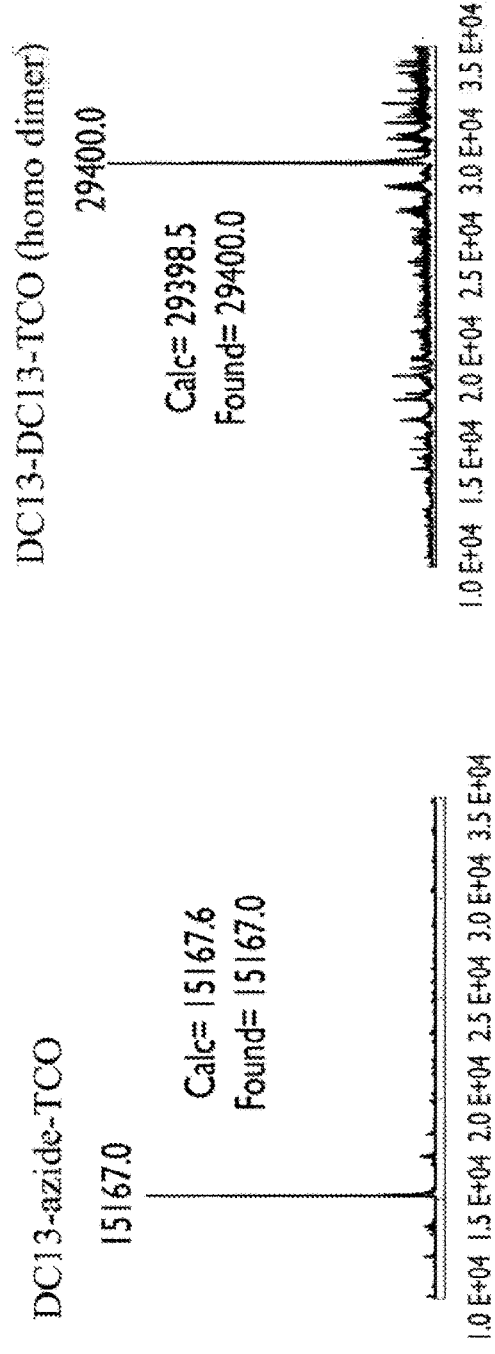
Figure 7G
Figure 7H

SEQUENCE LISTING

<160> NUMBER OF SEQ ID NOS: 81

<210> SEQ ID NO 1
<211> LENGTH: 378
<212> TYPE: DNA
<213> ORGANISM: Artificial Sequence
<220> FEATURE:
<223> OTHER INFORMATION: Synthetic Polynucleotide

<400> SEQUENCE: 1

```
caggtgcagc tgcaggagtc agggggagga ttggtgcagc ctgggggtc tctgagactc     60 tcctgtacag cctctggatt cacattcagt acttactaca tgagctgggt ccgcaaggct   120
ccagggaagg ggcccgagtg ggtctcagtt atgaatagta gtggtggtga cacaaggtat   180
gcagacttcg tgaagggccg attcaccatc tccagagaca cgccaagaa cacactgtat    240 ctccaaatga acagcctgaa acctgaggat acggccctgt attactgtgc gcaaggtaga   300
tcagatatat acccaacctt cacgcggggc caggggaccc aggtcaccgt ctcctcagga   360
ggactgccgg aaaccggc                                                  378
```

<210> SEQ ID NO 2
<211> LENGTH: 133
<212> TYPE: PRT
<213> ORGANISM: Artificial Sequence
<220> FEATURE:
<223> OTHER INFORMATION: Synthetic Polypeptide

<400> SEQUENCE: 2

```
Gln Val Gln Leu Gln Glu Ser Gly Gly Gly Leu Val Gln Pro Gly Gly
 1               5                  10                  15

Ser Leu Arg Leu Ser Cys Thr Ala Ser Gly Phe Thr Phe Ser Thr Tyr
            20                  25                  30

Tyr Met Ser Trp Val Arg Lys Ala Pro Gly Lys Gly Pro Glu Trp Val
        35                  40                  45

Ser Val Met Asn Ser Ser Gly Gly Asp Thr Arg Tyr Ala Asp Phe Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Leu Tyr Tyr Cys
                85                  90                  95

Ala Gln Gly Arg Ser Asp Ile Tyr Pro Thr Phe Thr Arg Gly Gln Gly
            100                 105                 110

Thr Gln Val Thr Val Ser Ser Gly Ser Leu Pro Glu Thr Gly Gly His
        115                 120                 125

His His His His His
        130
```

<210> SEQ ID NO 3
<211> LENGTH: 411
<212> TYPE: DNA
<213> ORGANISM: Artificial Sequence
<220> FEATURE:
<223> OTHER INFORMATION: Synthetic Polynucleotide

<400> SEQUENCE: 3

```
caggttcaac tgcaagagag tggcggggc ctggttcaga ccggtggttc tctccggctc     60
tcgtgtgccg caagtggagt agattttaac tggtatagca tgggttggtt caggcaagcc   120
cctggcaaag agcgggagta tgtggcttcg attgaccagg gaggcgagtt ggattacgca   180
atatcagtaa aggcagatt cacgatctcc cgagacaacg cgaagaatat ggtgtatctc    240
cagatgaatt cgttaaagcc cgaagacacc gctgtatact actgtgccgc agatttttcc   300
ggccggggtg cgtcaaaccc tgacaagtat aaatattggg gacagggaac ccaagtgacc   360
gtcagcagcg gtgggttgcc cgaaactgga ggacaccatc accatcacca t             411
```

<210> SEQ ID NO 4
<211> LENGTH: 137

<212> TYPE: PRT
<213> ORGANISM: Artificial Sequence
<220> FEATURE:
<223> OTHER INFORMATION: Synthetic Polypeptide

<400> SEQUENCE: 4

```
Gln Val Gln Leu Gln Glu Ser Gly Gly Gly Leu Val Gln Thr Gly Gly
1               5                   10                  15

Ser Leu Arg Leu Ser Cys Ala Ala Ser Gly Val Asp Phe Asn Trp Tyr
            20                  25                  30

Ser Met Gly Trp Phe Arg Gln Ala Pro Gly Lys Glu Arg Glu Tyr Val
        35                  40                  45

Ala Ser Ile Asp Gln Gly Gly Glu Leu Asp Tyr Ala Ile Ser Val Lys
    50                  55                  60

Gly Arg Phe Thr Ile Ser Arg Asp Asn Ala Lys Asn Met Val Tyr Leu
65                  70                  75                  80

Gln Met Asn Ser Leu Lys Pro Glu Asp Thr Ala Val Tyr Tyr Cys Ala
                85                  90                  95

Ala Asp Phe Ser Gly Arg Gly Ala Ser Asn Pro Asp Lys Tyr Lys Tyr
            100                 105                 110

Trp Gly Gln Gly Thr Gln Val Thr Val Ser Ser Gly Leu Pro Glu
        115                 120                 125

Thr Gly Gly His His His His His His
    130                 135
```

<210> SEQ ID NO 5
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 5

```
Leu Pro Glu Thr Gly Gly His His His His His His
1               5                   10
```

<210> SEQ ID NO 6
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 6

```
Gly Gly His His His His His His
1               5
```

<210> SEQ ID NO 7
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 7

```
Leu Pro Glu Thr
1
```

<210> SEQ ID NO 8
<211> LENGTH: 7
<212> TYPE: PRT
<213> ORGANISM: Artificial Sequence
<220> FEATURE:

```
<223> OTHER INFORMATION: Synthetic Polypeptide

<400> SEQUENCE: 8

Leu Pro Glu Thr Gly Gly Gly
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (6)..(7)
<223> OTHER INFORMATION: Xaa can be any naturally occurring amino acid

<400> SEQUENCE: 9

Leu Pro Glu Thr Gly Xaa Xaa
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 10

Leu Pro Glu Thr Gly Gly Gly Cys
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 11

Leu Pro Glu Thr Gly
1               5

<210> SEQ ID NO 12
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 12

Gly Gly Gly Cys
1

<210> SEQ ID NO 13
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
```

```
<400> SEQUENCE: 13

Leu Pro Xaa Thr Gly Xaa
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 14

Leu Pro Xaa Thr Gly Gly Gly
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 15

Leu Pro Xaa Thr Xaa
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 16

Asn Pro Xaa Thr Xaa
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 17

Leu Pro Xaa Ala Gly
```

```
<210> SEQ ID NO 18
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 18

Leu Pro Glu Thr Ala
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 19

Asn Pro Gln Thr Asn
1               5

<210> SEQ ID NO 20
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 20

Asn Pro Lys Thr Gly
1               5

<210> SEQ ID NO 21
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 21

Leu Pro Ser Thr Gly
1               5

<210> SEQ ID NO 22
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 22

Leu Pro Xaa Thr
1

<210> SEQ ID NO 23
<211> LENGTH: 5
<212> TYPE: PRT
<213> ORGANISM: Artificial Sequence
<220> FEATURE:
<223> OTHER INFORMATION: Synthetic Polypeptide
```

```
<400> SEQUENCE: 23

Leu Pro Lys Thr Gly
1               5

<210> SEQ ID NO 24
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 24

Leu Pro Ala Thr Gly
1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 25

Leu Pro Asn Thr Gly
1               5

<210> SEQ ID NO 26
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 26

Leu Pro Asn Ala Gly
1               5

<210> SEQ ID NO 27
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 27

Leu Pro Xaa Thr Ala
1               5

<210> SEQ ID NO 28
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 28

Leu Pro Asn Thr Ala
1               5

<210> SEQ ID NO 29
<211> LENGTH: 5
<212> TYPE: PRT
<213> ORGANISM: Artificial Sequence
```

```
<220> FEATURE:
<223> OTHER INFORMATION: Synthetic Polypeptide

<400> SEQUENCE: 29

Leu Pro Glu Thr Ala
1               5

<210> SEQ ID NO 30
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 30

Leu Gly Xaa Thr Gly
1               5

<210> SEQ ID NO 31
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 31

Leu Gly Ala Thr Gly
1               5

<210> SEQ ID NO 32
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 32

Ile Pro Xaa Thr Gly
1               5

<210> SEQ ID NO 33
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 33

Ile Pro Asn Thr Gly
1               5

<210> SEQ ID NO 34
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 34

Ile Pro Glu Thr Gly
```

```
<210> SEQ ID NO 35
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa is Gln or Lys
<220> FEATURE:
<221> NAME/KEY: misc_feature
<222> LOCATION: (4)..(4)
<223> OTHER INFORMATION: Xaa is Thr or absent
<220> FEATURE:
<221> NAME/KEY: misc_feature
<222> LOCATION: (5)..(5)
<223> OTHER INFORMATION: Xaa is Asn, Gly, or absent

<400> SEQUENCE: 35

Asn Pro Xaa Xaa Xaa
1               5

<210> SEQ ID NO 36
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 36

Asn Pro Gln Thr Asn
1               5

<210> SEQ ID NO 37
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 37

Asn Pro Lys Thr Gly
1               5

<210> SEQ ID NO 38
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 38

Asn Ser Lys Thr Ala
1               5

<210> SEQ ID NO 39
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 39

Asn Pro Gln Thr Gly
1               5
```

```
<210> SEQ ID NO 40
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 40

Asn Ala Lys Thr Asn
1               5

<210> SEQ ID NO 41
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 41

Asn Pro Gln Ser Ser
1               5

<210> SEQ ID NO 42
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa is Glu, Ala, Ser, or His

<400> SEQUENCE: 42

Asn Ala Xaa Thr Gly
1               5

<210> SEQ ID NO 43
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 43

Leu Pro Xaa Thr Ala
1               5

<210> SEQ ID NO 44
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 44

Leu Ala Xaa Thr Gly
1               5

<210> SEQ ID NO 45
```

```
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 45

Gln Val Pro Thr Gly Val
1               5

<210> SEQ ID NO 46
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 46

Thr Leu Xaa Thr Cys
1               5

<210> SEQ ID NO 47
<211> LENGTH: 206
<212> TYPE: PRT
<213> ORGANISM: S. aureus

<400> SEQUENCE: 47

Met Lys Lys Trp Thr Asn Arg Leu Met Thr Ile Ala Gly Val Val Leu
1               5                   10                  15

Ile Leu Val Ala Ala Tyr Leu Phe Ala Lys Pro His Ile Asp Asn Tyr
            20                  25                  30

Leu His Asp Lys Asp Lys Asp Glu Lys Ile Glu Gln Tyr Asp Lys Asn
        35                  40                  45

Val Lys Glu Gln Ala Ser Lys Asp Asn Lys Gln Ala Lys Pro Gln
    50                  55                  60

Ile Pro Lys Asp Lys Ser Lys Val Ala Gly Tyr Ile Glu Ile Pro Asp
65                  70                  75                  80

Ala Asp Ile Lys Glu Pro Val Tyr Pro Gly Pro Ala Thr Pro Glu Gln
                85                  90                  95

Leu Asn Arg Gly Val Ser Phe Ala Glu Glu Asn Glu Ser Leu Asp Asp
            100                 105                 110

Gln Asn Ile Ser Ile Ala Gly His Thr Phe Ile Asp Arg Pro Asn Tyr
        115                 120                 125

Gln Phe Thr Asn Leu Lys Ala Ala Lys Lys Gly Ser Met Val Tyr Phe
    130                 135                 140

Lys Val Gly Asn Glu Thr Arg Lys Tyr Lys Met Thr Ser Ile Arg Asp
145                 150                 155                 160

Val Lys Pro Thr Asp Val Glu Val Leu Asp Glu Gln Lys Gly Lys Asp
                165                 170                 175

Lys Gln Leu Thr Leu Ile Thr Cys Asp Asp Tyr Asn Glu Lys Thr Gly
            180                 185                 190

Val Trp Glu Lys Arg Lys Ile Phe Val Ala Thr Glu Val Lys
        195                 200                 205

<210> SEQ ID NO 48
<211> LENGTH: 206
<212> TYPE: PRT
```

<213> ORGANISM: S. aureus

<400> SEQUENCE: 48

Met Lys Lys Trp Thr Asn Arg Leu Met Thr Ile Ala Gly Val Val Leu
1               5                   10                  15

Ile Leu Val Ala Ala Tyr Leu Phe Ala Lys Pro His Ile Asp Asn Tyr
            20                  25                  30

Leu His Asp Lys Asp Lys Asp Glu Lys Ile Glu Gln Tyr Asp Lys Asn
        35                  40                  45

Val Lys Glu Gln Ala Ser Lys Asp Lys Gln Gln Ala Lys Pro Gln
    50                  55                  60

Ile Pro Lys Asp Lys Ser Lys Val Ala Gly Tyr Ile Glu Ile Pro Asp
65                  70                  75                  80

Ala Asp Ile Lys Glu Pro Val Tyr Pro Gly Pro Ala Thr Pro Glu Gln
                85                  90                  95

Leu Asn Arg Gly Val Ser Phe Ala Glu Glu Asn Glu Ser Leu Asp Asp
            100                 105                 110

Gln Asn Ile Ser Ile Ala Gly His Thr Phe Ile Asp Arg Pro Asn Tyr
        115                 120                 125

Gln Phe Thr Asn Leu Lys Ala Ala Lys Lys Gly Ser Met Val Tyr Phe
130                 135                 140

Lys Val Gly Asn Glu Thr Arg Lys Tyr Lys Met Thr Ser Ile Arg Asp
145                 150                 155                 160

Val Lys Pro Thr Asp Val Gly Val Leu Asp Glu Gln Lys Gly Lys Asp
                165                 170                 175

Lys Gln Leu Thr Leu Ile Thr Cys Asp Asp Tyr Asn Glu Lys Thr Gly
            180                 185                 190

Val Trp Glu Lys Arg Lys Ile Phe Val Ala Thr Glu Val Lys
            195                 200                 205

<210> SEQ ID NO 49
<211> LENGTH: 148
<212> TYPE: PRT
<213> ORGANISM: Artificial Sequence
<220> FEATURE:
<223> OTHER INFORMATION: Synthetic Polypeptide

<400> SEQUENCE: 49

Met Gln Ala Lys Pro Gln Ile Pro Lys Asp Lys Ser Lys Val Ala Gly
1               5                   10                  15

Tyr Ile Glu Ile Pro Asp Ala Asp Ile Lys Glu Pro Val Tyr Pro Gly
            20                  25                  30

Pro Ala Thr Arg Glu Gln Leu Asn Arg Gly Val Ser Phe Ala Glu Glu
        35                  40                  45

Asn Glu Ser Leu Asp Asp Gln Asn Ile Ser Ile Ala Gly His Thr Phe
    50                  55                  60

Ile Asp Arg Pro Asn Tyr Gln Phe Thr Asn Leu Lys Ala Ala Lys Lys
65                  70                  75                  80

Gly Ser Met Val Tyr Phe Lys Val Gly Asn Glu Thr Arg Lys Tyr Lys
                85                  90                  95

Met Thr Ser Ile Arg Asn Val Lys Pro Thr Ala Val Glu Val Leu Asp
            100                 105                 110

Glu Gln Lys Gly Lys Asp Lys Gln Leu Thr Leu Ile Thr Cys Asp Asp
        115                 120                 125

Tyr Asn Glu Glu Thr Gly Val Trp Glu Thr Arg Lys Ile Phe Val Ala
130                 135                 140

Thr Glu Val Lys
145

<210> SEQ ID NO 50
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa is Gln or Lys
<220> FEATURE:
<221> NAME/KEY: misc_feature
<222> LOCATION: (5)..(5)
<223> OTHER INFORMATION: Xaa is Ala or Ser

<400> SEQUENCE: 50

Leu Pro Xaa Thr Xaa Thr
1               5

<210> SEQ ID NO 51
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 51

Leu Pro Xaa Thr Xaa
1               5

<210> SEQ ID NO 52
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 52

Leu Pro Ser Thr Ser
1               5

<210> SEQ ID NO 53
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 53

Leu Pro Ile Thr Gly
1               5

<210> SEQ ID NO 54
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 54

Leu Pro Asp Thr Ala
1               5

<210> SEQ ID NO 55
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 55

Ser Pro Lys Thr Gly
1               5

<210> SEQ ID NO 56
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 56

Leu Ala Glu Thr Gly
1               5

<210> SEQ ID NO 57
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 57

Leu Ala Ala Thr Gly
1               5

<210> SEQ ID NO 58
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 58

Leu Ala His Thr Gly
1               5

<210> SEQ ID NO 59
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 59

Leu Ala Ser Thr Gly
1               5

<210> SEQ ID NO 60
<211> LENGTH: 5
<212> TYPE: PRT
<213> ORGANISM: Artificial Sequence
<220> FEATURE:
<223> OTHER INFORMATION: Synthetic Polypeptide

```
<400> SEQUENCE: 60

Leu Pro Leu Thr Gly
1               5

<210> SEQ ID NO 61
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 61

Leu Ser Arg Thr Gly
1               5

<210> SEQ ID NO 62
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 62

Val Pro Asp Thr Gly
1               5

<210> SEQ ID NO 63
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 63

Ile Pro Gln Thr Gly
1               5

<210> SEQ ID NO 64
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 64

Tyr Pro Arg Arg Gly
1               5

<210> SEQ ID NO 65
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 65

Leu Pro Met Thr Gly
1               5

<210> SEQ ID NO 66
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 66
```

```
Leu Ala Phe Thr Gly
1               5

<210> SEQ ID NO 67
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 67

Leu Pro Gln Thr Ser
1               5

<210> SEQ ID NO 68
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 68

Leu Ala Xaa Thr
1

<210> SEQ ID NO 69
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 69

Leu Pro Xaa Ala
1

<210> SEQ ID NO 70
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 70

Leu Gly Xaa Thr
1

<210> SEQ ID NO 71
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid
```

<400> SEQUENCE: 71

Ile Pro Xaa Thr
1

<210> SEQ ID NO 72
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 72

Asn Pro Xaa Thr
1

<210> SEQ ID NO 73
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 73

Asn Pro Gln Ser
1

<210> SEQ ID NO 74
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 74

Leu Pro Ser Thr
1

<210> SEQ ID NO 75
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 75

Asn Ser Lys Thr
1

<210> SEQ ID NO 76
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 76

Asn Pro Gln Thr
1

<210> SEQ ID NO 77
<211> LENGTH: 4
<212> TYPE: PRT

```
<213> ORGANISM: Artificial Sequence
<220> FEATURE:
<223> OTHER INFORMATION: Synthetic Polypeptide

<400> SEQUENCE: 77

Asn Ala Lys Thr
1

<210> SEQ ID NO 78
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 78

Leu Pro Ile Thr
1

<210> SEQ ID NO 79
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 79

Leu Ala Glu Thr
1

<210> SEQ ID NO 80
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 80

Asn Pro Gln Ser
1

<210> SEQ ID NO 81
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 81

Leu Pro Xaa Thr Gly
1               5
```

LABELING OF ANTIBODIES

RELATED APPLICATIONS

This application is a national stage filing under 35 U.S.C. § 371 of international PCT application, PCT/US2016/055074, filed Oct. 1, 2016, which claims priority under 35 U.S.C. § 119(e) to U.S. Provisional Application, U.S. Ser. No. 62/236,117, filed on Oct. 1, 2015 each of which is incorporated by reference herein.

GOVERNMENT SUPPORT

This invention was made with government support under R01-AI087879, DP1-GM106409, and R01-GM100518 awarded by National Institutes of Health. The government has certain rights in the invention.

BACKGROUND

Positron emission tomography (PET) is a powerful technology for medical and biological imaging and the scope of PET applications is expanding rapidly. The development of suitable PET tracers is critical to PET technology. Accordingly new PET tracers, such as peptide/protein based tracers would be useful to specifically label tissues in therapeutic and/or diagnostic applications.

SUMMARY

Some aspects of the disclosure are based on the recognition that antibody binding fragments, and in particular the single domain antibody fragment VHH, show an improved ability to detect antigens in vivo when site specifically conjugated to a hydrophilic polymer (e.g., PEG) and a radiolabel (e.g. $^{89}$Zr). Such antibodies are useful for inter alia detecting tumors and lymphocyte infiltration into tumors in vivo. Accordingly, the present disclosure provides antibodies that are site specifically labeled with a hydrophilic polymer and/or a radiolabel, as well as methods of making and using such antibodies.

The success of immunotherapies such as the administration of monoclonal antibodies against immune checkpoint inhibitors (e.g., CTLA4, PD-1 on T cells, and PD-L1) warrants the development of new methods, systems, and compositions for assessing whether an immunotherapy would be beneficial for treating patients. As one example, macrophages can affect tumor growth by establishing either a detrimental or favorable microenvironment. Thus, the ability to image the present of myeloid cells is of diagnostic and therpacutic relevance and, compared to tumor-specific markers[1], may be a more generally applicable approach for detection of tumor cells[2,3]. Immune cells often invade or surround solid tumors[1]. The success of immunotherapies such as the administration of monoclonal antibodies against immune checkpoint inhibitors (e.g., CTLA4, PD-1 on T cells, and PD-L1) may be assessed by imaging the presence and/or distribution of immune cells (e.g., myeloid and/or lymphoid cells) in a subject, for example, in a tumor of the subject. Accordingly, new methods and compositions to explore and assess the microenvironment of tumors non-invasively are needed.

Immune cells often infiltrate tumors and can thus serve as a proxy to assess the presence of a malignancy. The ability to image tumor-infiltrating cells depends on the availability of targeting molecules with the requisite affinity and specificity. Camelid-derived single domain antibody fragments (VHHs) Provided herein is the design and synthesis of site-specifically PEGylated VHHs and engineered bivalent VHHs fused site-specifically via their C-termini. VHHs, which recognize Class II MHC products and CD11b, were used to image immune cells, both in vitro and in vivo, by FACS, two-photon microscopy and positron emission tomography (PET). Both PEGylated and bivalent VHHs stained lymphoid organs and stained them more efficiently than their monovalent non-PEGylated counterparts. By PET imaging, modified VHHs detected engrafted melanoma and pancreatic tumors—as small as ~1 mm in size-by virtue of their association with myeloid cells. Modified VHHs showed significant improvement in fluorescence imaging, especially for the PEGylated VHHs.

In one aspect, a chemical approach was chosen to link two fully functional and properly refolded VHHs via their C-termini to ensure that their antigen binding capacity would not be compromised by modification of one of the N-termini, and that the two binding sites thus created would be equivalent, in the manner of a full-sized antibody. Accordingly, bivalent VHHs were produced through application of sortase-mediated enzymatic transformations in combination with click chemistry. Mono- and bivalent VHHs were compared in in vitro (FACS) experiments, by two-photon microscopy on lymph nodes and spleen excised from mice injected with VHHs, and by non-invasive in vivo immuno-PET imaging.

One minimally-invasive clinical diagnostic approach is the use of $^{18}$F-2-fluoro-2-deoxy-D-glucose positron emission tomography (FDG-PET), which distinguishes areas of high metabolic activity, such as tumors, from surrounding tissue with lesser glucose uptake[4]. These methods may not typically provide information on immune cells in the tumor microenvironment. They can be used to track immune cells, using isotopically labeled anti-CD11b, anti-Class II MHC, and anti CD8 antibody fragments[5-7].

The comparatively large size of intact full-sized antibodies results in a long circulatory half-life and may also hinder efficient tissue penetration[8]. These considerations have driven the search for smaller antibody-derived formats as alternative imaging tools[1, 6]. Thus, provided herein are camelid single domain antibody fragments (VHHs), as the smallest antigen binding derivatives obtainable from naturally occurring antibodies[9]. VHHs may be enzymatically modified and have been used in a variety of applications including imaging[10].

The production of bivalent single domain antibodies based on their monovalent equivalents could address issues of avidity, while retaining desirable properties such as small size. For example, the bivalent derivatives of single domain antibodies maybe small enough to penetrate tissues, be rapidly cleared from the circulation, yet benefit from increased avidity. On the other hand, tuning circulatory half-life could improve the staining efficiency of the targets by VHHs. Attachment of small PEG groups (e.g., PEGylation) or other hydrophilic polymers could be used as a tool to tune persistence of a VHH in the circulation. Moreover, PEGylation can decrease the immunogenicity of VHHs, which is important in cases when repeated administration is required but in rare cases even the PEG functionality itself may be immunogenic[12]. Thus, provided herein are methods for introducing site specific hydrophilic polymer (e.g., PEG) and radiolabel (e.g., $^{89}$Zr) modifications onto single domain antibodies (e.g., VHHs) and methods for producing site-specifically conjugated bivalent single domain antibodies. In some embodiments, the single domain antibodies provided herein are site specifically modified with PEG and a $^{89}$Zr.

However, it should be appreciated that additional hydrophilic polymers and other radiolabels may be used to modify the antibodies (e.g., single domain antibodies) provided herein.

The details of certain embodiments of the invention are set forth in the Detailed Description of Certain Embodiments, as described below. Other features, objects, and advantages of the invention will be apparent from the Definitions, Examples, Figures, and Claims.

BRIEF DESCRIPTION OF THE DRAWINGS

The accompanying drawings, which constitute a part of this specification, illustrate several exemplary embodiments of the invention and together with the description, serve to explain the principles of the invention. The embodiments disclosed in the drawings are exemplary and do not limit the scope of this disclosure.

(FIGS. 2E-2F) PEGylation of VHHs and characterization. Numbers indicate the following: #1: marker, #2: DC8-alexa647-azide, #3: DC8-alexa647-PEG-5 kDa, #4: DC8-alexa647-PEG-10 kDa, #5: DC8-alexa647-PEG-20 kDa. LPETG-XX is SEQ ID NO: 9; LPET-G$_3$ is SEQ ID NO: 8; LPET-G$_3$-Cys is SEQ ID NO: 10.

(FIG. 3C) Equal amount of DC8 with or without PEG, both equipped with Texas Red is injected IV. 3 h p.i., the mice are euthanized and spleens are excised for two-photon imaging. (FIG. 3D) Equal amount of DC8 with or without PEG (0.4 nmols), all equipped with Alexa647 is injected IV. 3 h p.i., the mice are euthanized and spleen is excised. Cells were harvested and analyzed with FACS.

FIGS. 4A-4I (FIG. 4A) show synthesis of $^{18}$F-Tetrazine. (FIG. 4B) $^{18}$F-labeling of VHH-dimers, monomers or PEG-VHHs. (FIG. 4C) radio-TLC analysis of the $^{18}$F-labeling reactions. (FIGS. 4D-4I) $^{18}$F-DC8-dimer and $^{18}$F-DC13-dimer detects lymphoid organs and reveals tumor-infiltrated immune cells. PET images are represented in both coronal and sagittal views for better visualization. CT images are provided for better visualization (FIG. 4H). (FIGS. 4D-4E) PET images of WT (FIG. 4D) and class II MHC−/− (FIG. 4E) mice 2 h p.i. of $^{18}$F-DC8 dimer; letters indicate: CV: cervical lymph nodes; BM: bone marrow; GB: gallbladder; LV: liver; KD: kidneys; Ints: intestines; BL: bladder; SP: spinal cord. (FIGS. 4F-4G) PET images of WT (FIG. 4F) and CD11b−/−(FIG. 4G) mice 2 h p.i. of $^{18}$F-DC13 dimer. (FIG. 4I) Tumor-associated class II MHC+ cells (FIG. 4I (coronal)) or CD11b+ cells (FIG. 4I (sagittal)) were visualized using $^{18}$F-DC13 dimer (FIG. 4I (coronal)) or $^{18}$F-DC8 dimer (FIG. 4I (sagittal)). Arrows are pointing at the tumors. In (FIG. 4I (sagittal)) stars are showing the lymph nodes. PET scale bars have arbitrary units. Images are representative of two to four mice with similar results.

(FIG. 5C) VHH monomer can block binding of $^{18}$F-VHH dimer onto the lymphoid organs. WT mice were injected with different amount of unlabeled DC8. $^{18}$F-DC8 dimer was injected 20 min later. PET SUVs are calculated based on PET images acquired 2 h p.i. of the $^{18}$F-labeled DC8 dimer. (FIG. 5D) WT mice were injected with same amount of either $^{18}$F-DC8 with or without labeled-PEGs. 3 h p.i., the mice were euthanized and activity in different organs were measured.

FIGS. 6A-6H show LC-MS analysis of VHHs, their corresponding sortagged products and dimers. DC8 and its derivatives (FIGS. 6A-6H).

FIGS. 7A-7H show LC-MS analysis of VHHs, their corresponding sortagged products and dimers. DC13 and its derivatives (FIGS. 7A-7H).

FIG. 11B, [$^{18}$F]-DC8-dimer; at 20 min).

FIG. 14B is a schematic representation of site-specific labeling of VHHs using sortase. LPETG-XX is SEQ ID NO: 9.

FIG. 15B is a schematic representation of preparing PEGylated $^{89}$Zr-labeled VHHs for PET imaging.

DETAILED DESCRIPTION OF CERTAIN EMBODIMENTS

Figure 1A:
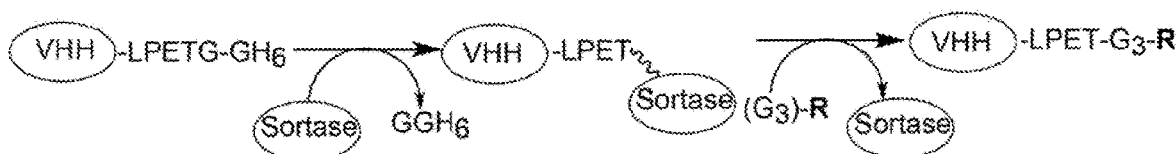
FIGS. 1A-1B show site-specific labeling of single domain antibodies (VHHs) using sortase and design (FIG. 1A) as well as (FIG. 1B) structures of the substrates. LPETG-GH$_6$ is SEQ ID NO: 5; GGH$_6$ is SEQ ID NO: 6; LPET is SEQ ID NO: 7; LPET-G$_3$ is SEQ ID NO: 8.

Antibodies are currently the fastest growing class of therapeutics. Although naked antibodies have proven their value as successful pharmaceuticals, they suffer from some limitations such as low tissue penetration and a long circulatory half-life. They have been conjugated to toxic payloads, PEGs or other polymers, or radioisotopes to increase and optimize their therapeutic efficacy. Although non-specific conjugation is suitable for most in vitro applications, for in vivo applications, site-specifically modified antibodies may have advantages. Provided herein is a novel approach in which an antibody fragment is tagged with two handles: one is used for the introduction of a fluorophore or radioisotope, and the second one is used to further modify the fragment with functionalities including a PEG moiety or a second antibody fragment. Such modifications may improve desired properties (e.g., circulatory half-life or avidity). Exemplary antibodies (e.g., single domain antibodies) provided herein, which recognize epitopes, such as Class II MHC, and CD11b showed high avidity and specificity. In some embodiments, antibodies conjugated to a hydrophilic polymer (e.g., PEG), and/or a fluorophore are referred to as constructs. Such constructs were used to image cancers and could detect tumors as small as about 1 mm in size.

The term "antibody", as used herein, refers to a protein belonging to the immunoglobulin superfamily. The terms antibody and immunoglobulin are used interchangeably. The term "antibody" encompasses not only intact (e.g., full-length) polyclonal or monoclonal antibodies, but also antigen-binding fragments thereof (such as Fab, Fab', F(ab')2, Fv), single chain (scFv), mutants thereof, fusion proteins comprising an antibody portion, humanized antibodies, chimeric antibodies, diabodies, linear antibodies, single chain antibodies, multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies. With some exceptions, mammalian antibodies are typically made of basic structural units each with two large heavy chains and two small light chains. There are several different types of antibody heavy chains, and several different kinds of antibodies, which are grouped into different isotypes based on which heavy chain they possess. Five different antibody isotypes are known in mammals, IgG, IgA, IgE, IgD, and IgM, which perform different roles, and help direct the appropriate immune response for each different type of foreign object they encounter. In some embodiments, an antibody is an IgG antibody, e.g., an antibody of the IgG1, 2, 3, or 4 human subclass. Antibodies from mammalian species (e.g., human, mouse, rat, goat, pig, horse, cattle, camel) are within the scope of the term, as are antibodies from non-mammalian species (e.g., from birds, reptiles, amphibia) are also within the scope of the term, e.g., IgY antibodies.

Only part of an antibody is involved in the binding of the antigen, and antigen-binding antibody fragments, their preparation and use, are well known to those of skill in the art. As is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology,* 7th Ed., Blackwell Scientific Publications, Oxford). Suitable antibodies and antibody fragments for use in the context of some embodiments of the present invention include, for example, human antibodies, humanized antibodies, domain antibodies, F(ab'), F(ab')$_2$, Fab, Fv, Fc, and Fd fragments, antibodies in which the Fc and/or FR and/or CDR1 and/or CDR2 and/or light chain CDR3 regions have been replaced by homologous human or non-human sequences; antibodies in which the FR and/or CDR1 and/or CDR2 and/or light chain CDR3 regions have been replaced by homologous human or non-human sequences; antibodies in which the FR and/or CDR1 and/or CDR2 and/or light chain CDR3 regions have been replaced by homologous human or non-human sequences; and antibodies in which the FR and/or CDR1 and/or CDR2 regions have been replaced by homologous human or non-human sequences. In some embodiments, so-called single chain antibodies (e.g., ScFv), (single) domain antibodies, and other intracellular antibodies may be used in the context of the present invention. Domain antibodies, camelid and camelized antibodies and fragments thereof, for example, VHH domains, or nanobodies, such as those described in patents and published patent applications of Ablynx NV and Domantis are also encompassed in the term antibody. Further, chimeric antibodies, e.g., antibodies comprising two antigen-binding domains that bind to different antigens, are also suitable for use in the context of some embodiments of the present invention. In some embodiments, the term antibody may also refer to "antibody mimetics," which are organic compounds the can specifically bind antigens, but are not structurally related to antibodies. For example, antibody mimetics known as "affibodies," or "affibody molecules," are small proteins engineered to bind e.g., target proteins or peptides with affinities comparable to monoclonal antibodies. In some embodiments, an affibody includes a protein scaffold based on the Z domain (the immunoglobulin G binding domain) of protein A, and in contrast to antibodies, affibody molecules are composed of alpha helices and lack disulfide bridges. Methods for engineering and producing affibodies are known, and include those described in Nord et al., "A combinatorial library of an α-helical bacterial receptor domain." *Prot. Eng.* 1995; 8 (6): 601-608; Nord et al., "Binding proteins selected from combinatorial libraries of an α-helical bacterial receptor domain." *Nature Biotechnol.* 1997; 15 (8): 772-777; Ståhl et al., "The use of gene fusions to protein A and protein G in immunology and biotechnology." *Pathol. Biol.* (Paris) 1997; 45 (1): 66-76; Rönnmark et al., "Construction and characterization of affibody-Fc chimeras produced in *Escherichia coli.*" *J. Immunol. Methods.* 2002; 261 (1-2): 199-211; Rönnmark et al., "Affibody-beta-galactosidase immunoconjugates produced as soluble fusion proteins in the *Escherichia coli* cytosol." *J. Immunol. Methods.* 2003; 281 (1-2): 149-160; Nord et al., "Recombinant human factor VIII-specific affinity ligands selected from phage-displayed combinatorial libraries of protein A." *Eur. J. Biochem.* 2001; 268 (15): 1-10; Engfeldt et al., "Chemical synthesis of triple-labeled three-helix bundle binding proteins for specific fluorescent detection of unlabeled protein." *Chem. BioChem.* 2005; 6 (6): 1043-1050; Ahlgren et al., "Targeting of HER2-expressing tumors with a site-specifically 99mTc-labeled recombinant affibody molecule, ZHER2:2395, with C-terminally engineered cysteine." *J. Nucl. Med.* 2009; 50 (5): 781-789; Orlova et al., "Evaluation of [(111/114m)In]CHX-A"-DTPA-ZHER2:342, an affibody ligand conjugate for targeting of HER2-expressing malignant tumors." *Q. J. Nucl. Med. Mol. Imaging.* 2007; 51 (4): 314-23; Tran et al., "(99m)Tc-maEEE-Z(HER2:342), an Affibody molecule-based tracer for the detection of HER2 expression in malignant tumors". *Bioconjug. Chem.* 2007; 18 (6): 1956-64; Orlova et al., "Tumor imaging using a picomolar affinity HER2 binding affibody molecule." *Cancer Res.* 2006; 66 (8): 4339-48; Holm et al., "Electrophilic Affibodies Forming Covalent Bonds to Protein Targets." *The Journal of Biological Chemistry* 2009; 284 (47): 32906-13;

Renberg et al., "Affibody molecules in protein capture microarrays: evaluation of multidomain ligands and different detection formats." *J. Proteome Res.* 2007; 6 (1): 171-179; Lundberg et al., "Site-specifically conjugated anti-HER2 Affibody molecules as one-step reagents for target expression analyses on cells and xenograft samples." *J. Immunol. Methods* 2007; 319 (1-2): 53-63; Tolmachev et al., "Radionuclide therapy of HER2-positive microxenografts using a 177Lu-labeled HER2-specific Affibody molecule." *Cancer Res.* 2007; 67 (6): 2773-82; and Gebauer & Skerra, "Engineered protein scaffolds as next-generation antibody therapeutics." *Current Opinion in Chemical Biology* 2009; 13 (3): 245-55; Siontorou C., "Nanobodies as novel agents for disease diagnosis and therapy." *Int. J. Nanomedicine* 2013; 8: 4215-4227; the entire contents of each are hereby incorporated by reference in their entirety.

The term "antigen-binding antibody fragment," as used herein, refers to a fragment of an antibody that comprises the paratope, or a fragment of the antibody that binds to the antigen the antibody binds to, with similar specificity and affinity as the intact antibody. Antibodies, e.g., fully human monoclonal antibodies, may be identified using phage display (or other display methods such as yeast display, ribosome display, bacterial display). Display libraries, e.g., phage display libraries, are available (and/or can be generated by one of ordinary skill in the art) that can be screened to identify an antibody that binds to an antigen of interest, e.g., using panning. See, e.g., Sidhu, S. (ed.) *Phage Display in Biotechnology and Drug Discovery* (Drug Discovery Series; CRC Press; 1$^{st}$ ed., 2005; Aitken, R. (ed.) *Antibody Phage Display: Methods and Protocols* (Methods in Molecular Biology) Humana Press; 2nd ed., 2009.

The term "single domain antibody," as used herein, refers to an antibody, in which the complementarity determining regions (CDRs) are part of a single domain polypeptide, that is, the complementarity determining regions are all on a single polypeptide chain. Examples of single domain antibodies include, but are not limited to, heavy chain antibodies, antibodies naturally devoid of light chains, single domain antibodies derived from conventional 4-chain antibodies, engineered antibodies, and single domain scaffolds other than those derived from antibodies. Single domain antibodies may be any of those known in the art, or any future single domain antibodies. Methods for making single domain antibodies and VHHs are known in the art and would be apparent to the skilled artisan. For example methods for making single domain antibodies and VHHs are provided in U.S. patent publication No.: US 2006/0034845, published on Feb. 16, 2006, the entire contents of which are incorporated by reference herein. Single domain antibodies may be derived from any species including, but not limited to, mouse, rat, human, camel, llama, goat, rabbit, and bovine. According to one aspect of the invention, a single domain antibody as used herein is a naturally occurring single domain antibody known as a heavy chain antibody devoid of light chains. Such single domain antibodies are disclosed in published international PCT application, WO 2013/024059, the entire contents of which are incorporated by reference herein. The variable domain derived from a heavy chain antibody naturally devoid of light chain is known as a VHH or nanobody to distinguish it from the conventional VH of four chain immunoglobulins. Such a VHH molecule can be derived from antibodies raised in Camelidae species, for example, camel, dromedary, llama, vicuña, alpaca, and guanaco. Other species besides Camelidac may produce heavy chain antibodies naturally devoid of light chain; such VHHs are within the scope of the invention.

As used herein, a "VHH" refers to the variable region of a heavy chain antibody, for example the heavy chain antibody from a camelid. VHHs, useful in the present invention and as known to the skilled artisan, may be heavy chain variable domains derived from immunoglobulins naturally devoid of light chains such as those derived from Camelidac as described in published international PCT Application, WO 2013/024059, published on Feb. 21, 2013 (and referred to hereinafter as VHH domains or nanobodies). Typically, VHH molecules are about 10× smaller than IgG molecules. For example, in some embodiments, VHH molecules are between 10 kDa and 50 kDa. In some embodiments, VHH molecules are between 10 kDa and 25 kDa. In some embodiments, VHH molecules are between 12 kDa and 16 kDa in size. In some embodiments, VHHs lend themselves to sortase-catalyzed enzymatic transformations for a variety of purposes, including the installation of radioisotopes and/or PEG modifications for administration to a subject and imaging (e.g., PET imaging). They are single polypeptides and are stable, resisting extreme pH and temperature conditions. They have the advantage of specificity, small size, and rapid circulatory clearance (<30 min). In some embodiments, the VHHs provided herein may be modified (e.g., with a polymer, such as PEG, and/or a detectable label) to yield improved properties for efficient detection of one or more molecules, proteins, or cells, for example, in vivo. Moreover, VHHs are resistant to the action of proteases which is not the case for conventional antibodies. Furthermore, in vitro expression of VHHs produces properly folded functional VHHs in high yield. In addition, antibodies generated in Camelids will recognize epitopes other than those recognized by antibodies generated in vitro through the use of antibody libraries or via immunization of mammals other than Camelids (in published international PCT Application, WO 2006/079372, published on Aug. 3, 2006; the entire contents of which are incorporated by reference herein). Since VHHs are known to bind 'unusual' epitopes such as cavities or grooves (WO 2006/079372), the affinity of such VHHs may be more suitable for diagnostic purposes. Single domain antibodies useful in the present invention may be produced my any method known in the art.

The term "binding agent," as used herein, refers to any molecule that binds another molecule with high affinity. In some embodiments, a binding agent binds its binding partner with high specificity. Examples for binding agents include, without limitation, antibodies, antibody fragments, nucleic acid molecules, receptors, ligands, aptamers, and adnectins.

The term "click chemistry" refers to a chemical philosophy introduced by K. Barry Sharpless of The Scripps Research Institute, describing chemistry tailored to generate covalent bonds quickly and reliably by joining small units comprising reactive groups together (see H. C. Kolb, M. G. Finn and K. B. Sharpless (2001). Click Chemistry: Diverse Chemical Function from a Few Good Reactions. *Angewandte Chemie International Edition* 40 (11): 2004-2021. Click chemistry does not refer to a specific reaction, but to a concept including, but not limited to, reactions that mimic reactions found in nature. In some embodiments, click chemistry reactions are modular, wide in scope, give high chemical yields, generate inoffensive byproducts, are stereospecific, exhibit a large thermodynamic driving force to favor a reaction with a single reaction product, and/or can be carried out under physiological conditions. In some embodiments, a click chemistry reaction exhibits high atom economy, can be carried out under simple reaction conditions, use readily available starting materials and reagents, uses no toxic solvents or uses a solvent that is benign or easily removed (preferably water), and/or provides simple product isolation by non-chromatographic methods (crystallisation or distillation). In some embodiments, the click chemistry reaction is a [2+3] dipolar cycloaddition. In certain embodiments, the click chemistry reaction is a Diels-Alder cycloaddition.

The term "click chemistry handle," as used herein, refers to a reactant, or a reactive group, that can partake in a click chemistry reaction. Exemplary click chemistry handles are demonstrated in U.S. Patent Publication 20130266512, which is incorporated by reference herein. For example, a strained alkyne, e.g., a cyclooctyne, is a click chemistry handle, since it can partake in a strain-promoted cycloaddition (see, e.g., Table 1). In general, click chemistry reactions require at least two molecules comprising click chemistry handles that can react with each other. Such click chemistry handle pairs that are reactive with each other are sometimes referred to herein as partner click chemistry handles. For example, an azide is a partner click chemistry handle to a cyclooctyne or any other alkyne. Exemplary click chemistry handles suitable for use according to some aspects of this invention are described herein, for example, in Tables 1 and 2. In some embodiments, the click chemistry partners are a conjugated diene and an optionally substituted alkene, In other embodiments, the click chemistry partners are an optionally substituted tetrazine and an optionally substituted trans-cyclooctene (TCO). In some embodiments, the click chemistry partners are optionally substituted tetrazine (Tz) and optionally substituted trans-cyclooctene (TCO). Tz and TCO react with each other in a reverse-electron demand Diels-Alder cycloaddition reaction (See e.g., Example 2, FIG. 4; Blackman et al., "The Tetrazine Ligation: Fast Bioconjugation based on Inverse-electron-demand Diels-Alder Reactivity." *J. Am. Chem. Soc.* 2008; 130, 13518-13519). In other embodiments, the click chemistry partners are an optionally substituted alkyne and an optionally substituted azide. For example, a difluorinated cyclooctyne, a dibenzocyclooctyne, a biarylazacyclooctynone, or a cyclopropyl-fused bicyclononyne can be paired with an azide as a click chemistry pair. In other embodiments, the click chemistry partners are reactive dienes and suitable tetrazine dienophiles. For example, TCO, norbornene, or biscyclononene can be paired with a suitable tetrazine dienophile as a click chemistry pair. In yet other embodiments, tetrazoles can act as latent sources of nitrile imines, which can pair with unactivated alkenes in the presence of ultraviolet light to create a click chemistry pair, termed a "photo-click" chemistry pair. The click chemistry pair may also be a cysteine and a maleimide. For example the cysteine from a peptide (e.g., GGGC (SEQ ID NO: 12)) may be reacted with a maleimide that is associated with a chelating agent (e.g., NOTA). Other suitable click chemistry handles are known to those of skill in the art (See, e.g., Table 1; Spicer et al., "Selective chemical protein modification." *Nature Communications.* 2014; 5:4740). For two molecules to be conjugated via click chemistry, the click chemistry handles of the molecules have to be reactive with each other, for example, in that the reactive moiety of one of the click chemistry handles can react with the reactive moiety of the second click chemistry handle to form a covalent bond. Such reactive pairs of click chemistry handles are well known to those of skill in the art and include, but are not limited to, those described in Table 1.

TABLE 1

Exemplary click chemistry handles and reactions.

| | | Exemplary rate constant ($M^{-1} s^{-1}$) |
|---|---|---|
| 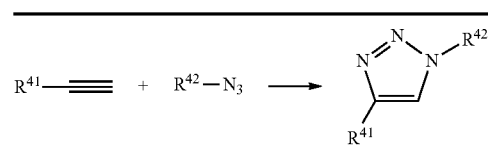 | 1,3-dipolar cycloaddition | $1 \times 10^{-3a}$ |
| 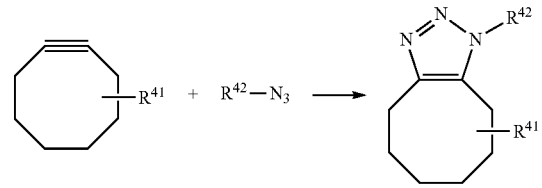 | strain-promoted cycloaddition | |
| 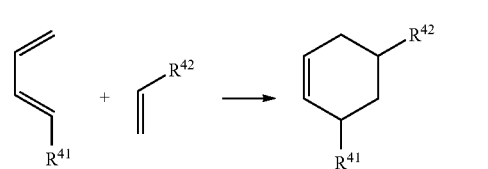 | Diels-Alder reaction | |
| 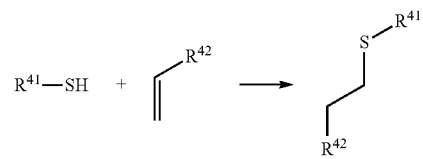 | Thiol-ene reaction | |

TABLE 1-continued

Exemplary click chemistry handles and reactions.

| Reaction | Exemplary rate constant ($M^{-1}\,s^{-1}$) |
|---|---|
| Strain-promoted cycloaddition | $8 \times 10^{-2a}$ |
| Strain-promoted cycloaddition | $2.3^a$ |
| Strain-promoted cycloaddition | $1^a$ |
| Strain-promoted cycloaddition | $0.1^a$ |

TABLE 1-continued
Exemplary click chemistry handles and reactions.
| Reaction | Exemplary rate constant (M$^{-1}$ s$^{-1}$) |
|---|---|
| 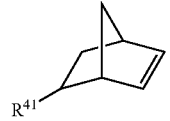 | Inverse-electron demand Diels-Alder (IEDDA) — 9[a] |
| 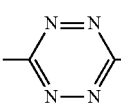 | Inverse-electron demand Diels-Alder (IEDDA) — 17,500[a]  35,000[b] |
| 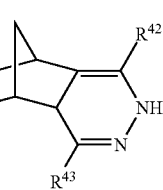 | Inverse-electron demand Diels-Alder (IEDDA) — >50,000[a]  880[b] |
| 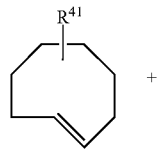 | 1,3-dipolar cycloaddition ("photo-click") — 0.9[a] |

TABLE 1-continued

Exemplary click chemistry handles and reactions.

| | | Exemplary rate constant ($M^{-1} s^{-1}$) |
|---|---|---|
| 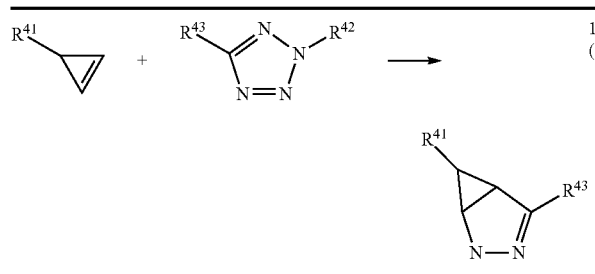 | 1,3-dipolar cycloaddition ("photo-click") | 58[a] |

Each of $R^{41}$, $R^{42}$, and $R^{43}$ is indpendently hydrogen, optionally substituted aliphatic, optionally substituted heteroaliphatic, optionally substituted aryl, optionally substituted heteroaryl, or optionally substituted heterocyclyl. In certain embodiments, at least one of $R^{41}$, $R^{42}$, and $R^{43}$ independently comprises a sortase recognition motif. In certain embodiments, one of $R^{41}$, $R^{42}$, and $R^{43}$ independently comprises a sortase recognition motif. In certain embodiments, two of $R^{41}$, $R^{42}$, and $R^{43}$ independently comprise a sortase recognition motif. In certain embodiments, each of $R^{41}$, $R^{42}$, and $R^{43}$ independently comprises a sortase recognition motif. In some embodiments, at least one of $R^{41}$, $R^{42}$, and $R^{43}$ is independently $R_R$-LPXT-[X]$_y$- (SEQ ID NO: 22), wherein each occurrence of X independently represents any amino acid residue; each occurrence of y is an integer between 0 and 10, inclusive; and each occurrence of $R_R$ independently represents a protein or an agent (e.g., a protein, peptide, a detectable label, a binding agent, a small molecule), and, optionally, a linker. Each instance of $R_3$ is independently H, substituted or unsubstituted alkyl (e.g., —CH$_3$), or substituted or unsubstituted aryl.
[a]Exemplary rate constant for small-molecule models.
[b]Exemplary on-protein rate constant.

In some embodiments, click chemistry handles used can react to form covalent bonds in the absence of a metal catalyst. Such click chemistry handles are well known to those of skill in the art and include the click chemistry handles described in Becer, Hoogenboom, and Schubert (Table 2), "Click Chemistry beyond Metal-Catalyzed Cycloaddition," *Angewandte Chemie International Edition* (2009) 48: 4900-4908:

TABLE 2

Exemplary click chemistry reactions.

| | Reagent A | Reagent B | Mechanism | Notes on reaction[a] |
|---|---|---|---|---|
| 0 | azide | alkyne | Cu-catalyzed [3 + 2] azide-alkyne cycloaddition (CuAAC) | 2 h at 60° C. in H$_2$O |
| 1 | azide | cyclooctyne | strain-promoted [3 + 2] azide-alkyne cycloaddition (SPAAC) | 1 h at RT |
| 2 | azide | activated alkyne | [3 + 2] Huisgen cycloaddition | 4 h at 50° C. |
| 3 | azide | electron-deficient alkyne | [3 + 2] cycloaddittion | 12 h at RT in H$_2$O |
| 4 | azide | aryne | [3 + 2] cycloaddition | 4 h at RT in THF with crown ether or 24 h at RT in CH$_3$CN |
| 5 | tetrazine | alkene | Diels-Alder retro-[4 + 2] cycloaddition | 40 min at 25° C. (100% yield) N$_2$ is the only by-product |
| 6 | tetrazole | alkene | 1,3-dipolar cycloaddition (photoclick) | few min UV irradiation and then overnight at 4° C. |
| 7 | dithioester | diene | hetero-Diels-Alder cycloaddition | 10 min at RT |
| 8 | anthracene | maleimide | [4 + 2] Diels-Alder reaction | 2 days at reflux in toluene |
| 9 | thiol | alkene | radical addition (thio click) | 30 min UV (quantitative conv.) or 24 h UV irradiation (>96%) |
| 10 | thiol | enone | Michael addition | 24 h at RT in CH$_3$CN |
| 11 | thiol | maleimide | Michael addition | 1 h at 40° C. in THF or 16 h at RT in dioxane |
| 12 | thiol | para-fluoro | nucleophilic substitution | overnight at RT in DMF or 60 min at 40° C. in DMF |
| 13 | amine | para-fluoro | nucleophilic substitution | 20 min MW at 95° C. in NMP as solvent |

[a]RT = room temperature, DMF = N,N-dimethylformamide, NMP = N-methylpyrolidone, THF = tetrahydrofuran, CH$_3$CN = acetonitrile.

Methods and compositions for using click chemistry in combination with sortagging technologies are known, and include those described by Ploegh et al., international PCT application, PCT/US2012/044584, filed Jun. 28, 2012, published as WO 2013/003555 on Jan. 3, 2013; and Ploegh et al., U.S. patent application U.S. Ser. No. 13/918,278, filed Jun. 14, 2013; the entire contents of each of which are incorporated herein by reference.

The term "conjugated" or "conjugation" refers to an association of two molecules, for example, two proteins or a protein and an agent, e.g., a small molecule, with one another in a way that they are linked by a direct or indirect covalent or non-covalent interaction. In certain embodiments, the association is covalent, and the entities are said to be "conjugated" to one another. In some embodiments, a protein is post-translationally conjugated to another molecule, for example, a second protein, a small molecule, a detectable label, a click chemistry handle, or a binding agent, by forming a covalent bond between the protein and the other molecule after the protein has been formed, and, in some embodiments, after the protein has been isolated. In some embodiments, two molecules are conjugated via a linker connecting both molecules. For example, in some embodiments where two proteins are conjugated to each other to form a protein fusion, the two proteins may be conjugated via a polypeptide linker, e.g., an amino acid sequence connecting the C-terminus of one protein to the N-terminus of the other protein. In some embodiments, two proteins are conjugated at their respective C-termini, generating a C-C conjugated chimeric protein. In some embodiments, two proteins are conjugated at their respective N-termini, generating an N-N conjugated chimeric protein. In some embodiments, conjugation of a protein to a peptide is achieved by transpeptidation using a sortase. See, e.g., Ploegh et al., International PCT Patent Application, PCT/US2010/000274, filed Feb. 1, 2010, published as WO/2010/087994 on Aug. 5, 2010, and Ploegh et al., International Patent Application, PCT/US2011/033303, filed Apr. 20, 2011, published as WO/2011/133704 on Oct. 27, 2011, the entire contents of each of which are incorporated herein by reference, for exemplary sortases, proteins, recognition motifs, reagents, and methods for sortase-mediated transpeptidation. In other embodiments, conjugation of a protein to a peptide or other moiety may be achieved using other enzymes known in the art, for example, formylglycine generating enzyme, sialyltransferase, phosphopantetheinyl-transferase, transglutaminase, farnesyltransferase, biotin ligase, lipoic acid ligase, or N-myristoyl transferase. Exemplary techniques and approaches for enzymatic labeling of proteins can be found in Rashidian, M., et al. "Enzymatic Labeling of Proteins: Techniques and Approaches", Bioconjugate Chem., 2013; 24, 1277-1294; which is incorporated by reference.

As used herein, a "detectable label" refers to a moiety that has at least one element, isotope, or functional group incorporated into the moiety which enables detection of the molecule, e.g., a protein or polypeptide, or other entity, to which the label is attached. Labels can be directly attached (i.e., via a bond) or can be attached by a tether (such as, for example, an optionally substituted alkylene; an optionally substituted alkenylene; an optionally substituted alkynylene; an optionally substituted heteroalkylene; an optionally substituted heteroalkenylene; an optionally substituted heteroalkynylene; an optionally substituted arylene; an optionally substituted heteroarylene; or an optionally substituted acylene, or any combination thereof, which can make up a tether). It will be appreciated that the label may be attached to or incorporated into a molecule, for example, a protein, polypeptide, or other entity, at any position.

In general, a label can fall into any one (or more) of five classes: a) a label which contains isotopic moieties, which may be radioactive or heavy isotopes, including, but not limited to, $^{2}H$, $^{3}H$, $^{13}C$, $^{14}C$, $^{15}N$, $^{18}F$, $^{31}P$, $^{32}P$, $^{35}S$, $^{67}Ga$, $^{76}Br$, $^{99m}Tc$ (Tc-99m), $^{111}In$, $^{123}I$, $^{125}I$, $^{131}I$, $^{153}Gd$, $^{169}Yb$, and $^{186}Re$; b) a label which contains an immune moiety, which may be antibodies or antigens, which may be bound to enzymes (e.g., such as horseradish peroxidase); c) a label which is a colored, luminescent, phosphorescent, or fluorescent moieties (e.g., such as the fluorescent label fluoresceinisothiocyanat (FITC); d) a label which has one or more photo affinity moieties; and e) a label which is a ligand for one or more known binding partners (e.g., biotin-streptavidin, FK506-FKBP). In certain embodiments, a label comprises a radioactive isotope, preferably an isotope which emits detectable particles, such as ß particles. In certain embodiments, the label comprises a fluorescent moiety. In certain embodiments, the label comprises a fluorophore. In some embodiments, the label is the fluorescent label fluoresceinisothiocyanat (FITC). In certain embodiments, the label comprises a ligand moiety with one or more known binding partners. In certain embodiments, the label comprises biotin. In some embodiments, a label is a fluorescent polypeptide (e.g., GFP or a derivative thereof such as enhanced GFP (EGFP)) or a luciferase (e.g., a firefly, Renilla, or Gaussia luciferase). It will be appreciated that, in certain embodiments, a label may react with a suitable substrate (e.g., a luciferin) to generate a detectable signal. Non-limiting examples of fluorescent proteins include GFP and derivatives thereof, proteins comprising chromophores that emit light of different colors such as red, yellow, and cyan fluorescent proteins, etc. Exemplary fluorescent proteins include, e.g., Sirius, Azurite, EBFP2, TagBFP, mTurquoise, ECFP, Cerulean, TagCFP, mTFP1, mUkG1, mAG1, AcGFP1, TagGFP2, EGFP, mWasabi, EmGFP, TagYFP, EYFP, Topaz, SYFP2, Venus, Citrine, mKO, mKO2, mOrange, mOrange2, TagRFP, TagRFP-T, mStrawberry, mRuby, mCherry, mRaspberry, mKate2, mPlum, mNeptune, T-Sapphire, mAmetrine, mKeima. See, e.g., Chalfie, M. and Kain, SR (eds.) Green fluorescent protein: properties, applications, and protocols (Methods of biochemical analysis, v. 47). Wiley-Interscience, Hoboken, N.J., 2006, and/or Chudakov, D M, et al., Physiol Rev. 90(3): 1103-63, 2010 for discussion of GFP and numerous other fluorescent or luminescent proteins. In some embodiments, a label comprises a dark quencher, e.g., a substance that absorbs excitation energy from a fluorophore and dissipates the energy as heat.

In some aspects, any of the antibodies (e.g. single domain antibodies) and/or methods of making said antibodies provided herein comprise a radionuclide. In some embodiments, the radionuclide is $^{2}H$, $^{3}H$, $^{11}C$, $^{13}C$, $^{14}C$, $^{61}Cu$, $^{62}Cu$, $^{13}N$, $^{15}N$, $^{15}O$, $^{18}F$, $^{31}P$, $^{32}P$, $^{35}S$, $^{67}Ga$, $^{68}Ga$, $^{76}Br$, $^{99m}Tc$ (Tc-99m), $^{111}In$, $^{123}I$, $^{124}I$, $^{125}I$, $^{131}I$, $^{153}Gd$, $^{89}Zr$, $^{86}Y$, $^{169}Yb$, $^{82}Rb$, or $^{186}Re$. However, in other embodiments, the radionuclide is not $^{18}F$. In other embodiments, the radionuclide is not $^{89}Zr$.

The term "linker," as used herein, refers to a chemical group or molecule covalently linked to a molecule, for example, a protein, and a chemical group or moiety, for example, a click chemistry handle. In some embodiments, the linker is positioned between, or flanked by, two groups, molecules, or moieties and connected to each one via a covalent bond, thus connecting the two. In some embodiments, the linker comprises one or more atoms. In some embodiments, the linker comprises between 1 and 500 atoms. In some embodiments, the linker comprises between 1 and 10, 1 and 15, 1 and 20, 1 and 50, 1 and 100, 1 and 150, 1 and 200, 1 and 250, 1 and 300, 1 and 350, 1 and 400, and 1 and 450 atoms. In some embodiments, the linker is an amino acid or a plurality of amino acids. In some embodiments, the linker comprises 1, 2, 3, 4, 5, 6, 7, 8, 9, 10, 11, 12, 13, 14, 15, 16, 17, 18, 19, 20, or more than 20 amino acids. In some embodiments, the linker comprises a polyglycine sequence. In some embodiments, the linker comprises a non-protein structure. In some embodiments, the linker is an organic molecule, group, polymer, or chemical moiety (e.g., poylethylene, polyethylene glycol).

The term "sortase," as used herein, refers to an enzyme able to carry out a transpeptidation reaction conjugating the C-terminus of a protein or peptide to the N-terminus of a protein or peptide via transamidation. Sortases are also referred to as transamidases, and typically exhibit both a protease and a transpeptidation activity. Various sortases from prokaryotic organisms have been identified. For example, some sortases from Gram-positive bacteria cleave and translocate proteins to proteoglycan moieties in intact cell walls. Among the sortases that have been isolated from *Staphylococcus aureus*, are sortase A (Srt A) and sortase B (Srt B). Thus, in certain embodiments, a transaminase used in accordance with the present invention is sortase A, e.g., from *S. aureus*, also referred to herein as SrtA$_{aureus}$. In certain embodiments, a transaminase is a sortase B. e.g., from *S. aureus*, also referred to herein as SrtB$_{aureus}$.

Sortases have been classified into four classes, designated A, B, C, and D, designated sortase A, sortase B, sortase C, and sortase D, respectively, based on sequence alignment and phylogenetic analysis of 61 sortases from Gram-positive bacterial genomes (Dramsi S, Tricu-Cuot P. Bierne H, Sorting sortases: a nomenclature proposal for the various sortases of Gram-positive bacteria. *Res Microbiol.* 156(3): 289-97, 2005; the entire contents of which are incorporated herein by reference). These classes correspond to the following subfamilies, into which sortases have also been classified by Comfort and Clubb (Comfort D, Clubb R T. "A comparative genome analysis identifies distinct sorting pathways in gram-positive bacteria" *Infect Immun.,* 72(5):2710-22, 2004; the entire contents of which are incorporated herein by reference): Class A (Subfamily 1), Class B (Subfamily 2), Class C (Subfamily 3), Class D (Subfamilies 4 and 5). The aforementioned references disclose numerous sortases and recognition motifs. See also Pallen, M. J.; Lam, A. C.; Antonio, M.; Dunbar, K. *TRENDS in Microbiology,* 2001, 9(3), 97-101; the entire contents of which are incorporated herein by reference. Those skilled in the art will readily be able to assign a sortase to the correct class based on its sequence and/or other characteristics such as those described in Drami, et al., supra.

The term "sortase A" is used herein to refer to a class A sortase, usually named SrtA in any particular bacterial species, e.g., SrtA from *S. aureus*. Likewise "sortase B" is used herein to refer to a class B sortase, usually named SrtB in any particular bacterial species, e.g., SrtB from *S. aureus*. The invention encompasses embodiments relating to a sortase A from any bacterial species or strain. The invention encompasses embodiments relating to a sortase B from any bacterial species or strain. The invention encompasses embodiments relating to a class C sortase from any bacterial species or strain. The invention encompasses embodiments relating to a class D sortase from any bacterial species or strain.

Amino acid sequences of Srt A and Srt B and the nucleotide sequences that encode them are known to those of skill in the art and are disclosed in a number of references cited herein, the entire contents of all of which are incorporated herein by reference. The amino acid sequence of a sortase-transaminase from *Staphylococcus aureus* also has substantial homology with sequences of enzymes from other Gram-positive bacteria, and such transamidases can be utilized in the ligation processes described herein. For example, for SrtA there is about a 31% sequence identity (and about 44% sequence similarity) with best alignment over the entire sequenced region of the *S. pyogenes* open reading frame. There is about a 28% sequence identity with best alignment over the entire sequenced region of the *A. naeslundii* open reading frame. It will be appreciated that different bacterial strains may exhibit differences in sequence of a particular polypeptide, and the sequences herein are exemplary.

In certain embodiments a transaminase bearing 18% or more sequence identity, 20% or more sequence identity, 30% or more sequence identity, 40% or more sequence identity, or 50% or more sequence identity with an *S. pyogenes, A. naeslundii, S. mutans, E. faecalis* or *B. subtilis* open reading frame encoding a sortase can be screened, and enzymes having transaminase activity comparable to Srt A or Srt B from *S. aureus* can be utilized (e.g., comparable activity sometimes is 10% of Srt A or Srt B activity or more).

Thus in some embodiments of the invention the sortase is a sortase A (SrtA). SrtA recognizes the motif (e.g., the sortase recognition motif) LPXTX (wherein each occurrence of X represents independently any amino acid residue) (SEQ ID NO: 15), with common recognition motifs being, e.g., LPKTG (SEQ ID NO: 23), LPATG (SEQ ID NO: 24), LPNTG (SEQ ID NO: 25). In some embodiments LPETG (SEQ ID NO: 11) is used as the sortase recognition motif. However, motifs falling outside this consensus may also be recognized. For example, in some embodiments the motif comprises an 'A' rather than a 'T' at position 4, e.g., LPXAG (SEQ ID NO: 17), e.g., LPNAG (SEQ ID NO: 26). In some embodiments the motif comprises an 'A' rather than a 'G' at position 5, e.g., LPXTA (SEQ ID NO: 27), e.g., LPNTA (SEQ ID NO: 28), e.g., LPETA (SEQ ID NO: 29). In some embodiments the motif comprises a 'G' rather than 'P' at position 2, e.g., LGXTG (SEQ ID NO: 30), e.g., LGATG (SEQ ID NO: 31). In some embodiments the motif comprises an 'I' rather than 'L' at position 1, e.g., IPXTG (SEQ ID NO: 32), e.g., IPNTG (SEQ ID NO:33) or IPETG (SEQ ID NO: 34). Additional suitable sortase recognition motifs will be apparent to those of skill in the art, and the invention is not limited in this respect. It will be appreciated that the terms "recognition motif" and "recognition sequence", with respect to sequences recognized by a transaminase or sortase, are used interchangeably.

In some embodiments of the invention the sortase is a sortase B (SrtB), e.g., a sortase B of *S. aureus, B. anthracis*, or *L. monocytogenes*. Motifs recognized by sortases (sortase recognition motifs) of the B class (SrtB) often fall within the consensus sequences NPXTX (SEQ ID NO: 16), e.g., NP[Q/K]-[T/s]-[N/G/s] (SEQ ID NO: 35), such as NPQTN (SEQ ID NO: 36) or NPKTG (SEQ ID NO: 37). For example, sortase B of *S. aureus* or *B. anthracis* cleaves the NPQTN (SEQ ID NO:36) or NPKTG (SEQ ID NO:37) motif of IsdC in the respective bacteria (see, e.g., Marraffini, L. and Schneewind, O., Journal of Bacteriology, 189(17), p. 6425-6436, 2007). Other recognition motifs found in putative substrates of class B sortases are NSKTA (SEQ ID NO: 38), NPQTG (SEQ ID NO: 39), NAKTN (SEQ ID NO:40), NPQSS (SEQ ID NO: 41). For example, SrtB from *L. monocytogenes* recognizes certain motifs lacking P at position 2 and/or lacking Q or K at position 3, such as NAKTN (SEQ ID NO: 40) and NPQSS (SEQ ID NO:41) (Mariscotti J F, García-Del Portillo F, Pucciarelli M G. The *Listeria monocytogenes* sortase-B recognizes varied amino acids at position two of the sorting motif. J Biol Chem. 2009 Jan. 7.)

In some embodiments, the sortase is a sortase C (Srt C). Sortase C may utilize LPXTX (SEQ ID NO: 15) as a recognition motif, with each occurrence of X independently representing any amino acid residue.

In some embodiments, the sortase is a sortase D (Srt D). Sortases in this class are predicted to recognize motifs with a consensus sequence NA-[E/A/S/H]-TG (SEQ ID NO: 42) (Comfort D, supra). Sortase D has been found, e.g., in *Streptomyces* spp., *Corynebacterium* spp., *Tropheryma whipplei, Thermobifida fusca*, and *Bifidobacterium longhum*. LPXTA (SEQ ID NO: 43) or LAXTG (SEQ ID NO:44) may serve as a recognition sequence for sortase D, e.g., of subfamilies 4 and 5, respectively subfamily-4 and subfamily-5 enzymes process the motifs LPXTA (SEQ ID NO: 27) and LAXTG (SEQ ID NO: 44), respectively). For example, *B. anthracis* Sortase C has been shown to specifically cleave the LPNTA (SEQ ID NO: 28) motif in *B. anthracis* BasI and BasH (see Marrafini, supra).

See Barnett and Scott for description of a sortase that recognizes QVPTGV (SEQ ID NO: 45) motif (Barnett, T C and Scott, JR, *Differential Recognition of Surface Proteins in Streptococcus pyogenes by Two Sortase Gene Homologs*. Journal of Bacteriology, Vol. 184, No. 8, p. 2181-2191, 2002; the entire contents of which are incorporated herein by reference). Additional sortases, including, but not limited to, sortases and sortase variants recognizing additional sortase recognition motifs are also suitable for use in some embodiments of this invention. For example, sortases described in Chen I. et al., "A general strategy for the evolution of bond-forming enzymes using yeast display." *Proc Natl Acad Sci USA*. 2011 Jul. 12; 108(28): 11399; Dorr, B. M., et al., "Reprogramming the specificity of sortase enzymes." *Proc. Natl. Acad. Sci. U.S.A.* 2014, 111, 13343-13348; the entire contents of each of which are incorporated herein by reference.

In some embodiments, a variant of a naturally occurring sortase may be used. Such variants may be produced through processes such as directed evolution, site-specific modification, etc. Considerable structural information regarding sortase enzymes, e.g., sortase A enzymes, is available, including NMR or crystal structures of SrtA alone or bound to a sortase recognition sequence (see, e.g., Zong Y, et al. J. Biol Chem. 2004, 279, 31383-31389). Three dimensional structure information is also available for other sortases, e.g., *S. pyogenes* SrtA (Racc, P R, et al., *J Biol Chem*. 2009, 284(11):6924-33). The active site and substrate binding pocket of *S. aureus* SrtA have been identified. One of ordinary skill in the art can generate functional variants by, for example, avoiding deletions or substitutions that would disrupt or substantially alter the active site or substrate binding pocket of a sortase. In some embodiments a functional variant of *S. aureus* SrtA comprises His at position 120, Cys at position 184, and Arg at position 197, wherein Cys at position 184 is located within a TLXTC (SEQ ID NO: 46) motif. Functional variants of other SrtA proteins may have His, Cys, Arg, and TLXTC (SEQ ID NO: 46) motifs at positions that correspond to the positions of these residues in *S. aureus* SrtA. In some embodiments, a sortase variant comprises a sequence at least 80%, 85%, 90%, 91%, 92%, 93%, 94%, 95%, 96%, 97%, 98%, or 99% identical to a wild type sortase A sequence or catalytic domain thereof, e.g., at least 80%, 85%, 90%, 91%, 92%, 93%, 94%, 95%, 96%, 97%, 98%, or 99% identical to amino acids 60-206 of SEQ ID NO: 47 or SEQ ID NO: 48, or at least 80%, 85%, 90%, 91%, 92%, 93%, 94%, 95%, 96%, 97%, 98%, or 99% identical to amino acids 26-206 of SEQ ID NO: 47 or SEQ ID NO: 48. In some embodiments, a sortase variant comprises 1, 2, 3, 4, 5, 6, 7, 8, 9, 10, 11, 12, 13, 14, or 15 amino acid substitutions relative to amino acids 60-206 of SEQ ID NO: 47 or relative to amino acids 26-206 of SEQ ID NO: 47 or SEQ ID NO: 48.

In some embodiments, a transaminase having higher transaminase activity than a naturally occurring sortase may be used. In some embodiments the activity of the transaminase is at least about 10, 15, 20, 40, 60, 80, 100, 120, 140, 160, 180, or 200 times as high as that of *S. aureus* sortase A. In some embodiments the activity is between about 10 and 50 times as high as that of *S. aureus* sortase A, e.g., between about 10 and 20 times as high, between about 20 and 30 times as high, between about 30 and 50 times as high. In some embodiments the activity is between about 50 and about 150 times as high as that of *S. aureus* sortase A, e.g., between about 50 and 75 times as high, between about 75 and 100 times as high, between about 100-125 times as high, or between about 125 and 150 times as high. For example, variants of *S. aureus* sortase A with up to a 140-fold increase in LPETG-coupling (SEQ ID NO: 11) activity compared with the starting wild-type enzyme have been identified (Chen, I., et al., *PNAS* 108(28): 11399-11404, 2011). In some embodiments such a sortase variant is used in a composition or method of the invention. In some embodiments a sortase variant comprises any one or more of the following substitutions relative to a wild type *S. aureus* SrtA: P94S or P94R, D160N, D165A, K190E, and K196T mutations.

One of ordinary skill in the art will appreciate that the foregoing descriptions of substitutions utilize standard notation of the form $X_1NX_2$, in which $X_1$ and $X_2$, represent amino acids and N represents an amino acid position, $X_1$ represents an amino acid present in a first sequence (e.g., a wild type *S. aureus* SrtA sequence), and $X_2$ represents an amino acid that is substituted for $X_1$ at position N, resulting in a second sequence that has $X_2$ at position N instead of $X_1$. It should be understood that the present disclosure is not intended to be limited in any way by the identity of the original amino acid residue $X_1$ that is present at a particular position N in a wild type SrtA sequence used to generate a SrtA variant and is replaced by $X_2$ in the variant. Any substitution which results in the specified amino acid residue at a position specified herein is contemplated by the disclosure. Thus a substitution may be defined by the position and the identity of $X_2$, whereas $X_1$ may vary depending, e.g., on the particular bacterial species or strain from which a particular SrtA originates. Thus in some embodiments, a sortase A variant comprises any one or more of the following: an S residue at position 94 (S94) or an R residue at position 94 (R94), an N residue at position 160 (N160), an A residue at position 165 (A165), an E residue at position 190 (E190), a T residue at position 196 (T196) (numbered according to the numbering of a wild type SrtA, e.g., SEQ ID NO: 47). For example, in some embodiments a sortase A variant comprises two, three, four, or five of the aforementioned mutations relative to a wild type *S. aureus* SrtA (e.g., SEQ ID NO: 47). In some embodiments a sortase A variant comprises an S residue at position 94 (S94) or an R residue at position 94 (R94), and also an N residue at position 160 (N160), an A residue at position 165 (A165), and a T residue at position 196 (T196). For example, in some embodiments a sortase A variant comprises P94S or P94R, and also D160N, D165A, and K196T. In some embodiments a sortase A variant comprises an S residue at position 94 (S94) or an R residue at position 94 (R94) and also an N residue at position 160 (N160), A residue at position 165 (A165), a E residue at position 190, and a T residue at position 196. For example, in some embodiments a sortase A variant comprises P94S or P94R, and also D160N, D165A, K190E, and K196T. In some embodiments a sortase A variant comprises an R residue at position 94 (R94), an N residue at position 160 (N160), a A residue at position 165 (A165), E residue at position 190, and a T residue at position 196. In some embodiments a sortase comprises P94R, D160N, D165A, K190E, and K196T.

It is to be further understood that the disclosure contemplates variants of any wild-type sortase A. Those skilled in the art will appreciate that wild-type sequences of sortase A may vary, e.g., SrtA from various species may have gaps, insertions, and/or may vary in length relative to the amino acid sequence of exemplary wild-type S. aureus SrtA. Those skilled in the art will appreciate that the positions described herein in regard to substitutions or other alterations pertain to the sequence of exemplary wild type S. aureus SrtA, unless otherwise indicated, and that such positions may be adjusted when making corresponding substitutions in different bacterial SrtA sequences in order to account for such gaps, insertions, and/or length differences. For example, as noted above, certain sortase variants comprise a substitution at amino acid position 94 (e.g., the amino acid is changed to an S residue). However, the amino acid at position 94 in S. aureus SrtA may correspond to an amino acid at a different position (e.g., position Z) in SrtA from a second bacterial species when the sequences are aligned. When generating a variant of the SrtA of the second bacterial species comprising a substitution at "position 94" (based on the wild type S. aureus SrtA sequence numbering), it is the amino acid at position Z of the SrtA from the second bacterial species that should be changed (e.g., to S) rather than the amino acid at position 94. Those skilled in the art will understand how to align any original wild-type sortase A sequence to be used for generating a SrtA variant with an exemplary wild-type S. aureus sortase A sequence for purposes of determining the positions in the original wild-type sortase A sequence that correspond to the exemplary wild-type S. aureus sortase A sequence when taking into account gaps and/or insertions in the alignment of the two sequences.

In some embodiments, amino acids at position 94, 160, 165, 190, and/or 196 are altered in a variant as compared with the amino acids present at those positions in a wild type S. aureus SrtA, and the other amino acids of the variant are identical to those present at the corresponding positions in a wild type SrtA, e.g., a wild type S. aureus SrtA. In some embodiments, one or more of the other amino acids of a variant, e.g., 1, 2, 3, 4, 5, 6, 7, 8, 9, or 10 of the other amino acids differ from those present at corresponding position(s) in a wild type SrtA, e.g., a wild type S. aureus SrtA. In some embodiments a variant may have any of the properties or degrees of sequence identity specified in the definition of "variants" above.

An exemplary wild type S. aureus SrtA sequence (Gene ID: 1125243, NCBI RefSeq Acc. No. NP_375640.1) is shown below, with the afore-mentioned positions underlined:

(SEQ ID NO: 47)
MKKWTNRLMTIAGVVLILVAAYLFAKPHIDNYLHDKDKDEKIEQYDKNVK

-continued

EQAS<u>K</u>DNKQQAKPQIPKDKSKVAGYIEIPDADIKEPVYPGPAT<u>P</u>EQLNRG

VSFAEENESLDDQNISIAGHTFIDRPNYQFTNLKAAKKGSMVYFKVGNET

RKYKMTSIR<u>D</u>VKPT<u>D</u>VEVLDEQKGKDKQLTLITCDDYNE<u>K</u>TGVWE<u>K</u>RKIF

VATEVK.

One of ordinary skill in the art will appreciate that different subspecies, strains, and isolates may differ in sequence at positions that do not significantly affect activity. For example, another exemplary wild type S. aureus SrtA sequence (Gene ID: 3238307, NCBI RefSeq Acc. No. YP_187332.1; GenBank Acc. No. AAD48437) has a K residue at position 57 and a G residue at position 167, as shown below in SEQ ID NO: 48:

(SEQ ID NO: 48)
MKKWTNRLMTIAGVVLILVAAYLFAKPHIDNYLHDKDKDEKIEQYDKNVK

EQAS<u>K</u>D<u>K</u>KQQAKPQIPKDKSKVAGYIEIPDADIKEPVYPGPAT<u>P</u>EQLNRG

VSFAEENESLDDQNISIAGHTFIDRPNYQFTNLKAAKKGSMVYFKVGNET

RKYKMTSIR<u>D</u>VKPT<u>D</u>VGVLDEQKGKDKQLTLITCDDYNE<u>K</u>TGVWE<u>K</u>RKIF

VATEVK

Either or both of these amino acids (i.e., K57 and/or G167) may be present in or introduced into any SrtA sequence, e.g., any S. aureus SrtA sequence, whether naturally occurring or generated by man. Furthermore, as described herein, any sortase sequence may further comprise a tag (e.g., 6XHis), a spacer, or both. For example, the N- or C-terminus may be extended to encompass a tag, optionally separated from the rest of the sequence by a spacer, In some embodiments a sortase variant comprising the following sequence may be used, in which amino acid substitutions relative to a wild type S. aureus SrtA of SEQ ID NO: 47 or SEQ ID NO: 48 are shown in underlined bold letters:

(SEQ ID NO: 49)
MQAKPQIPKDKSKVAGYIEIPDADIKEPVYPGPAT<u>R</u>EQLNRGVSFAEENE

SLDDQNISIAGHTFIDRPNYQFTNLKAAKKGSMVYFKVGNETRKYKMTSI

R<u>N</u>VKPT<u>A</u>VEVLDEQKGKDKQLTLITCDDYNE<u>E</u>TGVWE<u>T</u>RKIFVATEVK.

As will be appreciated, amino acids 2-148 of the above sequence correspond to amino acids 60-206 of the full length S. aureus SrtA sequence (the catalytic domain). For example, the "R" residue at position 36 of SEQ ID NO: 49 corresponds to the "P" residue at position 94 in SEQ ID NO: 47 or 48. It is also contemplated in some embodiments to use sortase variants that have other substitutions at one or more of positions 94, 160, 165, 190, and 196 (numbered according to the numbering of SEQ ID NO: 47 or 48), e.g., wherein such substitutions utilize an amino acid that would be a conservative substitution at the relevant position as compared with the sequence of SEQ ID NO: 49.

The use of sortases found in any gram-positive organism, such as those mentioned herein and/or in the references (including databases) cited herein is contemplated in the context of some embodiments of this invention. Also contemplated is the use of sortases found in gram negative bacteria, e.g., *Colwellia psychrerythraea, Microbulbifer degradans, Bradyrhizobium japonicum, Shewanella onei-*

*densis*, and *Shewanella putrefaciens*. Such sortases recognize sequence motifs outside the LPXTX (SEQ ID NO: 15) consensus, for example, LP[Q/K]T[A/S]T (SEQ ID NO: 50). In keeping with the variation tolerated at position 3 in sortases from gram-positive organisms, a sequence motif LPXT[A/S] (SEQ ID NO: 51), e.g., LPXTA (SEQ ID NO:27) or LPSTS (SEQ ID NO: 52) may be used.

Those of skill in the art will appreciate that any sortase recognition motif known in the art can be used in some embodiments of this invention, and that the invention is not limited in this respect. For example, in some embodiments the sortase recognition motif is selected from: LPKTG (SEQ ID NO: 23), LPITG (SEQ ID NO: 53), LPDTA (SEQ ID NO: 54), SPKTG (SEQ ID NO:55), LAETG (SEQ ID NO: 56), LAATG (SEQ ID NO: 57), LAHTG (SEQ ID NO: 58), LASTG (SEQ ID NO: 59), LPLTG (SEQ ID NO: 60), LSRTG (SEQ ID NO: 61), LPETG (SEQ ID NO:11), VPDTG (SEQ ID NO: 62), IPQTG (SEQ ID NO: 63), YPRRG (SEQ ID NO: 64), LPMTG (SEQ ID NO:65), LAFTG (SEQ ID NO: 66), LPQTS (SEQ ID NO: 67), it being understood that in various embodiments of the invention the fifth residue may be replaced with any other amino acid residue. For example, the sequence used may be LPXT (SEQ ID NO: 22), LAXT (SEQ ID NO: 68), LPXA (SEQ ID NO: 69), LGXT (SEQ ID NO: 70), IPXT (SEQ ID NO: 71), NPXT (SEQ ID NO: 72), NPQS (SEQ ID NO: 73), LPST (SEQ ID NO: 74), NSKT (SEQ ID NO: 75), NPQT (SEQ ID NO: 76), NAKT (SEQ ID NO: 77), LPIT (SEQ ID NO: 78), LAET (SEQ ID NO: 79), or NPQS (SEQ ID NO: 80). The invention encompasses embodiments in which 'X' in any sortase recognition motif disclosed herein or known in the art is amino acid, for example, any naturally occurring or any non-naturally occurring amino acid. In some embodiments, X is selected from the 20 standard amino acids found most commonly in proteins found in living organisms. In some embodiments, e.g., where the recognition motif is LPXTG (SEQ ID NO: 81) or LPXT (SEQ ID NO: 22), X is D, E, A, N, Q. K, or R. In some embodiments, X in a particular recognition motif is selected from those amino acids that occur naturally at position 3 in a naturally occurring sortase substrate. For example, in some embodiments X is selected from K, E, N, Q, A in an LPXTG (SEQ ID NO: 81) or LPXT (SEQ ID NO: 22)motif where the sortase is a sortase A. In some embodiments X is selected from K, S, E, L, A, N in an LPXTG (SEQ ID NO: 81) or LPXT (SEQ ID NO: 22) motif and a class C sortase is used.

In some embodiments, a sortase recognition sequence further comprises one or more additional amino acids, e.g., at the N- or C-terminus. For example, one or more amino acids (e.g., up to five amino acids) having the identity of amino acids found immediately N-terminal to, or C-terminal to, a five amino acid recognition sequence in a naturally occurring sortase substrate may be incorporated. Such additional amino acids may provide context that improves the recognition of the recognition motif.

The term "sortase recognition motif," as used herein, refers to any molecule that is recognized by a sortase, for example, any molecule that can partake in a sortase-mediated transpeptidation reaction. In some embodiments, "sortase recognition motif" and "sortase recognition sequence" are used interchangeably. A typical sortase-mediated transpeptidation reaction involves a substrate comprising a C-terminal sortase recognition motif, e.g., an LPXTX (SEQ ID NO: 15) motif, and a second substrate, referred to herein as a "sortase substrate." A sortase substrate is a chemical moiety that can partake in a sortase-mediated transpeptidation reaction with a sortase recognition motif. In some embodiments, the sortase substrate is a polyglycine or polyalanine. In some embodiments, the sortase substrate comprises an alkylamine group. In some embodiments, the sortase substrate is N-terminal. In some embodiments, the sortase substrate is C-terminal In some embodiments, a sortase substrate, or substrate recognition motif though described as being "C-terminal" or N-terminal," is not required to be at the immediate C- or N-terminus. For example, in some embodiments, other amino acids, for example a tag (e.g., a 6xHis-tag), are found at the immediate C-terminus of a protein comprising a C-terminal sortase recognition motif, and the C-terminal sortase recognition motif is adjacent (e.g., within 5, 10, 15 or 20 amino acids) thereto. A sortase recognition motif may be a peptide or a protein, for example, a peptide comprising a sortase recognition motif such as an LPXTX (SEQ ID NO: 15). In some embodiments, a sortase substrate is a polyglycine a polyalanine, or an alkylamine group wherein the peptide is conjugated to an agent, e.g., a radiolabeled compound or small molecule. Accordingly, both proteins and non-protein molecules can be sortase substrates. Some examples of sortase substrates are described in more detail elsewhere herein and additional suitable sortase substrates will be apparent to the skilled artisan. The invention is not limited in this respect.

The term "sortagging." as used herein, refers to the process of adding a tag or agent, e.g., a moiety or molecule, for example, a radiolabeled compound or small molecule, onto a target molecule, for example, a target protein for use in PET applications via a sortase-mediated transpeptidation reaction. Examples of additional suitable tags include, but are not limited to, amino acids, nucleic acids, polynucleotides, sugars, carbohydrates, polymers, lipids, fatty acids, and small molecules. Other suitable tags will be apparent to those of skill in the art and the invention is not limited in this aspect. In some embodiments, a tag comprises a sequence useful for purifying, expressing, solubilizing, and/or detecting a polypeptide. In some embodiments, a tag can serve multiple functions. In some embodiments, a tag comprises an HA, TAP. Myc, 6xHis, Flag, streptavidin, biotin, or GST tag, to name a few examples. In some embodiments, a tag is cleavable, so that it can be removed, e.g., by a protease. In some embodiments, this is achieved by including a protease cleavage site in the tag, e.g., adjacent or linked to a functional portion of the tag. Exemplary proteases include, e.g., thrombin, TEV protease, Factor Xa, PreScission protease, etc. In some embodiments, a "self-cleaving" tag is used. Sec, e.g., Wood et al., International PCT Application PCT/US2005/05763, filed on Feb. 24, 2005, and published as WO/2005/086654 on Sep. 22, 2005.

The term "subject" includes, but is not limited to, vertebrates, more specifically a mammal (e.g., a human, horse, pig, rabbit, dog, sheep, goat, non-human primate, cow, cat, guinea pig or rodent), a fish, a bird or a reptile or an amphibian. In some embodiments, the subject is a human subject. As used herein, "patient" refers to a subject afflicted with a disease or disorder. The term "patient" includes human and veterinary subjects of any sex or stage of development.

The term "target protein," as used herein in the context of sortase-mediated modification of proteins, refers to a protein that is modified by the conjugation of an agent, for example a radioactive agent that renders the protein suitable for diagnostic and/or therapeutic applications, such as PET imaging. The term "target protein" may refer to a wild type or naturally occurring form of the respective protein, or to an engineered form, for example, to a recombinant protein variant comprising a sortase recognition motif not contained in a wild-type form of the protein. The term "modifying a target protein," as used herein in the context of sortase-mediated protein modification, refers to a process of altering a target protein comprising a sortase recognition motif via a sortase-mediated transpeptidation reaction. Typically, the modification leads to the target protein being conjugated to an agent, for example, a peptide, protein, detectable label, or small molecule. In certain embodiments, the modification provides radiolabeled proteins.

Antibodies and Single Domain Antibodies

Some aspects of the disclosure provide antibodies (e.g., single domain antibodies) comprising a hydrophilic polymer and a detectable label. Other aspects of the disclosure provide methods for conjugating hydrophilic polymers and/or detectable labels to antibodies (e.g., single domain antibodies). In some embodiments, such antibodies are useful for imaging, for example a tumor, a tissue, or an organ in a subject. It should be appreciated that any of the antibodies provided herein may bind to a particular antigen. In some embodiments, any of the antibodies provided herein may be produced, for example, by immunizing a subject (e.g., research animal) with an antigen, or using other methods, such as phage display. In some embodiments, an antibody is said to bind to an antigen if it is capable of binding to said antigen with an affinity better than $10^{-6}$M. In some embodiments, an antibody is said to bind to an antigen if it is capable of binding to said antigen with an affinity better than $10^{-6}$ M, $10^{-7}$ M, $10^{-8}$ M, $10^{-9}$ M, $10^{-10}$ M, or $10^{-11}$ M.

Any of the antibodies (e.g., single domain antibodies) provided herein may be humanized. Methods of humanizing antibodies are known in the art and would be apparent to the skilled artisan. Technology to humanize camelid VHHs has been developed (see e.g., Vincke et al., J. Biol. Chem. 2009, 284, 3273-3284; which is incorporated herein by reference), and several VHHs have been used already in a number of phase I and phase II clinical trials for therapeutic applications (see, e.g., De Meyer et al., Trends Biotechnol. 2014, 32, 263-270; which is incorporated herein by reference). Accordingly, in some embodiments, methods for using VHHs (e.g., any of the VHHs provided herein) are provided. In some embodiments, the methods include detecting an epitope in a subject. In some embodiments, the methods include detecting a lymphocyte, e.g., in a tumor of a subject. In some embodiments, the methods include determining whether a subject will respond to a therapeutic agent.

In some embodiments, any of the antibodies provided herein bind to any immune cell. Some examples of immune cells include T-cells, B-cells, plasma cells, macrophages, dendritic cells, neutrophils, eosinophils, or mast cells. In some embodiments, the antibody binds to a marker of inflammation. For example, in some embodiments, the antibody useful in diagnostic applications involving PET. Use of antibodies for PET based applications is referred to as immunoPET (See, e.g., Knowles et al., "Advances in immuno-positron emission tomography: antibodies for molecular imaging in oncology." *J Clin Oncol.* 2012; 30:3884-3892; the entire contents of which are hereby incorporated by reference). Such antibodies include monoclonal antibodies known to target or bind cancerous cells or tissues in a subject's body. For example, a non-limiting list of antibodies approved by the U.S. Food and Drug Administration (FDA) and the European Medicines Agency is provided in Table 3 of Salsano and Treglia, "PET imaging using radiolabeled antibodies: future direction in tumor diagnosis and correlate applications." *Research and Reports in Nuclear Medicine.* 2013: 3; 9-17, the entire contents of which are hereby incorporated by reference. The table is reproduced below.

TABLE 3

List of monoclonal antibodies approved by the US Food and Drug Administration and the European Medicines Agency in cancer therapy.

| Antibody | Brand name | Type | Target: antibody type | Application | Company | Approval year EU | Approval year USA |
|---|---|---|---|---|---|---|---|
| Rituximab | Rituxan, MabThera | Chimeric IgG1 | CD20 | Non-Hodgkin lymphoma | Genentech | 1998 | 1997 |
| Trastuzumab | Herceptin | Humanized IgG1 | HER2 | Beast cancer | Genentech/Roche | 2000 | 1998 |
| Gemtuzumab ozogamicin | Mylotarg* | Humanized IgG4, immunotoxin | CD33 | Acute myeloid leukemia | Wyeth/Pfizer | NA | 2000 |
| Alemtuzumab | MabCampath, Campath-IH | Humanized IgG1 | CD52 | Chronic myeloid leukemia | Genzyme | 2001 | 2001 |
| Ibritumomab tiuxecan | Zevalin | Murine IgG1 | CD20 | Non-Hodgkin lymphoma | Biogen Idec | 2004 | 2002 |
| Tositumomab | Bexxar | Murine IgG2a | CD20 | Non-Hodgkin lymphoma | Corixa/GSK | NA | 2003 |
| Cecuximab | Erbitux | Chimeric IgG1 | EGFR | Colorectal cancer, head and neck cancer | Imclone/Lilly | 2004 | 2004 |
| Bevacizumab | Avastin | Humanized IgG1 | VEGF | Colorectal cancer, non-small cell lung cancer | Genentech/Roche | 2005 | 2004 |
| Panitumumab | Vectibix | Human IgG2 | EGFR | Colorectal cancer | Amgen | 2007 | 2006 |
| Ofatumumab | Arzerra | Human IgG1 | CD20 | Chronic lymphocytic leukemia | Genmab | 2010 | 2009 |
| Denosumab | Prolia | Human IgG2 | RANK ligand | Bone metastases, giant cell tumor of bone | Amgen | 2010 | 2010 |
| Ipilimumab | Yervoy | Human IgG1 | CTLA-4 | Melanoma | BMS | 2011 | 2011 |
| Brentuximab vedotin | Adcetris | Chimeric IgG1, drug-conjugate | CD30 | Anaplastic large cell lymphoma, Hodgkin lymphoma | Seattle Genetics | 2012 | 2011 |

TABLE 3-continued

List of monoclonal antibodies approved by the US Food and Drug Administration
and the European Medicines Agency in cancer therapy.

| Antibody | Brand name | Type | Target: antibody type | Application | Company | Approval year EU | Approval year USA |
|---|---|---|---|---|---|---|---|
| Pertuzumab | Perjeta | Humanized IgG1 | HER2 | Breast cancer | Genentech/Roche | 2013 | 2012 |
| Ado-trastuzumab emtansine | Kadcyla | Humanized IgG1, drug-conjugate | HER2 | Breast cancer | Genentech/Roche | in review | 2013 |

Note:
*withdrawn in 2010.
Abbreviations: CTLA 4, cytotoxic T-lymphocyte antigen 4; EGFR, epidermal growth factor receptor; HER, human epidermal receptor; NA, not approved; VEGF, vascular endothelial growth factor.

Any of the antibodies, or fragments thereof, disclosed in Table 3 of Salsano and Treglia can be labeled according to the methods provided herein. Other antibodies amenable to labeling as described herein include, but are not limited to, those described in Wright and Lapi, "Designing the magic bullet? The advancement of immuno-PET into clinical use." *J. Nucl. Med.* 2013 August; 54(8):1171-4; the entire contents of which are hereby incorporated by reference. These antibodies (see below) were successfully labeled with isotopes and were used in PET based diagnostic and/or therapeutic applications. However, the antibodies were labeled via chemical means that are not always amenable to quickly generating labeled antibodies with isotopes having a short half-life. Thus, such antibodies can be quickly and efficiently labeled with any desired isotope according to the methods, compositions, reagents, and kits provided herein. Antibodies disclosed by Wright and Lapi, include:

Humanized A33 (huA33), which recognizes A33 antigen, which is known to be expressed in greater than 95% of human colon adenocarcinomas. In a study utilizing radiolabeled huA33 (Carrasquillo et al., "$^{124}$I-huA33 antibody PET of colorectal cancer." *J. Nucl. Med.* 2011; 52:1173-1180; the entire contents of which are hereby incorporated by reference), 25 patients with primary or metastatic colorectal cancer (CRC) were administered 44.4-396 MBq (median, 343 MBq) of $^{124}$I-huA33 with a total of 10 mg of huA33. No adverse side effects were observed during the treatment that could be attributed to the huA33. The antibody could be administered via intravenous administration or hepatic arterial infusion (HAI), with HAI giving no detectable advantage over intravenous injection. Eleven patients had 12 primary tumors, 10 of which were detected via immuno-PET. Ten patients had liver metastases, all of which were detected by $^{124}$I-huA33. Four of 7 patients with nodal metastases displayed uptake of the $^{124}$I-huA33, and 2 of 5 patients had lung lesions that were visualized by immuno-PET.

Radretumab (L19SIP), which targets an epitope contained in the extra-domain B of fibronectin, was labeled with $^{124}$I and used to establish provisional doses of $^{131}$I-labeled radretumab in 6 patients with brain metastasis (Poli et al., "Radretumab radioimmunotherapy in patients with brain metastasis: a $^{124}$I-L19SIP dosimetric PET study. *Cancer Immunol Res.* 2013:OF1-OF10; the entire contents of which are hereby incorporated by reference).

Girentuximab (cG250), a chimeric antibody that binds carbonic anhydrase IX (CAIX), expressed in >95% of clear cell renal carcinoma (ccRCC), was labeled with $^{124}$I and used to detect such cancers (Divgi et al., "Positron emission tomography/computed tomography identification of clear cell renal cell carcinoma: results from the REDECT Trial." *J. Clin. Oncol.* 2013; 31:187-194; the entire contents of which are hereby incorporated by reference).

Panitumumab, a fully humanized antibody that binds epidermal growth factor receptor (EGFR), was successfully labeled with $^{89}$Zr and used to image colorectal tumor xenografts (Nayak et al., "PET and MR imaging of metastatic peritoneal and pulmonary colorectal cancer in mice with human epidermal growth factor receptor 1-targeted $^{89}$Zr-Labeled panitumumab." *J. Nucl. Med.* 2012; 53:113-120; Chang et al., "Development and characterization of $^{89}$Zr-labeled panitumumab for immuno-positron emission tomographic imaging of the epidermal growth factor receptor." *Mol. Imaging.* 2013; 12:17-27; the entire contents of each are hereby incorporated by reference).

U36, a chimeric antibody that recognizes the v6 region of CD44, was labeled with $^{89}$Zr to image head and neck squamous cell carcinoma (Börjesson et al. "Radiation dosimetry of $^{89}$Zr-labeled chimeric monoclonal antibody U36 as used for immuno-PET in head and neck cancer patients." *J. Nucl. Med.* 2009; 50:1828-1836; the entire contents of which are hereby incorporated by reference).

Trastuzumab, cetuximab, and bevacizumab (see Table 4 above), were also successfully labeled with $^{89}$Zr and used in PET applications (Dijkers et al., "Biodistribution of $^{89}$Zr-trastuzumab and PET imaging of HER2-positive lesions in patients with metastatic breast cancer." *Clin. Pharmacol. Ther.* 2010; 87:586-592; www.cancer.gov/clinicaltrials/search/results?protocolsearchid511815785. Accessed Jul. 15, 2013; the entire contents of each are hereby incorporated by reference).

In some embodiments, any of the antibodies provided herein binds to a tumor antigen. In general, a tumor antigen can be any antigenic substance produced by a tumor cell (e.g., tumorigenic cells, or in some embodiments tumor stromal cells, e.g., tumor-associated cells such as cancer-associated fibroblasts). In many embodiments, a tumor antigen is a molecule (or portion thereof) that is differentially expressed by tumor cells as compared with non-tumor cells. In other embodiments, a tumor antigen is expressed on the surface of the cell. Tumor antigens may include, e.g., proteins that are normally produced in very small quantities and are expressed in larger quantities by tumor cells, proteins that are normally produced only in certain stages of development, proteins whose structure (e.g., sequence or post-translational modification(s)) is modified due to a mutation in tumor cells, or normal proteins that are (under normal conditions) sequestered from the immune system. Tumor antigens may be useful in, e.g., identifying or detecting tumor cells (e.g., for purposes of diagnosis and/or for purposes of monitoring subjects who have received treatment for a tumor, e.g., to test for recurrence) and/or for purposes of targeting various agents (e.g., therapeutic agents) to tumor cells. For example, in some embodiments, a radiolabeled antibody is provided comprising an antibody or antibody fragment that binds a tumor antigen, thereby allowing detection of the tumor in vivo, e.g., using PET. In some embodiments, a tumor antigen is an expression product of a mutated gene, e.g., an oncogene or mutated tumor suppressor gene, an overexpressed or aberrantly expressed cellular protein, an antigen encoded by an oncogenic virus (e.g., HBV; HCV; herpesvirus family members such as EBV, KSV; papilloma virus, etc.), or an oncofetal antigen. Oncofetal antigens are normally produced in the early stages of embryonic development and largely or completely disappear by the time the immune system is fully developed. Examples are alphafetoprotein (AFP, found, e.g., in germ cell tumors and hepatocellular carcinoma) and carcinoembryonic antigen (CEA, found, e.g., in bowel cancers and occasionally in lung and breast cancers). Tyrosinase is an example of a protein normally produced in very low quantities but whose production is greatly increased in certain tumor cells (e.g., melanoma cells). Other exemplary tumor antigens include, e.g., CA-125 (found, e.g., in ovarian cancer); MUC-1 (found, e.g., in breast cancer); epithelial tumor antigen (found, e.g., in breast cancer); melanoma-associated antigen (MAGE; found, e.g., in malignant melanoma); and prostatic acid phosphatase (PAP, found in prostate cancer). In some embodiments, a tumor antigen is at least in part exposed at the cell surface of tumor cells. In some embodiments, a tumor antigen comprises an abnormally modified polypeptide or lipid, e.g., an aberrantly modified cell surface glycolipid or glycoprotein. It will be appreciated that a tumor antigen may be expressed by a subset of tumors of a particular type and/or by a subset of cells in a tumor. Additional exemplary tumor antigens are known in the art and are within the scope of this disclosure. For example exemplary tumor antigens are described in WO 2014/183066 and US 20160122707, the entire contents of each are incorporated by reference herein.

Other exemplary therapeutic/diagnostic antibodies, or fragments thereof, that are useful in the production of radiolabeled antibodies or proteins according to the methods provided herein include, but are not limited to, the following antibodies, or fragments thereof (the target of the antibody is listed in parentheses together with exemplary non-limiting therapeutic indications):

Abciximab (glycoprotein IIb/IIIa; cardiovascular disease), Adalimumab (TNF-α, various auto-immune disorders, e.g., rheumatoid arthritis), Alemtuzumab (CD52; chronic lymphocytic leukemia), Basiliximab (IL-2Rα receptor (CD25); transplant rejection), Bevacizumab (vascular endothelial growth factor A; various cancers, e.g., colorectal cancer, non-small cell lung cancer, glioblastoma, kidney cancer; wet age-related macular degeneration), Catumaxomab (CD3 and EpCAM, malignant ascites), Cetuximab (EGF receptor, various cancers, e.g., colorectal cancer, head and neck cancer), Certolizumab (e.g., Certolizumab pegol) (TNF alpha; Crohn's disease, rheumatoid arthritis), Daclizumab (IL-2Rα receptor (CD25); transplant rejection), Eculizumab (complement protein C5; paroxysmal nocturnal hemoglobinuria), Efalizumab (CD11a; psoriasis), Gemtuzumab (CD33; acute myelogenous leukemia (e.g., conjugated to calicheamicin)), Ibritumomab tiuxetan (CD20; Non-Hodgkin lymphoma (e.g., labeled with yttrium-90 or indium-111)), Infliximab (TNF alpha; various auto-immune disorders, e.g., rheumatoid arthritis) Muromonab-CD3 (T Cell CD3 receptor; transplant rejection), Natalizumab (alpha-4 (α4) integrin; multiple sclerosis, Crohn's disease), Omalizumab (IgE; allergy-related asthma), Palivizumab (epitope of RSV F protein; Respiratory Syncytial Virus infection), Panitumumab (EGF receptor; cancer, e.g., colorectal cancer), Ranibizumab (vascular endothelial growth factor A; wet age-related macular degeneration) Rituximab (CD20; non-Hodgkin lymphoma), Tositumomab (CD20; non-Hodgkin lymphoma), Trastuzumab (ErbB2; breast cancer), and any antigen-binding fragments thereof.

In some embodiments, any of the antibodies, or fragments thereof, (e.g., radiolabeled and/or PEGylated), described herein, may be used to image an immune response. The in vivo imaging of the inflammatory response, e.g., by labeling sites of inflammation using the methods and compositions provided herein, allows for non-invasive diagnosis, monitoring, and treatment of inflammatory disorders, as described herein. Other exemplary inflammatory markers to which radiolabeled proteins of the instant disclosure may bind include, but are not limited to, cytokines, tumor necrosis factor (TNF)-α. IL-6, IL-1 beta, IL-8, IL-10, IL-12, IL-16, IL-18, monocyte chemoattractant protein-1 (MCP-1), GRO-α (Growth Related Oncogene-α), matrix metalloproteinase-8 (MMP-8), CSFs (colony-stimulating factors), epithelial cell-derived neutrophil-activating peptide-78 (ENA-78), regulated on activation normal T cell expressed and secreted (RANTES) CCL5, CXCL6 (granulocyte chemotactic protein-2), CXCL9 MIG, CXCL10; IP-10, CXCL11, CXCL13 (BCA-1), Exodus-1 (CCL20), MIF (macrophage migration inhibitory factor): MIP-1alpha (CCL3), MIP-1beta (CCL4), CD11b, CD11c, CD13, CD15, CD66, CD14, CD64, CD66b, CD18, CD16, CD62L, CD67, HLA-DR, sHLA-G, Dihydroepiandrotendione (DHEA)-S, Cortisol CRF (corticotrophin-releasing factor), CRF-binding protein, alpha-defensin, beta-defensin, neutrophil defensins (HNP 1-3), bactericidal/permeability-increasing protein (BPI), calprotectin (MRP8/14), surfactant protein-A, surfactant protein-D, serum amyloid P component, serum amyloid A, complement factors, mannan-binding lectin, fibrinogen, prothrombin, factor VIII, von Willebrand factor, plasminogen, mannan-bindinglectin, c-reactive protein, Pentraxin 3, scavenger receptors, C-type lectins, Toll-like receptor (TLR)-4, TLR-2, TLR-3, TLR-6, intracellular pattern recognition receptors (Nod1, Nod2, RIG-1, MDA-5), RAGE (receptor for advanced glycation endproduct), alpha 2-macroglobulin, ferritin, hepcidin, ceruloplasmin, haptoglobin, orosomucoid, alpha 1-antitrypsin, alpha 1-antichymotrypsin, lipopolysaccharide-binding protein (LBP), albumin, transferrin (including lactoferrin), transthyretin, retinol-binding protein, antithrombin, transcortin, adrenocorticotropin, Urocortin, estriol, MMP-1, MMP-2, TIMP-2, MMP-3, MMP-7, MMP-9, arachidonate lipoxygenase metabolites, prostaglandins, prostacyclins, thromboxanes, leukotrienes, Catalase, Caspase-1 (NALP3 inflammasome), leptin, adiponectin, resistin, visfatin, Retinol binding protein 4 (RBP4), endotoxin, Epidermal growth factor (EGF), insulin-like growth factor binding protein-1 (IGFBP-1), neutrophil elastase, leukocyte elastase (ELA2, neutrophil), SLPI (secretory leukocyte protease inhibitor), S100 calcium binding protein B, Heat shock protein, Endothel in-1, -2, Angiopoietin-2, Calcium-binding protein, Soluble Triggering receptor expressed on myeloid cells 1 (sTREM1), Protein-Z (vitamin K-dependent plasma glycoprotein), and Tissue factor and Platelet activating factor (PAF).

In some embodiments, any of the antibodies, or fragments thereof, (e.g., radiolabeled and/or PEGylated), described herein, may be used to image immune cells independent of an immune response. This may be done using antibodies that detect specific immune cell markers that are not indicative of an active immune response. As one example, naïve T cells may be imaged using any of the radiolabelled antibodies or antibody fragments, described herein, that bind to the naïve T cell markers CD3, CD4, CD45RA, CD45RB, CD197, or CD62L. Further information on various immune cell types may be found in, e.g., Zhu, J., et al., Differentiation of effector CD4 T cell populations. Annu. Rev. Immunol., 28 (2010), pp. 445-489; S. Crotty, Follicular helper CD4 T cells (TFH), Annu. Rev. Immunol., 29 (2011), pp. 621-663. Of course it would be understood that certain of these markers (e.g., CD3, CD4) would also be expressed on T cells involved in an immune response and could be used as targets for imaging an immune response.

In some embodiments, any of the antibodies, or fragments thereof, (e.g., radiolabeled and/or PEGylated), described herein may be used to non-invasively image tumor and/or T cell markers. In some embodiments, any of the antibodies, or fragments thereof, (e.g., radiolabeled and/or PEGylated), described herein may be used to non-invasively image a tumor cell and/or a T cell. In some embodiments, the radiolabeled antibodies or antibody fragments detect markers including, but not limited to PD-L1, PD-1, PD-2, CTLA-4, CD3, CD4, CD8, and CD28.

In some embodiments, any of the antibodies, or fragments thereof, (e.g., radiolabeled and/or PEGylated) described herein bind to proteins involved in immune checkpoint pathways. "Immune checkpoint pathways" or "immune checkpoints" are naturally existing inhibitory pathways of the immune system that play important roles in maintaining self-tolerance and modulating the duration and level of effector output (e.g., in the case of T cells, the levels of cytokine production, proliferation or target killing potential) of physiological immune responses in order to minimize damage to the tissues of the individual mounting the immune response. Such pathways may, for example, downmodulate T cell activity or enhance regulatory T cell immunosuppressive activity. Examples of immune checkpoint pathways include, but are not limited to the PD-1 pathway and the CTLA-4 pathway and the TIM3 pathway. Tumors frequently co-opt certain immune-checkpoint pathways as a major mechanism of immune resistance, e.g., against T cells that are specific for tumor antigens. Furthermore, chronic antigen exposure, such as occurs in cancer, can lead to high levels of expression of immune checkpoint proteins (e.g., PD1, PD-L1, PD-L2) by immune cells, which can induce a state of T cell exhaustion or anergy. Certain immune checkpoint proteins such as CTLA4 and PD1 are highly expressed on T regulatory ($T_{Reg}$) cells and may enhance their proliferation. Many tumours are highly infiltrated with $T_{Reg}$ cells that likely suppress effector immune responses, Thus, blockade of the PD1 pathway and/or the CTLA4 pathway may enhance antitumour immune responses by diminishing the number and/or suppressive activity of intratumoral $T_{Reg}$ cells. Certain aspects of the invention utilize the radiolabeled proteins (e.g., radiolabeled antibodies or antibody fragments) for diagnosing or monitoring a disease or condition (e.g., cancer) or the response of a disease or condition (e.g., cancer) to therapy. For example, the radiolebeled antibodies or antibody fragments may be used to detect whether a tumor expresses an immune checkpoint marker (e.g., an immune checkpoint protein) and/or to detect whether a tumor contains immune cells that express an immune checkpoint marker (e.g., an immune checkpoint protein). In other embodiments, the inventive radiolabeled proteins (e.g., radiolabeled antibodies or antibody fragments) bind to an immune checkpoint modulator. In some embodiments the immune checkpoint modulator is an immune checkpoint inhibitor. "Immune checkpoint inhibitor" refers to any agent that inhibits (suppresses, reduces activity of) an immune checkpoint pathway. In some embodiments the immune checkpoint modulator is an immune checkpoint activator. "Immune checkpoint activator" refers to any agent that activates (stimulates, increases activity of) an immune checkpoint pathway.

Immune checkpoint inhibitors, e.g., monoclonal antibodies that bind to immune checkpoint proteins such as CTLA4, PD1, PD-L1 have shown notable efficacy in treating a variety of different cancers, including cancers that are advanced, have failed to respond to conventional chemotherapeutic agents, and/or have a poor prognosis, such as metastatic melanoma (sec, e.g., Pardoll, DM., The blockade of immune checkpoints in cancer immunotherapy, Nat Rev Cancer. 2012; 12(4):252-64). However, not all subjects with tumors of a particular type may experience benefit from treatment with a given immune checkpoint inhibitor. One or ordinary skill would appreciate that a benefit could be, e.g., stable disease rather than progressive disease, eventual reduced number and/or volume of tumor lesions, increased mean survival, etc. Detection of immune checkpoint markers using any of the methods, described herein, may be used to determine whether or not to administer a therapeutic and/or to select a therapeutic (e.g., from among multiple different therapeutic options). For example, a radiolabeled antibody or antibody fragment that binds PD-L1 can be used to detect whether a tumor within a patient expresses PD-L1. Patients having a PD-L1 positive tumor may then be administered a therapeutic that targets the PD1 pathway, e.g., a therapeutic (such as an antibody) that targets PD1 or PD-L1. A radiolabeled protein (e.g., radiolabeled antibody or antibody fragment) that binds PD1 can be used to detect whether a tumor within a patient is positive for PD1 (e.g., due to the presence of immune cells that express high levels of PD1). Patients having a PD1 positive tumor may then be administered a therapeutic agent that targets the PD1 pathway, In some embodiments a radiolabeled protein (e.g., radiolabeled antibody or antibody fragment) that binds TIM3 can be used to detect whether a tumor within a patient is positive for TIM3 (e.g., due to the presence of immune cells that express high levels of TIM3). Patients having a TIM3 positive tumor may then be administered a therapeutic that targets the TIM3 pathway, e.g., a therapeutic (such as an antibody) that targets TIM3. In some embodiments a radiolabeled protein (e.g., radiolabeled antibody or antibody fragment) that binds CTLA4 can be used to detect whether a tumor within a patient is positive for CTLA4 (e.g., due to the presence of immune cells that express high levels of CTLA4). Patients having a CTLA4 positive tumor may then be administered a therapeutic that targets the CTLA4 pathway, e.g., a therapeutic (such as an antibody) that targets CTLA4. In some embodiments a subject with a tumor may be imaged with two, three, or more radiolabeled proteins (e.g., antibodies, antibody fragments) that bind to different immune checkpoint proteins (e.g., proteins involved in different immune checkpoint pathways). One or more immune checkpoint pathways that are positive in the tumor are identified. The patient is then treated with one or more agent(s) that target those immune checkpoint pathways for which a tumor (or one or more tumor(s)) in the subject is positive. In some embodiments, if the tumor is negative for a particular immune checkpoint pathway or immune checkpoint protein, an alternative treatment may be administered instead of an immune checkpoint inhibitor that would target that immune checkpoint pathway or immune checkpoint protein. Other aspects of the invention utilize the radiolabeled antibodies or antibody fragments for monitoring the response to a therapeutic or monitoring expression of a protein, such as an immune checkpoint inhibitor protein. For example, a radiolabeled antibody or antibody fragment, described herein, may be used to detect whether an immune response has been generated or enhanced or suppressed at a site of interest, such as at the site of a tumor or a site of infection, or whether the tumor expresses an immune checkpoint protein (e.g., PD-L1). In some embodiments a radiolabeled protein that binds to an immune cell, e.g., a T cell, may be administered to a subject before, concurrently, and/or after administration of a treatment intended to enhance or inhibit an immune response. Images may be compared from before and after treatment to assess the effect of the treatment on the immune response. In some embodiments, the inventive radiolabeled proteins may be used to monitor the response to a therapeutic at least every 1 day, at least every 5 days, at least every 10 days, at least every 15 days, at least every 30 days, at least every 45 days, at least every 60 days, at least every 120 days, at least every 180 days, at least every 240 days or at least every year. In some embodiments a subject may be monitored for, e.g., up to 3, 6, 9 months, up to 1, 2, 5, years, or more. In some embodiments, a therapeutic agent that targets an immune checkpoint inhibitor pathway is a monoclonal antibody. In some embodiments, the monoclonal antibody is a chimeric, humanized, or human monoclonal antibody. In some embodiments, the antibody is an IgG antibody, e.g., an IgG1 or IgG4 antibody. In some embodiments, a therapeutic agent that targets the CTLA4 pathway is a monoclonal antibody that binds to CTLA4, such as ipilimumab (Yervoy) or tremelimumab. In some embodiments, a therapeutic agent that targets the PD1 pathway is a monoclonal antibody that binds to PD1, such as nivolumab (a fully human IgG4 monoclonal antibody), pidilizumab (also known as CT-011, a humanized IgG1 monoclonal antibody), or pembrolizumab (Keytruda, formerly lambrolizumab; also known as MK-3475), a humanized IgG4 monoclonal antibody), or MEDI0680 (AMP-514, a humanized IgG4mAb against PD-1). In some embodiments, a therapeutic agent that targets the PD1 pathway is a monoclonal antibody that binds to PD-L1 such as BMS-936559 (a fully human IgG4 monoclonal antibody), MPDL3280A (human monoclonal, Genentech), MSB0010718C (Merck Serono), or MEDI4736. In some embodiments, a therapeutic agent that targets the PD1 pathway is a monoclonal antibody that binds to PD-L2. In some embodiments, a therapeutic agent that targets the PD1 pathway is a recombinant fusion protein comprising extracellular domain of PD-L2 such as AMP-224. A variety of PD1 pathway inhibitors, e.g., antibodies that bind to PD-1, PD-L1, or PD-L2 are described in U.S. Pat. Pub. No. 20040213795, 20110195068, 20120039906, 20120114649, 20130095098, 20130108651, 20130109843, 20130237580, and 20130291136, all of which are incorporated by reference herein.

In some embodiments, the subject suffers from a solid tumor. In some embodiments, the subject suffers from melanoma, renal cell carcinoma, non-small-cell lung cancer, ovarian cancer, brain cancer (e.g., glioblastoma), lymphoma (e.g., Non-Hodgkin lymphoma), hepatocellular, esophageal, breast (e.g., triple negative breast cancer), multiple myeloma, or pancreatic cancer. In some embodiments, the subject has a metastatic cancer, stage III cancer, or stage IV cancer.

It would be understood that the immune checkpoint inhibitor could be administered as a single agent or in combination with one or more other anti-tumor agents.
Properties In some embodiments, any of the antibodies, or fragments thereof, (e.g., radiolabeled and/or PEGylated), described herein, are capable of reaching their targets and are cleared quickly from the circulation. Whole antibodies and their fragments have different characteristics that determine their targeting properties, such as how quickly they reach the target antigen and clear from the blood, which organ clears the antibody from the blood, penetration into the tumor and amount of the injected radiolabeled antibody or antibody fragment binding to the target. Once antibodies target their respective antigens, they generally bind with high avidity, which in turn determines their tumor residence time, whereas the unbound antibody is processed by various organs in the body and eventually degraded and excreted. Whole IgG, which is the principal antibody form used, clears very slowly from the blood, requiring several days before a sufficient amount leaves the circulation to allow the specific concentration taken into the tumor to be distinguished from blood and adjacent tissue radioactivity. Its slow clearance is in part owing to its large size (approximately 150,000 Da) that impedes its extravasation, resulting in a slow tumor accretion. As the molecular size of an antibody is reduced from a divalent F(ab')2 fragment (approximately 100,000 Da) to the monovalent binding Fab fragment (approximately 50,000 Da), there is a progressively faster clearance from the blood. Molecular engineering has enabled the formation of even smaller antibody structures, such as scFv (approximately 25,000 Da), which are cleared even more rapidly from the blood. See Goldenberg D. M. et al., "Novel radiolabeled antibody conjugates." Oncogene. 2007, 26, 3734-3744; the entire contents of which are hereby incorporated by reference. Accordingly, in some embodiments any of the antibodies, or fragments thereof, (e.g., radiolabeled and/or PEGylated), described herein, have a molecular weight of less than 60 kDa, less than 55 kDa, less than 50 kDa, less than 45 kDa, less than 40 kDa, less than 35 kDa, less than 30 kDa, less than 25 kDa less than 20 kDa, less than 15 kDa, less than 10 kDa, or less than 5 kDa. In other embodiments the radiolabelled proteins (e.g., antibodies or antibody fragments), described herein, have a molecular weight ranging from 5 kDa-15 kDa, from 5 kDa-20 kDa, from 5 kDa-25 kDa, from 5 kDa-30 kDa, from 5 kDa-35 kDa, from 5 kDa-40 kDa, from 5 kDa-45 kDa, from 5 kDa-55 kDa, from 5 kDa-60 kDa, from 15 kDa-20 kDa, from 15 kDa-25 kDa, from 15 kDa-30 kDa, from 15 kDa-35 kDa, from 15 kDa-40 kDa, from 15 kDa-45 kDa, from 15 kDa-50 kDa, from 15 kDa-55 kDa, from 15 kDa-60 kDa, from 25 kDa-35 kDa, from 25 kDa-45 kDa, from 25 kDa-55 kDa, from 25 kDa-60 kDa, from 35 kDa-45 kDa, from 35 kDa-55 kDa, from 35 kDa-60 kDa, from 45 kDa-55 kDa, from 45 kDa-60 kDa, or from 50 kDa-60 kDa. In yet other embodiments, any of the antibodies, or fragments thereof, (e.g., radiolabeled and/or PEGylated), described herein, are expediently cleared from the circulation following injection into a patient. In some embodiments, at least 95% of the radiolabelled proteins (e.g., antibodies or antibody fragments) are cleared from the blood within 20 minutes, within 30 minutes, within 40 minutes, within 60 minutes, within 80 minutes, within 30 minutes, within 40 minutes, within 60 minutes, within 90 minutes, within 2 hours, within 3 hours, within 4 hours, within 6 hours, within 8 hours, within 10 hours or within 12 hours. In other embodiments, at least 95% of the radiolabelled proteins (e.g., antibodies or antibody fragments) are cleared from the body within 20 minutes, within 30 minutes, within 40 minutes, within 60 minutes, within 80 minutes, within 30 minutes, within 40 minutes, within 60 minutes, within 90 minutes, within 2 hours, within 3 hours, within 4 hours, within 6 hours, within 8 hours, within 10 hours or within 12 hours.

Hydrophilic Polymers

Some aspects of the disclosure are related to the use hydrophilic polymers and methods of conjugating hydrophilic polymers to an antibody (e.g., a single domain antibody). As used herein, a "hydrophilic polymer" refers to a molecule (e.g., a macromolecule) comprised of three or more repeating units that contain polar or charged functional groups, rendering them soluble in water. In some embodiments, the hydrophilic polymer is soluble to at least 50 mg/mL in water, to at least 100 mg/mL in water, to at least 150 mg/mL in water, to at least 200 mg/mL in water, to at least 250 mg/mL in water, to at least 300 mg/mL in water, to at least 400 mg/mL in water, to at least 500 mg/mL in water, to at least 600 mg/mL in water, to at least 700 mg/mL in water, to at least 800 mg/mL in water, to at least 900 mg/mL in water, or at least 1000 mg/mL in water at 20° C. In some embodiments, the hydrophilic polymer is a linear polymer. In some embodiments, the hydrophilic polymer is a branched polymer, which may be configured in any number of ways. In some embodiments, the hydrophilic polymer is a suitable size and/or has a suitable linear or branched structure for conferring improved properties to any of the antibodies provided herein. In some embodiments, the hydrophilic polymer is from 5 kDa to 1000 kDa in size. In some embodiments, the polymer is at least 5 kDa, at least 10 kDa, at least 15 kDa, at least 20 kDa, at least 25 kDa, at least 30 kDa, at least 40 kDa, at least 50 kDa, at least 70 kDa, at least 100 kDa, at least 150 kDa, at least 200 kDa, at least 300 kDa, at least 400 kDa, at least 500 kDa, at least 600 kDa, at least 700 kDa, at least 800 kDa, at least 900 kDa, or at least 1000 kDa in size.

In some embodiments, the hydrophilic polymer useful in the present invention is synthetic polymer. In certain embodiments, the hydrophilic polymer is not a polypeptide, polynucleotide, or polysaccharide. Examples of hydrophilic synthetic polymers include, without limitation polyethylene glycol (PEG), polyvinyl pyrrolidone (PVP), polyvinyl alcohol (PVA), polyacrylic acid (PAA), polyacrylamide, N-(2-hydroxypropyl) methacrylamide (HPMA), divinyl ether-maleic anhydride (DIVEMA), polyoxazoline, polyphosphoester (PPE), polyethyleneimine (PEI), and polyphosphazene. However, it should be appreciated that other synthetic polymers may be used and are considered to be within the scope of this disclosure.

In some embodiments, any of the hydrophilic polymers provided herein are natural polymers. Examples of natural polymers include, without limitation, polysaccharides, xanthan gum, pectins, chitosan derivatives, dextran, carrageenan, guar gum, cellulose ethers (e.g., Sodium CMC, HPC, and HPMC), hyaluronic acid (HA), albumin, and starch or starch based derivatives. However, it should be appreciated that other synthetic polymers may be used and are within the scope of this disclosure. Additional hydrophilic polymers would be apparent to the skilled artisan and are within the scope of this disclosure. For example, exemplary hydrophilic polymers have been described previously in Veeran, G. K., et al., "Water Soluble Polymers for Pharmaceutical Applications" *Polymers* 2011, 3, 1972-2009; the entire contents of which are incorporated by reference herein. It should be appreciated that, in some embodiments, PEGylation also refers to the addition of any hydrophilic polymer, for example any of the hydrophilic polymers provided herein.

Chelating Moieties

Some aspects of the disclosure provide chelating moieties and methods for conjugating chelating moieties to antibodies (e.g., single domain antibodies). As used here a "chelating moiety" is an agent whose molecules can form several bonds to a single metal ion. In some embodiments, the chelating moiety is an agent that binds to a radionuclide. In some embodiments, the chelating moiety is an agent that binds to rubidium-82, copper-61, copper-62, copper-64, yttrium-86, gallium-68, zirconium-89. However, it should be appreciated that the chelating moiety may be an agent that binds to additional radioactive metals. Exemplary chelating moieties include, without limitation, 1,4,7-triazacyclononane-triacetic acid (NOTA), 1,4,7,10-tetraazacyclododecane-tetraacetic acid (DOTA), triazacyclononane-phosphinate (TRAP), or desferrioxamine (DFO). However, it should be appreciated that additional chelating moieties may be used and are within the scope of this invention. Exemplary metallic radionuclides and chelators have been described in the art and are within the scope of this disclosure. For example, exemplary metallic radionuclides and chelators have been described in Liu X., et al., "A Brief Review of Chelators for Radiolabeling Oligomers" Materials, 2010, 3, 3204-3217, the entire contents of which are incorporated by reference herein.

Chemistry Definitions

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastercomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Elicl, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, IN 1972). The invention additionally encompasses compounds as individual isomers substantially free of other isomers, and alternatively, as mixtures of various isomers.

In a formula, --- is absent, a coordination bond between a ligand and a metal, or a single bond.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic," as used herein, includes both saturated and unsaturated, nonaromatic, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl," "alkynyl," and the like. Furthermore, as used herein, the terms "alkyl," "alkenyl," "alkynyl," and the like encompass both substituted and unsubstituted groups. In certain embodiments, as used herein, "aliphatic" is used to indicate those aliphatic groups (cyclic, acyclic, substituted, unsubstituted, branched or unbranched) having 1-20 carbon atoms ($C_{1-20}$ aliphatic). In certain embodiments, the aliphatic group has 1-10 carbon atoms ($C_{1-10}$ aliphatic). In certain embodiments, the aliphatic group has 1-6 carbon atoms ($C_{1-6}$ aliphatic). In certain embodiments, the aliphatic group has 1-5 carbon atoms ($C_{1-5}$ aliphatic). In certain embodiments, the aliphatic group has 1~4 carbon atoms ($C_{1-4}$ aliphatic). In certain embodiments, the aliphatic group has 1-3 carbon atoms ($C_{1-3}$ aliphatic). In certain embodiments, the aliphatic group has 1-2 carbon atoms ($C_{1-2}$ aliphatic). Aliphatic group substituents include, but are not limited to, any of the substituents described herein, that result in the formation of a stable moiety.

The term "heteroaliphatic", as used herein, refers to aliphatic moieties that contain one or more oxygen, sulfur, nitrogen, phosphorus, or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$, wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The term "alkyl," as used herein, refers to saturated, straight- or branched-chain hydrocarbon radicals derived from a hydrocarbon moiety containing between one and twenty carbon atoms by removal of a single hydrogen atom. In some embodiments, the alkyl group employed in the invention contains 1-20 carbon atoms ($C_{1-20}$alkyl). In another embodiment, the alkyl group employed contains 1-15 carbon atoms ($C_{1-15}$alkyl). In another embodiment, the alkyl group employed contains 1-10 carbon atoms ($C_{1-10}$alkyl). In another embodiment, the alkyl group employed contains 1-8 carbon atoms ($C_{1-8}$alkyl). In another embodiment, the alkyl group employed contains 1-6 carbon atoms ($C_{1-6}$alkyl). In another embodiment, the alkyl group employed contains 1-5 carbon atoms ($C_{1-5}$alkyl). In another embodiment, the alkyl group employed contains 1-4 carbon atoms ($C_{1-4}$alkyl). In another embodiment, the alkyl group employed contains 1-3 carbon atoms ($C_{1-3}$alkyl). In another embodiment, the alkyl group employed contains 1-2 carbon atoms ($C_{1-2}$alkyl). Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like, which may bear one or more substituents. Alkyl group substituents include, but are not limited to, any of the substituents described herein, that result in the formation of a stable moiety. The term "alkylene," as used herein, refers to a biradical derived from an alkyl group, as defined herein, by removal of two hydrogen atoms. Alkylene groups may be cyclic or acyclic, branched or unbranched, substituted or unsubstituted. Alkylene group substituents include, but are not limited to, any of the substituents described herein, that result in the formation of a stable moiety.

The term "alkenyl," as used herein, denotes a monovalent group derived from a straight- or branched-chain hydrocarbon moiety having at least one carbon-carbon double bond by the removal of a single hydrogen atom. In certain embodiments, the alkenyl group employed in the invention contains 2-20 carbon atoms ($C_{2-20}$alkenyl). In some embodiments, the alkenyl group employed in the invention contains 2-15 carbon atoms ($C_{2-15}$alkenyl). In another embodiment, the alkenyl group employed contains 2-10 carbon atoms ($C_{2-10}$alkenyl). In still other embodiments, the alkenyl group contains 2-8 carbon atoms ($C_{2-8}$alkenyl). In yet other embodiments, the alkenyl group contains 2-6 carbons ($C_{2-6}$alkenyl). In yet other embodiments, the alkenyl group contains 2-5 carbons ($C_{2-5}$alkenyl). In yet other embodiments, the alkenyl group contains 2-4 carbons ($C_{2-4}$alkenyl). In yet other embodiments, the alkenyl group contains 2-3 carbons ($C_{2-3}$alkenyl). In yet other embodiments, the alkenyl group contains 2 carbons ($C_2$alkenyl). Alkenyl groups include, for example, ethenyl, propenyl, butenyl, 1-methyl-2-buten-1-yl, and the like, which may bear one or more substituents. Alkenyl group substituents include, but are not limited to, any of the substituents described herein, that result in the formation of a stable moiety. The term "alkenylene," as used herein, refers to a biradical derived from an alkenyl group, as defined herein, by removal of two hydrogen atoms. Alkenylene groups may be cyclic or acyclic, branched or unbranched, substituted or unsubstituted. Alkenylene group substituents include, but are not limited to, any of the substituents described herein, that result in the formation of a stable moiety.

The term "alkynyl," as used herein, refers to a monovalent group derived from a straight- or branched-chain hydrocarbon having at least one carbon-carbon triple bond by the removal of a single hydrogen atom. In certain embodiments, the alkynyl group employed in the invention contains 2-20 carbon atoms ($C_{2-20}$alkynyl). In some embodiments, the alkynyl group employed in the invention contains 2-15 carbon atoms ($C_{2-15}$alkynyl). In another embodiment, the alkynyl group employed contains 2-10 carbon atoms ($C_{2-10}$alkynyl). In still other embodiments, the alkynyl group contains 2-8 carbon atoms ($C_{2-8}$alkynyl). In still other embodiments, the alkynyl group contains 2-6 carbon atoms ($C_{2-6}$alkynyl). In still other embodiments, the alkynyl group contains 2-5 carbon atoms ($C_{2-5}$alkynyl). In still other embodiments, the alkynyl group contains 2-4 carbon atoms ($C_{2-4}$alkynyl). In still other embodiments, the alkynyl group contains 2-3 carbon atoms ($C_{2-3}$alkynyl). In still other embodiments, the alkynyl group contains 2 carbon atoms ($C_2$alkynyl). Representative alkynyl groups include, but are not limited to, ethynyl, 2-propynyl (propargyl), 1-propynyl, and the like, which may bear one or more substituents. Alkynyl group substituents include, but are not limited to, any of the substituents described herein, that result in the formation of a stable moiety. The term "alkynylene," as used herein, refers to a biradical derived from an alkynylene group, as defined herein, by removal of two hydrogen atoms. Alkynylene groups may be cyclic or acyclic, branched or unbranched, substituted or unsubstituted. Alkynylene group substituents include, but are not limited to, any of the substituents described herein, that result in the formation of a stable moiety.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("hetero$C_{2-10}$ alkenyl"). In some embodiments, a heteroalkenyl group has 2 to 9 carbon atoms at least one double bond, and 1 or more heteroatoms within the parent chain ("hetero$C_{2-9}$ alkenyl"). In some embodiments, a heteroalkenyl group has 2 to 8 carbon atoms, at least one double bond, and 1 or more heteroatoms within the parent chain ("hetero$C_{2-8}$ alkenyl"). In some embodiments, a heteroalkenyl group has 2 to 7 carbon atoms, at least one double bond, and 1 or more heteroatoms within the parent chain ("hetero$C_{2-7}$ alkenyl"). In some embodiments, a heteroalkenyl group has 2 to 6 carbon atoms, at least one double bond, and 1 or more heteroatoms within the parent chain ("hetero$C_{2-6}$ alkenyl"). In some embodiments, a heteroalkenyl group has 2 to 5 carbon atoms, at least one double bond, and 1 or 2 heteroatoms within the parent chain ("hetero$C_{2-5}$ alkenyl"). In some embodiments, a heteroalkenyl group has 2 to 4 carbon atoms, at least one double bond, and 1 or 2 heteroatoms within the parent chain ("hetero$C_{2-4}$ alkenyl"). In some embodiments, a heteroalkenyl group has 2 to 3 carbon atoms, at least one double bond, and 1 heteroatom within the parent chain ("hetero$C_{2-3}$ alkenyl"). In some embodiments, a heteroalkenyl group has 2 to 6 carbon atoms, at least one double bond, and 1 or 2 heteroatoms within the parent chain ("hetero$C_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted hetero$C_{2-10}$ alkenyl. In certain embodiments, the heteroalkenyl group is a substituted hetero$C_{2-10}$ alkenyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("hetero$C_{2-10}$ alkynyl"). In some embodiments, a heteroalkynyl group has 2 to 9 carbon atoms, at least one triple bond, and 1 or more heteroatoms within the parent chain ("hetero$C_{2-9}$ alkynyl"). In some embodiments, a heteroalkynyl group has 2 to 8 carbon atoms, at least one triple bond, and 1 or more heteroatoms within the parent chain ("hetero$C_{2-8}$ alkynyl"). In some embodiments, a heteroalkynyl group has 2 to 7 carbon atoms, at least one triple bond, and 1 or more heteroatoms within the parent chain ("hetero$C_{2-7}$ alkynyl"). In some embodiments, a heteroalkynyl group has 2 to 6 carbon atoms, at least one triple bond, and 1 or more heteroatoms within the parent chain ("hetero$C_{2-6}$ alkynyl"). In some embodiments, a heteroalkynyl group has 2 to 5 carbon atoms, at least one triple bond, and 1 or 2 heteroatoms within the parent chain ("hetero$C_{2-5}$ alkynyl"). In some embodiments, a heteroalkynyl group has 2 to 4 carbon atoms, at least one triple bond, and 1 or 2 heteroatoms within the parent chain ("hetero$C_{2-4}$ alkynyl"). In some embodiments, a heteroalkynyl group has 2 to 3 carbon atoms, at least one triple bond, and 1 heteroatom within the parent chain ("hetero$C_{2-3}$ alkynyl"). In some embodiments, a heteroalkynyl group has 2 to 6 carbon atoms, at least one triple bond, and 1 or 2 heteroatoms within the parent chain ("hetero$C_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

The term "carbocyclyl" or "carbocyclic" refers to a radical of a non-aromatic cyclic hydrocarbon group having from 3 to 14 ring carbon atoms ("C$_{3-14}$ carbocyclyl") and zero heteroatoms in the non-aromatic ring system. In some embodiments, a carbocyclyl group has 3 to 10 ring carbon atoms ("C$_{3-10}$ carbocyclyl"). In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 4 to 6 ring carbon atoms ("C$_{4-6}$ carbocyclyl"). In some embodiments, a carbocyclyl group has 5 to 6 ring carbon atoms ("C$_{5-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted C$_{3-14}$ carbocyclyl. In certain embodiments, the carbocyclyl group is a substituted C$_{3-14}$ carbocyclyl.

In some embodiments, "carbocyclyl" is a monocyclic, saturated carbocyclyl group having from 3 to 14 ring carbon atoms ("C$_{3-14}$ cycloalkyl"). In some embodiments, a cycloalkyl group has 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 4 to 6 ring carbon atoms ("C$_{4-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted C$_{3-14}$ cycloalkyl. In certain embodiments, the cycloalkyl group is a substituted C$_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14× electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

The term "unsaturated" or "partially unsaturated" refers to a moiety that includes at least one double or triple bond.

Affixing the suffix "ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

The term "halo" or "halogen" refers to fluorine (fluoro, —F), chlorine (chloro, —Cl), bromine (bromo, —Br), or iodine (iodo, —I).

The term "amino" refers to the group —NH$_2$. The term "substituted amino," by extension, refers to a monosubstituted amino, a disubstituted amino, or a trisubstituted amino.

In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, —NHP(=O)(OR$^{cc}$)$_2$, and —NHP(=O)(NR$^{bb}$)$_2$, wherein R$^{aa}$, R$^{bb}$ and Rec are as defined herein, and wherein R$^{bb}$ of the group —NH(R$^{bb}$) is not hydrogen.

The term "disubstituted amino" refers to an amino group wherein the nitrogen atom directly attached to the parent molecule is substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{aa}$, —NR$^{bb}$P(=O)(OR)$_2$, and —NR$^{bb}$P(=O)(NR$^{bb}$)$_2$, wherein R$^{aa}$, R$^{bb}$, and Rec are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N(R$^{bb}$)$_3$ and —N(R$^{bb}$)$_3$$^+$X$^-$, wherein R$^{bb}$ and X$^-$ are as defined herein.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R)$_2$, —SO$_2$N(R)$_2$, —SO$_2$R$^{cc}$, —SO$_2$OR$^{cc}$, —SOR$^{aa}$, —C(=S)N(RC)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, Rec and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, 1-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylidencamine, N-diphenylmethylencamine, N-[(2-pyridyl)mesityl] methylencamine, N-(N',N'-dimethylaminomethylene) amine, N,N'-isopropylidenediamine, N-p-nitrobenzylidencamine, N-salicylidencamine, N-5-chlorosalicylidencamine, N-(5-chloro-2-hydroxyphenyl) phenylmethylencamine, N-cyclohexylidencamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfonamide, o-nitrobenzenesulfonamide (Nps), 2,4 dinitrobenzenesulfonamide, pentachlorobenzenesulfonamide, 2-nitro-4-methoxybenzenesulfonamide, triphenylmethylsulfenamide, and 3-nitropyridinesulfonamide (Npys).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N (R$^{bb}$)$_2$, —C(=NR$^{bb}$)R$^{aa}$, —C(=NR$^{bb}$)OR$^{aa}$, —C(=NR$^{bb}$) N(R$^{bb}$)$_2$, —S(=O)R$^{aa}$, —SO$_2$R$^{aa}$, —Si(R$^{aa}$)$_3$, —P(RC)$_2$, —P(R$^{cc}$)$_3$, —P(=O)$_2$R$^{aa}$, —P(=O)(R$^{aa}$)$_2$, —P(=O) (OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$, are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, 1-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), 1-butyldiphenylsilyl (TBDPS), tribenzylsilyl, tri-p-xylylsilyl, triphenylsilyl, diphenylmethylsilyl (DPMS), 1-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, 1-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate. 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on an sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(RC)_2$, —$P(RC)_3$, —$P(=O)_2R^{aa}$, —$P(=O)(R^{aa})_2$, —$P(=O)(OR)_2$, —$P(=O)_2N(R^{bb})_2$, and —$P(=O)(NR^{bb})_2$, wherein $R^{aa}$, $R^{bb}$, and Rec are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

The terms "aminooxy," or "aminooxy group," are used interchangeably herein and refer to functional groups having the general formula:

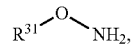

wherein $R^{31}$ is optionally substituted aliphatic, optionally substituted heteroaliphatic, optionally substituted aryl, optionally substituted heteroaryl, or optionally substituted heterocyclyl. In some embodiments, $R^{31}$ is an amino acid, wherein the point of attachment for the oxygen is on the side chain of the amino acid. In certain embodiments, the amino acid is within a polypeptide.

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The terms "carbonyl." or "carbonyl group." are used interchangeably herein and refer to functional groups composed of a carbon atom double-bonded to any oxygen atom. Carbonyls have the general formula:

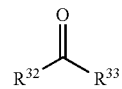

wherein each of $R^{32}$ and $R^{33}$ independently represents hydroxyl, optionally substituted amino, optionally substituted aliphatic, optionally substituted heteroaliphatic, optionally substituted aryl, optionally substituted heteroaryl, or optionally substituted heterocyclyl. Examples of carbonyls include, but are not limited to, aldehydes, ketones, carboxylic acids, esters, amides, enones, acyl halides, acid anhydrides, and imides. In some embodiments, a carbonyl-containing compound refers to a compound having an aldehyde group, or a compound capable of forming an aldehyde group through isomerization. For example, in some embodiments, certain sugars (e.g., reducing sugars) such as glucose, form aldehydes through isomerization. A sugar is classified as a reducing sugar if it has an open-chain form with an aldehyde group or a free hemiacetal group. Monosaccharides which contain an aldehyde group are known as aldoses, and those with a ketone group are known as ketoses. The aldehyde can be oxidized via a redox reaction in which another compound is reduced. Thus, a reducing sugar is one that is capable of reducing certain chemicals. Sugars with ketone groups in their open chain form are capable of isomerizing via a series of tautomeric shifts to produce an aldehyde group in solution. Therefore, ketone-bearing sugars like fructose are considered reducing sugars but it is the isomer containing an aldehyde group which is reducing since ketones cannot be oxidized without decomposition of the sugar. This type of isomerization is catalyzed by the base present in solutions which test for the presence of aldehydes.

The term "hydrazide," as used herein, refers to functional groups having the general formula:

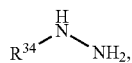

wherein $R^{34}$ is optionally substituted aliphatic, optionally substituted heteroaliphatic, optionally substituted aryl, optionally substituted heteroaryl, or optionally substituted heterocyclyl. In some embodiments, $R^{34}$ is an amino acid, wherein the point of attachment for the oxygen is on the side chain of the amino acid. In certain embodiments, the amino acid is within a polypeptide.

The term "hydrazone," as used herein, refers to compound having the general formula:

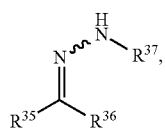

wherein each of $R^{35}$, $R^{36}$, and $R^{37}$ is independently optionally substituted aliphatic, optionally substituted heteroaliphatic, optionally substituted aryl, optionally substituted heteroaryl, or optionally substituted heterocyclyl. The term "hydrazone linkage," as used herein, refers to the formula:

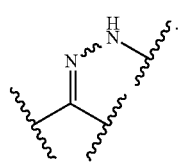

Hydrzones can be prepared from, for example, joining of a compound comprising a hydrazide group and a compound comprising a carbonyl.

The term "acyl," as used herein, is a subset of a substituted alkyl group, and refers to a group having the general formula —C(=O)$R^A$, —C(=O)O$R^A$, —C(=O)—O—C(=O)$R^A$, —C(=O)S$R^A$, or —C(=O)N($R^A$)$_2$, wherein each instance of $R^A$ is independently hydrogen, optionally substituted aliphatic, optionally substituted heteroaliphatic, optionally substituted aryl, optionally substituted heteroaryl, or optionally substituted heterocyclyl. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety.

The term "azide" or "azido," as used herein, refers to a group of the formula (—N$_3$).

Definitions of specific functional groups and chemical terms are described in more detail below. The chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. Sec, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, IN 1972). The invention additionally encompasses compounds as individual isomers substantially free of other isomers, and alternatively, as mixtures of various isomers.

In a formula, --- is absent, a coordination bond between a ligand and a metal, or a single bond.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic," as used herein, includes both saturated and unsaturated, nonaromatic, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl," "alkynyl," and the like. Furthermore, as used herein, the terms "alkyl," "alkenyl," "alkynyl," and the like encompass both substituted and unsubstituted groups. In certain embodiments, as used herein, "aliphatic" is used to indicate those aliphatic groups (cyclic, acyclic, substituted, unsubstituted, branched or unbranched) having 1-20 carbon atoms ($C_{1-20}$ aliphatic). In certain embodiments, the aliphatic group has 1-10 carbon atoms ($C_{1-10}$ aliphatic). In certain embodiments, the aliphatic group has 1-6 carbon atoms ($C_{1-6}$ aliphatic). In certain embodiments, the aliphatic group has 1-5 carbon atoms ($C_{1-5}$ aliphatic). In certain embodiments, the aliphatic group has 1~4 carbon atoms ($C_{1-4}$ aliphatic). In certain embodiments, the aliphatic group has 1-3 carbon atoms ($C_{1-3}$ aliphatic). In certain embodiments, the aliphatic group has 1-2 carbon atoms ($C_{1-2}$ aliphatic). Aliphatic group substituents include, but are not limited to, any of the substituents described herein, that result in the formation of a stable moiety.

The term "heteroaliphatic", as used herein, refers to aliphatic moieties that contain one or more oxygen, sulfur, nitrogen, phosphorus, or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The term "alkyl," as used herein, refers to saturated, straight- or branched-chain hydrocarbon radicals derived from a hydrocarbon moiety containing between one and twenty carbon atoms by removal of a single hydrogen atom. In some embodiments, the alkyl group employed in the invention contains 1-20 carbon atoms ($C_{1-20}$alkyl). In another embodiment, the alkyl group employed contains 1-15 carbon atoms ($C_{1-15}$alkyl). In another embodiment, the alkyl group employed contains 1-10 carbon atoms ($C_{1-10}$alkyl). In another embodiment, the alkyl group employed contains 1-8 carbon atoms ($C_{1-8}$alkyl). In another embodiment, the alkyl group employed contains 1-6 carbon atoms ($C_{1-6}$alkyl). In another embodiment, the alkyl group employed contains 1-5 carbon atoms ($C_{1-5}$alkyl). In another embodiment, the alkyl group employed contains 1-4 carbon atoms ($C_{1-4}$alkyl). In another embodiment, the alkyl group employed contains 1-3 carbon atoms ($C_{1-3}$alkyl). In another embodiment, the alkyl group employed contains 1-2 carbon atoms ($C_{1-2}$alkyl). Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like, which may bear one or more substituents. Alkyl group substituents include, but are not limited to, any of the substituents described herein, that result in the formation of a stable moiety. The term "alkylene," as used herein, refers to a biradical derived from an alkyl group, as defined herein, by removal of two hydrogen atoms. Alkylene groups may be cyclic or acyclic, branched or unbranched, substituted or unsubstituted. Alkylene group substituents include, but are not limited to, any of the substituents described herein, that result in the formation of a stable moiety.

The term "alkenyl," as used herein, denotes a monovalent group derived from a straight- or branched-chain hydrocarbon moiety having at least one carbon-carbon double bond by the removal of a single hydrogen atom. In certain embodiments, the alkenyl group employed in the invention contains 2-20 carbon atoms ($C_{2-20}$alkenyl). In some embodiments, the alkenyl group employed in the invention contains 2-15 carbon atoms ($C_{2-15}$alkenyl). In another embodiment, the alkenyl group employed contains 2-10 carbon atoms ($C_{2-10}$alkenyl). In still other embodiments, the alkenyl group contains 2-8 carbon atoms ($C_{2-8}$alkenyl). In yet other embodiments, the alkenyl group contains 2-6 carbons ($C_{2-6}$alkenyl). In yet other embodiments, the alkenyl group contains 2-5 carbons ($C_{2-5}$alkenyl). In yet other embodiments, the alkenyl group contains 2-4 carbons ($C_{2-4}$alkenyl). In yet other embodiments, the alkenyl group contains 2-3 carbons ($C_{2-3}$alkenyl). In yet other embodiments, the alkenyl group contains 2 carbons ($C_2$alkenyl). Alkenyl groups include, for example, ethenyl, propenyl, butenyl, 1-methyl-2-buten-1-yl, and the like, which may bear one or more substituents. Alkenyl group substituents include, but are not limited to, any of the substituents described herein, that result in the formation of a stable moiety. The term "alkenylene," as used herein, refers to a biradical derived from an alkenyl group, as defined herein, by removal of two hydrogen atoms. Alkenylene groups may be cyclic or acyclic, branched or unbranched, substituted or unsubstituted. Alkenylene group substituents include, but are not limited to, any of the substituents described herein, that result in the formation of a stable moiety.

The term "alkynyl," as used herein, refers to a monovalent group derived from a straight- or branched-chain hydrocarbon having at least one carbon-carbon triple bond by the removal of a single hydrogen atom. In certain embodiments, the alkynyl group employed in the invention contains 2-20 carbon atoms ($C_{2-20}$alkynyl). In some embodiments, the alkynyl group employed in the invention contains 2-15 carbon atoms ($C_{2-15}$alkynyl). In another embodiment, the alkynyl group employed contains 2-10 carbon atoms ($C_{2-10}$ alkynyl). In still other embodiments, the alkynyl group contains 2-8 carbon atoms ($C_{2-8}$alkynyl). In still other embodiments, the alkynyl group contains 2-6 carbon atoms ($C_{2-6}$alkynyl). In still other embodiments, the alkynyl group contains 2-5 carbon atoms ($C_{2-5}$alkynyl). In still other embodiments, the alkynyl group contains 2-4 carbon atoms ($C_{2-4}$alkynyl). In still other embodiments, the alkynyl group contains 2-3 carbon atoms ($C_{2-3}$alkynyl). In still other embodiments, the alkynyl group contains 2 carbon atoms ($C_2$alkynyl). Representative alkynyl groups include, but are not limited to, ethynyl, 2-propynyl (propargyl), 1-propynyl, and the like, which may bear one or more substituents.

Alkynyl group substituents include, but are not limited to, any of the substituents described herein, that result in the formation of a stable moiety. The term "alkynylene," as used herein, refers to a biradical derived from an alkynylene group, as defined herein, by removal of two hydrogen atoms. Alkynylene groups may be cyclic or acyclic, branched or unbranched, substituted or unsubstituted. Alkynylene group substituents include, but are not limited to, any of the substituents described herein, that result in the formation of a stable moiety.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("heteroC$_{1-10}$ alkyl"). In some embodiments, a heteroalkyl group is a saturated group having 1 to 9 carbon atoms and 1 or more heteroatoms within the parent chain ("heteroC$_{1-9}$ alkyl"). In some embodiments, a heteroalkyl group is a saturated group having 1 to 8 carbon atoms and 1 or more heteroatoms within the parent chain ("heteroC$_{1-8}$ alkyl"). In some embodiments, a heteroalkyl group is a saturated group having 1 to 7 carbon atoms and 1 or more heteroatoms within the parent chain ("heteroC$_{1-7}$ alkyl"). In some embodiments, a heteroalkyl group is a saturated group having 1 to 6 carbon atoms and 1 or more heteroatoms within the parent chain ("heteroC$_{1-6}$ alkyl"). In some embodiments, a heteroalkyl group is a saturated group having 1 to 5 carbon atoms and 1 or 2 heteroatoms within the parent chain ("heteroC$_{1-5}$ alkyl"). In some embodiments, a heteroalkyl group is a saturated group having 1 to 4 carbon atoms and 1 or 2 heteroatoms within the parent chain ("heteroC$_{1-4}$ alkyl"). In some embodiments, a heteroalkyl group is a saturated group having 1 to 3 carbon atoms and 1 heteroatom within the parent chain ("heteroC$_{1-3}$ alkyl"). In some embodiments, a heteroalkyl group is a saturated group having 1 to 2 carbon atoms and 1 heteroatom within the parent chain ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms within the parent chain ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and 1 or 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

The term "carbocyclyl" or "carbocyclic" refers to a radical of a non-aromatic cyclic hydrocarbon group having from 3 to 14 ring carbon atoms ("C$_{3-14}$ carbocyclyl") and zero heteroatoms in the non-aromatic ring system. In some embodiments, a carbocyclyl group has 3 to 10 ring carbon atoms ("C$_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4] diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14× electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

The term "unsaturated" or "partially unsaturated" refers to a moiety that includes at least one double or triple bond.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

The term "halo" or "halogen" refers to fluorine (fluoro, —F), chlorine (chloro, —Cl), bromine (bromo, —Br), or iodine (iodo, —I).

The term "amino" refers to the group —NH$_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH($R^{bb}$), —NHC(=O)$R^{aa}$, —NHCO$_2R^{aa}$, —NHC(=O)N($R^{bb}$)$_2$, —NHC(=N$R^{bb}$)N($R^{bb}$)$_2$, —NHSO$_2R^{aa}$, —NHP(=O)(O$R^{cc}$)$_2$, and —NHP(=O)(N$R^{bb}$)$_2$, wherein $R^{aa}$, $R^{bb}$ and Rec are as defined herein, and wherein $R^{bb}$ of the group —NH($R^{bb}$) is not hydrogen.

The term "disubstituted amino" refers to an amino group wherein the nitrogen atom directly attached to the parent molecule is substituted with two groups other than hydrogen, and includes groups selected from —N($R^{bb}$)$_2$, —N$R^{bb}$C(=O)$R^{aa}$, —N$R^{bb}$CO$_2R^{aa}$, —N$R^{bb}$C(=O)N($R^{bb}$)$_2$, —N$R^{bb}$C(=N$R^{bb}$)N($R^{bb}$)$_2$, —N$R^{bb}$SO$_2R^{aa}$, —N$R^{bb}$P(=O)(OR(C)$_2$, and —N$R^{bb}$P(=O)(N$R^{bb}$)$_2$, wherein $R^{aa}$, $R^{bb}$, and Rec are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N($R^{bb}$)$_3$ and —N($R^{bb}$)$_3^+$X$^-$, wherein $R^{bb}$ and X$^-$ are as defined herein.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(RC)$_2$, —C(=O)$R^{aa}$, —C(=O)N($R^{cc}$)$_2$, —CO$_2R^{aa}$, —SO$_2R^{aa}$, —C(=N$R^{cc}$)$R^{aa}$, —C(=N$R^{cc}$)OR$^{aa}$, —C(=N$R^{cc}$)N($R^{cc}$)$_2$, —SO$_2$N($R^{cc}$)$_2$, —SO$_2R^{cc}$, —SO$_2$OR$^{cc}$, —SOR$^{aa}$, —C(=S)N($R^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-1-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-1-butylphenyl)-1-methylethyl carbamate (1-Bumcoc), 2-(2'- and 4'-pyridyl)

ethyl carbamate (Pyoc), 2-(N,N-dicyclohexylcarboxamido) ethyl carbamate, 1-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonoethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, 1-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-1-butylphenyl carbamate, 4 (trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), ß-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethylencamine, N-[(2-pyridyl)mesityl]methyleneamine, N-(N',N'-dimethylaminomethylene)amine, N,N'-isopropylidenediamine, N-p-nitrobenzylideneamine, N-salicylidencamine, N-5-chlorosalicylidencamine, N-(5-chloro-2-hydroxyphenyl)phenylmethylencamine, N-cyclohexylidencamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfonamide, o-nitrobenzenesulfonamide (Nps), 2,4-dinitrobenzenesulfonamide, pentachlorobenzenesulfonamide, 2-nitro-4-methoxybenzenesulfonamide, triphenylmethylsulfonamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N (R$^{bb}$)$_2$, —C(=NR$^{bb}$)R$^{aa}$, C(=NR$^{bb}$)OR$^{aa}$, —C(=NR$^{bb}$)N (R$^{bb}$)$_2$, —S(=O)R$^{aa}$, —SO$_2$R$^{aa}$, —Si(R$^{aa}$)$_3$, —P(R$^{cc}$)$_2$, —P(RC)$_3$, —P(=O)$_2$R$^{aa}$, —P(=O)(R$^{aa}$)$_2$, —P(=O) (OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$, are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), 1-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), 1-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, 1-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), tricthylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), 1-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, 1-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on an sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(RC)_2$, —$P(RC)_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and Rec are as defined herein. Sulfur protecting groups are well known in the art and include those described in detail in *Protecting Groups in Organic Synthesis*, T. W. Greene and P. G. M. Wuts, 3rd edition, John Wiley & Sons, 1999, incorporated herein by reference.

The terms "aminooxy," or "aminooxy group," are used interchangeably herein and refer to functional groups having the general formula:

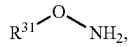

wherein $R^{31}$ is optionally substituted aliphatic, optionally substituted heteroaliphatic, optionally substituted aryl, optionally substituted heteroaryl, or optionally substituted heterocyclyl. In some embodiments, $R^{31}$ is an amino acid, wherein the point of attachment for the oxygen is on the side chain of the amino acid. In certain embodiments, the amino acid is within a polypeptide.

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The terms "carbonyl," or "carbonyl group," are used interchangeably herein and refer to functional groups composed of a carbon atom double-bonded to any oxygen atom. Carbonyls have the general formula:

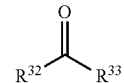

wherein each of $R^{32}$ and $R^{33}$ independently represents hydroxyl, optionally substituted amino, optionally substituted aliphatic, optionally substituted heteroaliphatic, optionally substituted aryl, optionally substituted heteroaryl, or optionally substituted heterocyclyl. Examples of carbonyls include, but are not limited to, aldehydes, ketones, carboxylic acids, esters, amides, enones, acyl halides, acid anhydrides, and imides. In some embodiments, a carbonyl-containing compound refers to a compound having an aldehyde group, or a compound capable of forming an aldehyde group through isomerization. For example, in some embodiments, certain sugars (e.g., reducing sugars) such as glucose, form aldehydes through isomerization. A sugar is classified as a reducing sugar if it has an open-chain form with an aldehyde group or a free hemiacetal group. Monosaccharides which contain an aldehyde group are known as aldoses, and those with a ketone group are known as ketoses. The aldehyde can be oxidized via a redox reaction in which another compound is reduced. Thus, a reducing sugar is one that is capable of reducing certain chemicals. Sugars with ketone groups in their open chain form are capable of isomerizing via a series of tautomeric shifts to produce an aldehyde group in solution. Therefore, ketone-bearing sugars like fructose are considered reducing sugars but it is the isomer containing an aldehyde group which is reducing since ketones cannot be oxidized without decomposition of the sugar. This type of isomerization is catalyzed by the base present in solutions which test for the presence of aldehydes.

The term "hydrazide," as used herein, refers to functional groups having the general formula:

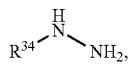

wherein $R^{34}$ is optionally substituted aliphatic, optionally substituted heteroaliphatic, optionally substituted aryl, optionally substituted heteroaryl, or optionally substituted heterocyclyl. In some embodiments, $R^{34}$ is an amino acid, wherein the point of attachment for the oxygen is on the side chain of the amino acid. In certain embodiments, the amino acid is within a polypeptide.

The term "hydrazone," as used herein, refers to compound having the general formula:

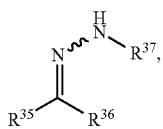

wherein each of $R^{35}$, $R^{36}$, and $R^{37}$ is independently optionally substituted aliphatic, optionally substituted heteroaliphatic, optionally substituted aryl, optionally substituted heteroaryl, or optionally substituted heterocyclyl. The term "hydrazone linkage," as used herein, refers to the formula:

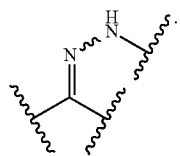 [SMILES: *NN=C(*)*]

Hydrzones can be prepared from, for example, joining of a compound comprising a hydrazide group and a compound comprising a carbonyl.

The term "acyl," as used herein, is a subset of a substituted alkyl group, and refers to a group having the general formula —C(=O)$R^A$, —C(=O)O$R^A$, —C(=O)—O—C(=O)$R^A$, —C(=O)S$R^A$, or —C(=O)N($R^A$)$_2$, wherein each instance of $R^A$ is independently hydrogen, optionally substituted aliphatic, optionally substituted heteroaliphatic, optionally substituted aryl, optionally substituted heteroaryl, or optionally substituted heterocyclyl. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety.

The term "azide" or "azido," as used herein, refers to a group of the formula (—N$_3$).

Radiolabled Proteins

Aspects of the disclosure provide antibodies, or fragments thereof, (e.g., single domain antibodies) comprising a radiolabel and/or a hydrophilic polymer. It should be appreciated that any of the linkages provided herein may be used to link proteins (e.g., antibodies) to a radiolabel and/or a hydrophilic polymer. It should also be appreciated that agents, such as the chelating moieties and radionuclides provided below may be substituted with another agents, such as any of the chelating moieties and radionuclides provided herein Another aspect of the present invention provides radiolabeled proteins. The radiolabeled proteins can be prepared from modified proteins of Formula (I).

In certain embodiments, provided herein is a modified protein of Formula (I):

wherein
L$^1$ is a linker comprising at least four amino acids formed by enzymatic conjugation between two enzyme recognition sequences; and
R$^1$ comprises a reactive group capable of undergoing a click chemistry reaction.

As generally defined herein, L$^1$ is a linker formed by enzymatic conjugation between two enzyme recognition sequences. In certain embodiments, L$^1$ comprises at least four amino acids. In certain embodiments, L$^1$ comprises at least five amino acids. In certain embodiments, L$^1$ comprises at least six amino acids. In certain embodiments, L$^1$ comprises at least seven amino acids. In certain embodiments, L$^1$ is a linker formed by sortase-mediated transpeptidation of two sortase recognition sequences. In certain embodiments, L$^1$ is -LPXTGGGK-, -LPXTGGG-, -NPXTGGGK-, NPXTGGG-, -LPXTAAA-, -NPXTAAA-,-LPXTGGGGG-, or -LPGAG-, wherein each instance of X is independently an amino acid. In certain embodiments, X is E. In certain embodiments, X is Q. In certain embodiments, X is K.

In certain embodiments, the modified protein is formed by enzymatic conjugation of

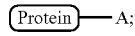

and a compound of Formula (a): B—R$^1$ (a), wherein each of A and B is independently an enzyme recognition sequence. In certain embodiments, the modified protein is formed by sortase-mediated transpeptidation of

and the compound of Formula (a): B—R$^1$ (a), wherein A comprises a C-terminal sortase recognition sequence, and B comprises a N-terminal sortase recognition sequence; or A comprises a N-terminal sortase recognition sequence, and B comprises a C-terminal sortase recognition sequence.

In certain embodiments, A comprises LPXTX or NPXTX, and B comprises an oligoglycine or an oligoalanine sequence; wherein each instance of X is independently an amino acid. In certain embodiments, B comprises LPXTX or NPXTX, and A comprises an oligoglycine or an oligoalanine sequence; wherein each instance of X is independently an amino acid. In certain embodiments, A is LPETG, LPETA, NPQTN, or NPKTG, and B is GGG or AAA. In certain embodiments, A comprises an oligoglycine or an oligoalanine sequence, and B comprises LPXTX or NPXTX, wherein each instance of X is independently an amino acid. In certain embodiments, B is LPETG, LPETA, NPQTN, or NPKTG, and A is GGG or AAA.

As used herein, the enzyme recognition sequence is an amino acid sequence recognized by a transamidase enzyme. In certain embodiments, the transamidase recognition sequence is a sortase recognition sequence or a sortase recognition motif. In certain embodiments, the sortase is sortase A (SrtA). In certain embodiments, the sortase is sortase B (SrtB).

As generally defined herein, $R^1$ is a reactive group capable of undergoing a click chemistry reaction.

Click chemistry is a chemical approach introduced by Sharpless in 2001 and describes chemistry tailored to generate substances quickly and reliably by joining small units together. See, e.g., Kolb, Finn and Sharpless *Angewandte Chemie International Edition* (2001) 40: 2004-2021; Evans, *Australian Journal of Chemistry* (2007) 60: 384-395). Exemplary coupling reactions (some of which may be classified as "Click chemistry") include, but are not limited to, formation of esters, thioesters, amides (e.g., such as peptide coupling) from activated acids or acyl halides; nucleophilic displacement reactions (e.g., such as nucleophilic displacement of a halide or ring opening of strained ring systems); azide-alkyne Huisgon cycloaddition; thiol-yne addition; imine formation; Michael additions (e.g., maleimide addition); Diels-Alder reaction and inverse electron demand Diels-Alder reaction; and [4+1] cycloadditions (e.g. between isonitriles (isocyanides) and tetrazines). In certain embodiments, the click chemistry reaction is a Diels-Alder reaction. It is to be understood that the click chemistry reaction may be followed by additional one or more chemical transformations. In certain embodiments, the click chemistry reaction is a Diels-Alder reaction followed by an retro-Diels-Alder reaction.

In certain embodiments, $R^1$ is a reactive group capable of undergoing a [3+2] cycloaddition. In certain embodiments, $R^1$ comprises a dipolarophile. In certain embodiments, $R^1$ comprises an alkynyl group. In certain embodiments, $R^1$ comprises a 1,3-dipole. In certain embodiments, $R^1$ comprises an azido. In certain embodiments, $R^1$ is a reactive group capable of undergoing a Diels-Alder cycloaddition. In certain embodiments, $R^1$ comprises a conjugated diene. In certain embodiments, $R^1$ comprises a tetrazine or a quadricyclane. In certain embodiments, $R^1$ comprises a tetrazine. In certain embodiments, $R^1$ comprises an unsubstituted tetrazine. In certain embodiments. $R^1$ comprises a substituted tetrazine.

In certain embodiments, $R^1$ is of Formula (i):

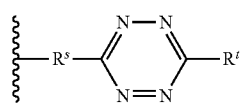
(i)

wherein $R^t$ is hydrogen, optionally substituted aliphatic, optionally substituted heteroaliphatic, optionally substituted aryl, optionally substituted heteroaryl, or optionally substituted heterocyclyl; and $R^s$ is a bond, optionally substituted aliphatic, optionally substituted heteroaliphatic, optionally substituted arylene, optionally substituted heteroarylene, or optionally substituted heterocyclylene.

As generally defined herein, $R^t$ is hydrogen, optionally substituted aliphatic, optionally substituted heteroaliphatic, optionally substituted aryl, optionally substituted heteroaryl, or optionally substituted heterocyclyl. In certain embodiments, $R^t$ is hydrogen. In certain embodiments, $R^t$ is optionally substituted aliphatic. In certain embodiments, $R^t$ is optionally substituted $C_{1-6}$ alkyl. In certain embodiments. $R^t$ is unsubstituted $C_{1-6}$ alkyl. In certain embodiments, $R^t$ is methyl or ethyl. In certain embodiments, $R^t$ is substituted $C_{1-6}$ alkyl. In certain embodiments, $R^t$ is optionally substituted aryl. In certain embodiments, $R^t$ is optionally substituted phenyl. In certain embodiments, $R^t$ is optionally substituted heteroaryl. In certain embodiments, $R^t$ is optionally substituted pyridine.

As generally defined herein, $R^s$ is a bond, optionally substituted aliphatic, optionally substituted heteroaliphatic, optionally substituted arylene, optionally substituted heteroarylene, or optionally substituted heterocyclylene. In certain embodiments, $R^s$ is a bond. In certain embodiments, $R^s$ is optionally substituted aliphatic. In certain embodiments. $R^s$ is optionally substituted $C_{1-6}$ alkyl. In certain embodiments, $R^s$ is unsubstituted $C_{1-6}$ alkyl. In certain embodiments, $R^s$ is methyl or ethyl. In certain embodiments, $R^s$ is substituted $C_{1-6}$ alkyl. In certain embodiments, $R^s$ is optionally substituted heteroaliphatic. In certain embodiments, $R^s$ is optionally substituted arylene. In certain embodiments. $R^s$ is optionally substituted phenyl. In certain embodiments. $R^s$ is optionally substituted heteroarylene. In certain embodiments, $R^s$ is optionally substituted pyridine.

In certain embodiments, $R^1$ comprises a dienophile. In certain embodiments, $R^1$ comprises an optionally substituted alkene. In certain embodiments. $R^1$ comprises a cyclooctene.

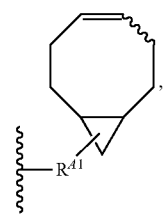

In certain embodiments. $R^1$ comprises a substituted cyclooctene of the formula:

wherein $R^{41}$ is a bond, optionally substituted aliphatic, optionally substituted heteroaliphatic, optionally substituted arylene, optionally substituted heteroarylene, or optionally substituted heterocyclylene. $R^1$ comprises a substituted cyclooctene of the formula:

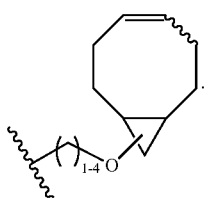

In certain embodiments, R¹ comprises a trans-cyclooctene. In certain embodiments, R¹ comprises a substituted trans-cyclooctene of the formula

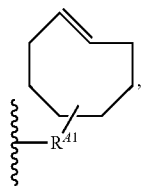

wherein $R^{41}$ is as defined herein. In certain embodiments, R¹ comprises a substituted trans-cyclooctene of the formula

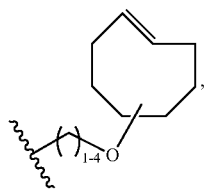

wherein $R^{41}$ is as defined herein. In certain embodiments, R¹ comprises an unsubstituted trans-cyclooctene.

Another aspect of the invention provides a radioactive protein of Formula (II)

(II)

wherein
L¹ is a linker comprising at least four amino acids formed by enzymatic conjugation between two enzyme recognition sequences; and
L² is optionally substituted aliphatic, optionally substituted heteroaliphatic, optionally substituted arylene, optionally substituted heteroarylene, or optionally substituted heterocyclylene.

In certain embodiments, the linker L² is formed by a click chemistry reaction. In certain embodiments, the linker L² is formed by a [3+2] cycloaddition. In certain embodiments, the linker L² is formed by a Diels-Alder cycloaddition. In certain embodiments, the linker L² is formed by a Diels-Alder cycloaddition followed by one or more chemical transformations. In certain embodiments, the linker L² is formed by a Diels-Alder cycloaddition followed by retro-Diels-Alder reaction.

As generally defined herein, L² is optionally substituted aliphatic, optionally substituted heteroaliphatic, optionally substituted arylene, optionally substituted heteroarylene, or optionally substituted heterocyclylene. In certain embodiments, L² is optionally substituted aliphatic. In certain embodiments, L² is optionally substituted heteroaliphatic. In certain embodiments, L² is optionally substituted arylene. In certain embodiments, L² is optionally substituted cycloalkylene. In certain embodiments, L² is optionally substituted heteroarylene.

In certain embodiments, the radioactive protein of Formula (II) is formed by a click chemistry reaction of the modified protein of Formula (I) and a compound of Formula (b): ¹⁸F-R² (b), wherein R² is a reactive group capable of undergoing the click chemistry reaction.

As generally defined herein, R² is a reactive group capable of undergoing a click chemistry reaction. In certain embodiments, R² is a reactive unsaturated group capable of undergoing a [3+2] cycloaddition. In certain embodiments, R² comprises a dipolarophile. In certain embodiments, R² comprises an alkynyl group. In certain embodiments, R² comprises a 1,3-dipole. In certain embodiments, R² comprises an azido. In certain embodiments, R² is a reactive group capable of undergoing a Diels-Alder cycloaddition. In certain embodiments, R² comprises a conjugated diene. In certain embodiments, R² comprises a tetrazine or a quadricyclane. In certain embodiments, R² comprises a tetrazine. In certain embodiments, R² comprises an unsubstituted tetrazine. In certain embodiments, R² comprises a substituted tetrazine.

In certain embodiments, R² is of Formula (i):

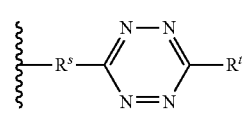

(i)

wherein
$R^t$ is hydrogen, optionally substituted aliphatic, optionally substituted heteroaliphatic, optionally substituted aryl, optionally substituted heteroaryl, or optionally substituted heterocyclyl; and
$R^s$ is a bond, optionally substituted aliphatic, optionally substituted heteroaliphatic, optionally substituted arylene, optionally substituted heteroarylene, or optionally substituted heterocyclylene.

In certain embodiments, R² comprises a dienophile. In certain embodiments, R² comprises an optionally substituted alkene. In certain embodiments, R² comprises a cyclooctene. In certain embodiments, R² comprises a trans-cyclooctene. In certain embodiments, R² comprises a substituted trans-cyclooctene. In certain embodiments, R² comprises an unsubstituted trans-cyclooctene.

In certain embodiments, a compound of Formula (b): ¹⁸F-R² (b), is of Formula (b-1):

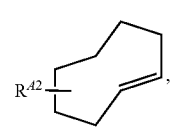

(b-1)

wherein $R^{42}$ is optionally substituted aliphatic, optionally substituted heteroaliphatic, optionally substituted aryl, optionally substituted heteroaryl, or optionally substituted heterocyclyl; and $R^{42}$ comprises ¹⁸F. In certain embodiments, $R^{42}$ is optionally substituted aliphatic. In certain embodiments, $R^{A2}$ is optionally substituted heteroaliphatic. In certain embodiments, $R^{A2}$ is —O—$C_{1-6}$alkylene, wherein the $C_{1-6}$alkylene comprises $^{18}F$.

In certain embodiments, a compound of Formula (b) is of Formula (b-1-a):

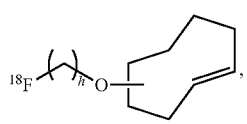

(b-1-a)

wherein h is an integer of 1 to 5, inclusive.

Compounds of Formula (b-1-a) can be prepared from a compound of Formula (b-1-a-i):

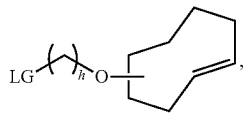

(b-1-a-i)

with a proper nucleophile comprising $^{18}F$, wherein h is as defined herein, LG is a leaving group. In certain embodiments, the compounds of Formula (b-1) can be prepared according to Scheme S6 or Scheme S6-a.

The term "leaving group" is given its ordinary meaning in the art of synthetic organic chemistry and refers to an atom or a group capable of being displaced by a nucleophile. Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, -OTs), methanesulfonate (mesylate, -OMs), p-bromobenzenesulfonyloxy (brosylate, -OBs), or trifluoromethanesulfonate (triflate, -OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties. In certain embodiments, LG is -OTs.

In certain embodiments, a compound of Formula (b) is of Formula (b-1-b):

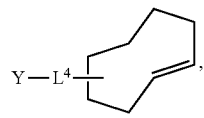

(b-1-b)

wherein $L^4$ and Y are as defined herein.

In certain embodiments, a compound of Formula (b) is of Formula (b-1-c):

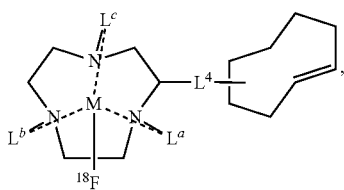

(b-1-c)

wherein $L^4$, M, $L^a$, $L^b$, and $L^c$ are as defined herein, and --- indicates a coordination bond or absent, as valency permits. In certain embodiments, ---- is a single coordination bond. In certain embodiments, --- is absent.

In certain embodiments, a compound of Formula (b) is of the formula:

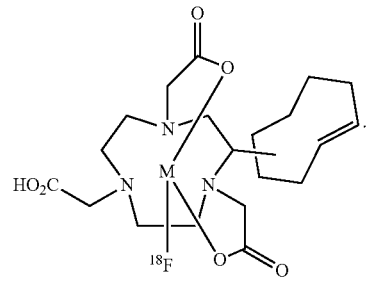

In certain embodiments, a compound of Formula (b): $^{18}F-R^2$ (b), is of Formula (b-2):

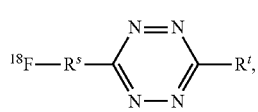

(b-2)

wherein $R^s$ and $R^t$ are as defined herein.

In certain embodiments, a compound of Formula (b) is of Formula (b-2-a):

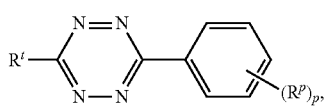

(b-2-a)

wherein $R^t$, $R^p$, and p are as defined herein.

In certain embodiments, a compound of Formula (b) is of Formula (b-2-a1):

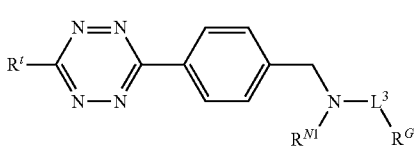

(b-2-a1)

wherein $R^t$, $R^{N1}$, $L^3$, $R^{q1}$, and q1 are as defined herein; and $R^G$ is an optionally substituted carbohydrate group; provided that $R^G$ comprises $^{18}F$.

A "carbohydrate group" or a "carbohydrate" refers to a monosaccharide or a polysaccharide (e.g., a disaccharide or oligosaccharide). Exemplary monosaccharides include, but are not limited to, natural sugars, such as allose, altrose, glucose, mannose, gulose, idose, galactose, talose, ribose, arabinose, xylose, and lyxose. Disaccharides are two joined monosaccharides. Exemplary disaccharides include, but are not limited to, sucrose, maltose, cellobiose, and lactose. Typically, an oligosaccharide includes between three and ten monosaccharide units (e.g., raffinose, stachyose). The carbohydrate group may be a natural sugar or a modified sugar. Exemplary modified sugars include, but are not limited to, sugars where the hydroxyl group is replaced with an amino group and/or alkyl group (e.g., such as desosamine), 2'-deoxyribose wherein a hydroxyl group is removed, 2'-fluororibose wherein a hydroxyl group is replace with a fluorine, or N-acetylglucosamine, or a nitrogen-containing form of glucose (e.g., 2'-fluororibose, deoxyribose, and hexose), and the like. Various carbohydrates are further described below and herein. Carbohydrates may exist in many different forms, for example, conformers, cyclic forms, acyclic forms, stereoisomers, tautomers, anomers, and isomers. In certain embodiments, $R^G$ is an optionally substituted glucose.

In certain embodiments, a compound of Formula (b) is of Formula (b-2-a2):

(b-2-a2)

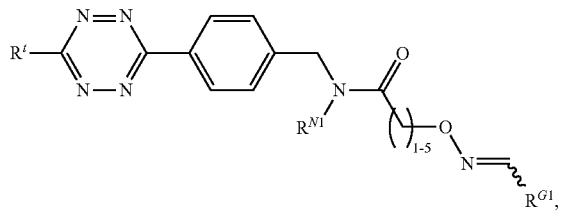

wherein $R^t$, $R^{N1}$ are as defined herein; and $R^{G1}$ is an optionally substituted carbohydrate group or a fragment thereof; provided that $R^{G1}$ comprises 18F.

The oxime compounds of Formula (b-2-a2)

(b-2-a2)

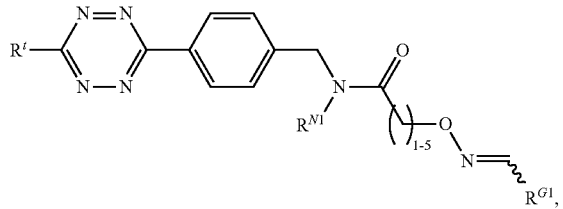

can be prepared from optionally substituted tetrazine-aminooxy and a radiolabeled optionally substituted aldehyde of the formula $R^{as}$—CHO, wherein $R^{as}$ is optionally substituted aliphatic, optionally substituted heteroaliphatic, optionally substituted aryl, optionally substituted heteroaryl, or optionally substituted heterocyclyl (Scheme S1). In certain embodiments, $R^{as}$ is an optionally substituted carbohydrate group or a fragment thereof. In certain embodiments, $R^{as}$ is an optionally substituted glucose or a fragment thereof. In certain embodiments, the reaction is carried out in the presence of a catalyst. In certain embodiments, the catalyst is m-phenylenediamine, p-phenylenediamine, or p-anisidine. In certain embodiments, the catalyst is m-phenylenediamine. In certain embodiments, the molar ratio of the optionally substituted tetrazine-aminooxy to the catalyst is from about 10:1 to 1:10. In certain embodiments, the molar ratio of the optionally substituted tetrazine-aminooxy to the catalyst is from about 1:1 to 1:8. In certain embodiments, the molar ratio of the optionally substituted tetrazine-aminooxy to the catalyst is from about 1:1 to 1:6. In certain embodiments, the molar ratio of the optionally substituted tetrazine-aminooxy to the catalyst is from about 1:2 to 1:4. In certain embodiments, the molar ratio of the optionally substituted tetrazine-aminooxy to the catalyst is about 1:4.

Scheme S1.

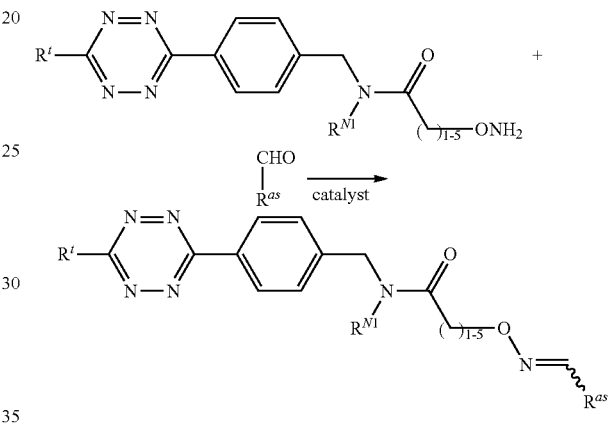

In certain embodiments, $R^{as}$ is an optionally substituted carbohydrate group or a fragment thereof, provided $R^{as}$ comprises 18F. In certain embodiments, $R^{as}$ is an optionally substituted glucose or a fragment thereof. In certain embodiments, $R^{as}$ is 18F-FDG of a fragment thereof.

As provided in Scheme S1, the resulting oxime product can be easily purified from the reaction mixture to the change in hydrophilicity.

In certain embodiments of Scheme S1, the excess of tetrazine-aminooxy can be captured by reacting with another water soluble carbohydrate. In certain embodiments, the water soluble carbohydrate is glucosamine 6-sulfate.

In certain embodiments, a compound of Formula (b) is of Formula (b-2-a2):

(b-2-a2)

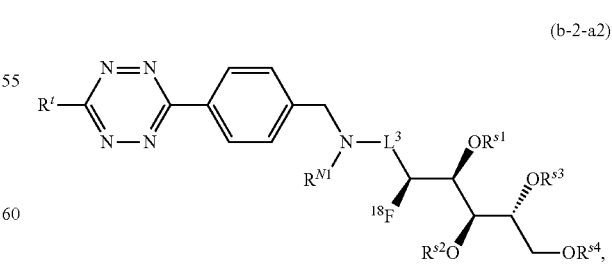

wherein $R^t$, $R^{N1}$, $L^3$, $R^{s1}$, $R^{s2}$, $R^{s3}$, and $R^{s4}$ are as defined herein.

In certain embodiments, a compound of Formula (b) is of Formula (b-2-a3):

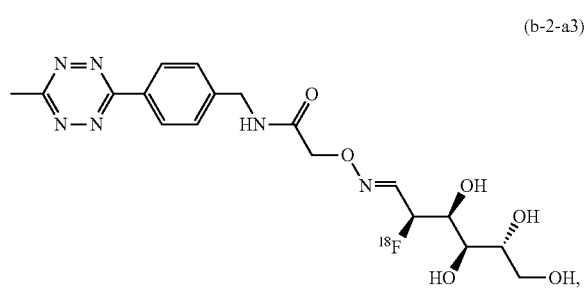 [SMILES: Cc1nnc(-c2ccc(CNC(=O)CO/N=C/[C@H]([18F])[C@@H](O)[C@H](O)[C@H](O)CO)cc2)nn1]
(b-2-a3)

wherein $R^t$, $R^{N1}$, $L^3$, $R^{s1}$, $R^{s2}$, $R^{s3}$, and $R^{s4}$ are as defined herein.

In certain embodiments, a compound of Formula (b) is of Formula (b-2-b):

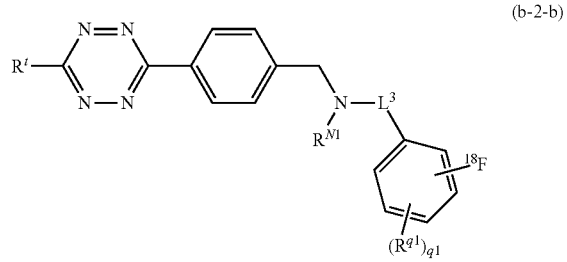
(b-2-b)

wherein $R^t$, $R^{N1}$, $L^3$, $R^{q1}$, and q1 are as defined herein.

In certain embodiments, a compound of Formula (b) is of Formula (b-2-b1):

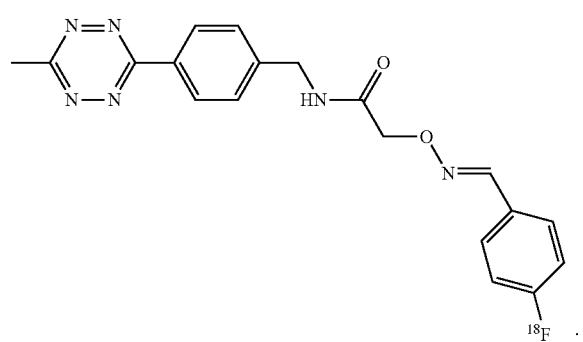
(b-2-b1)

In certain embodiments, a compound of Formula (b) is of Formula (b-3):

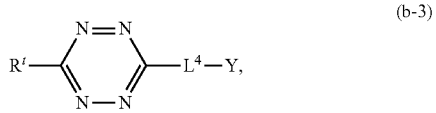
(b-3)

wherein $R^t$, $L^4$, and Y are as defined herein.

In certain embodiments, a compound of Formula (b) is of Formula (b-3-a):

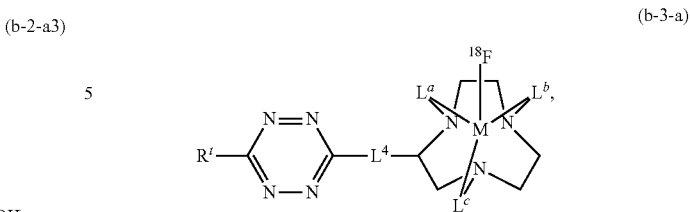
(b-3-a)

wherein $R^t$, $L^4$, $L^a$, $L^b$, and $L^c$ are as defined herein.

In certain embodiments, a compound of Formula (b) is of the following formula:

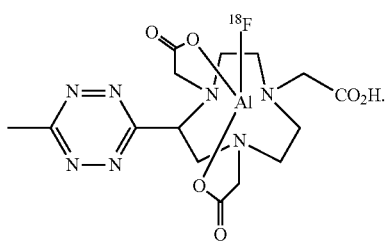

In certain embodiments, the linker $L^2$ is of Formula (ii):

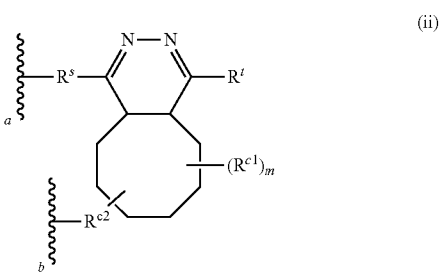
(ii)

wherein
  $R^t$ is hydrogen, optionally substituted aliphatic, optionally substituted heteroaliphatic, optionally substituted aryl, optionally substituted heteroaryl, or optionally substituted heterocyclyl;
  $R^s$ is a bond, optionally substituted aliphatic, optionally substituted heteroaliphatic, optionally substituted arylene, optionally substituted heteroarylene, or optionally substituted heterocyclylene;
  each instance of $R^{c1}$ is hydrogen, optionally substituted aliphatic, optionally substituted heteroaliphatic, optionally substituted aryl, optionally substituted heteroaryl, or optionally substituted heterocyclyl; or optionally two $R^{c1}$ taken with the intervening atoms to form an optionally substituted carbocyclyl or optionally substituted heterocyclyl ring;
  $R^{c2}$ is a bond, optionally substituted aliphatic, optionally substituted heteroaliphatic, optionally substituted arylene, optionally substituted heteroarylene, or optionally substituted heterocyclylene;
  m is 0, 1, 2, 3, 4, 5, 6, 7, or 8, as valency permits;
  a indicates point of attachment to $L^1$; and
  b indicates point of attachment to $^{18}F$.

In certain embodiments, m is 0. In certain embodiments, m is 1. In certain embodiments, m is 2. In certain embodiments, m is 3. In certain embodiments, m is 4.

As generally defined herein, each instance of $R^{c1}$ is independently hydrogen, optionally substituted aliphatic, optionally substituted heteroaliphatic, optionally substituted aryl, optionally substituted heteroaryl, or optionally substituted heterocyclyl. In certain embodiments, $R^{c1}$ is hydrogen. In certain embodiments, $R^{c1}$ is optionally substituted aliphatic. In certain embodiments, $R^{c1}$ is optionally substituted alkyl. In certain embodiments, $R^{c1}$ is optionally substituted heteroaliphatic. In certain embodiments, two $R^{c1}$ taken with the intervening atoms to form an optionally substituted carbocyclyl. In certain embodiments, two $R^{c1}$ taken with the intervening atoms to form an optionally substituted cyclopropyl.

As generally defined herein, $R^{c2}$ is a bond, optionally substituted aliphatic, optionally substituted heteroaliphatic, optionally substituted arylene, optionally substituted heteroarylene, or optionally substituted heterocyclylene. In certain embodiments, $R^{c2}$ is a bond. In certain embodiments, $R^{c2}$ is optionally substituted aliphatic. In certain embodiments, $R^{c2}$ is optionally substituted alkyl. In certain embodiments, $R^{c2}$ is optionally substituted heteroaliphatic. In certain embodiments, $R^{c2}$ is optionally substituted alkoxy. In certain embodiments, $R^{c2}$ is an optionally substituted amino group.

In certain embodiments, the linker $L^2$ is of Formula (ii-a):

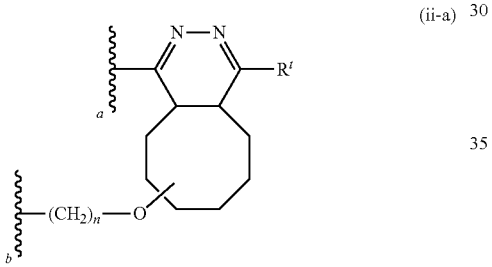

(ii-a)

wherein n is an integer between 1 and 8, inclusive.

In certain embodiments, n is 1. In certain embodiments, n is 2. In certain embodiments, n is 3. In certain embodiments, n is 4. In certain embodiments, n is 5. In certain embodiments, n is 6. In certain embodiments, n is 7. In certain embodiments, n is 8.

In certain embodiments, the linker $L^2$ is of Formula (ii-b):

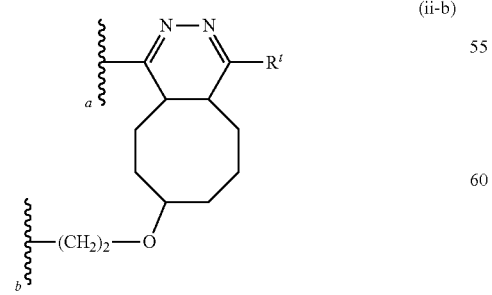

(ii-b)

wherein n is an integer between 1 and 8, inclusive.

In certain embodiments, the linker $L^2$ is of Formula (iii):

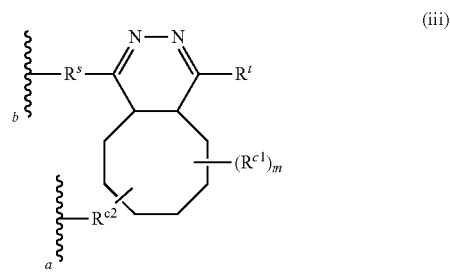

(iii)

wherein
- $R^t$ is hydrogen, optionally substituted aliphatic, optionally substituted heteroaliphatic, optionally substituted aryl, optionally substituted heteroaryl, or optionally substituted heterocyclyl;
- $R^s$ is a bond, optionally substituted aliphatic, optionally substituted heteroaliphatic, optionally substituted arylene, optionally substituted heteroarylene, or optionally substituted heterocyclylene;
- each instance of $R^{c1}$ is hydrogen, optionally substituted aliphatic, optionally substituted heteroaliphatic, optionally substituted aryl, optionally substituted heteroaryl, or optionally substituted heterocyclyl;
- $R^{c2}$ is a bond, optionally substituted aliphatic, optionally substituted heteroaliphatic, optionally substituted arylene, optionally substituted heteroarylene, or optionally substituted heterocyclylene;
- m is 0, 1, 2, 3, 4, 5, 6, 7, or 8, as valency permits;
- a indicates point of attachment to $L^1$; and
- b indicates point of attachment to $^{18}F$.

In certain embodiments, the linker $L^2$ is of Formula (iii-a):

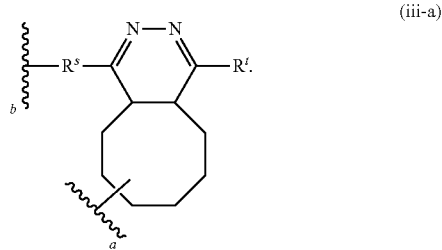

(iii-a)

In certain embodiments, wherein $-L^2-F^{18}$ is of Formula (iii-b):

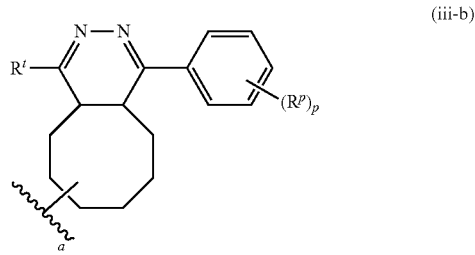

(iii-b)

wherein
each instance of $R^p$ is independently hydrogen, optionally substituted aliphatic, optionally substituted heteroaliphatic, optionally substituted aryl, optionally substituted heteroaryl, optionally substituted heterocyclyl, hydroxyl, or optionally substituted amino; provided at least one $R^p$ is not hydrogen and comprises $F^{18}$; and
p is 1, 2, 3, 4, or 5.

In certain embodiments, p is 1. In certain embodiments, p is 2. In certain embodiments, p is 3. In certain embodiments, p is 4. In certain embodiments, p is 3. In certain embodiments, p is 5.

As generally defined herein, $R^p$ is hydrogen, optionally substituted aliphatic, optionally substituted heteroaliphatic, optionally substituted aryl, optionally substituted heteroaryl, optionally substituted heterocyclyl, hydroxyl, or optionally substituted amino; wherein at least one $R^p$ is not hydrogen and comprises $F^{18}$. In certain embodiments, $R^p$ is hydrogen. In certain embodiments, $R^p$ is optionally substituted aliphatic. In certain embodiments, $R^p$ is optionally substituted $C_{1-6}$ alkyl. In certain embodiments, $R^p$ is unsubstituted $C_{1-6}$ alkyl. In certain embodiments, $R^p$ is methyl or ethyl. In certain embodiments, $R^p$ is substituted $C_{1-6}$ alkyl. In certain embodiments, $R^p$ is optionally substituted aryl. In certain embodiments, $R^p$ is optionally substituted phenyl. In certain embodiments, $R^p$ is optionally substituted heteroaryl. In certain embodiments, $R^p$ is optionally substituted pyridine. In certain embodiments, least one $R^p$ is not hydrogen and comprises $F^{18}$.

In certain embodiments, wherein $-L^2-F^{18}$ is of Formula (iii-b1):

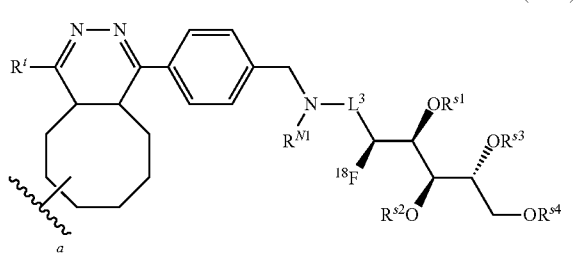

(iii-b1)

wherein
$L^3$ is a bond, optionally substituted aliphatic, optionally substituted heteroaliphatic, optionally substituted arylene, optionally substituted heteroarylene, or optionally substituted heterocyclylene;

$R^{N1}$ is independently hydrogen, optionally substituted aliphatic, optionally substituted heteroaliphatic, optionally substituted aryl, or optionally substituted heteroaryl, or a nitrogen protecting group; and each of $R^{s1}$, $R^{s2}$, $R^{s3}$, and $R^{s4}$ is independently hydrogen, optionally substituted aliphatic, optionally substituted heteroaliphatic, optionally substituted aryl, or optionally substituted heteroaryl, or an oxygen protecting group.

As generally defined herein, $L^3$ is a bond, optionally substituted aliphatic, optionally substituted heteroaliphatic, optionally substituted arylene, optionally substituted heteroarylene, or optionally substituted heterocyclylene. In certain embodiments, $L^3$ is a bond. In certain embodiments, $L^3$ is optionally substituted aliphatic. In certain embodiments, $L^3$ is optionally substituted heteroaliphatic. In certain embodiments, $L^3$ comprises an oxime moiety. In certain embodiments, $L^3$ is of the formula

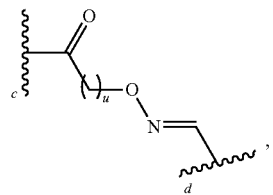

wherein c indicates the point of attachment to $-N-R^{N1}-$;
d indicates the point of attachment to $-CH_{18}F-$; and u is 1, 2, 3, 4, or 5. In certain embodiments, $L^3$ is C=O.

In certain embodiments, $R^{N1}$ is independently hydrogen. In certain embodiments, $R^{N1}$ is optionally substituted aliphatic. In certain embodiments, $R^{N1}$ is optionally substituted alkyl. In certain embodiments, $R^{N1}$ is an amino protectin group.

In certain embodiments, $R^{s1}$ is independently hydrogen. In certain embodiments, $R^{s1}$ is optionally substituted aliphatic. In certain embodiments, $R^{s1}$ is optionally substituted alkyl. In certain embodiments, $R^{s1}$ is an oxygen protectin group. In certain embodiments, $R^{s1}$ is acyl (e.g. acetyl).

In certain embodiments, $R^{s2}$ is independently hydrogen. In certain embodiments, $R^{s2}$ is optionally substituted aliphatic. In certain embodiments, $R^{s2}$ is optionally substituted alkyl. In certain embodiments, $R^{s2}$ is an oxygen protectin group. In certain embodiments, $R^{s2}$ is acyl (e.g. acetyl).

In certain embodiments, $R^{s3}$ is independently hydrogen. In certain embodiments, $R^{s3}$ is optionally substituted aliphatic. In certain embodiments, $R^{s3}$ is optionally substituted alkyl. In certain embodiments, $R^{s3}$ is an oxygen protectin group. In certain embodiments, $R^{s3}$ is acyl (e.g. acetyl).

In certain embodiments, $R^{s4}$ is independently hydrogen. In certain embodiments, $R^{s4}$ is optionally substituted aliphatic. In certain embodiments, $R^{s4}$ is optionally substituted alkyl. In certain embodiments, $R^{s4}$ is an oxygen protectin group. In certain embodiments, $R^{s4}$ is acyl (e.g. acetyl).

In certain embodiments, $R^{s1}$, $R^{s2}$, $R^{s3}$, and $R^{s4}$ are all hydrogen.

In certain embodiments, $R^{N1}$, $R^{s1}$, $R^{s2}$, $R^{s3}$, and $R^{s4}$ are all hydrogen.

In certain embodiments, $R^{N1}$, $R^{s1}$, $R^{s2}$, $R^{s3}$, and $R^{s4}$ are all hydrogen; and $R^t$ is optionally substituted aliphatic. In certain embodiments, $R^{N1}$, $R^{s1}$, $R^{s2}$, $R^{s3}$, and $R^{s4}$ are all hydrogen; and $R^t$ is optionally substituted $C_{1-6}$ alkyl. In certain embodiments, $R^{N1}$, $R^{s1}$, $R^{s2}$, $R^{s3}$, and $R^{s4}$ are all hydrogen; and $R^t$ is methyl or ethyl.

In certain embodiments, wherein $-L^2-F^{18}$ is of the formula:

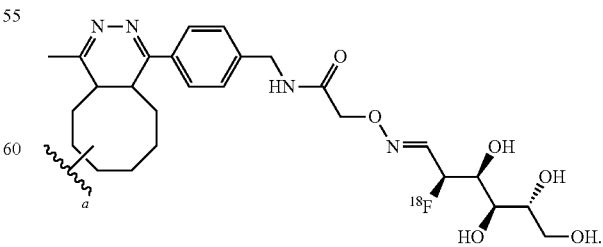

In certain embodiments, wherein $-L^2-F^{18}$ is of Formula (iii-b2):

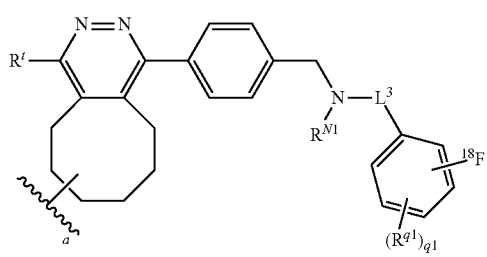

(iii-b2)

In certain embodiments, -L²-F¹⁸ is of Formula (iii-b3):

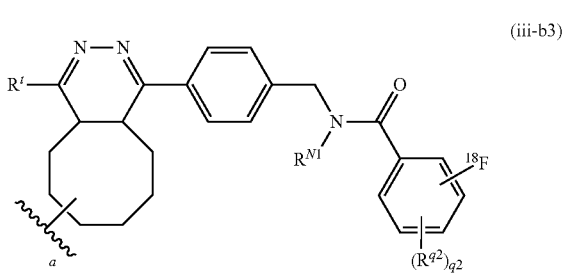

(iii-b3)

wherein
- L³ is a bond, optionally substituted aliphatic, optionally substituted heteroaliphatic, optionally substituted arylene, optionally substituted heteroarylene, or optionally substituted heterocyclylene;
- $R^{N1}$ is independently hydrogen, optionally substituted aliphatic, optionally substituted heteroaliphatic, optionally substituted aryl, or optionally substituted heteroaryl, or a nitrogen protecting group;
- each instance of $R^{91}$ is independently hydrogen, optionally substituted aliphatic, optionally substituted heteroaliphatic, optionally substituted aryl, optionally substituted heteroaryl, optionally substituted heterocyclyl, hydroxyl, or optionally substituted amino; and
- q1 is 0, 1, 2, 3, or 4.

In certain embodiments, $R^t$ is optionally substituted aliphatic and $R^{91}$ is hydrogen. In certain embodiments, $R^t$ is optionally substituted $C_{1-6}$ alkyl; L³ is

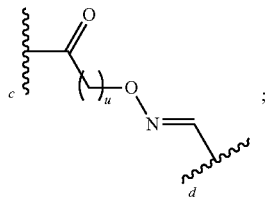

u is 1; and $R^{91}$ is hydrogen.

In certain embodiments, -L²-F¹⁸ is of the formula:

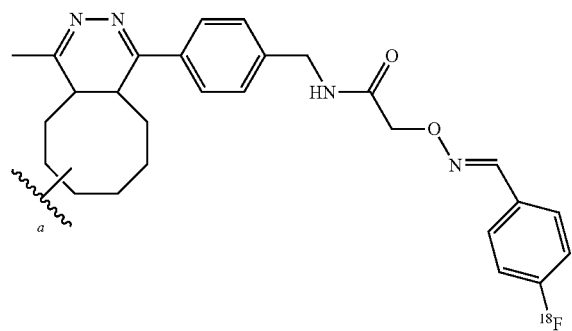

wherein
- $R^{N1}$ is independently hydrogen, optionally substituted aliphatic, optionally substituted heteroaliphatic, optionally substituted aryl, or optionally substituted heteroaryl, or a nitrogen protecting group; and
- each instance of $R^{92}$ is independently hydrogen, optionally substituted aliphatic, optionally substituted heteroaliphatic, optionally substituted aryl, optionally substituted carbocyclyl, optionally substituted heteroaryl, optionally substituted heterocyclyl, hydroxyl, or optionally substituted amino; and
- q2 is 0, 1, 2, 3, or 4.

In certain embodiments, q2 is 0. In certain embodiments, q2 is 1. In certain embodiments, q1 is 2. In certain embodiments, q2 is 3. In certain embodiments, q2 is 4.

In certain embodiments, $R^{92}$ is hydrogen. In certain embodiments, $R^{92}$ is optionally substituted aliphatic. In certain embodiments, $R^{92}$ is optionally substituted $C_{1-6}$ alkyl.

In certain embodiments, $R^t$ is optionally substituted aliphatic and $R^{92}$ is hydrogen.

In certain embodiments, -L²-F¹⁸ is of the formula:

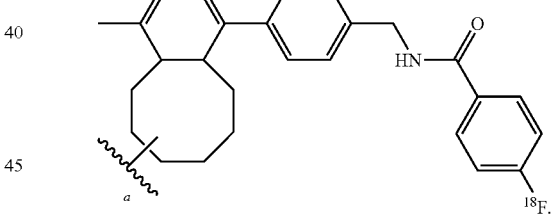

In certain embodiments, wherein -L²-F¹⁸ is of Formula (iii-b4):

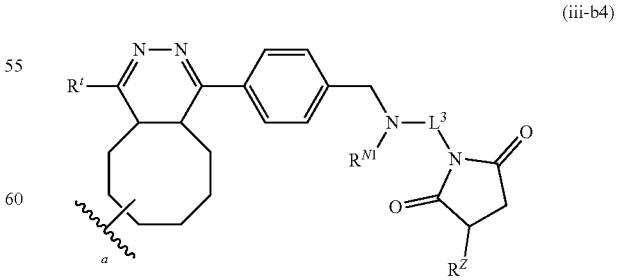

(iii-b4)

wherein
- L³ is a bond, optionally substituted aliphatic, optionally substituted heteroaliphatic, optionally substituted arylene, optionally substituted heteroarylene, or optionally substituted heterocyclylene;

$R^{N1}$ is independently hydrogen, optionally substituted aliphatic, optionally substituted heteroaliphatic, optionally substituted aryl, or optionally substituted heteroaryl, or a nitrogen protecting group; and $R^Z$ is independently hydrogen, optionally substituted aliphatic, optionally substituted heteroaliphatic, optionally substituted aryl, or optionally substituted heteroaryl, wherein $R^Z$ comprise $^{18}F$.

In certain embodiments, wherein $-L^2-F^{18}$ is of Formula (iii-b4-a):

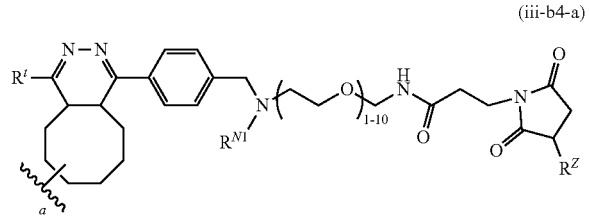

(iii-b4-a)

In certain embodiments, $R^2$ is an optionally substituted thiol.

In certain embodiments, $-L^2-F^{18}$ is of Formula (iii-c):

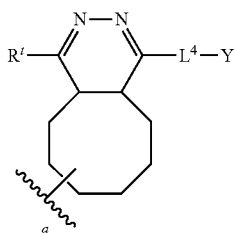

(iii-c)

wherein

Y is a ligand capable of chelating to a pharmaceutically acceptable metal complex comprising $F^{18}$; and $L^4$ is a bond, optionally substituted aliphatic, optionally substituted heteroaliphatic, optionally substituted arylene, optionally substituted cycloalkylene, optionally substituted heteroarylene, or optionally substituted heterocyclylene.

As generally defined herein, Y is a ligand capable of chelating to a pharmaceutically acceptable metal complex comprising $F^{18}$. As used herein, a ligand refers to an ion or molecule (functional group) that binds to a central metal atom to form a coordination complex. The bonding between metal and ligand generally involves formal donation of one or more of the ligand's electron pairs. The nature of metal-ligand bonding can range from covalent to ionic. Exemplary monodentate ligands include, but are not limited to, CO, organonitriles (e.g., $CH_3CN$, $CH_3CH_2CN$), monosubstituted amines, disubstituted amines, trisubstituted amines, heterocyclyls (e.g., pyridine, piperidine), dialkylcyanamides, triphenylphosphine oxide, THF, DMF, or NMF. Exemplary bidentate ligands include, but are not limited to, 1,5-cyclooctadiene, norbornadiene, 1,2-ethylenediamine, tetramethylethylenediamine, 1,2-dimethoxyethane, diglyme, or 2,5-dithiahexane. Exemplary tridentate ligands include, but are not limited to, conjugated cyclic triene (e.g., cycloheptatriene), conjugated acyclic triene, arenes (e.g., benzene, toluene, xylene, mesitylene, naphthalene), tetraazamacrocyles (e.g., tetraazacyclododecane), polyamines (e.g., diethylenetriamine), and trithiocyclononane. In certain embodiments, the ligand is a polydentate ligand. In certain embodiments, the ligand comprises 1,4,7-triazacyclononane-triacetic acid (NOTA), 1,4,7,10-tetraazacyclododecane-tetraacetic acid (DOTA), or triazacyclononane-phosphinate (TRAP).

The phrase "pharmaceutically acceptable" means that the metal complex is suitable for administration to a subject. In certain embodiments, the metal complex is a halide metal complex. In certain embodiments, the metal is a pharmaceutically acceptable metal. In certain embodiments, the metal is IIA or IIIA group metal. In certain embodiments, the metal is an early transition metal. In certain embodiments, the metal is Al.

In certain embodiments, $L^4$ is a bond. In certain embodiments, $L^4$ is an optionally substituted aliphatic. In certain embodiments, $L^4$ is an optionally substituted heteroaliphatic.

In certain embodiments, $-L^2-F^{18}$ is of Formula (iii-c1):

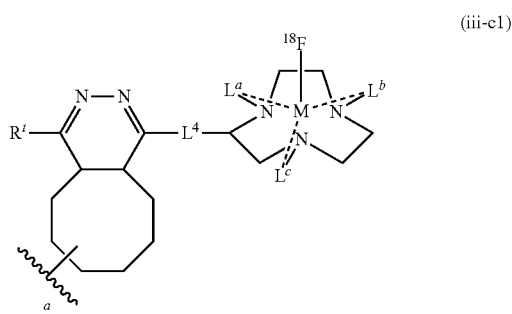

(iii-c1)

wherein

M is a pharmaceutically acceptable metal;

each of $L^a$, $L^b$, and $L^c$ is independently optionally substituted aliphatic, optionally substituted heteroaliphatic, optionally substituted arylene, optionally substituted cycloalkylene, optionally substituted heteroarylene, or optionally substituted heterocyclylene; and "---" indicates a coordination bond or absend, as valency permits.

In certain embodiments, $L^a$ is optionally substituted aliphatic. In certain embodiments, $L^a$ is optionally substituted heteroaliphatic. In certain embodiments, $L^a$ is optionally substituted heteroalkylene. In certain embodiments, $L^a$ is $-(CH_2)_{1-3}-C(=O)O-$, wherein the chelation point to M is O. In certain embodiments, $L^a$ is $-CH_2-C(=O)O-$. In certain embodiments, $L^a$ is $-(CH_2)_{1-3}-C(=O)OH$, wherein the chelation point to M is O. In certain embodiments, $L^a$ is $-CH_2-C(=O)OH$.

In certain embodiments, $L^b$ is optionally substituted aliphatic. In certain embodiments, $L^b$ is optionally substituted heteroaliphatic. In certain embodiments, $L^b$ is optionally substituted heteroalkylene. In certain embodiments, $L^b$ is $-(CH_2)_{1-3}-C(=O)O-$ wherein the chelation point to M is O. In certain embodiments, $L^b$ is $-CH_2-C(=O)O-$. In certain embodiments, $L^b$ is $-(CH_2)_{1-3}-C(=O)OH$, wherein the chelation point to M is O. In certain embodiments, $L^b$ is $-CH_2-C(=O)OH$.

89

In certain embodiments, $L^c$ is optionally substituted aliphatic. In certain embodiments, $L^c$ is optionally substituted heteroaliphatic. In certain embodiments, $L^c$ is optionally substituted heteroalkylene. In certain embodiments, $L^c$ is —(CH$_2$)$_{1-3}$—C(=O)O— wherein the point of attachment to M is O. In certain embodiments, $L^c$ is —CH$_2$—C(=O)O—. In certain embodiments, $L^c$ is —(CH$_2$)$_{1-3}$—C(=O)OH, wherein chelation point to M is O. In certain embodiments, $L^c$ is —CH$_2$—C(=O)OH.

As generally defined herein, "---" indicates the chelation formed between M and the ligand, as valency permits. In certain embodiments, M forms one chelating bond with the ligand. In certain embodiments, M forms two chelating bonds with the ligand. In certain embodiments, M forms three chelating bonds with the ligand.

90

In certain embodiments, -L$^2$-F$^{18}$ is of Formula (iii-c2):

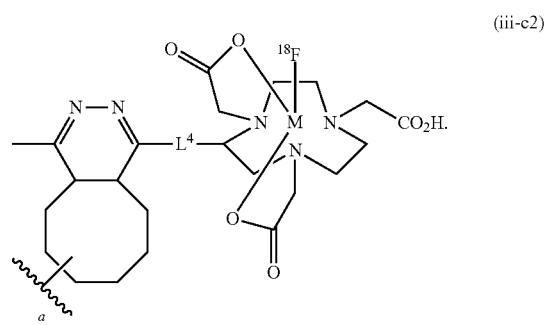

(iii-c2)

In certain embodiments, the radioactive protein is one of the following formulae:

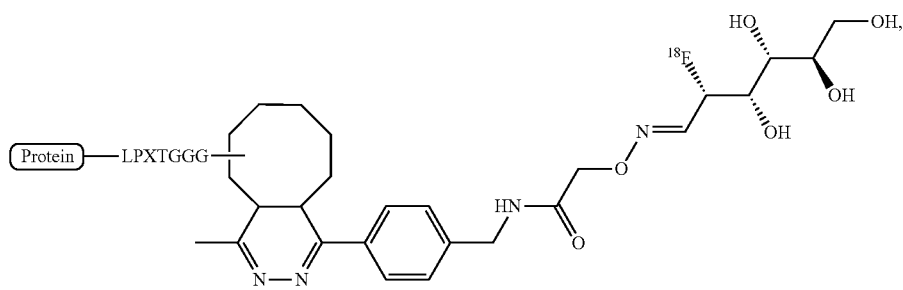

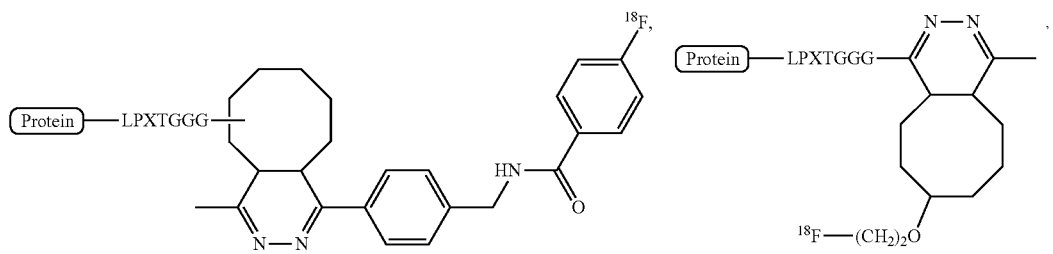

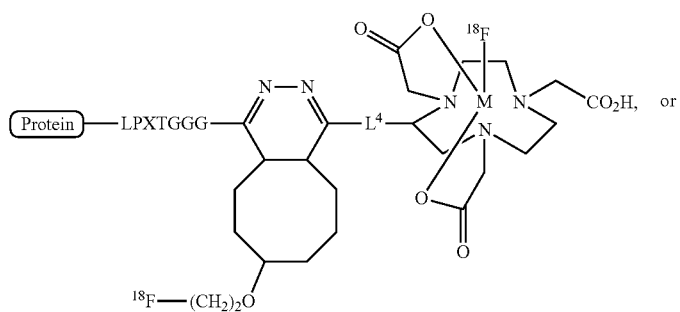

or

-continued

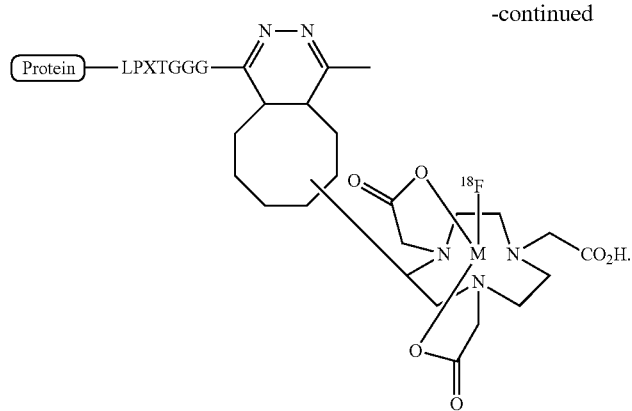

In certain embodiments, the linker $L^2$ is of one of the following formulae:

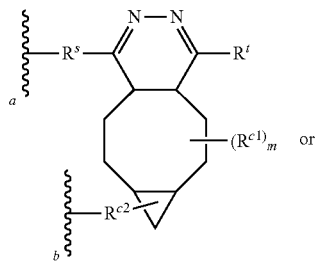
(iv-a)

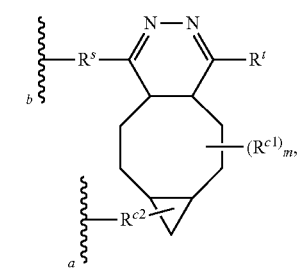
(iv-b)

wherein $R^s$, $R^t$, $R^{c1}$, $R^{c2}$, and m are as defined herein.

In certain embodiments, provided herein is a radioactive protein of Formula (III)

(III)

wherein
$L^1$ is as defined herein; and
$R^3$ comprises a ligand capable of chelating to a pharmaceutically acceptable radioactive metal complex.

In certain embodiments, $L^1$-$R^3$ is of the following formula:

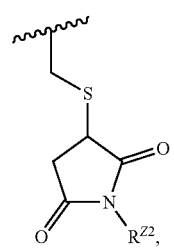

wherein $R^{72}$ is optionally substituted aliphatic, optionally substituted heteroaliphatic, optionally substituted aryl, or optionally substituted heteroaryl, or a nitrogen protecting group; wherein $R^{72}$ comprises a ligand capable of chelating to a pharmaceutically acceptable radioactive metal complex.

In certain embodiments, $R^3$ comprises mono-dentecate ligand. In certain embodiments, $R^3$ comprises a polydentecate ligand. In certain embodiments, $R^3$ comprises 1,4,7-triazacyclononane-triacetic acid (NOTA), 1,4,7,10-tetraazacyclododecane-tetraacetic acid (DOTA), or triazacyclononane-phosphinate (TRAP).

In certain embodiments, the metal is $^{64}Cu^{2+}$. In certain embodiments, the metal is $^{68}Ga^{3+}$.

In certain embodiments, the radioactive protein is one of the following formulae:

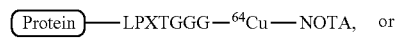

In certain embodiments, provided herein is a radioactive protein of Formula (IV)

(IV)

wherein
$L^1$ is a linker comprising at least four amino acids formed by enzymatic conjugation between two enzyme recognition sequences;
$R^4$ comprises a radioactive optionally substituted carbohydrate; and
$R^4$ is linked to the C-terminus of the adjacent amino acid in $L^1$.

As generally defined herein, $R^4$ comprises a radioactive optionally substituted carbohydrate. In certain embodiments, $R^4$ comprises a radioactive optionally substituted glucose. In certain embodiments, $R^4$ comprises a radioactive glucose comprising 18F. In certain embodiments, $R^4$ comprises an optionally substituted glucose comprising 18F. In certain embodiments, $R^4$ is linked to the C-terminus of the adjacent amino acid in $L^1$. In certain embodiments, $R^4$ is linked to the side chain of the adjacent amino acid in $L^1$.

In certain embodiments, $R^4$ is of Formula (iv):

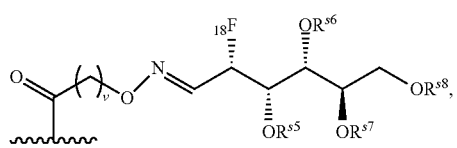

(iv)

wherein v is 1, 2, 3, 4, or 5; and each of $R^{s5}$, $R^{s6}$, $R^{s7}$, and $R^{s8}$ is independently hydrogen, optionally substituted aliphatic, optionally substituted heteroaliphatic, optionally substituted aryl, or optionally substituted heteroaryl, or an oxygen protecting group.

In certain embodiments, $R^{s5}$ is independently hydrogen. In certain embodiments, $R^{s5}$ is optionally substituted aliphatic. In certain embodiments, $R^{s5}$ is optionally substituted alkyl. In certain embodiments, $R^{s5}$ is an oxygen protectin group. In certain embodiments, $R^{s5}$ is acyl (e.g. acetyl).

In certain embodiments, $R^{s6}$ is independently hydrogen. In certain embodiments, $R^{s6}$ is optionally substituted aliphatic. In certain embodiments, $R^{s6}$ is optionally substituted alkyl. In certain embodiments, $R^{s6}$ is an oxygen protectin group. In certain embodiments, $R^{s6}$ is acyl (e.g. acetyl).

In certain embodiments, $R^{s7}$ is independently hydrogen. In certain embodiments, $R^{s7}$ is optionally substituted aliphatic. In certain embodiments, $R^{s7}$ is optionally substituted alkyl. In certain embodiments, $R^{s7}$ is an oxygen protectin group. In certain embodiments, $R^{s7}$ is acyl (e.g. acetyl).

In certain embodiments, $R^{s8}$ is independently hydrogen. In certain embodiments, $R^{s8}$ is optionally substituted aliphatic. In certain embodiments, $R^{s8}$ is optionally substituted alkyl. In certain embodiments, $R^{s8}$ is an oxygen protectin group. In certain embodiments, $R^{s8}$ is acyl (e.g. acetyl).

In certain embodiments, $R^4$ is of the formula:

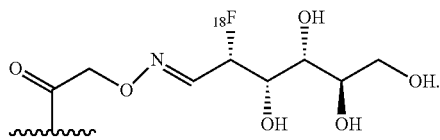

In certain embodiments, the radioactive protein is of the following formula:

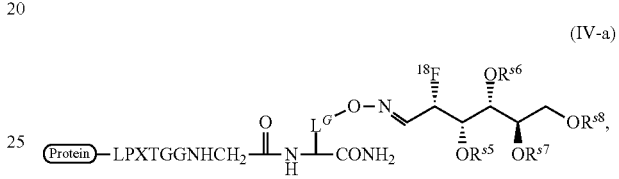

(IV-a)

wherein $R^{s5}$, $R^{s6}$, $R^{s7}$, and $R^{s8}$ are as defined herein; and $L^G$ is optionally substituted aliphatic or optionally substituted heteroaliphatic.

In certain embodiments, $L^G$ is optionally substituted aliphatic. In certain embodiments, $L^G$ is optionally substituted $C_{1-10}$ alkyl. In certain embodiments, $L^G$ is optionally substituted heteroaliphatic. In certain embodiments, $L^G$ is of the formula:

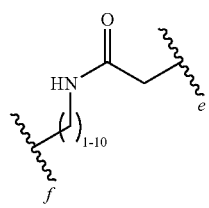

wherein e indicates the point of attachment to oxygen and f indicates the point of attachment to the alpha carbon of the amino acid.

In certain embodiments, the radioactive protein is of the following formula:

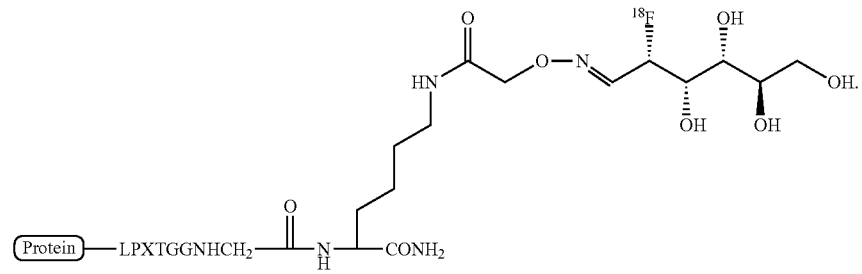

In certain embodiments,

[Protein]

is an antibody, a nuclear factor, a neuropeptide, a receptor protein, an enzyme, a structural protein, or a fragment thereof. In certain embodiments,

[Protein]

is an antibody or a fragment thereof. In certain embodiments,

[Protein]

is VHH or a fragment thereof.

Synthesis of Intermediates and Radiolabeled Proteins

The oxime compounds of Formula (b-2-a2)

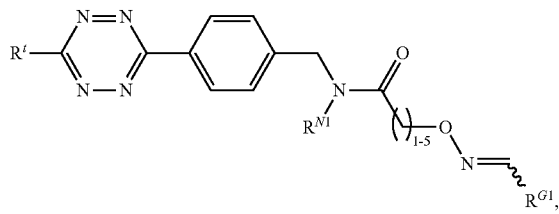

(b-2-a2)

can be prepared from optionally substituted tetrazine-aminooxy and a radiolabeled optionally substituted aldehyde or optionally substituted ketone of the formula $R^{as}$—CO—$R^{bs}$, wherein $R^{G1}$ is as defined herein; each of $R^{as}$ and $R^{bs}$ is independently hydrogen, optionally substituted aliphatic, optionally substituted heteroaliphatic, optionally substituted aryl, optionally substituted heteroaryl, or optionally substituted heterocyclyl; provided $R^{as}$ and $R^{bs}$ are not both hydrogen (Scheme S1).

Scheme S1.

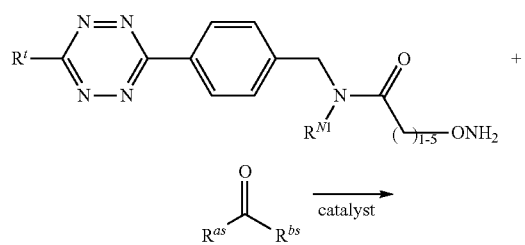

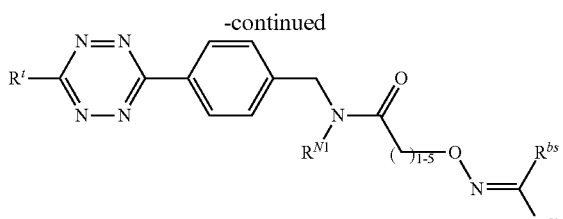

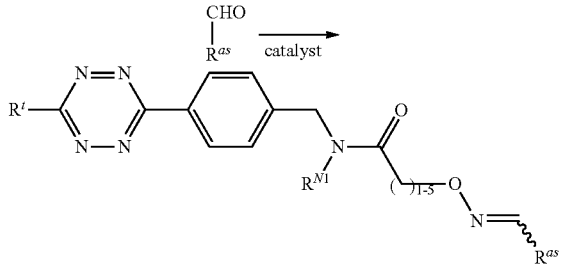

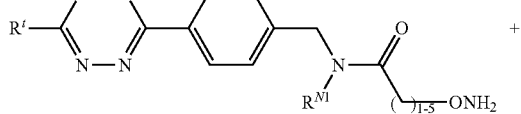

In certain embodiments, $R^{as}$ is an optionally substituted carbohydrate group or a fragment thereof. In certain embodiments, $R^{as}$ is an optionally substituted glucose or a fragment thereof. In certain embodiments, the reaction is carried out in the presence of a catalyst. In certain embodiments, the catalyst is m-phenylenediamine, p-phenylenediamine, or p-anisidine. In certain embodiments, the catalyst is m-phenylenediamine. In certain embodiments, the molar ratio of the optionally substituted tetrazine-aminooxy to the catalyst is from about 10:1 to 1:10. In certain embodiments, the molar ratio of the optionally substituted tetrazine-aminooxy to the catalyst is from about 1:1 to 1:8. In certain embodiments, the molar ratio of the optionally substituted tetrazine-aminooxy to the catalyst is from about 1:1 to 1:6. In certain embodiments, the molar ratio of the optionally substituted tetrazine-aminooxy to the catalyst is from about 1:2 to 1:4. In certain embodiments, the molar ratio of the optionally substituted tetrazine-aminooxy to the catalyst is about 1:4.

In certain embodiments, $R^{as}$ is an optionally substituted carbohydrate group or a fragment thereof, provided $R^{as}$ comprises 18F. In certain embodiments, $R^{as}$ is an optionally substituted glucose or a fragment thereof. In certain embodiments, $R^{as}$ is 18F-FDG of a fragment thereof.

As provided in Scheme S1, the resulting oxime product can be easily purified from the reaction mixture to the change in hydrophilicity.

In certain embodiments of Scheme S1, the excess of tetrazine-aminooxy can be captured by reacting with another water soluble carbohydrate. In certain embodiments, the water soluble carbohydrate is glucosamine 6-sulfate.

The compound of Formula (b-2-b)

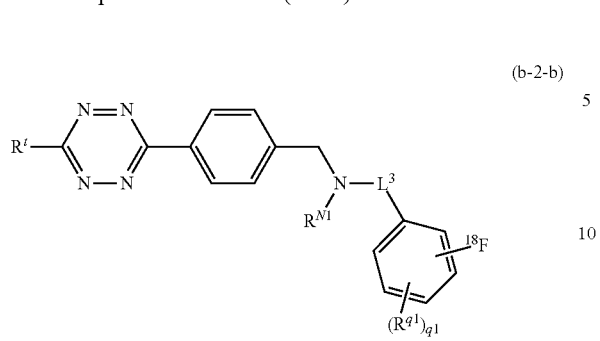

can be prepared from reacting an optionally substituted tetrazine comprising a nucleophic group with an electrophile comprising 18F such as $^{18}$F-SFB. Exemplary synthesis of Formula (b-2-b) is provided in Scheme S2.

Scheme S2

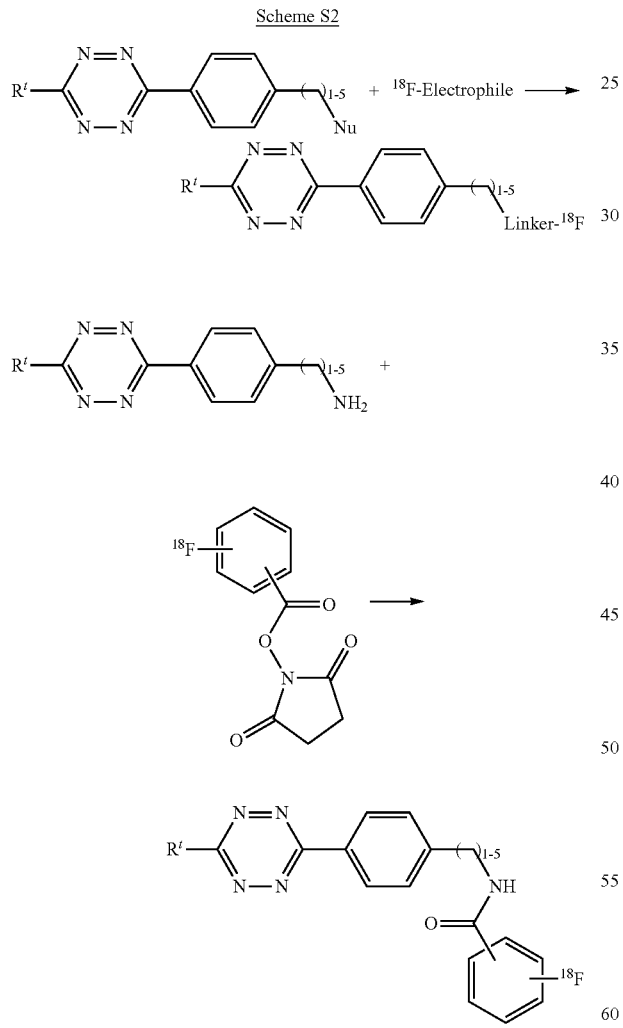

In certain embodiments, the Nu is an amino group. In certain embodiments, the electrophile is an optionally substituted N-succinimidyl comprising 18F. In certain embodiments, the optionally substituted N-succinimidyl is 18F-SFB of the formula

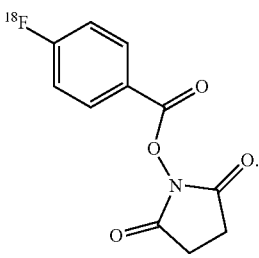 [SMILES: O=C(ON1C(=O)CCC1=O)c1ccc([18F])cc1]

Figure 11A:
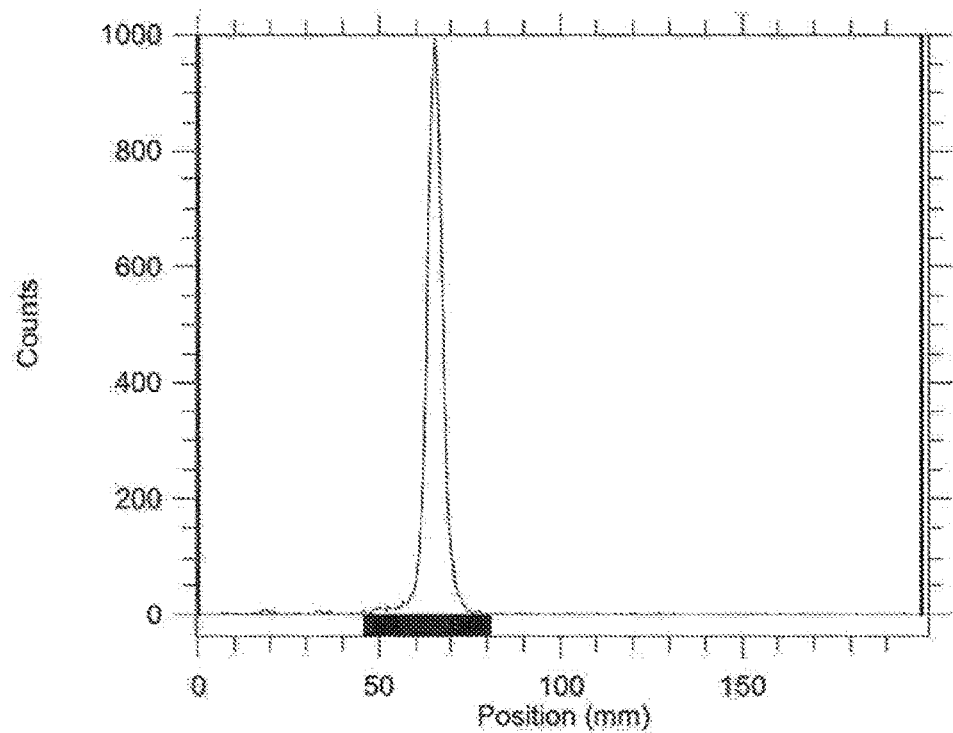
FIGS. 11A-11B show the PD-10 cartridge was eluted with PBS (10×500 µL), and each fragment was collected into a new 1.5 mL tube. The desired product [$^{18}$F]-VHHs usually eluted at tubes #4-7. Characterization (using [$^{18}$F]-DC8-dimer as an example): rTLC chromatography (FIG. 11A, [18F]-Tz 5.
Figure 11B:
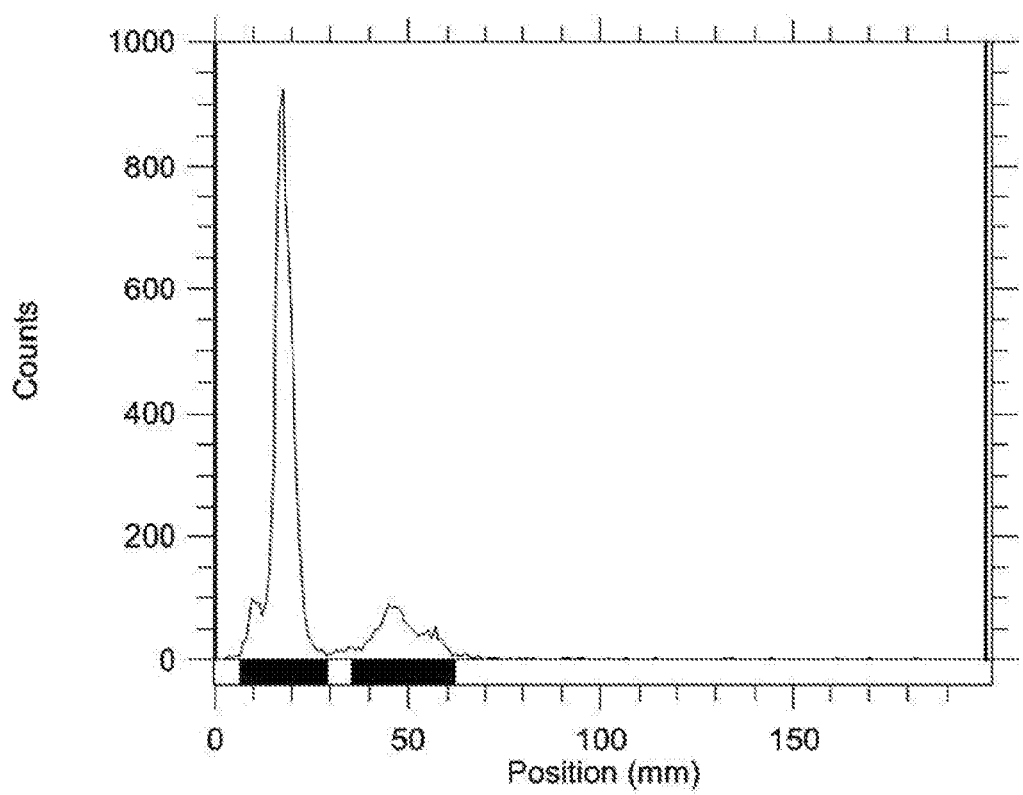

Exemplary synthesis of $^{18}$F-SFB can be found in FIG. 11.

The radioactive protein of Formula (II) can be prepared from a modified protein of Formula (I) with a compound of Formula (b): $^{18}$F—R$^2$ (b), wherein R$^2$ is a reactive group capable of undergoing the click chemistry reaction (Scheme S3):

Scheme S3.

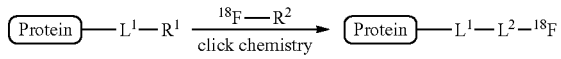

In certain embodiments, R$^1$ is the first click chemistry handle and R$^2$ is the second click chemistry handle. In certain embodiments, R$^2$ is the first click chemistry handle and R$^1$ is the second click chemistry handle.

Click chemistry should be modular, wide in scope, give high chemical yields, generate inoffensive byproducts, be stereospecific, be physiologically stable, exhibit a large thermodynamic driving force (e.g., >84 KJ/mol to favor a reaction with a single reaction product), and/or have high atom economy. Several reactions have been identified which fit this concept:

(1) The Huisgen 1,3-dipolar cycloaddition (e.g., the Cu(I)-catalyzed stepwise variant, often referred to simply as the "click reaction"; see, e.g., Tornoe et al., *Journal of Organic Chemistry* (2002) 67: 3057-3064). Copper and ruthenium are the commonly used catalysts in the reaction. The use of copper as a catalyst results in the formation of 1,4-regioisomer whereas ruthenium results in formation of the 1,5-regioisomer;

(2) Other cycloaddition reactions, such as the Diels-Alder cycloaddition;

(3) Nucleophilic addition to small strained rings like epoxides and aziridines;

(4) Nucleophilic addition to activated carbonyl groups; and (4) Addition reactions to carbon-carbon double or triple bonds.

In certain embodiments, the click chemistry is a Diels-Alder cycloaddition. Exemplary Diels-Alder cycloadditions can be found in U.S. Patent Publication No. 20130266512, which is incorporated by reference herein;

The radioactive protein of Formula (III) can be prepared from a compound comprising an aminooxy moiety with an optionally substituted aldehyde (Scheme S4):

Scheme S4.

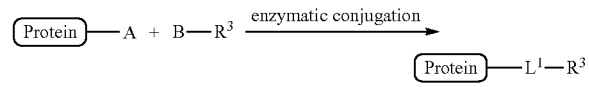

-continued

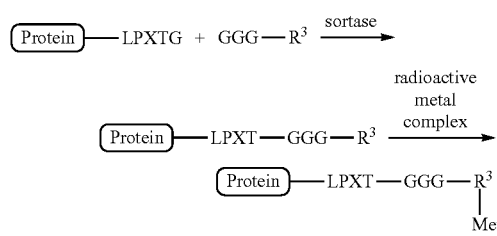

The radioactive protein of Formula (IV) can be prepared from a compound comprising an aminooxy moiety with an optionally substituted aldehyde or an optionally substituted ketone (Scheme S5), wherein $L^G$ is as defined herein.

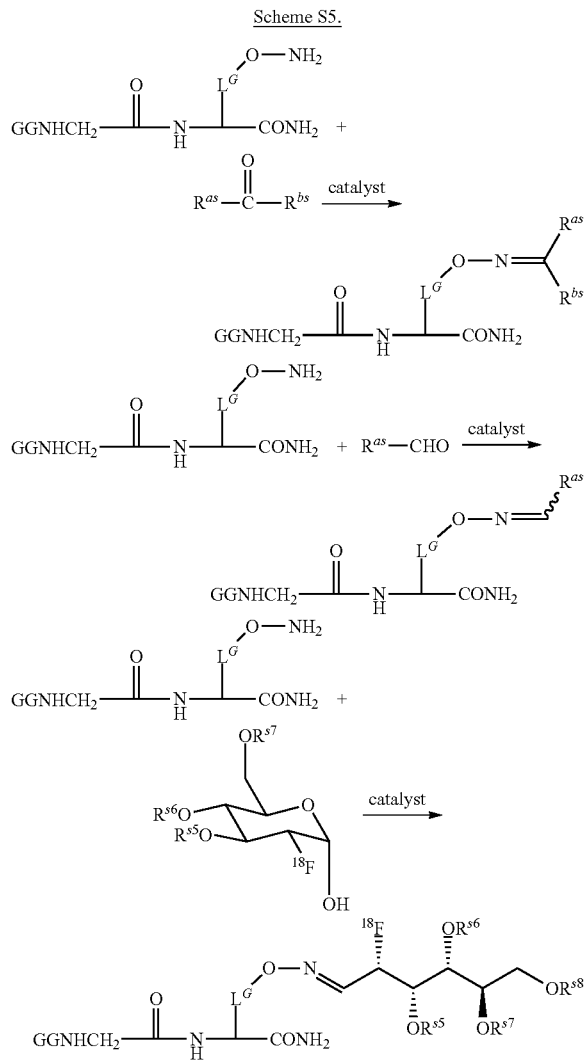

In certain embodiments, the aldehyde is an optionally substituted carbohydrate comprising an aldehyde group or is capable of forming one through isomerism. In certain embodiments, the optionally substituted aldehyde is an optionally substituted monosaccharide. In certain embodiments, the optionally substituted aldehyde is optionally substituted glucose, optionally substituted glyceraldehyde, or optionally substituted galactose. In certain embodiments, the optionally substituted aldehyde is optionally substituted glucose.

In certain embodiments, the catalyst is m-phenylenediamine (mPDA), o-phenylenediamine, p-phenylenediamine, o-aminophenol, m-aminophenol, p-aminophenol, o-aminobenzoic acid, 5-methoxyanthranilic acid, 3,5-diaminobenzoic acid or aniline. In certain embodiments, the catalyst is m-phenylenediamine (mPDA).

In certain embodiments, the radioactive optionally substituted cyclooctene is synthesized by a nucleophilic reaction with an $^{18}F$ anion with a substituted cyclooctene comprising a leaving group $L^G$ (Scheme S6), wherein $L^G$ is as defined herein and $L^{61}$ is optionally substituted aliphatic, optionally substituted heteroaliphatic, optionally substituted arylene, optionally substituted heteroarylene, or optionally substituted heterocyclylene.

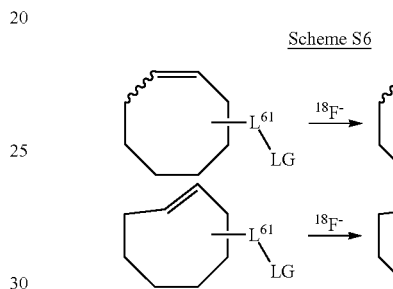

In certain embodiments, $L^{61}$ is optionally substituted hereoaliphatic. In certain embodiments, $L^{61}$ is straight chain heteroaliphatic. In certain embodiments, $L^{61}$ is $-O-C_{1-8}$alkylene. In certain embodiments, $L^{61}$ is $-O-(CH_2)_{1-8}-$.

In certain embodiments, the radioactive optionally substituted cyclooctene is synthesized as shown in Scheme S6-a, wherein $L^{61}$ is as defined herein.

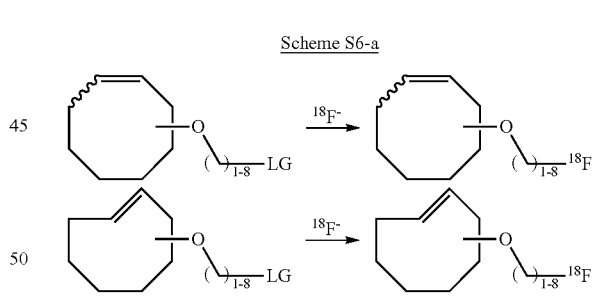

In certain embodiments, the $^{18}F^-$ anion is from an inorganic salt comprising $^{18}F^-$ anion. In certain embodiments, the $^{18}F^-$ anion is from a metal salt comprising $^{18}F^-$ anion. In certain embodiments, the $^{18}F^-$ anion is from IA, IIA, or IIIA metal fluoride. In certain embodiments, the $^{18}F^-$ anion is from transition metal complex comprising $^{18}F^-$.

In certain embodiments, the enzymatic conjugation is a modification using a formylglycine generating enzyme (FGE). In certain embodiments, the protein is an antibody. In certain embodiments, the enzyme is FGE. In certain embodiments, the FGE recognition sequence is CXPXR. In certain embodiments, the FGE recognition sequence is LCTPSRGSLFTGR. In certain embodiments, the radioactive protein is prepared according to Scheme E1.

Scheme E1

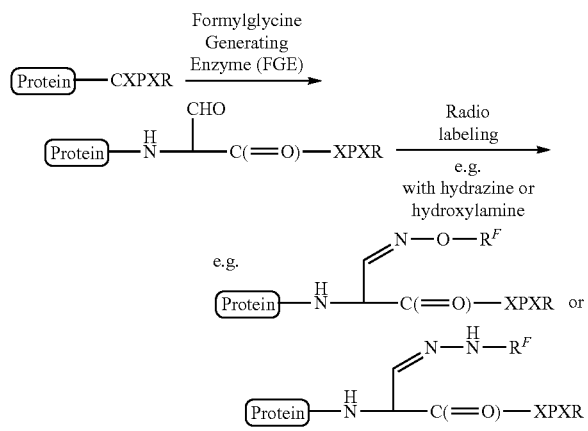

$R^F$ is a reactive group capable of undergoing a click chemistry reaction, comprising a radioactive optionally substituted carbohydrate, or comprising a ligand capable of chelating to a pharmaceutically acceptable radioactive metal complex.
X = an independently amino acid.

It is to be understood that the —CHO group generated from the FGE modification can undergo any suitable reaction to incorporate a radioactive label, for example, a click chemistry handle, a radioactive carbohydrate, or a ligand capable of chelating to a pharmaceutically acceptable radioactive metal complex. Exemplary transformations such as reacting with hydrazine or hydroxylamine are shown in the Scheme E1.

In certain embodiments, the enzymatic conjugation is a modification using sialyltransferases. In certain embodiments, the protein is a cell surface polypeptide. In certain embodiments, the protein is a glycan. An exemplary sialylation is shown in Scheme E2, wherein $R^4$ is as defined herein.

Scheme E2

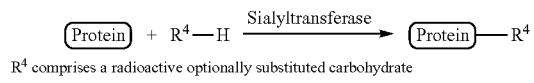

$R^4$ comprises a radioactive optionally substituted carbohydrate

In certain embodiments, $R^4$ comprises radioactive optionally substituted glucose. In certain embodiments, $R^4$ comprises $^{18}$F-FDG. In certain embodiments, $R^4$ comprises radioactive optionally substituted aldolase. In certain embodiments, $R^4$ comprises radioactive optionally substituted mannose.

In certain embodiments, the enzymatic conjugation is a modification using phosphopantetheinyltransferases (PPTases). In certain embodiments, the protein is peptide carrier protein (PCP). In certain embodiments, the protein is acyl carrier protein (ACP). In certain embodiments, the PPT recognition sequence comprises a serine residue. In certain embodiments, the PPTase recognition sequence is DSLEFIASKLA, VLDSLEFIASKLA, or GSQDVLDSLEFIASKLA. In certain embodiments, the phosphopantetheinyltransferase is Sfp. An exemplary modification using PPTase is shown in Scheme E3, wherein $R^F$ is as defined herein Scheme E3

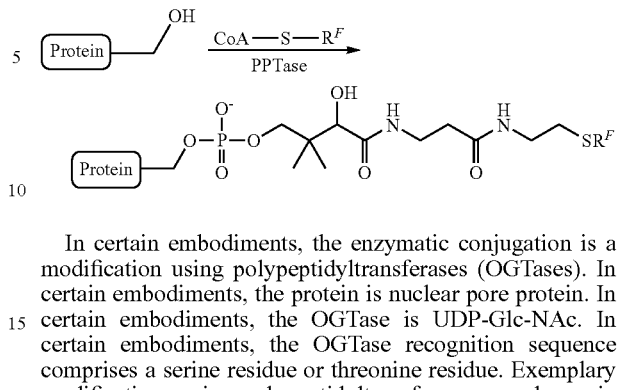

In certain embodiments, the enzymatic conjugation is a modification using polypeptidyltransferases (OGTases). In certain embodiments, the protein is nuclear pore protein. In certain embodiments, the OGTase is UDP-Glc-NAc. In certain embodiments, the OGTase recognition sequence comprises a serine residue or threonine residue. Exemplary modifications using polypeptidyltransferases are shown in Scheme E4, wherein $R^F$ is as defined herein.

Scheme E4

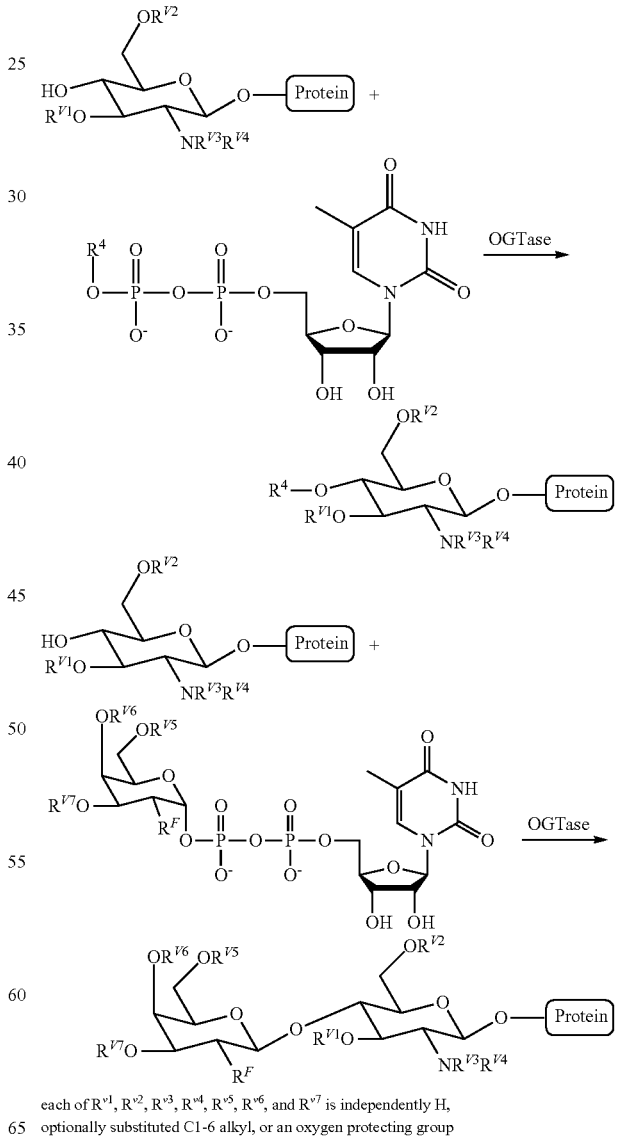

each of $R^{v1}$, $R^{v2}$, $R^{v3}$, $R^{v4}$, $R^{v5}$, $R^{v6}$, and $R^{v7}$ is independently H, optionally substituted C1-6 alkyl, or an oxygen protecting group In certain embodiments, the enzymatic conjugation is a modification using transglutaminase (TGases). In certain embodiments, the protein is an antibody. In certain embodiments, the TGase recognition sequence comprises a glutamine (Q) residue. In certain embodiments, the TGase recognition sequence comprises XXQXX. In certain embodiments, the protein recognition sequence is GGGSLLQG, PNPQLPF, PKPQQFM, or GQQQLG. In certain embodiments, the protein recognition sequence comprises a lysine (K) residue. In certain embodiments, the protein recognition sequence is MRHKGS. An exemplary modification using TGases is shown in Scheme E5, wherein $R^F$ is as defined herein.

Scheme E5

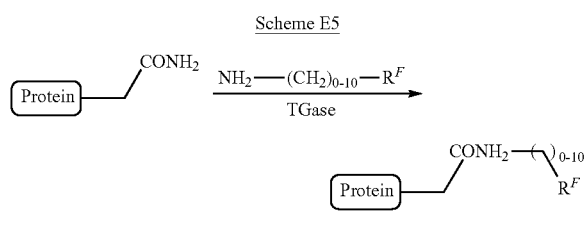

In certain embodiments, the enzymatic conjugation is a modification using protein farnesyltransferase (PFTase). In certain embodiments, the protein is an antibody. In certain embodiments, the PFTase recognition sequence comprises CaaX, wherein each instance of a is independently an aliphatic amino acid and X is as defined herein. Exemplary modifications using PFTases are shown in Scheme E6, wherein $R^F$ is as defined herein.

Scheme E6

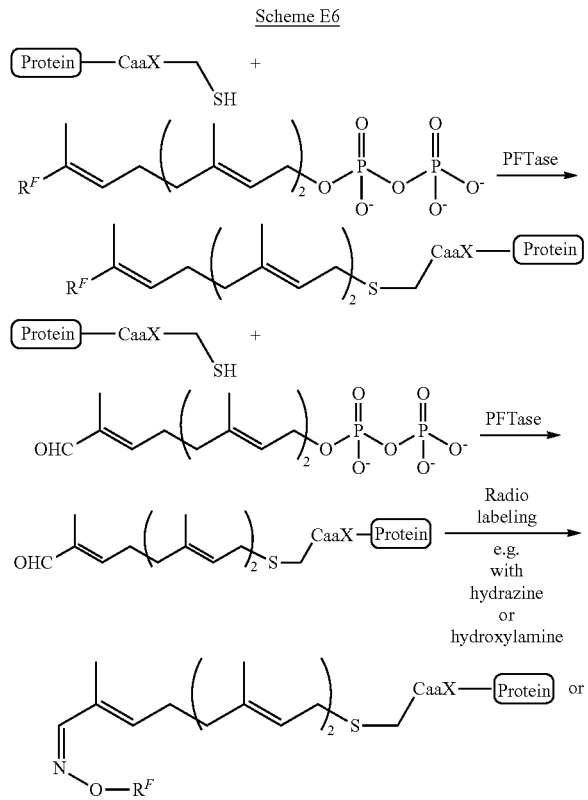

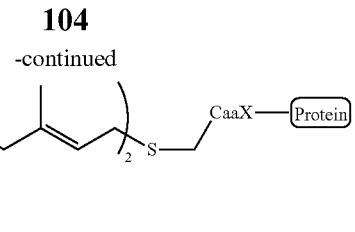

In certain embodiments, the enzymatic conjugation is a modification using biotin ligases. In certain embodiments, the protein is an antibody. In certain embodiments, the biotin ligase recognition sequence comprises lysine (K). In certain embodiments, the biotin ligase recognition sequence comprises GLNDIFEAQKIEWHE. In certain embodiments, the enzyme is E. coli biotin ligase, BirA. An exemplary modification using biotin ligases is shown in Scheme E7, wherein $R^F$ is as defined herein.

Scheme E7

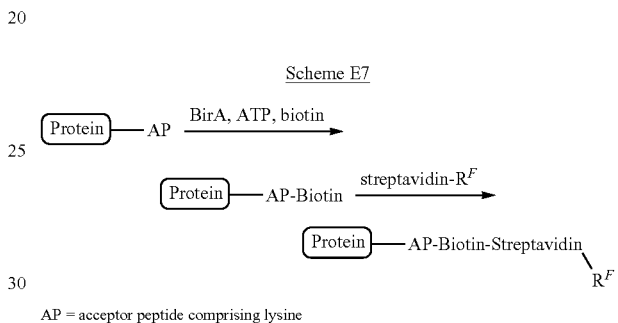

AP = acceptor peptide comprising lysine

In certain embodiments, the enzymatic conjugation is a modification using lipoic acid ligases (LplAs). In certain embodiments, the protein is an antibody. In certain embodiments, the protein is a growth factor receptor. In certain embodiments, the LplA recognition sequence comprises GFEIDKVWYDLDA. In certain embodiments, the enzyme is E. coli Lpl. An exemplary modification using LplAs is shown in Scheme E8, wherein $R^F$ is as defined herein.

Scheme E8

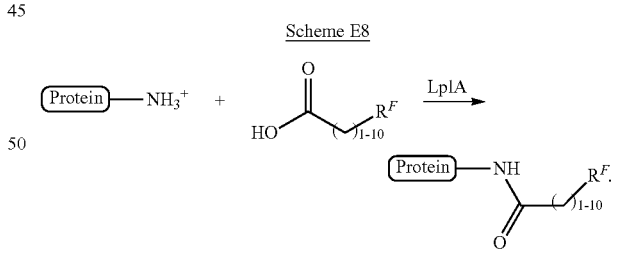

In certain embodiments, the enzymatic conjugation is a modification using N-myristoyltransferase (NMT). In certain embodiments, the protein is an antibody. In certain embodiments, the protein is a tyrosine kinase. In certain embodiments, the protein is a HIV-1 matrix protein. In certain embodiments, the protein is a HIV Gag. In certain embodiments, the protein is an ADP-ribosylating factor. In certain embodiments, the NMT recognition sequence comprises GXXXS/T, wherein X is any amino acid. An exemplary modification using NMT is shown in Scheme E9, wherein $R^F$ is as defined herein.

Scheme E9

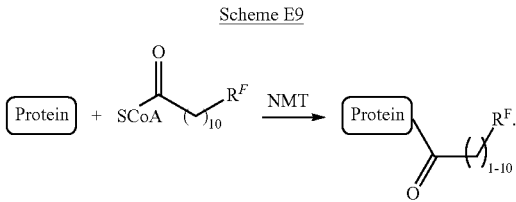

In certain embodiments, $R^F$ is a reactive group capable of undergoing a click chemistry reaction. In certain embodiments, $R^F$ is $R^1$ as defined herein. In certain embodiments, $R^F$ is optionally substituted tetrazine. In certain embodiments, $R^F$ is optionally substituted tetrazine comprising $^{18}$F. In certain embodiments, $R^F$ is optionally substituted tetrazine comprising $^{18}$F-FDG or a fragment thereof. In certain embodiments, $R^F$ is optionally substituted tetrazine comprising $^{18}$F-SFB or a fragment thereof. In certain embodiments, $R^F$ is optionally substituted cyclooctene. In certain embodiments, $R^F$ is optionally substituted trans-cyclooctene. In certain embodiments, $R^F$ is optionally substituted trans-cyclooctene comprising $^{18}$F. In certain embodiments, $R^F$ is comprises a ligand capable of chelating to a pharmaceutically acceptable radioactive metal complex. In certain embodiments, $R^F$ is $R^3$ as defined herein. In certain embodiments, $R^F$ comprises a ligand capable of chelating to a pharmaceutically acceptable metal complex comprising $F^{18}$. In certain embodiments, $R^F$ is Y as defined herein. In certain embodiments, $R^F$ comprises a radioactive optionally substituted carbohydrate. In certain embodiments, $R^F$ is $R^4$ as defined herein. In certain embodiments, $R^F$ comprises $^{18}$F-FDG or a fragment thereof.

Kits

Some aspects of this invention provide kits useful for labeling proteins with radioactive agents and/or hydrophilic polymers, and/or for generating radiolabeled sortase substrate peptides.

In some embodiments, the kit comprises a radiolabeled protein generated according to an inventive method provided herein. In some embodiments, the kit comprises (i) a single domain antibody comprising a sortase recognition sequence, (ii) a sortase substrate comprising a first click chemistry handle, and (iii) a hydrophilic polymer conjugated to a second click chemistry handle. In some embodiments, the kit comprises (i) a first single domain antibody comprising a first click chemistry handle, and (ii) a second single domain antibody comprising a second click chemistry handle. In some embodiments, the kit comprises (i) a first single domain antibody comprising a sortase recognition sequence, (ii) a first sortase substrate, wherein the first sortase substrate comprises a first click chemistry handle, (iii) a second single domain antibody comprising a sortase recognition sequence, and (iv) a second sortase substrate, wherein the second sortase substrate comprises a second click chemistry handle. In some embodiments, the kit further comprises a radionuclide. In some embodiments, the radionuclide is carbon-11, carbon-14, nitrogen-13, oxygen-15, fluorine-18, rubidium-82, copper-61, copper-62, copper-64, yttrium-86, gallium-68, zirconium-89, or iodine-124. In some embodiments, the kit further comprises a sortase A from *Staphylococcus aureus* (SrtAaureus), sortase A from *Streptococcus pyogenes* (SrtApyogenes), sortase B from *S. aureus* (SrtBaureus), sortase B from *Bacillus anthracis* (SrtBanthracis), or sortase B from *Listeria monocytogenes* (SrtBmonocytogenes).

In some embodiments, the kit further comprises a buffer or reagent useful for carrying out a sortase-mediated transpeptidation reaction.

EXAMPLES

In order that the invention described herein may be more fully understood, the following examples are set forth. The examples described in this application are offered to illustrate the methods, compositions, and systems provided herein and are not to be construed in any way as limiting their scope.

Example 1. Enzyme-Mediated Dual-Labeling of Antibodies for Multimodal Imaging and to Manipulate their Characteristics Structures of VHHs show that their C-terminus is positioned away from the antigen binding site[13]. Therefore a chemical approach was chosen to link two fully functional VHHs via their C-termini to ensure that their antigen binding capacity would not be compromised by modification of one of the N-termini in the resulting fusion, and that the two binding sites thus created would be equivalent, which may be more difficult to ascertain for genetic fusions.

Figure 1B:
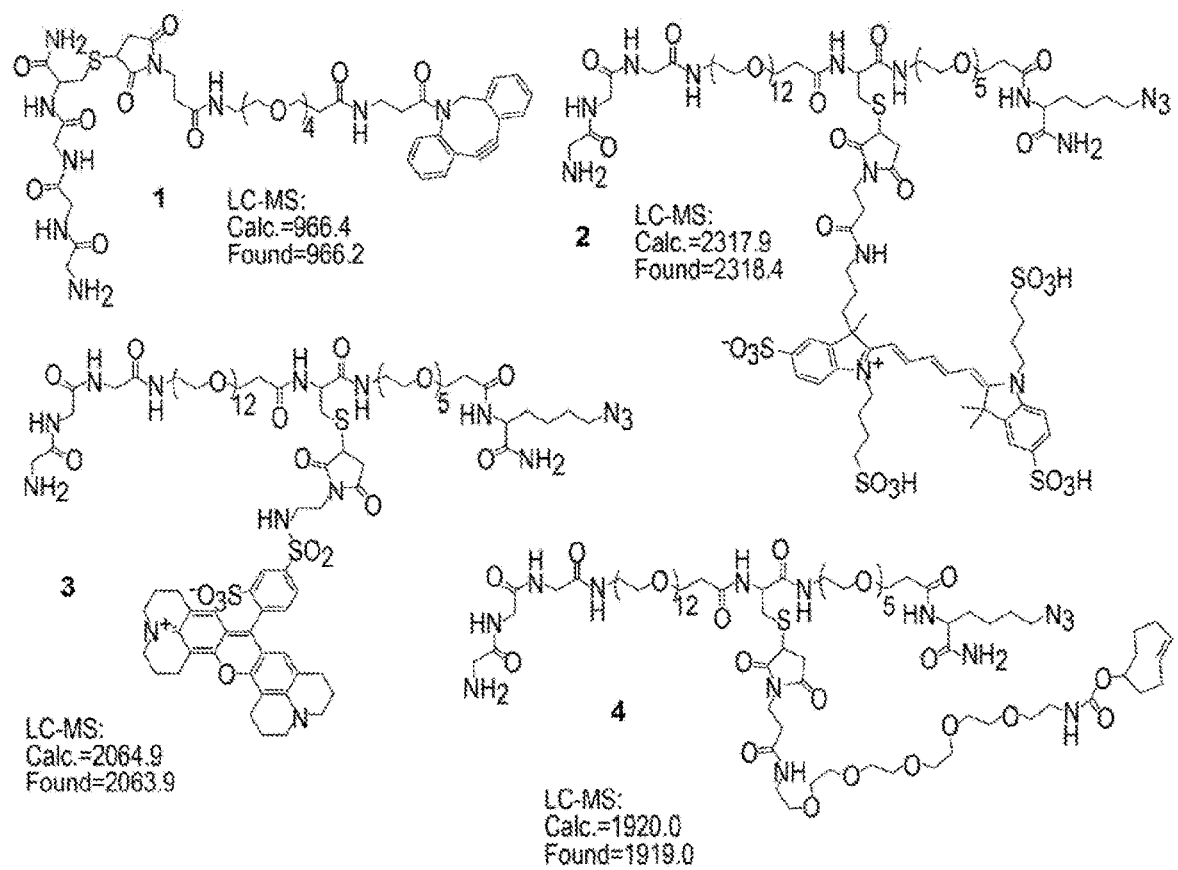
Figures 2A, 2B:
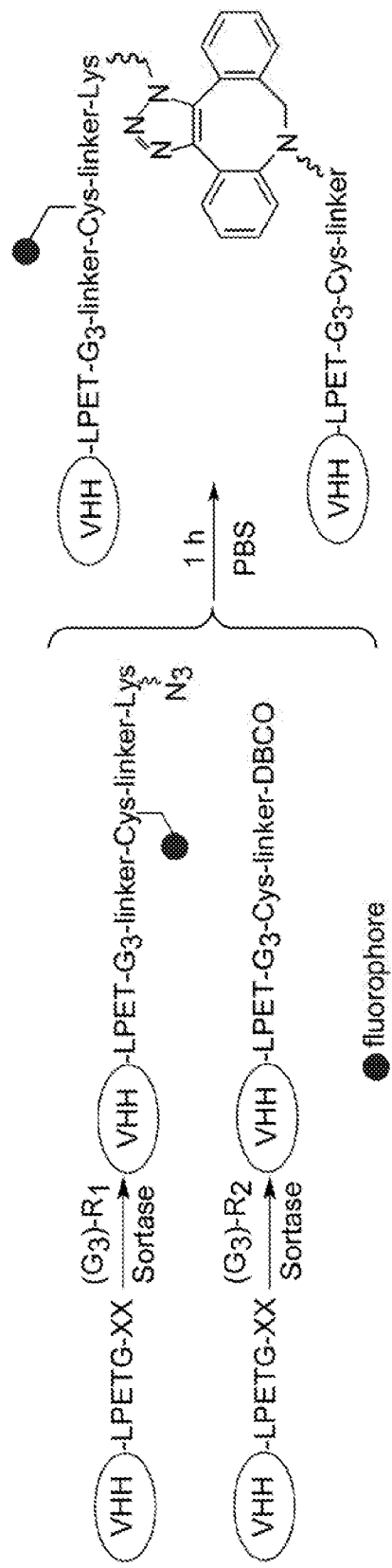
FIGS. 2A-2F show synthesis of VHH-derivatives (FIG. 2A and FIG. 2B). Characterizations were performed on all the products (FIG. 2C and FIG. 2D). Here is shown the LC-MS and SDS-PAGE analysis for DC13. Numbers indicate the followings: #1: marker, #2: DC13, #3: DC13-DBCO, #4: DC13-azide-Texas Red, #5: DC13-dimer-Texas Red, #6: DC13-azide-Alexa647. #7: DC13-dimer-Alexa647.
Figure 2C:
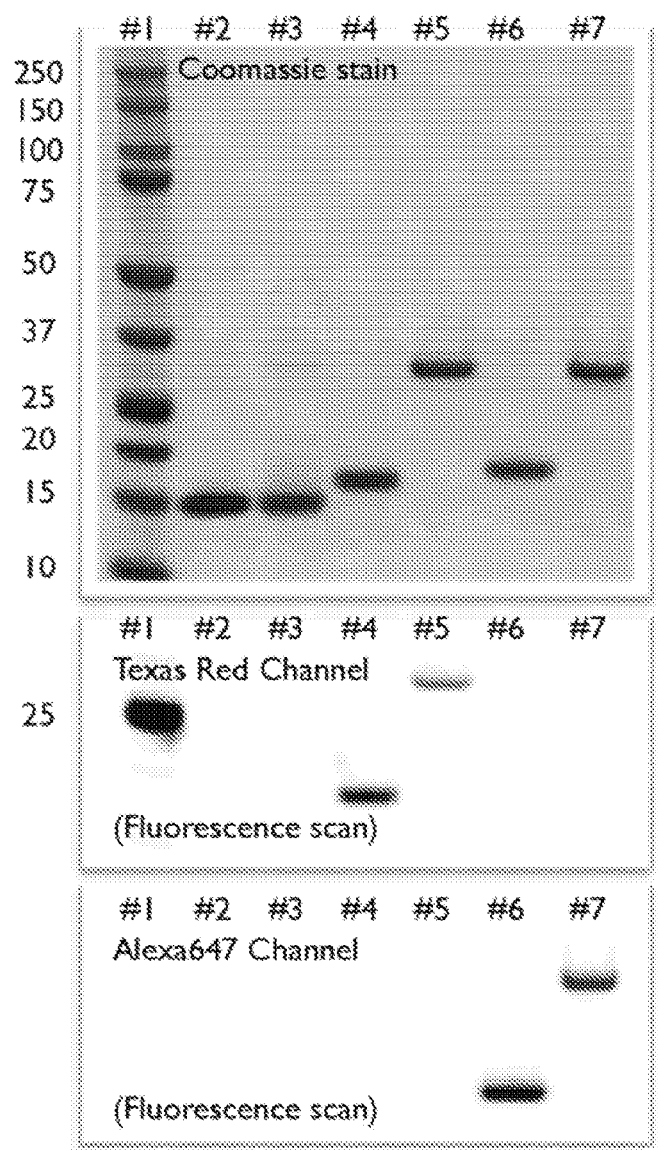
Figure 2D:
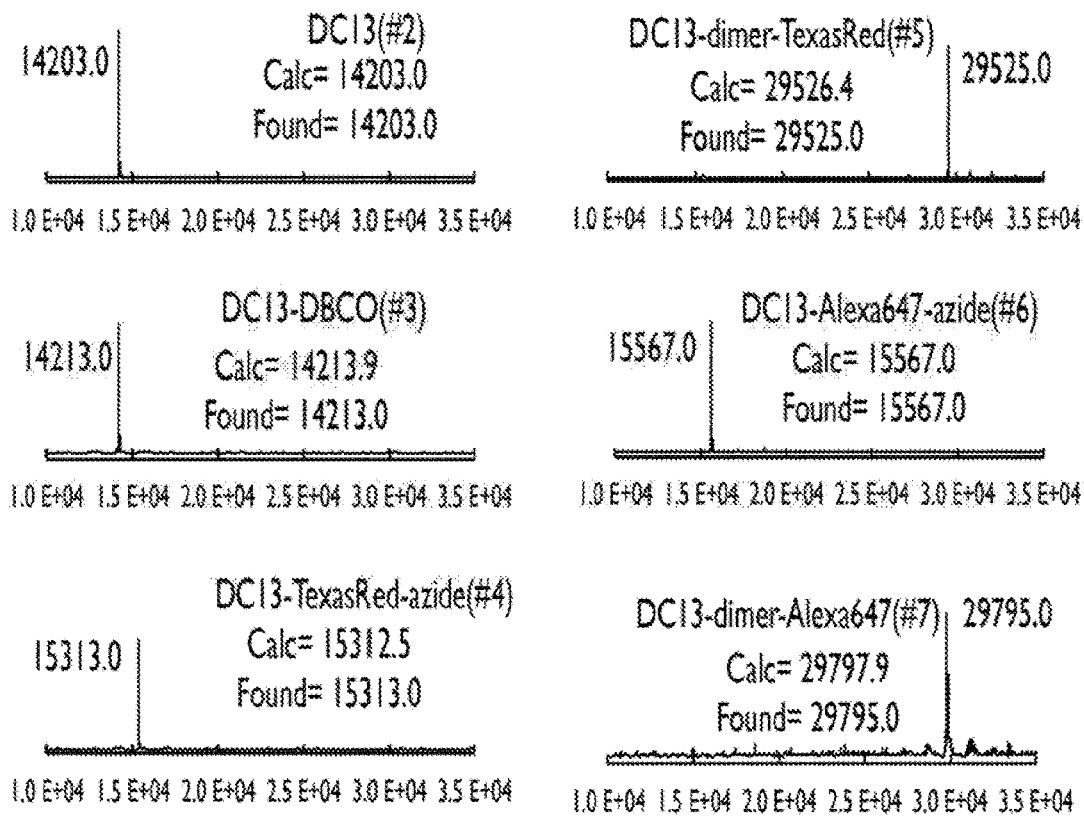
Figure 2E:
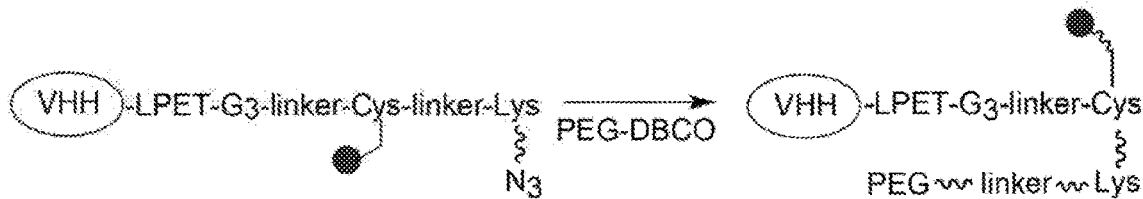
Figure 2F:
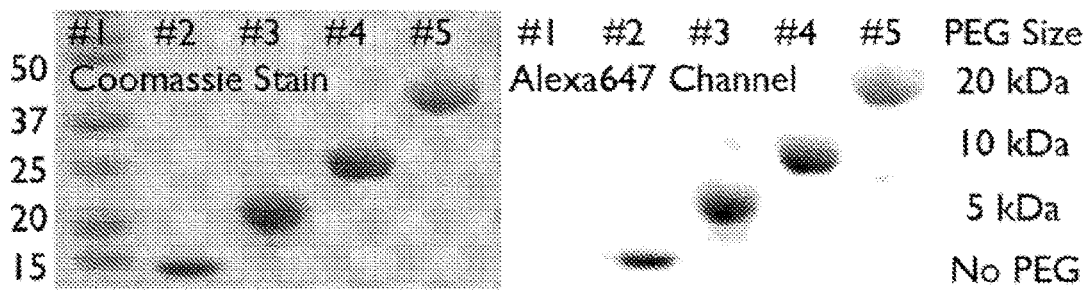
Figure 3A:
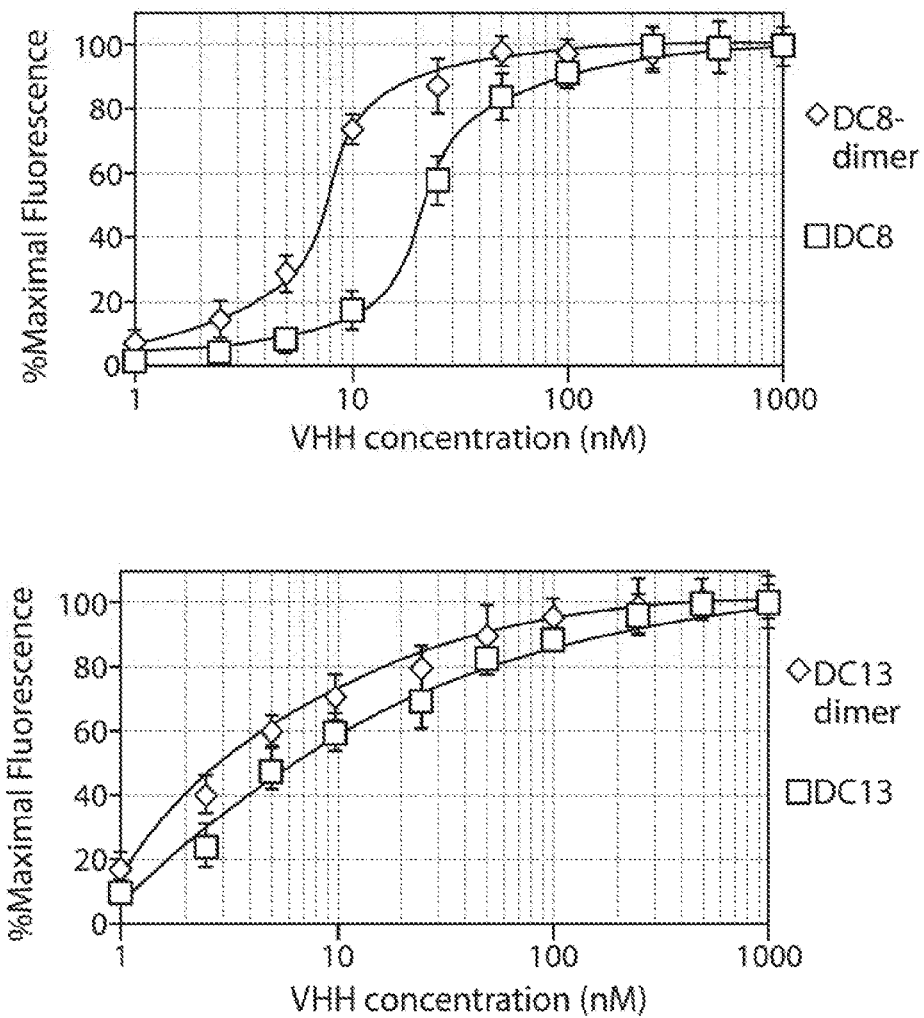
FIGS. 3A-3D (FIGS. 3A-3B) show dimers that are able to stain their targets with increased efficiency compared to their corresponding monomers; for FIG. 3A: cells were stained in vitro with the indicated concentrations of Alexa647-labeled VHH monomers or dimers; for FIG. 3B: equal amount of DC8 monomer and DC8-dimer is injected IV. 2 h p.i., the mice are euthanized and spleens are excised for two-photon imaging.
Figure 3B:
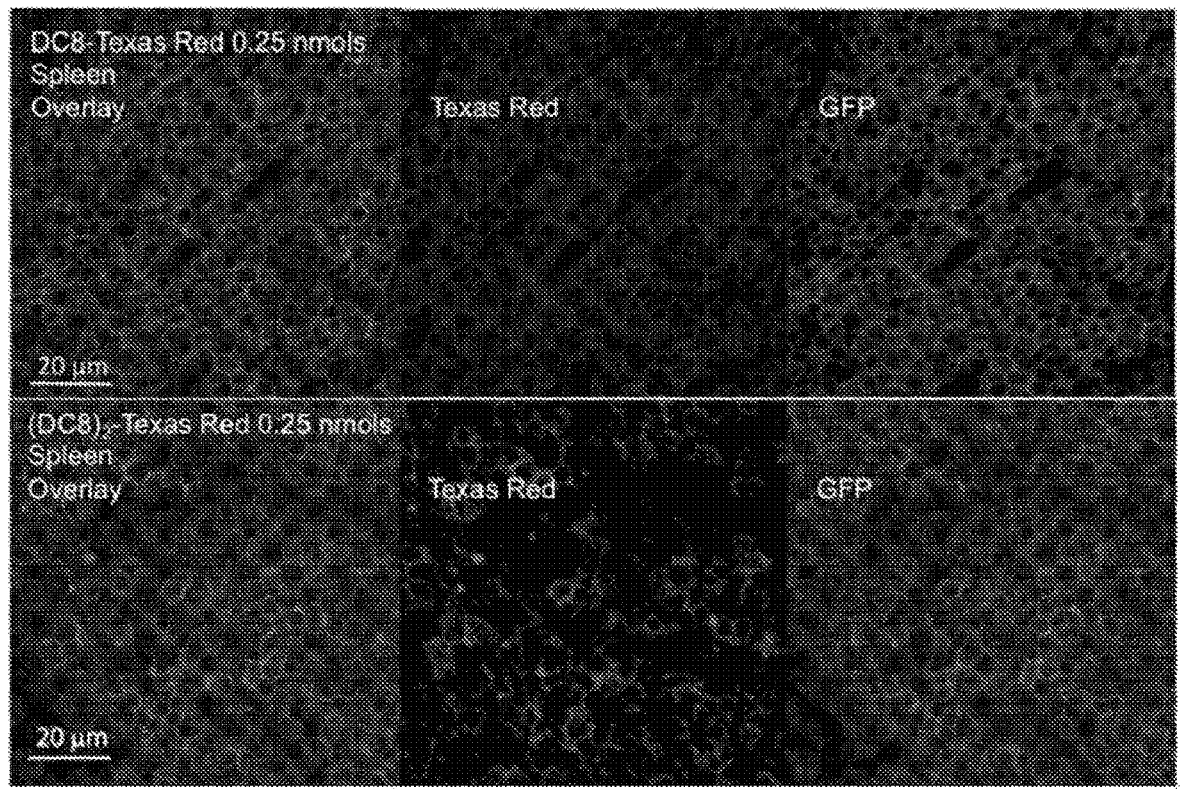
Figure 3C:
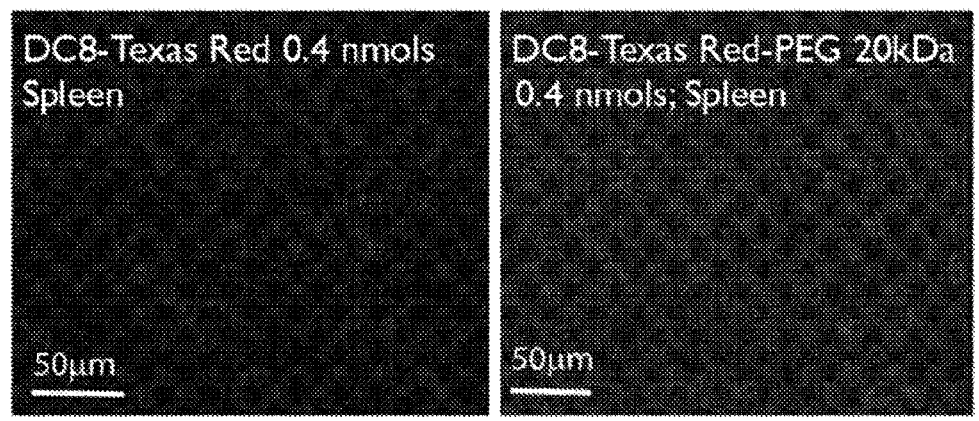
Figure 3D:
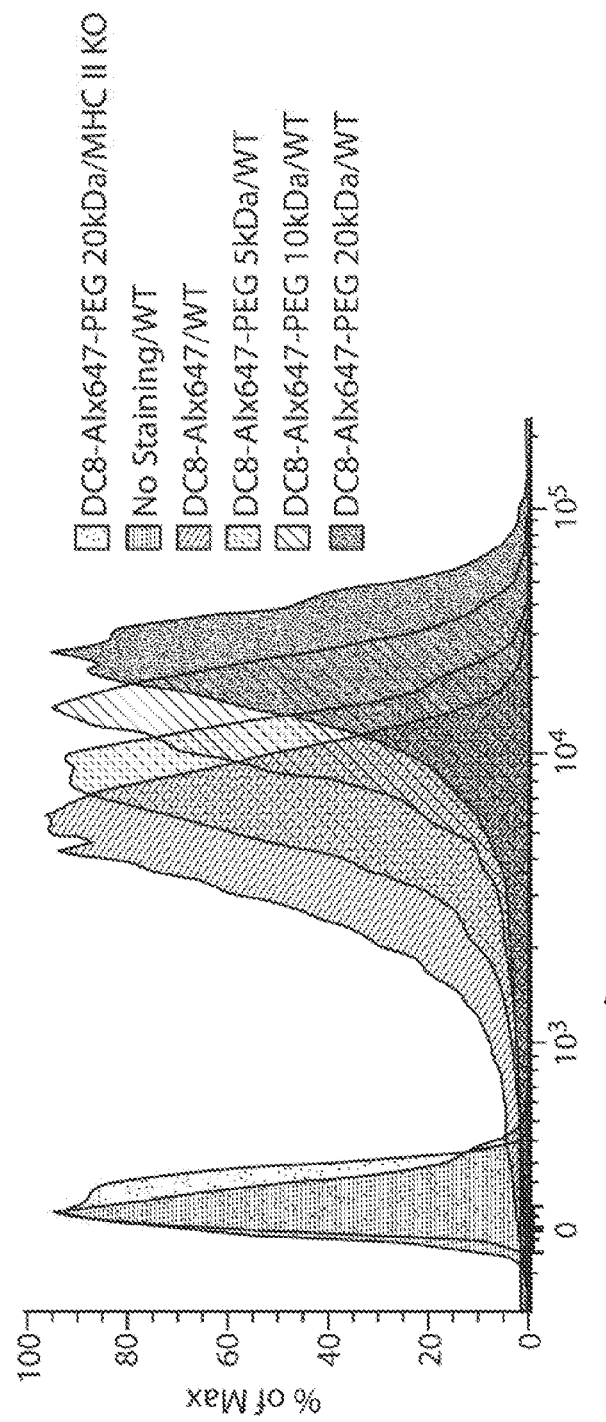
Figures 4D, 4E, 4F:
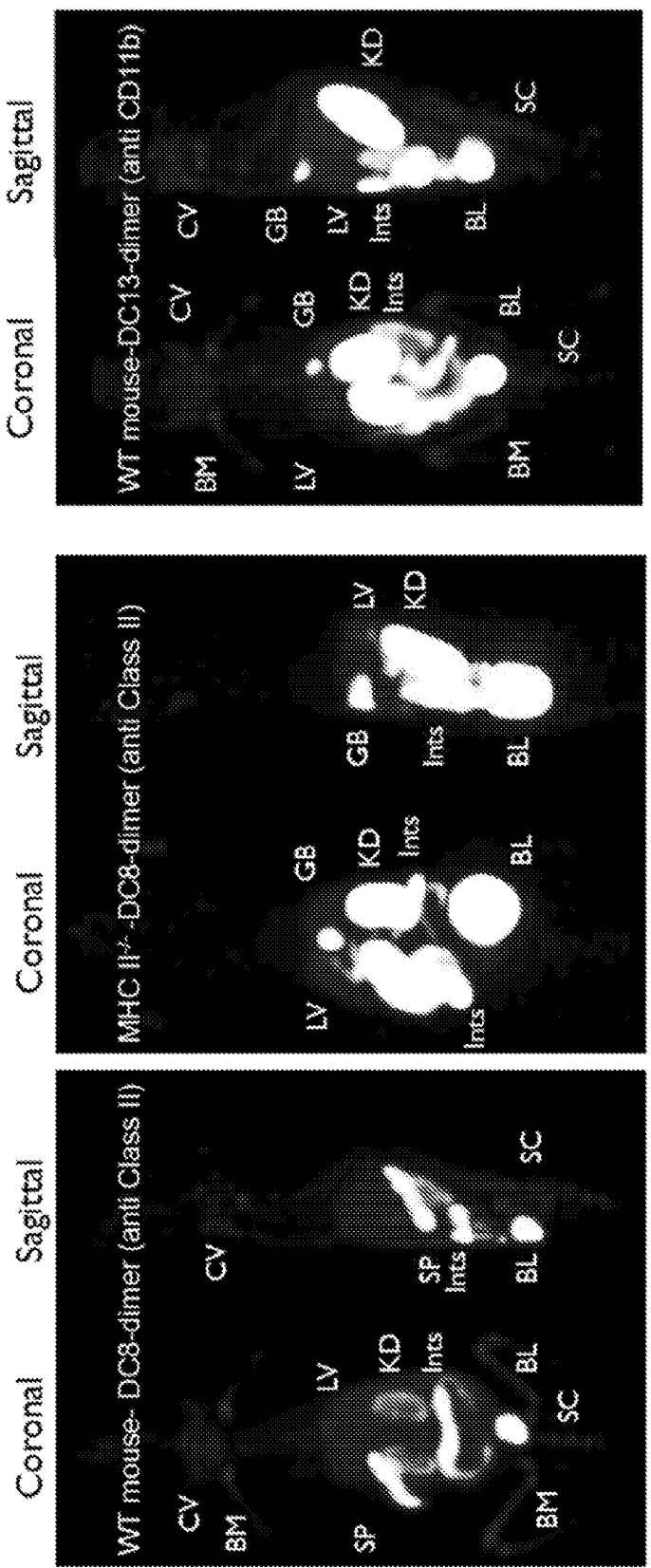
Figures 4G, 4H, 4I:
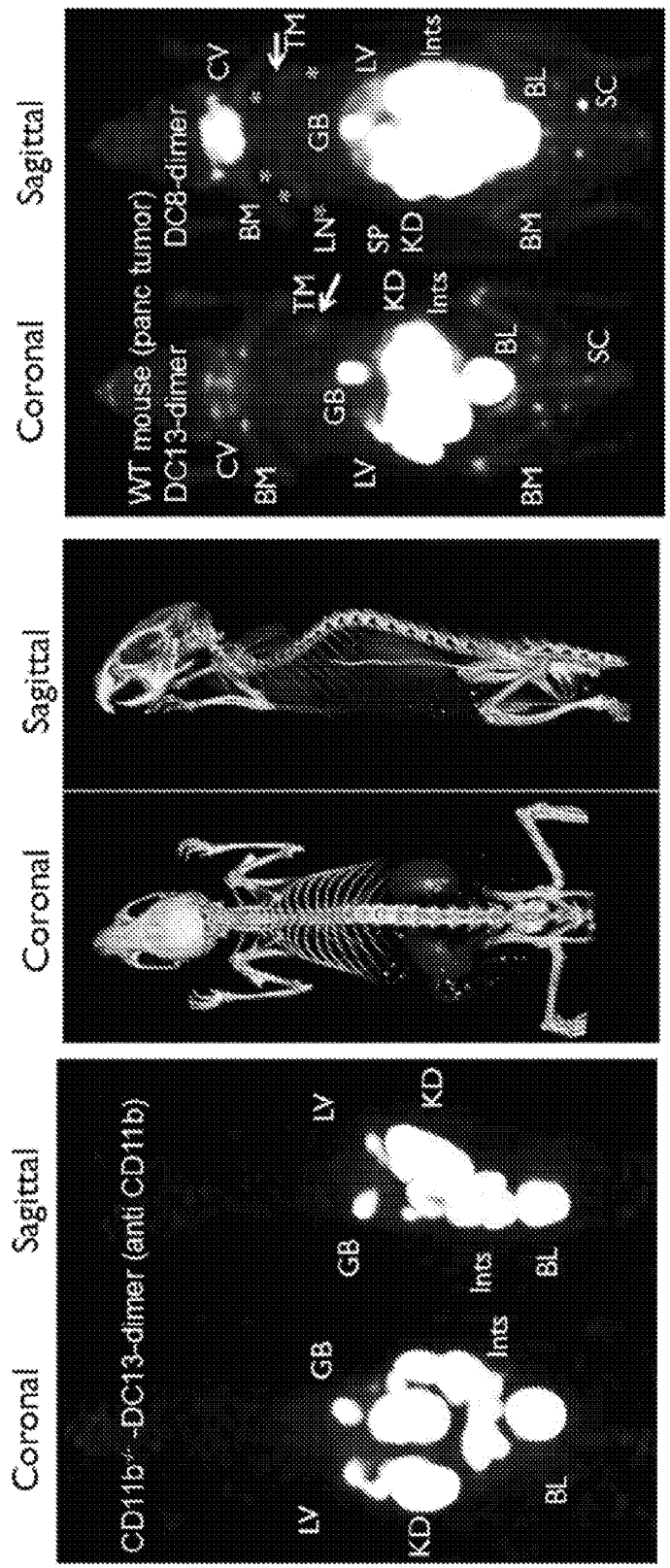
Figure 5A:
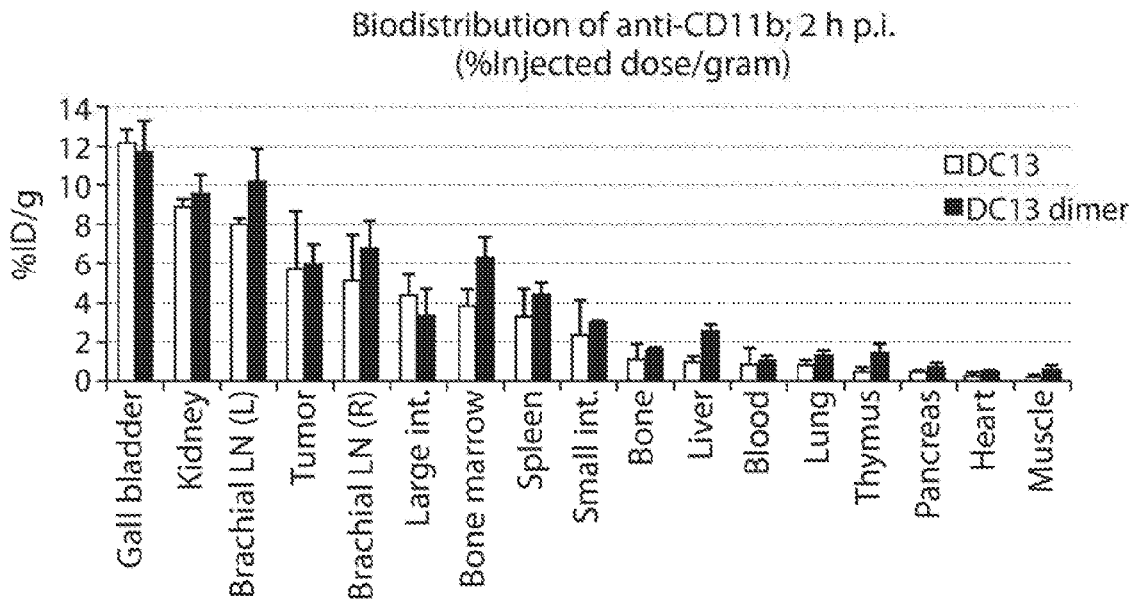
FIGS. 5A-5D (FIGS. 5A-5B) show postmortem biodistribution of $^{18}$F-VHHs in all organs. Mice were injected with same amount of either $^{18}$F-VHH or $^{18}$F-VHH dimer. 3 h p.i., mice were euthanized and activity in different organs were measured.
Figure 5B:
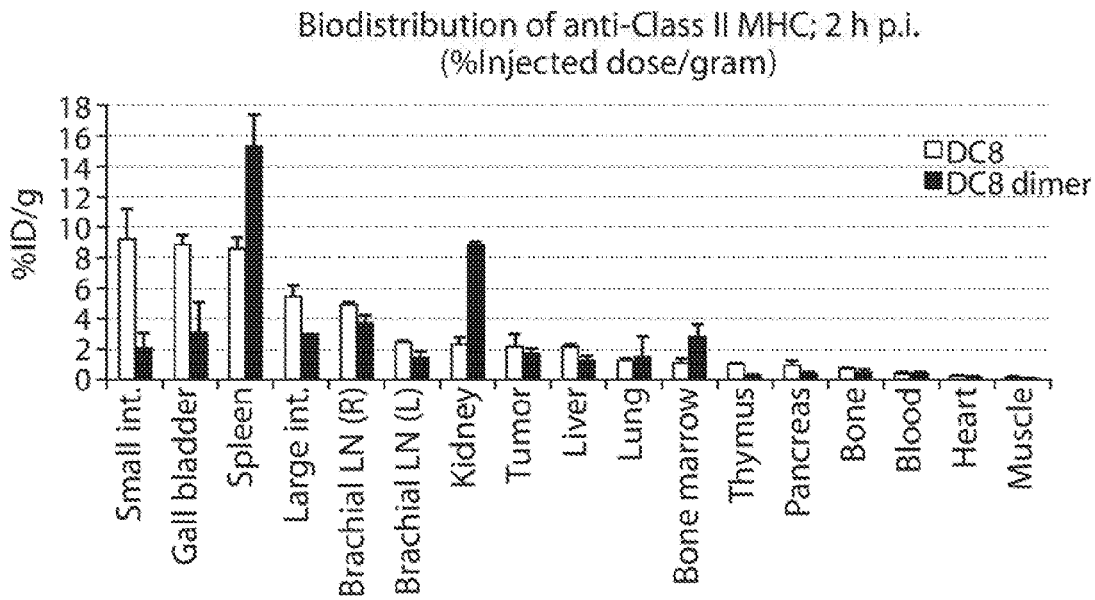
Figure 5C:
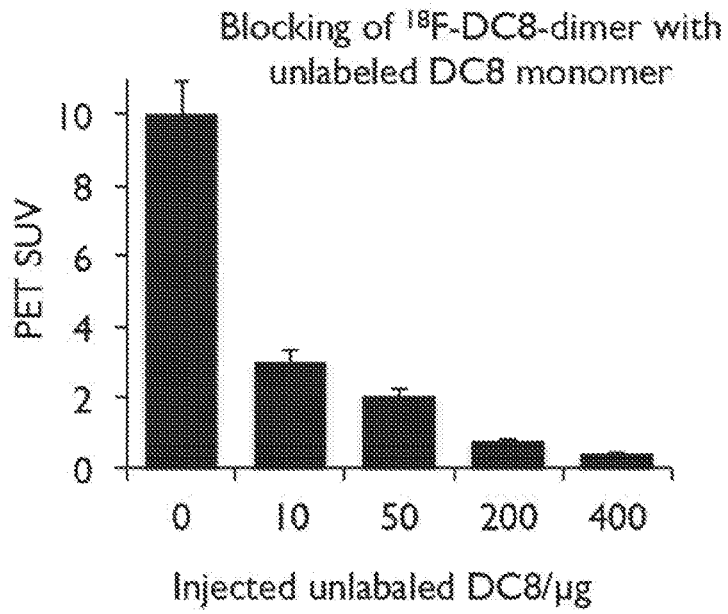

Four sortase substrates were designed and synthesized for production of dimers or PEGylated VHHs (FIG. 1). The substrates either contain two bioorthogonal handles or a handle and a flourophore. The Alexa647-labeled substrate was designed such that the reaction products could be used in FACS experiments to estimate relative in vitro binding affinities. The Texas Red-modified substrate was designed to enable two-photon microscopy and to estimate relative in vivo binding affinities; the TCO-modified substrate was produced to allow rapid installation of a tetrazine-functionalized radioactive tag for PET, in this case an isotopically labelled $^{18}$F-labeled-tetrazine radioactive tag for PET (t1/2=110 min.18F t1/2<2 h). The dimers were produced as exemplified in FIG. 2. For DC8 (anti Class II), splenocytes were stained with different concentrations of monomers and dimers and analyzed by FACS. For DC13 (anti CD11b), the CD11b+ mutuDC dendritic cell line was used. For Class II MHC and CD11b, VHH dimers bind approximately 3.3 and 2.3-fold better than their corresponding monomers respectively (FIG. 3). The in vivo binding characteristics of the VHH dimers versus monomers were evaluated. Due to the more abundant expression of Class II MHC molecules on splenocytes compared to that of CD11b, the in vivo binding affinity for anti-Class II dimers was explored. Mice were injected i.v. with equal amounts of monomers and dimers (0.25 nmol) of DC8. 2 h p.i., mice were euthanized and lymphoid organs were excised for examination. Monomers and dimers yielded different staining patterns (FIG. 3B), with the dimer showing interspersed yet more pronounced staining than the monomer, corroborating the FACS results. To render monomers and dimers suitable for immuno-PET, dimer VHHs were produced using substrate 4. To produce the $^{18}$F-tetrazine, a method was applied that was automated in its key steps to minimize operator radiation exposure in the course of preparation (FIG. 4A). The $^{18}$F-labeled anti Class II and anti CD11b dimers were produced and applied them to PET imaging (FIG. 4). PET showed that both the dimers stained lymphoid organs (FIG. 4). The anti Class II MHC dimer showed stronger staining of lymphoid organs, particularly the spleen, compared to the anti CD11b dimer (FIGS. 4D and 4F). This may be attributed to the fact that in spleen there are fewer CD11b+ cells compared to Class II MHC+ cells and less CD11b expressed per cell. Specificity was established by blocking the targets of these VHHs by introduction of unlabeled VHHs as competitors prior to imaging. PET imaging conducted 2 h p.i. of $^{18}$F-labeled VHHs showed effective blocking of signal in the lymphoid organs, further underlining the specificity of the signals (FIG. 5C). To further confirm the specificity of the dimers in the absence of competing VHHs, MHC II$^{-/-}$ and CD11b$^{-/-}$ mice were imaged. No PET signals were detected in lymphoid organs, further confirming the specificity of both dimers (FIGS. 4E-4G). Monomers and dimers do not differ in uptake in kidneys and intestine, organs commonly targeted non-specifically by VHHs in the course of their clearance[14]. These experiments helped set the stage to explore ability of VHH dimers to image tumors. Two types of tumors were imaged with the developed bivalent VHHs by engraftment of mice with the B16 melanoma or the pancreatic tumor cell line panc02. Both the dimers readily detected the lymphoid organs as well as the B16 melanoma tumor or the panc02 graft. Upon excision, the panc-tumors were no more than ~ 1-2 mm in diameter, showing the method to be sensitive. Postmortem biodistribution analysis correlated well with the FACS and two-photon results as well (FIGS. 5A-5B). It was examined whether circulatory half-life could be manipulated to further improve the signal to noise ratio. PEGylation of VHHs results in increased circulatory half-life, where the increase correlates with the size of the attached PEG group[15]. VHHs sortagged with substrate 2 or 3 were reacted with DBCO-functionalized PEG (5 kDa, 10 kDa or 20 kDa) to yield the final PEGylated VHHs (FIGS. 2E-2F). B6 mice received 5 µg of PEGylated VHH and were euthanized 3 h later, followed by dissection of lymph nodes and spleen for FACS and two-photon microscopy. FACS showed a significant increase in staining of the PEGylated DC8-Alexa647 versus the non-PEGylated DC8. An approximate 30%, 100%, and 220% increase in staining was observed for 5 kDa, 10 kDa, or 20 kDa PEG-conjugated DC8, respectively, establishing a correlation between the size of the attached PEG moiety and their staining efficiency (FIG. 3D). When DC8-Alexa647-PEG-20 kDa were injected, which showed the strongest binding in vivo, into a MHC II-mouse, FACS analysis showed no staining in the spleen (FIG. 3D). This confirmed that PEGylation does not affect the specificity of the VHHs.

Figure 5D:
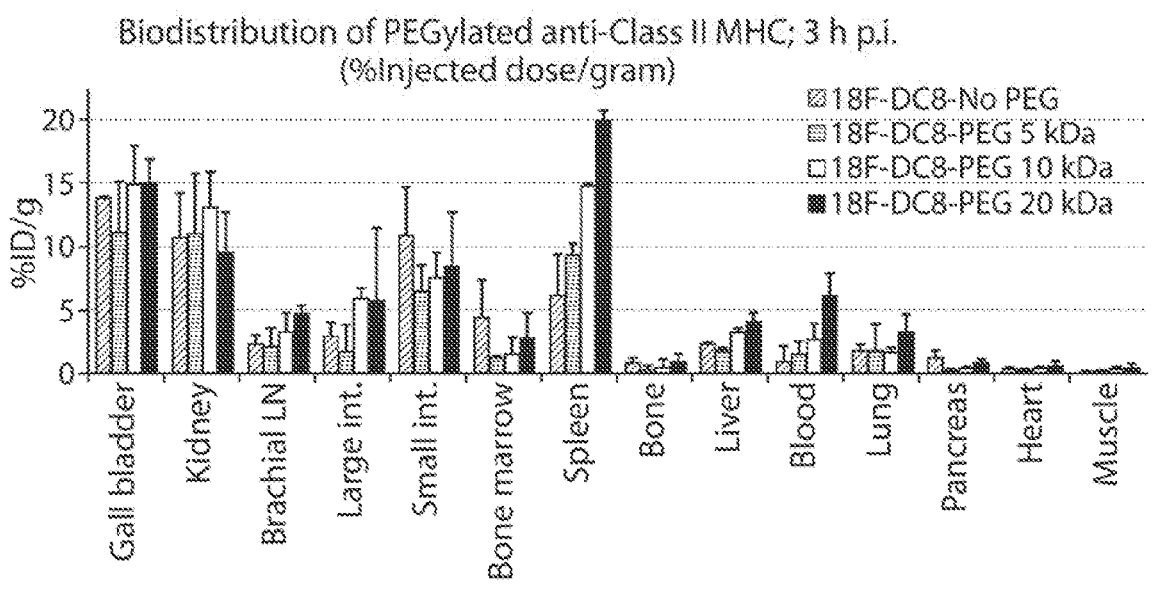

The PEGylated VHHs were explored for their suitability in PET imaging. VHH DC8 was PEGylated and modified with an $^{18}$F radionuclide. PEGylated VHHs showed increased staining of the lymphoid organs, confirming FACS and two-photon microscopy (FIG. 5D). The longer circulatory half-life of PEGylated VHHs may increase the likelihood of a VHH binding to its target, as long as target accessibility is not compromised by PEGylation. The $^{18}$F-labeled-DC8-PEG-20 kDa had the highest PET signal in blood at the time of imaging (3 h p.i) (FIG. 5D). While the larger 20 kDa PEG can significantly increase the staining efficiency in lymphoid organs, it can delay circulatory clearance, a factor to consider when isotopes with short half-lives, such as 18F or 11C, are being used. However, a 10 kDa or a 5 kDa PEG-modified VHH can still significantly increase staining efficiency and yet be rapidly cleared. For labeling of VHHs, the use of isotopes with longer half-lives, such as $^{89}$Zr or $^{64}$Cu, the use of a 20 kDa PEG moiety may improve staining.

In summary, the methods provided herein may produce site-specifically PEGylated or bivalent single domain antibodies equipped with a fluorophore and/or radionuclide ($^{18}$F) for the different imaging modalities. The reaction conditions are compatible with full retention of biological activity of the fusion partners. By cytofluorimetry, dimers bind approximately 3 times more avidly to their targets. Two-photon microscopy demonstrated that Texas Red-labeled bivalent single domain derivatives bind more efficiently to their targets. PEGylated fluorescent VHHs showed improved staining in vivo, with larger PEG substituents giving stronger signals in FACS. In immuno-PET experiments, bivalent $^{18}$F-labeled VHHs better stained lymphoid organs in vivo than monomers. $^{18}$F-labeled PEGylated VHHs showed improved staining, with higher MW PEG substituents giving stronger signals. Finally, immuno-PET of two different models of tumor-bearing mice, showed that the DC8-dimer and DC13-dimer detected not only lymphoid organs, but also showed the location of ectopic melanoma and pancreatic tumor grafts as small as about 1 mm in size. Overall, these data provide support that derivatives of single domain antibodies are a valuable addition to the current imaging and radiodiagnostic approaches.

REFERENCES

[1] T. Olafsen, S. J. Sirk, S. Olma, C. K.-F. Shen, A. M. Wu, *Tumor Biol.* 2012, 33, 669-677.

[2] E. J. Lipson, W. H. Sharfman, C. G. Drake, I. Wollner, J. M. Taube, R. A. Anders, H. Xu, S. Yao, A. Pons, L. Chen, et al., *Clin. Cancer Res. Off. J. Am. Assoc. Cancer Res.* 2013, 19. 462-468.

[3] T. R. Simpson, F. Li, W. Montalvo-Ortiz, M. A. Sepulveda, K. Bergerhoff, F. Arce, C. Roddie, J. Y. Henry, H. Yagita, J. D. Wolchok, et al., *J. Exp. Med.* 2013, 210, 1695-1710.

[4] R. Boellaard, M. J. O'Doherty, W. A. Weber, F. M. Mottaghy, M. N. Lonsdale, S. G. Stroobants, W. J. G. Oyen, J. Kotzerke, O. S. Hoekstra, J. Pruim, et al., *Eur. J. Nucl. Med. Mol. Imaging* 2010, 37, 181-200.

[5] M. Rashidian, E. J. Keliher, A. M. Bilate, J. N. Duarte, G. R. Wojtkiewicz, J. T. Jacobsen, J. Cragnolini, L. K. Swee, G. D. Victora, R. Weissleder, et al., *Proc. Natl. Acad. Sci. U.S.A.* 2015, DOI 10.1073/pnas. 1502609112.

[6] R. Tavare, M. N. McCracken, K. A. Zettlitz, S. M. Knowles, F. B. Salazar, T. Olafsen, O. N. Witte, A. M. Wu, *Proc. Natl. Acad. Sci.* 2014, 111, 1108-1113.

[7] M. Rashidian, E. J. Keliher, M. Dougan, P. K. Juras, M. Cavallari, G. R. Wojtkiewicz, J. T. Jacobsen, J. G. Edens, J. M. J. Tas, G. Victora, et al., *ACS Cent. Sci.* 2015, 150603073029009.

[8] E. C. Dijkers, T. H. Oude Munnink, J. G. Kosterink, A. H. Brouwers, P. L. Jager, J. R. de Jong. G. A. van Dongen, C. P. Schröder, M. N. Lub-de Hooge, E. G. de Vries, *Clin. Pharmacol. Ther.* 2010, 87. 586-592.

[9] M. Rashidian, E. J. Keliher, A. M. Bilate, J. Doarte, G. Wojtkiewicz, J. Jacobsen, G. Victora. R. Weissleder, H. L. Ploegh, *Proc. Natl. Acad. Sci. U.S.A.* 2015.

[10] T. De Meyer, S. Muyldermans, A. Depicker, *Trends Biotechnol.* 2014, 32, 263-270.

[11] P. Holliger, T. Prospero, G. Winter, *Proc. Natl. Acad. Sci. U.S.A* 1993, 90, 6444-6448.

[12] H. Schellekens, W. E. Hennink. V. Brinks, *Pharm. Res.* 2013, 30, 1729-1734.

[13] E. De Genst, K. Silence, K. Decanniere, K. Conrath, R. Loris, J. Kinne, S. Muyldermans, L. Wyns, *Proc. Natl. Acad. Sci. U.S.A* 2006, 103, 4586-4591.

[14] V. Cortez-Retamozo, M. Lauwereys, G. Hassanzadeh Gh, M. Gobert, K. Conrath, S. Muyldermans, P. De Baetselier, H. Revets, *Int. J. Cancer J. Int. Cancer* 2002, 98, 456-462.

[15] Y. Vugmeyster, C. A. Entrican, A. P. Joyce, R. F. Lawrence-Henderson, B. A. Leary, C. S. Mahoney, H. K. Patel, S. W. Raso, S. H. Olland, M. Hegen, et al., *Bioconjug. Chem.* 2012, 23, 1452-1462.

Example 2. Materials and Methods

Synthesis of (Gly)$_3$-PEG$_{12}$-Cys(TCO)-PEG$_5$-Lys(azide)

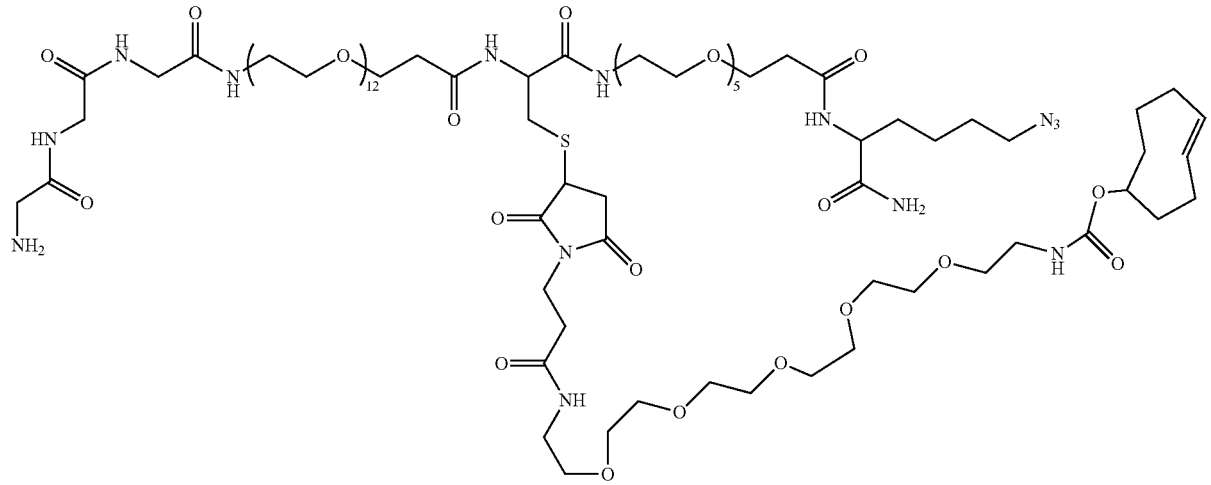

The peptide (Gly)$_3$-PEG$_{12}$-Cys-PEG$_5$-Lys(azide) was synthesized by standard solid phase peptide synthesis. Maleimide-TCO (from Conju-bio) was dissolved in 0.05 M NaHCO$_3$ buffer pH 8.3. The peptide was added and left to stir at room temperature for 1 h until LC-MS indicated near-complete conversion to the product. The solution was filtered and purified by reverse phase-HPLC with a semi-preparative column (Phenomenex, C$_{18}$ column, Gemini, 5 μm, 10×250 mm) at a flow rate of 5.0 mL/min.; solvent A: 0.1% formic acid in H$_2$O, solvent B: 0.1% formic acid in CH$_3$CN. Product eluted at 35-40% solvent B. Fractions containing pure product were collected and lyophilized. LC-MS calculated for C$_{83}$H$_{151}$N$_{14}$O$_{34}$S [M+H]$^+$ 1920.0, found 1919.0.

Synthesis of (Gly)$_3$-PEG$_{12}$-Cys(Texas Red)-PEG$_5$-Lys(azide)

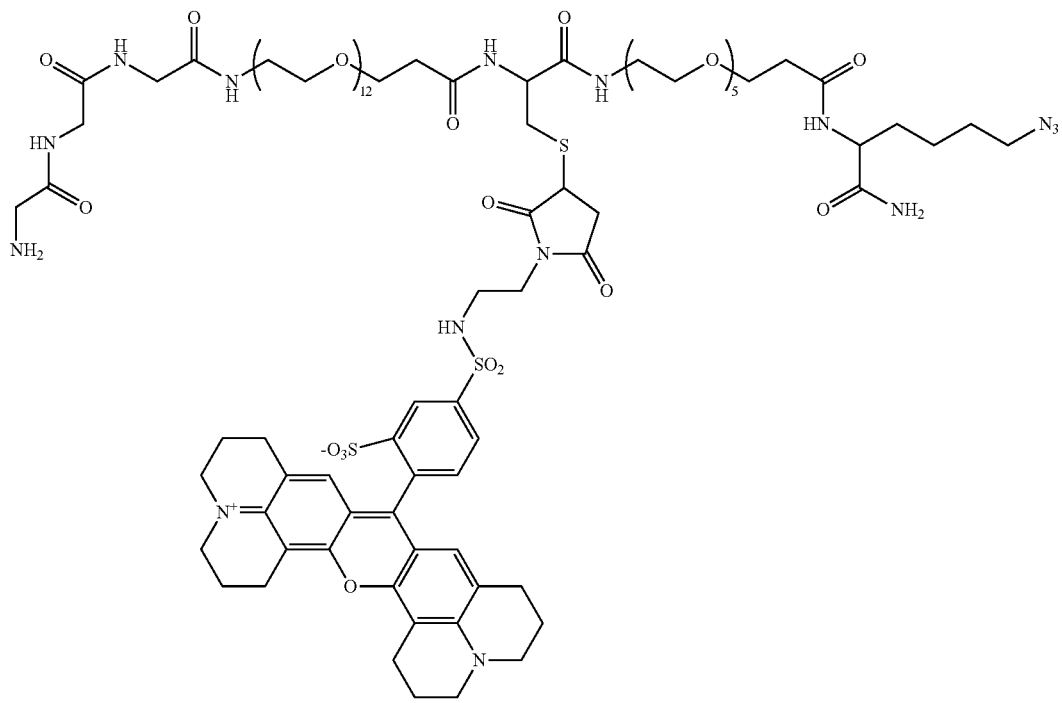

The peptide (Gly)$_3$-PEG$_{12}$-Cys-PEG$_5$-Lys(azide) was synthesized by standard solid phase peptide synthesis and was dissolved in 0.05 M NaHCO$_3$ buffer pH 8.3. Maleimide-Texas Red (from Vector Labs) was dissolved in DMSO and then was added to the solution and left to stir at room temperature for 1 h until LC-MS indicated near-complete conversion to the product. The solution was filtered and purified by reverse phase-HPLC with a semi-preparative column (Phenomenex, C$_{18}$ column, Gemini, 5 µm, 10×250 mm) at a flow rate of 5.0 mL/min.; solvent A: 0.1% TFA in H$_2$O, solvent B: 0.1% TFA in CH$_3$CN. Product eluted at 40-45% solvent B. Fractions containing pure product were collected and lyophilized. LC-MS calculated for C$_{92}$H$_{142}$N$_{15}$O$_{32}$S$_3$ [M+H]$^+$ 2064.9, found 2063.9.

Synthesis of (Gly)$_3$-PEG$_{12}$-Cys(Alexa647)-PEG$_5$-Lys(azide)

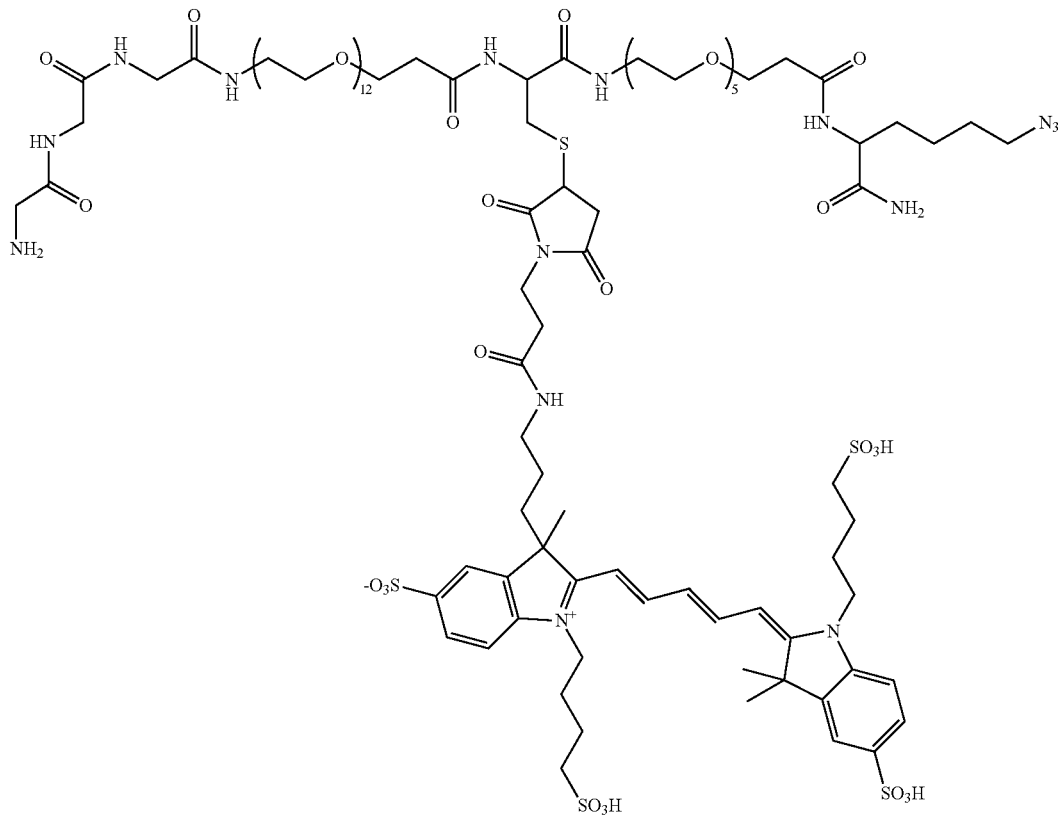

The peptide (Gly)$_3$-PEG$_{12}$-Cys-PEG$_5$-Lys(azide) was synthesized by standard solid phase peptide synthesis. Maleimide-Alexa647 (from Life Technology) was dissolved in 0.05 M NaHCO$_3$ buffer pH 8.3. The peptide was added and left to stir at room temperature for 1 h until LC-MS indicated near-complete conversion to the product. The solution was filtered and purified by reverse phase-HPLC with a semi-preparative column (Phenomenex, C$_{18}$ column, Gemini, 5 µm, 10×250 mm) at a flow rate of 5.0 mL/min.; solvent A: 0.1% TFA in H$_2$O, solvent B: 0.1% TFA in CH$_3$CN. Product eluted at 30-35% solvent B. Fractions containing pure product were collected and lyophilized. LC-MS calculated for C$_{97}$H$_{158}$N$_{15}$O$_{39}$S$_5$ [M+H]$^+$ 2317.9, found 2318.4.

Synthesis of (Gly)₃-DBCO

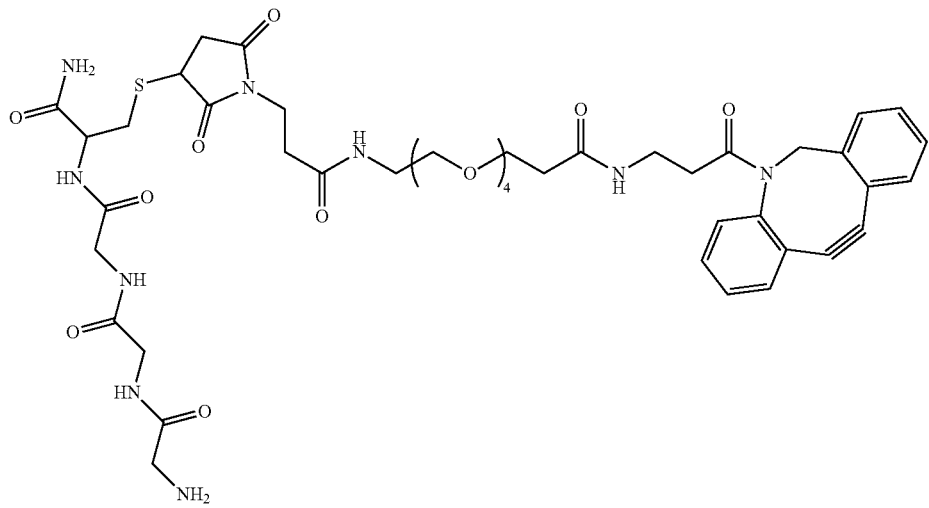

The tetrapeptide (Gly)₃-Cys (SEQ ID NO: 12) was synthesized by standard solid phase peptide synthesis and was dissolved in 0.05 M NaHCO₃ buffer pH 8.3. Maleimide-DBCO (from Click Chemistry Tools) was dissolved in DMSO and then was added to the solution and left to stir at room temperature for 1 h until LC-MS indicated near-complete conversion to the product. The solution was filtered and purified by reverse phase-HPLC with a semi-preparative column (Phenomenex, $C_{18}$ column, Gemini, 5 μm, 10×250 mm) at a flow rate of 5.0 mL/min.; solvent A: 0.1% TFA in H₂O, solvent B: 0.1% TFA in CH₃CN. Product eluted at 35-40% solvent B. Fractions containing pure product were collected and lyophilized. LC-MS calculated for $C_{45}H_{60}N_9O_{13}S$ [M+H]⁺ 966.4, found 966.4.

Enzymatic Incorporation of Substrates into Proteins Using Sortase.

The penta-mutant sortase A, with an improved $k_{cat}$, was used (1). Reaction mixtures (1 mL) contained Tris·HCl (50 mM, pH 7.5), CaCl₂ (10 mM), NaCl (150 mM), triglycine-containing probe (500 u M), LPETG-containing (SEQ ID NO: 11) substrate (100 μM), and sortase (5 μM) (2, 3). After incubation at 4° C. with agitation for 2 h, reaction products were analyzed by LC-MS. Yields were generally >90%. When the yield was below 90%, the reaction was allowed to proceed for an additional two hours, with addition of sortase to 10 μM and triglycine-containing probe to 1 mM. Ni-NTA beads were added to the reaction mixture with agitation for 5 min at 25° C. followed by centrifugation to remove sortase and any remaining unreacted His-tagged substrate. The final product was purified by size exclusion chromatography in PBS or Tris·HCl (50 mM, pH 7.5). The labeled protein was stored at −80° C. with 5% glycerol for up to six months.

Dimerization of VHHs.

The general procedure was as follows: the DBCO-VHH (1.3 eq, in PBS) was added to the azide-X-VHH (where X is either TCO, Texas Red or Alexa647) and the reaction was left to proceed at room temperature for ~1-3 hours with constant agitation, where LC-MS analysis revealed (generally) above 80% conversion to the corresponding dimer. The dimer was then purified via size exclusion chromatography (FPLC) using PBS as the eluting solvent. The labeled dimer was stored at −80° C. with 5% glycerol for up to six months.

PEGylation of VHHs.

The general procedure was as follows: the DBCO-PEG (4 eq, in PBS) was added to the azide-X-VHH (where X is either TCO, Texas Red or Alexa647) and the reaction was left to proceed at room temperature for ~1-2 hours with constant agitation, where SDS-PAGE analysis revealed (generally) above 80% conversion to the corresponding PEGylated product. The final PEGylated product was purified via size exclusion chromatography (FPLC) using PBS as the eluting solvent. The labeled PEGylated protein was stored at −80° C. with 5% glycerol for up to six months.

Two-Photon Imaging.

Two-photon imaging was performed with Olympus BX61 upright microscope (Olympus 25×1.05 NA Plan Objective), fitted with a SpectraPysics MaiTai DeepSee laser. Images were acquired using 910 nm excitation and following filters; CFP (460-510), GFP (495-540) and a third filter (575-630) for the Texas Red signal. Second harmonics (collagen) were also detected in the CFP filter. Images were acquired with 5 μm Z-resolution with Olympus Fluo View FC1000 software. Tile images were saved as JPEG files. Images were processed to obtain a scale bar in Imaris v 7.4.0; no intensity or contrast adjustments were made.

Synthesis and characterization of [¹⁹F]SFB-Tetrazine

Figure 13A:
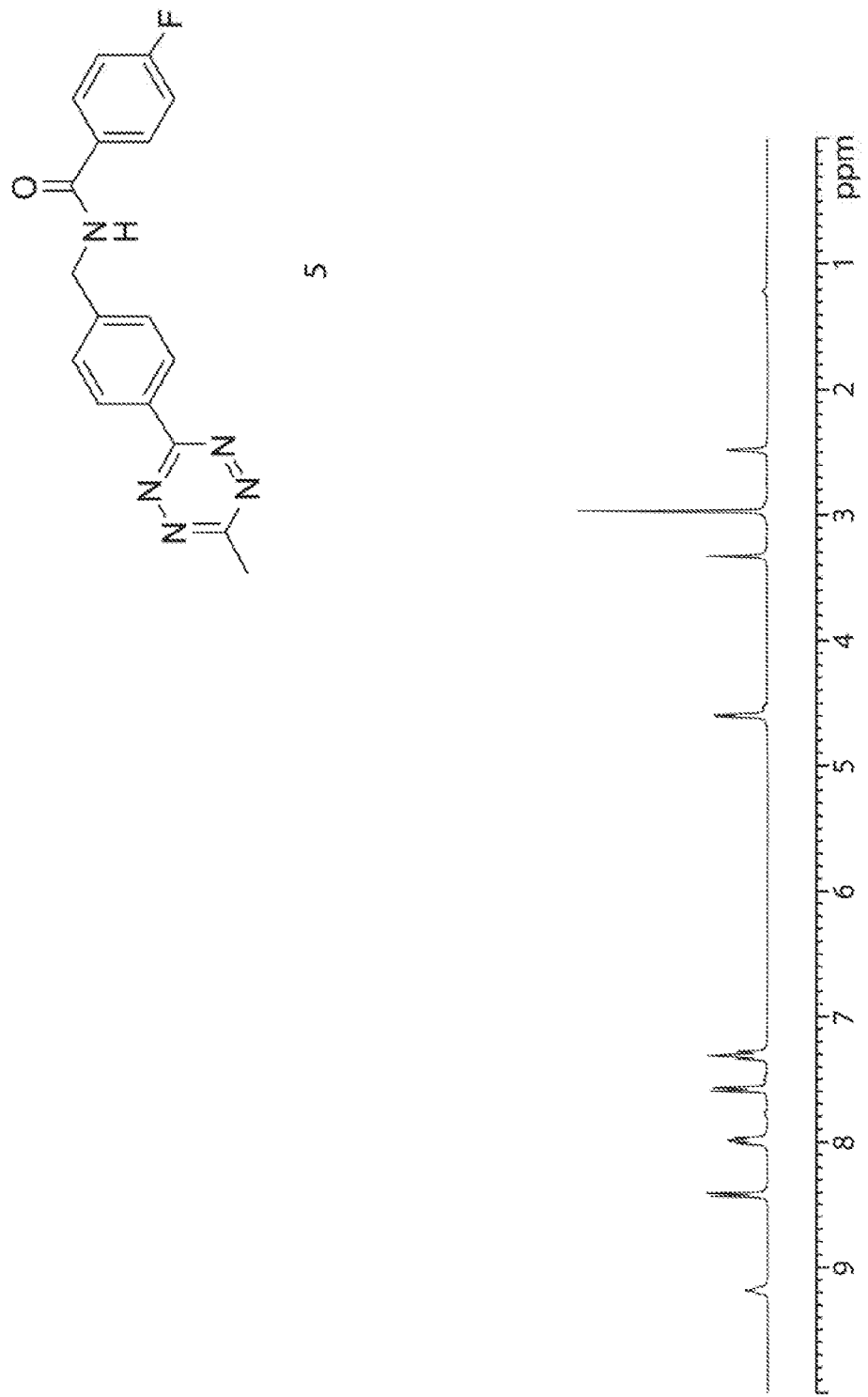
FIGS. 13A-13B show NMR spectra of [$^{19}$F]tetrazine 5: $^1$H-NMR (FIG. 13A) and $^{13}$C-NMR (FIG. 13B).
Figure 13B:
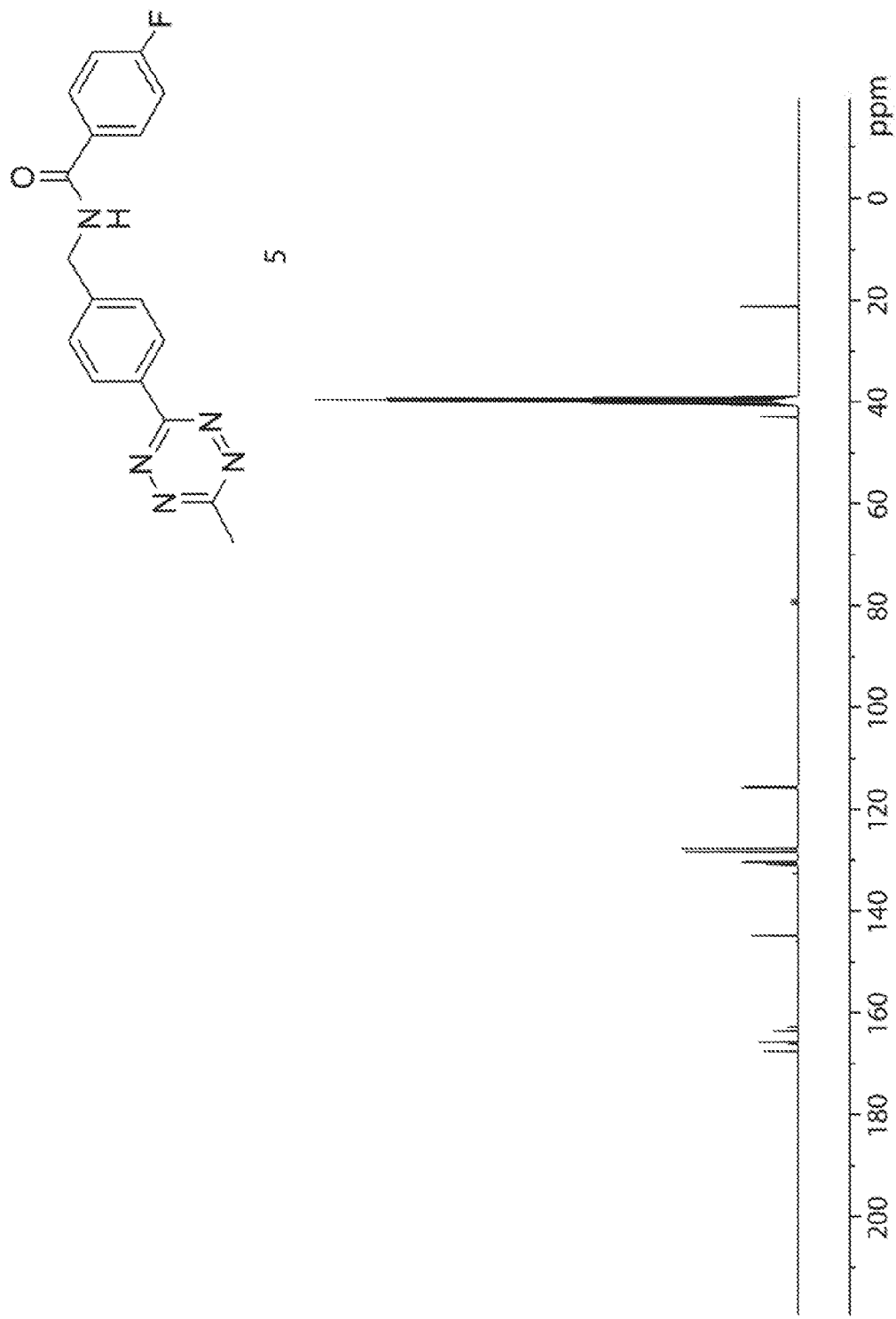
Figure 14A:
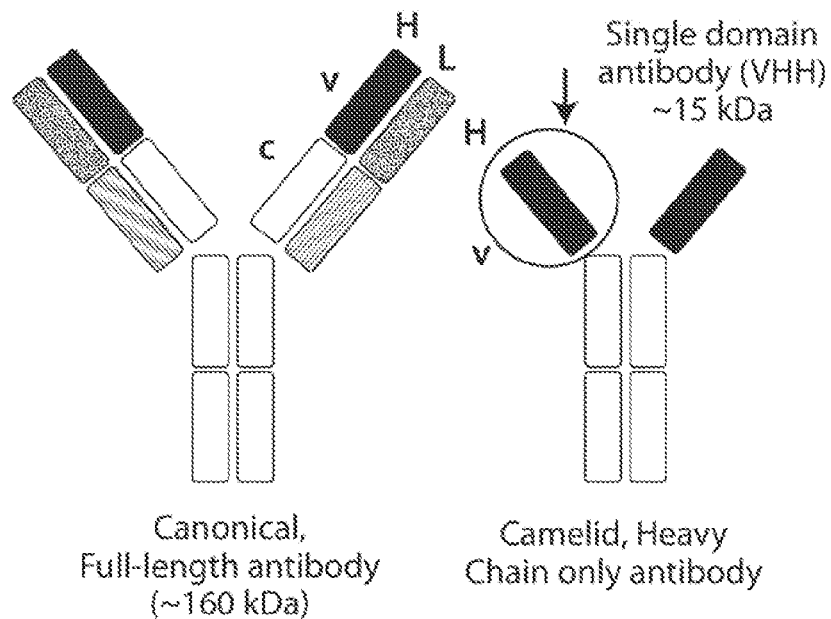
FIGS. 14A-14B show a schematic of a camelid heavy chain only antibody and a conventional IgG. A VHH portion is shown within the circle indicated by the arrow (FIG. 14A).
Figure 14B:
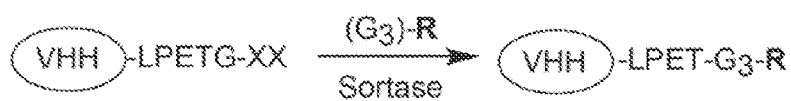

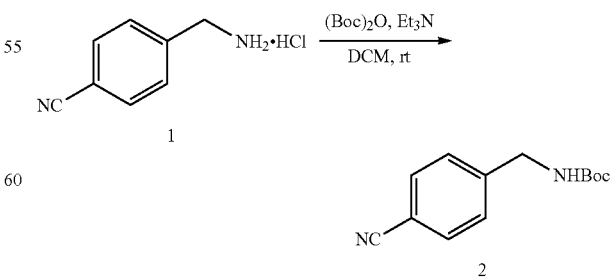

tert-butyl (4-cyanobenzyl)carbamate (2): 4-(Aminomethyl)benzonitrile hydrochloride 1 (2.82 g, 16.7 mmol) and triethylamine (4.7 mL, 33.7 mmol) were dissolved in anhydrous $CH_2Cl_2$ (50 mL) at 0° C. To this stirred solution was added di-tert-butyl dicarbonate (4.38 g, 20.1 mmol), and the reaction allowed to warm to room temperature and stirred for 16 hours. The reaction mixture was evaporated in vacuo, and the residue was re-dissolved in diethyl ether (50 mL), which was washed successively with 0.5 M aq. HCl (2×25 mL), saturated $NaHCO_3$ (2×25 mL) and brine (25 mL). The organic layer was dried with $MgSO_4$, filtered and evaporated in vacuo to give an off-white solid. The residue was purified by flash column chromatography (Hexanes/EtOAc=10/1) to afford tert-butyl (4-cyanobenzyl) carbamate 2 (3.69 g, yield 95%) as a colorless solid. It was further characterized according to the literature procedure (4). FIGS. 13A-13B show 1H-NMR and 13C-NMR spectra, respectively.

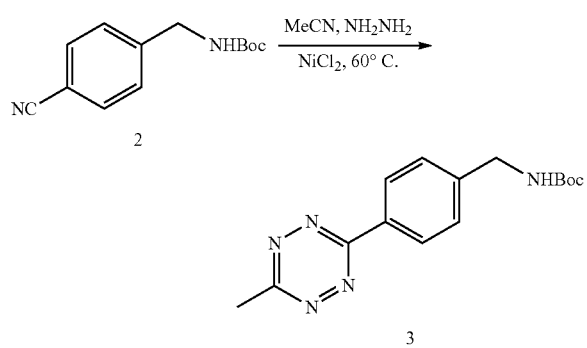

tert-butyl (4-(6-methyl-1,2,4,5-tetrazin-3-yl)benzyl) carbamate (3): A stirred mixture of carbamate 2 (1.5 g, 6.46 mmol), MeCN (3.4 mL, 64.6 mmol) and anhydrous $NiCl_2$ (418 mg, 3.23 mmol) was treated dropwise with hydrazine (5 mL, 161.5 mmol). The purple reaction mixture was stirred at 60° C. for 24 hours. Afterwards a solution of $NaNO_2$ (8.8 g, 127 mmol) in $H_2O$ (65 mL) was carefully added. HCl (2 N solution) was added until the evolution of nitrous oxides ceased. The dark red solution was extracted with ethyl acetate (3×60 mL). The extract was combined and dried over $MgSO_4$ and concentrated. The residue was purified by column chromatography (Hexanes/EtOAc=8/1) to afford tert-butyl (4-(6-methyl-1,2,4,5-tetrazin-3-yl)benzyl) carbamate 3 (1.22 g, yield 63%) as a red solid. It was further characterized according to the literature (5).

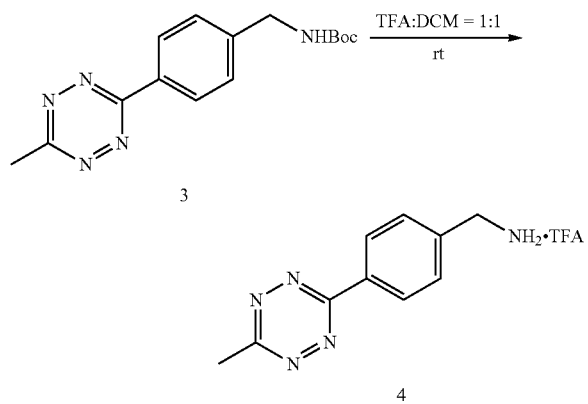

(4-(6-methyl-1,2,4,5-tetrazin-3-yl)phenyl)methanamine (4): In a 100 mL reaction vessel was charged the solution of tetrazine 3 (301 mg, 1.0 mmol) in DCM (12 mL). Trifluoroacetic acid (12 mL) was added dropwise. The mixture was stirred at room temperature for 2 h. Afterwards the mixture was evaporated and suspended into $Et_2O$ (20 mL) for recrystallization at −20° C. The supernatant was decanted and the residue was dried under vacuum for 2 hours to afford (4-(6-methyl-1,2,4,5-tetrazin-3-yl)phenyl)methanamine 4 (200 mg, yield 99%) as red solid. The product was further characterized according to the literature (6).

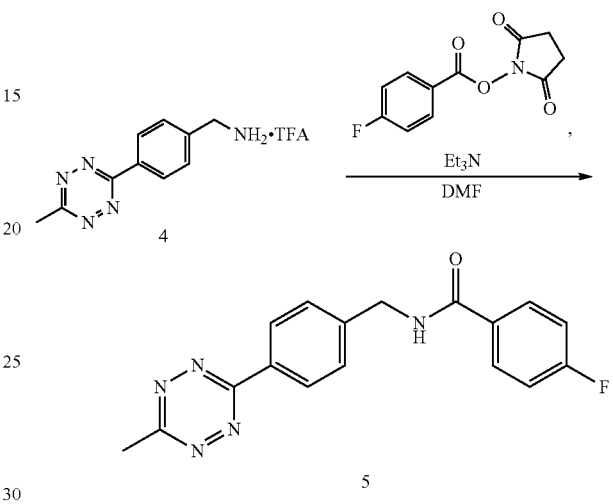

4-fluoro-N-(4-(6-methyl-1,2,4,5-tetrazin-3-yl)benzyl)benzamide (5): A solution of the tetrazine amine TFA salt 4 (50 mg, 0.25 mmol) in anhydrous DMF (3.5 mL) was added 2,5-dioxopyrrolidin-1-yl 4-fluorobenzoate (50 mg, 0.223 mmol) and $Et_3N$ (0.35 mL, 2.5 mmol). The resulting solution was then stirred at room temperature overnight under argon gas. The reaction mixture was quenched with water (15 mL), and then extracted with ethyl ether (10 mL×3). The organic layers were combined, washed with brine, dried over $MgSO_4$, filtered and evaporated under reduced pressure. The crude product was purified by flash chromatography (Hexanes/EtOAc=7/1) to afford 4-fluoro-N-(4-(6-methyl-1,2,4,5-tetrazin-3-yl)benzyl)benzamide 5 (29 mg, 36%) as a red solid powder.

$^1$H NMR (300 MHz, DMSO) δ 9.18 (t, J=6.1 Hz, 1H), 8.43 (d, J=8.4 Hz, 2H), 7.99 (dd, J=5.5, 3.3 Hz, 2H), 7.58 (d, J=8.2 Hz, 2H), 7.31 (t, J=7.8 Hz, 2H), 4.60 (d, J=6.1 Hz, 2H), 2.97 (s, 3H); $^{13}$C NMR (75 MHz, DMSO) δ 167.5, 165.9 (d, J=23.3 Hz), 163.6, 162.8, 144.8, 131.0 (d, J=3.1 Hz), 130.8, 130.3 (d, J=8.9 Hz), 128.5, 127.9, 115.7 (d, J=21.7 Hz), 43.0, 21.3; HRMS calc'd for $C_{17}H_{15}FN_5O^+[M+H]^+$, 324.1261; found 324.1265.

Radiochemical synthesis of [$^{18}$F]-Tetrazine ([$^{18}$F]-5)

General methods for radioisotope production: a GE PETtrace 16.5 MeV cyclotron was used for [$^{18}$F]fluoride production by the $^{18}O(p,n)^{18}F$ nuclear reaction to irradiate $^{18}$O-enriched water. [$^{18}$F]fluoride was delivered to a lead-shielded hot cell in $^{18}$O-enriched water by nitrogen gas pressure.

General methods for analysis of radiofluorination reactions: radioactivity was quantified using a Capintec Radioisotope Calibrator (CRC-712M) ion chamber. Radiochemical incorporation yields were determined by radioTLC.

EMD TLC Silica gel 60 plates (10×2 cm) were spotted with an aliquot (1-5 µL) of crude reaction mixture approximately 1.5 cm from the bottom of the plate (baseline). TLC plates were developed in a chamber containing ethyl acetate until within 2 cm of the top of the plate (front). Analysis was performed using a Bioscan AR-2000 radio-TLC imaging scanner and WinScan software. Radiochemical identity and purity were determined by radioHPLC. A Phenomenex Luna C18, 250×4.6 mm, 5 µm HPLC column was used with a Waters 1515 Isocratic HPLC Pump equipped with a Waters 2487 Dual & Absorbance Detector, a Bioscan Flow-Count equipped with a NaI crystal, and Breeze software.

Manual Radiolabeling.

CONTROL:

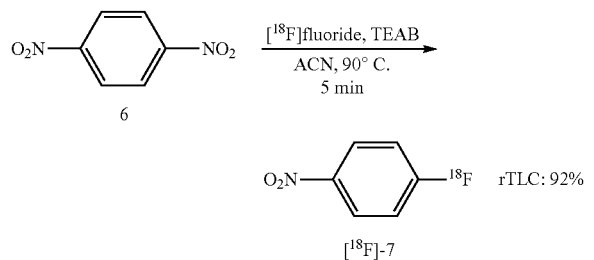

EXPERIMENT:

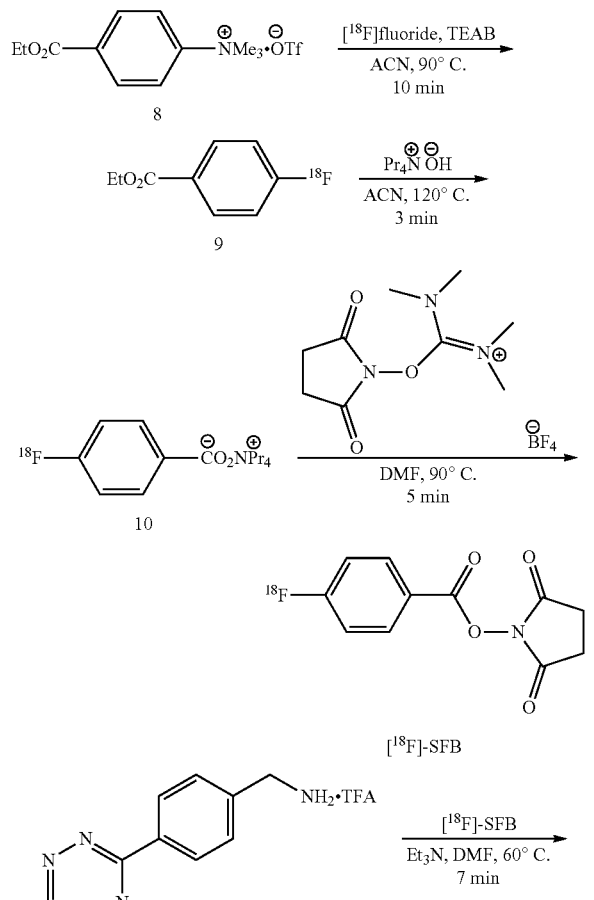

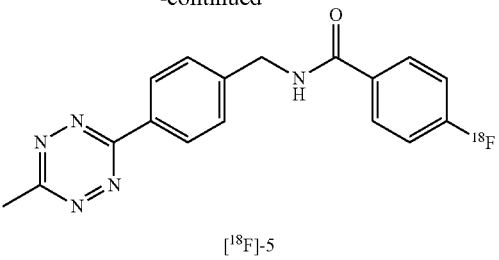

[$^{18}$F]-5

[$^{18}$F]Fluoride was prepared for radiofluorination by the following method: a solution of base (tetraethylammonium bicarbonate (TEAB), 6 mg) in acetonitrile and water (1 mL, v/v 7:3) was added to an aliquot of target water (≤ 1 mL) containing the appropriate amount of [$^{18}$F]fluoride in a V-shaped vial sealed with a teflon-lined septum. The vial was heated to 110° C. while nitrogen gas was passed through a P$_2$O$_5$-Drierite™ column followed by the vented vial. When no liquid was visible in the vial, it was removed from heat, anhydrous acetonitrile (1 mL) was added, and the heating was resumed until dryness. This step was repeated an additional three times. The vial was then cooled at room temperature under nitrogen pressure. The contents were resolubilized in CH$_3$CN (0.6 mL). A solution of TEA[$^{18}$F] (0.2 mL) was added into another V-shaped vial charged with 1,4-dinitrobenzene 6 (2 mg) and CH$_3$CN (0.2 mL). The mixture was heated at 90° C. for 5 min, and then quenched with HPLC mobile phase (40% CH$_3$CN, 60% 0.1 M NH$_4$·HCO$_2$ (aq), 0.2 mL). TLC plate was spotted with crude mixture (2 µL) and developed with 100% EtOAc to determine the radiochemical conversion. The RCC value (92%) revealed that the TEA[$^{18}$F] solution was ready for radiolabeling. (total time: 8 min)

Note: The quality of TEA[$^{18}$F] is crucial for the following radiolabeling, thus the control is necessary to evaluate the quality.

Figure 8:
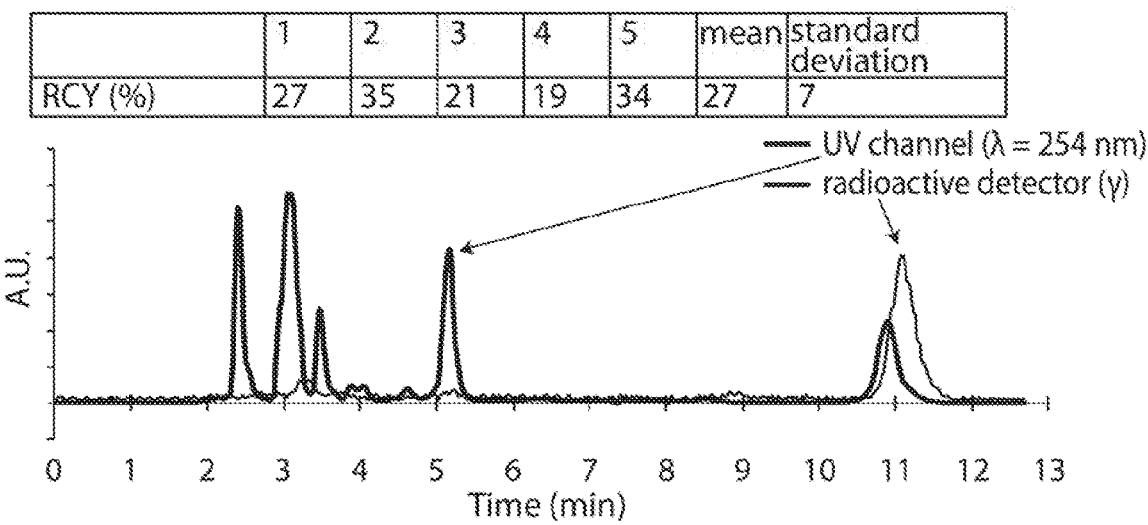
FIG. 8 shows a table of radiochemical yield (non-decay corrected) and a radio HPLC chromatogram. The column was luna 5u C18 100 Å 250×4.6 mm, the mobile phase was 60% CH$_3$CN, 40% 0.1 M NH$_4$·HCO$_2$ (aq), and the flow rate was 1 mL/min.

Ethyl 4-(trimethylammonium triflate)benzoate 8 (4.8 mg) in anhydrous MeCN (0.6 mL) was added to the above dried TEA[$^{18}$F] solution (0.4 mL) and the mixture was heated at 90° C. for 10 min to produce ethyl 4-[18F]fluorobenzoate 9. The ethyl ester was subsequently hydrolyzed to form 10 using tetrapropylammonium hydroxide (20 µL, 1.0 M in water) at 120° C. for 3 min, and then the mixture azeotropically dried using MeCN (1 mL). Subsequently, a solution of N,N,N',N'-Tetramethyl-O-(N-succinimidyl) uronium tetrafluoroborate (10 mg) in DMF (0.3 mL) was added and the solution heated at 90° C. for 5 min. The mixture was cooled down to ambient temperature. Afterwards a solution of tetrazine amine TFA salt 4 (1.7 mg) in DMF (0.3 mL) was added into the mixture, followed by addition of Et$_3$N (20 µL). Then the reaction was heated at 60° C. for 7 min, quenched with HPLC mobile phase (60% CH$_3$CN, 40% 0.1 M NH$_4$·HCO$_2$ (aq), 2 mL). The solution was diluted with water (15 mL), passed through C$_{18}$ cartridge, washed with water (10 mL), and eluted with acetonitrile (1.5 mL) to determine the radiochemical yield (RCY) and identity via co-injection with standard [1$^{9F}$]-5. FIG. 8 shows a table of radiochemical yield (non-decay corrected) and a radioHPLC chromatogram. The column was luna 5u C18 100 Å 250×4.6 mm, the mobile phase was 60% CH$_3$CN, 40% 0.1 M NH$_4$·HCO$_2$ (aq), and the flow rate was 1 mL/min.

Automated Synthesis by GE TracerLab FX$_{FN}$ Method.

Figure 9:
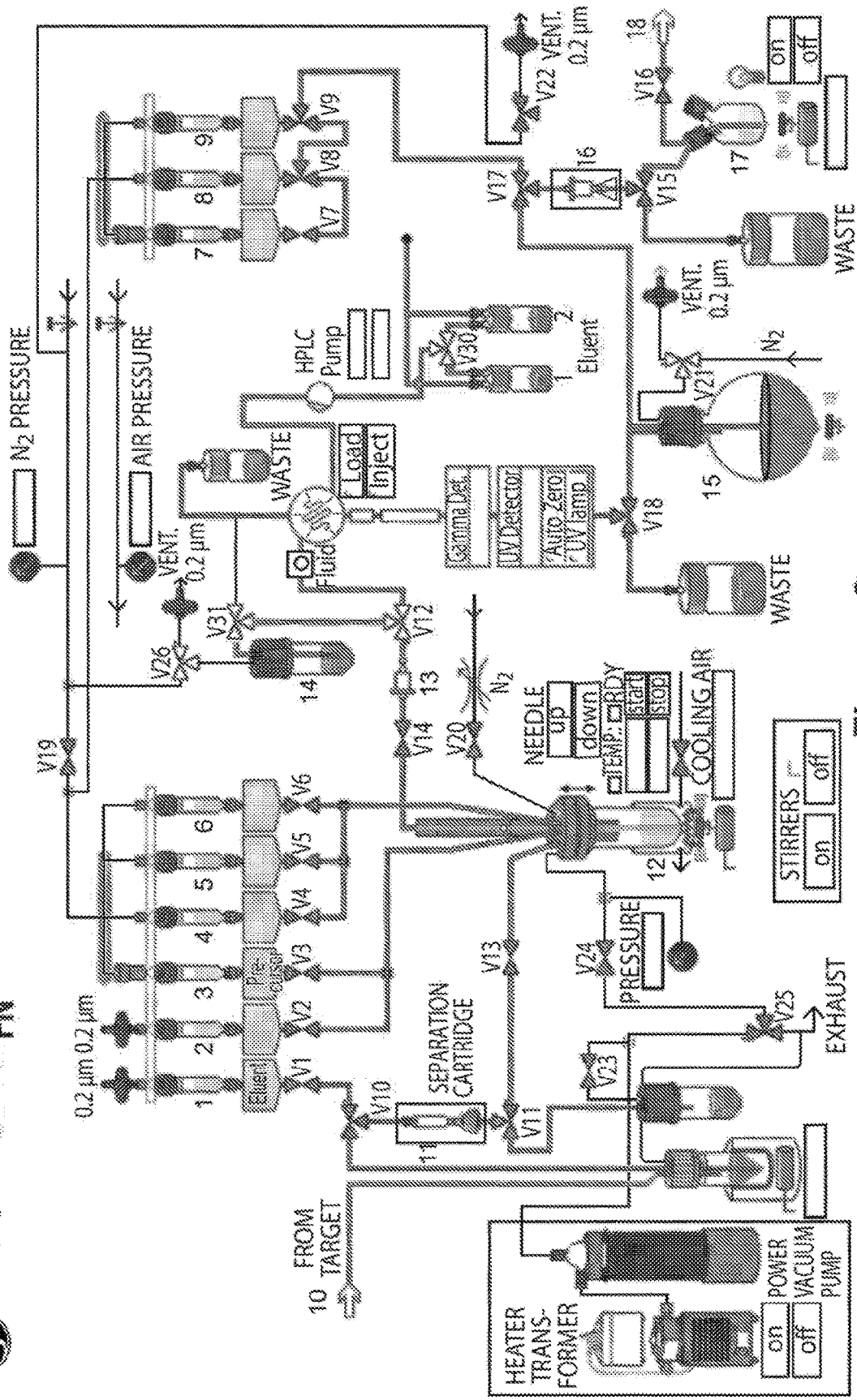
FIG. 9 shows a schematic of the GE TRACERlab™ FXFN radiosynthesis module automated synthesis manifold for [$^{18}$F]-5.

Following completion of bombardment, the [$^{18}$F]fluoride was transferred to the GE TRACERlab™ FX$_{FN}$ radiosynthesis module via helium gas overpressure. A schematic diagram of the GE medical systems commercial TRACERlab™ $FX_{FN}$ radiosynthesis module used for the synthesis of [$^{18}$F]-5 is shown in FIG. 9.

Automated synthesis involves the following: (1) azeotropic drying of [$^{18}$F]fluoride; (2) [$^{18}$F]fluorination; and (3) HPLC purification, followed by solid-phase formulation of the final product. The synthesis module was operated in the following sequences with numerical references to FIG. 9.

[$^{18}$F]Fluoride was produced by the $_{18}$O(p,n)$^{18}$F nuclear reaction using a GE cyclotron and delivered to the radiosynthesis module via 10. The [$^{18}$F]fluoride was quantitatively trapped on a QMA carbonate ion exchange solid phase extraction (SPE) light cartridge (Waters; activated with 6 mL of trace grade $H_2O$).

Automated synthesis began with the elution of resin-bound [$^{18}$F]fluoride using a solution of tetraethylammonium bicarbonate (6 mg in 500 μL $H_2O$ and 500 μL $CH_3CN$), pre-loaded into 1 and delivered to the reactor (12).

The reaction mixture (12) was dried azeotropically at 85° C. under N2 flow and vacuum over 5 min, then at 110° C. under N2 flow and vacuum for 2 min, then cooled down to 90° C.

·Ethyl 4-(trimethylammonium triflate)benzoate 8 (5 mg in 1.0 mL $CH_3CN$) pre-loaded into 3 was added to 12. The reactor was sealed via the closure of valve V13, V20 and V24 and the reaction mixture was maintained at 90° C. for 10 min.

The reaction mixture was then cooled to 40° C., vented via valve V24, and tetrapropylammonium hydroxide (1.0 M in water, 20 μL in 0.5 mL $CH_3CN$) pre-loaded into 4 was added to 12. The reactor was sealed via the closure of valve V24 and the reaction mixture was heated to 120° C. and this temperature was maintained for 3 min, then cooled down to 70° C.

The reaction mixture (12) was dried azeotropically by addition of 1 mL anhydrous $CH_3CN$, preloaded into 5, at 70° C. under N2 flow and vacuum over 6 min.

N,N,N',N'-Tetramethyl-O-(N-succinimidyl) uronium tetrafluoroborate (TSTU, 10 mg) in DMF (0.5 mL) pre-loaded into 6 was added to 12. The reactor was sealed via the closure of valve V24 and the reaction mixture was heated to 90° C. and this temperature was maintained for 5 min, then cooled down to 60° C.

A mixture of tetrazine amine TFA salt 4 (6.0 mg) and $Et_3N$ (40 μL) in DMF (0.5 mL) pre-loaded into 2 was added to 12. The reaction mixture was maintained at 60° C. for 7 min.

The crude reaction mixture was eluted into 14, which was preloaded with 20:80 $CH_3CN$/0.1 M ammonium formate solution (3 mL). The contents of 14 were transferred to the HPLC loop via N2 pressure using a fluid detector, injected onto a semi-preparative column (Luna C18 semi-preparative, 250×10.00 mm, 5p), and eluted with 40:60 $CH_3CN$/0.1 M ammonium formate by volume at a flow rate of 5 mL/min. The eluent was monitored by UV (2=254 nm) and radiochemical detectors connected in series.

Figure 10:
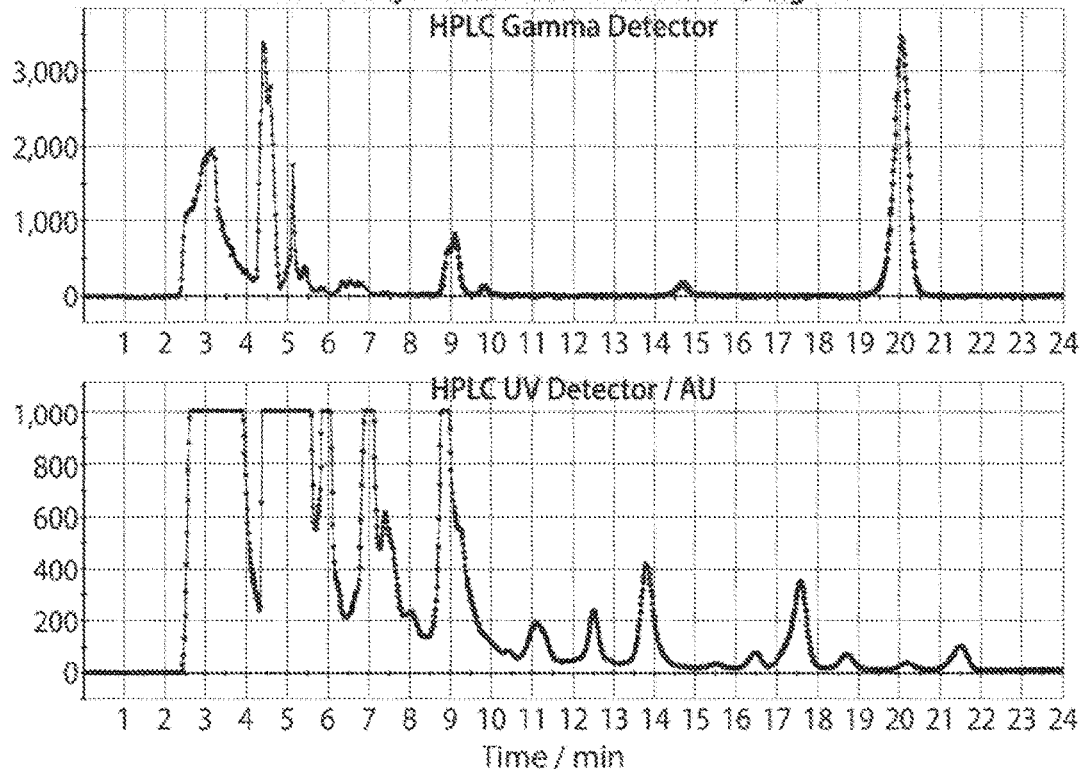
FIG. 10 shows a semi-preparative HPLC trace of a typical radiosynthesis of [$^{18}$F]-5.

A typical semi-preparative HPLC chromatogram is shown in FIG. 10. The fraction containing the major radiochemical product ($t_R$=20.1 min) was collected, via valve 18, into a large dilution vessel (15), which was preloaded with 23 mL of sterile water for injection (United States Pharmacopeia (USP); Hospira). The diluted HPLC fraction was then loaded onto a C18 SPE cartridge (16) (Waters; preactivated with 5 mL EtOH followed by 10 mL $H_2O$).

Cartridge 16 was washed with 10 mL sterile water for injection, USP, preloaded into 7, to remove traces of salts, HPLC mobile phase, and [$^{18}$F]fluoride. Then 16 was eluted with 1.5 mL $CH_3CN$, preloaded in 8, into collection vial 17.

Analyses of radioactive mixtures were performed by HPLC with an in-line UV (λ=254 nm) detector in series with a CsI PIN diode radioactivity detector. Uncorrected radiochemical yields of [$^{18}$F]-5 were 10±3% (n=8) relative to starting [$^{18}$F]fluoride.

Synthesis and Characterization of [$^{18}$F]-VHHs

Figure 12:
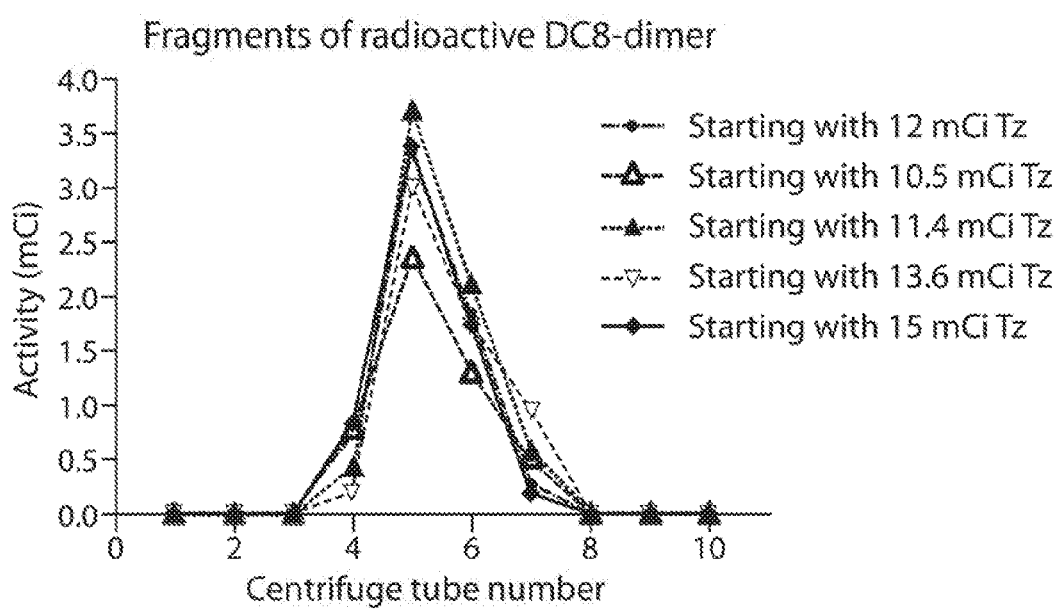
FIG. 12 shows fragments collection through PD-10 cartridge. After size-exclusion chromatography, a 47±9% (n=5, non-decay corrected) radiochemical yield was obtained.

General procedure: the solution of [$^{18}$F]-Tetrazine 5 obtained from $FX_{FN}$ was concentrated at 70° C. under N2 flow for 10 min, then cooled down to room temperature. A centrifuge tube (1.5 mL) was loaded with PBS (150 μL) and a solution of [$^{18}$F]-Tetrazine 5 in $CH_3CN$ (50 μL), then the radioactivity was measured by a dose calibrator (10~15 mCi). VHH-TCO (either monomer or dimer) in PBS (100 μL) was added into the centrifuge tube at the last step. The reaction was allowed to proceed with constant agitation at room temperature for ~20 min. The mixture was analyzed by radio-TLC (100% EtOAc, $R_f$[$^{18}$F]-Tz 5=0.6, $R_f$ [$^{18}$F]-VHHs=0.0) showing more than 80% radiochemical conversion. The reaction mixture was loaded onto a PD-10 size-exclusion cartridge (GE Healthcare), and PBS (2×500 μL) was used to assist transfer. Afterwards the activity of the reaction centrifuge tube was measured by the dose calibrator (<50 μCi), confirming a complete transfer. The PD-10 cartridge was eluted with PBS (10×500 μL), and each fragment was collected into a new 1.5 mL tube. The desired product [$^{18}$F]-VHHs usually eluted at tubes #4-7. Characterization (using [$^{18}$F]-DC8-dimer as an example): rTLC chromatography (FIG. 11 (left panel) [$^{18}$F]-Tz 5; FIG. 11 (right) [$^{18}$F]-DC8-dimer; at 20 min). Fragments collection through PD-10 cartridge can be found in FIG. 12. After size-exclusion chromatography, a 47±9% (n=5, non-decay corrected) radiochemical yield was obtained.

MicroPET Imaging Studies.

All procedures and animal protocols were approved by the Massachusetts General Hospital subcommittee on research animal care. [$^{18}$F]VHHs (20-40 μCi) was injected into the tail-vein of each animal. Mice were serially imaged using a microPET (Sofie, G4-PET). For all imaging experiments, mice were anesthetized using 2% isoflurane in $O_2$ at a flow rate of ~1.5 L/min, positioned in a prone position along the long axis of the microPET scanner and imaged. Images were reconstructed using a filtered back projection reconstruction algorithm. For image analysis, cylindrical regions of interest (ROIs) were manually drawn from three dimensional filtered back projection (FBP) reconstructed PET images using AMIDE software. Regional radioactivity was expressed as the percentage standardized uptake value [% SUV=% ID/mL×body weight (g)]. Two- and three-dimensional visualizations were produced using the DICOM viewer OsiriX (©Pixmeo SARL, 2003-2014).

Sequences of DC8, and DC13
DC8:
  Nucleic Acid:

(SEQ ID NO: 1)
CAGGTGCAGCTGCAGGAGTCAGGGGGAGGATTGGTGCAGCCTGGGGGGTC

TCTGAGACTCTCCTGTACAGCCTCTGGATTCACATTCAGTACTTACTACA

TGAGCTGGGTCCGCAAGGCTCCAGGGAAGGGGCCCGAGTGGGTCTCAGTT

ATGAATAGTAGTGGTGGTGACACAAGGTATGCAGACTTCGTGAAGGGCCG

ATTCACCATCTCCAGAGACAACGCCAAGAACACACTGTATCTCCAAATGA

ACAGCCTGAAACCTGAGGATACGGCCCTGTATTACTGTGCGCAAGGTAGA

TCAGATATATACCCAACCTTCACGCGGGGCCAGGGGACCCAGGTCACCGT

CTCCTCAGGAGGACTGCCGGAAACCGGC

Peptide:

(SEQ ID NO: 2)
QVQLQESGGGLVQPGGSLRLSCTASGFTFSTYYMSWVRKAPGKGPEWVSV

MNSSGGDTRYADFVKGRFTISRDNAKNTLYLQMNSLKPEDTALYYCAQGR

SDIYPTFTRGQGTQVTVSSGSLPETGGHHHHHH

DC13:
  Nucleic Acid:

(SEQ ID NO: 3)
CAGGTTCAACTGCAAGAGAGTGGCGGGGGCCTGGTTCAGACCGGTGGTTC

TCTCCGGCTCTCGTGTGCCGCAAGTGGAGTAGATTTTAACTGGTATAGCA

TGGGTTGGTTCAGGCAAGCCCCTGGCAAAGAGCGGGAGTATGTGGCTTCG

ATTGACCAGGGAGGCGAGTTGGATTACGCAATATCAGTAAAGGGCAGATT

CACGATCTCCCGAGACAACGCGAAGAATATGGTGTATCTCCAGATGAATT

CGTTAAAGCCCGAAGACACCGCTGTATACTACTGTGCCGCAGATTTTTCC

GGCCGGGGTGCGTCAAACCCTGACAAGTATAAATATTGGGGACAGGGAAC

CCAAGTGACCGTCAGCAGCGGTGGGTTGCCCGAAACTGGAGGACACCATC

ACCATCACCAT

Peptide:

(SEQ ID NO: 4)
QVQLQESGGGLVQTGGSLRLSCAASGVDFNWYSMGWFRQAPGKEREYVAS

IDQGGELDYAISVKGRFTISRDNAKNMVYLQMNSLKPEDTAVYYCAADFS

GRGASNPDKYKYWGQGTQVTVSSGGLPETGGHHHHHH

REFERENCES

1. Chen I, Dorr B M, Liu D R (2011) A general strategy for the evolution of bond-forming enzymes using yeast display. *Proc Natl Acad Sci USA* 108(28):11399-11404.
2. Theile C S, et al. (2013) Site-specific N-terminal labeling of proteins using sortase-mediated reactions. *Nat Protoc* 8(9):1800-1807.
3. Witte M D, et al. (2012) Preparation of unnatural N-to-N and C-to-C protein fusions. *Proc Natl Acad Sci* 109(30): 11993-11998.
4. Mok N Y, Chadwick J, Kellett K A B, Casas-Arce E, Hooper N M, Johnson A P, Fishwick C W G (2013) Discovery of biphenylacetamide-derived inhibitors of BACE1 using de novo structure-based molecular design. *J Med Chem* 56(5):1843-1852.
5. Yang J, Karver M R, Li W, Sahu S, Devaraj N K (2012) Metal-catalyzed one-pot synthesis of tetrazines directly from aliphatic nitriles and hydrazine. *Angew Chem Int Ed* 51(21): 5222-5225.
6. Evans H L, Carroll L, Aboagye E O, Spivey A C (2014) Bioorthogonal chemistry for 68Ga radiolabelling of DOTA-containing compounds. *J Label Compd Radiopharm* 57(4):291-297.

Example 3. Immuno-PET of Tumor Cells In Vivo

Figure 15A:
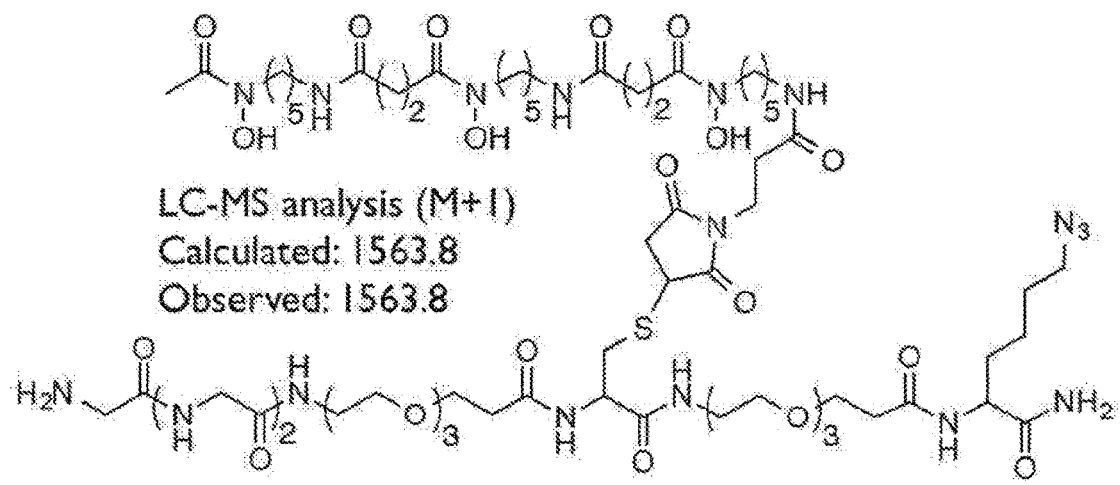
FIGS. 15A-15B shows the structure of the synthesized bi-orthogonal sortase substrate (FIG. 15A). The azide functionality allows installment of PEG groups, and DFO chelator is used to install radiometal $^{89}$Zr allowing PET imaging.
Figure 15B:
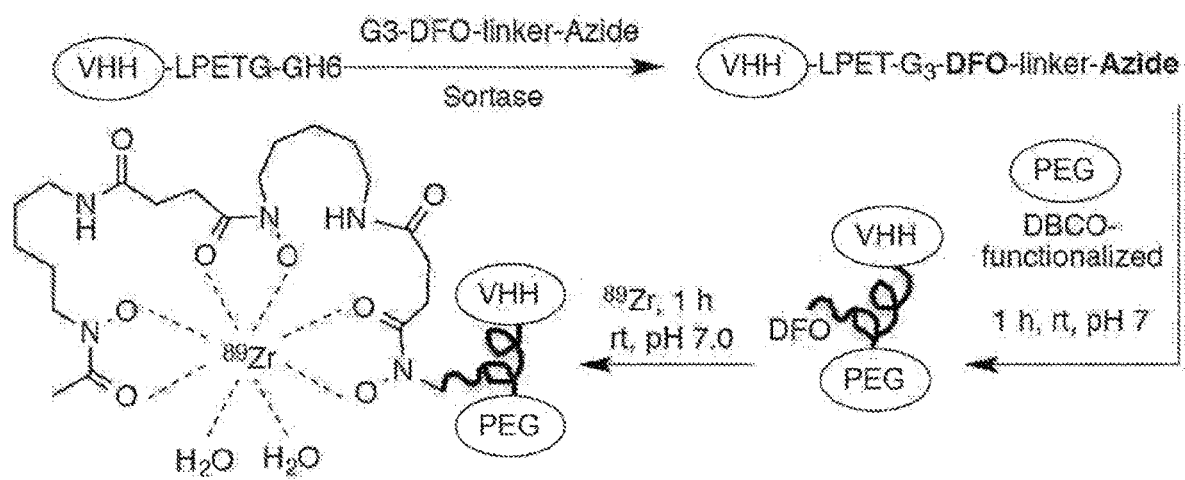
Figure 16A:
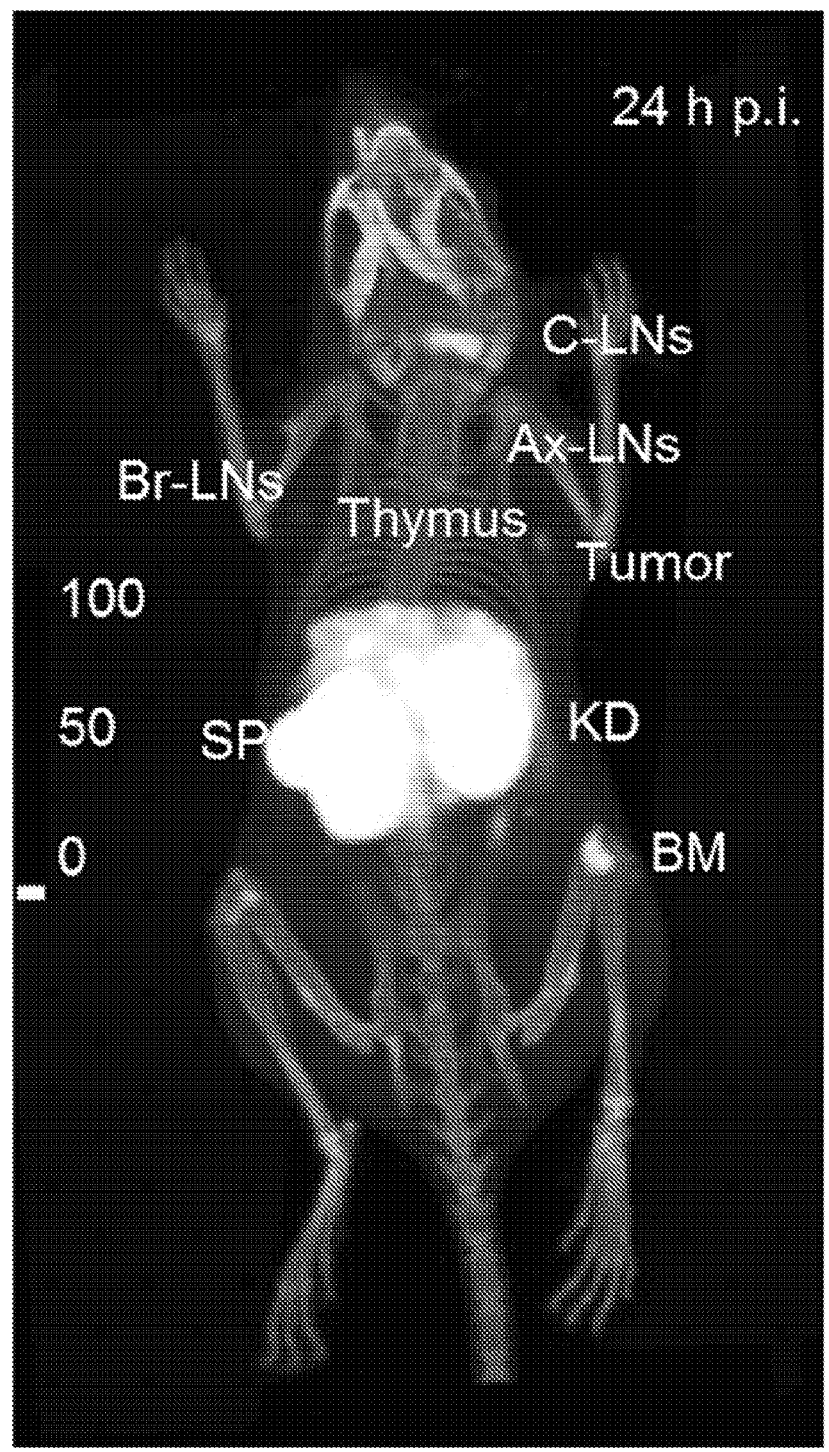
FIGS. 16A-16B shows that $^{89}$Zr-PEGylated-VHH7 detects secondary lymphoid organs and B16 tumor in a wild-type B6 mouse injected with B16 tumor cells (FIG. 16A), and $^{89}$Zr-PEGylated-VHH7 detects secondary lymphoid organs a wild-type B6 mouse not injected with B16 tumor cells (FIG. 16B).
Figure 16B:
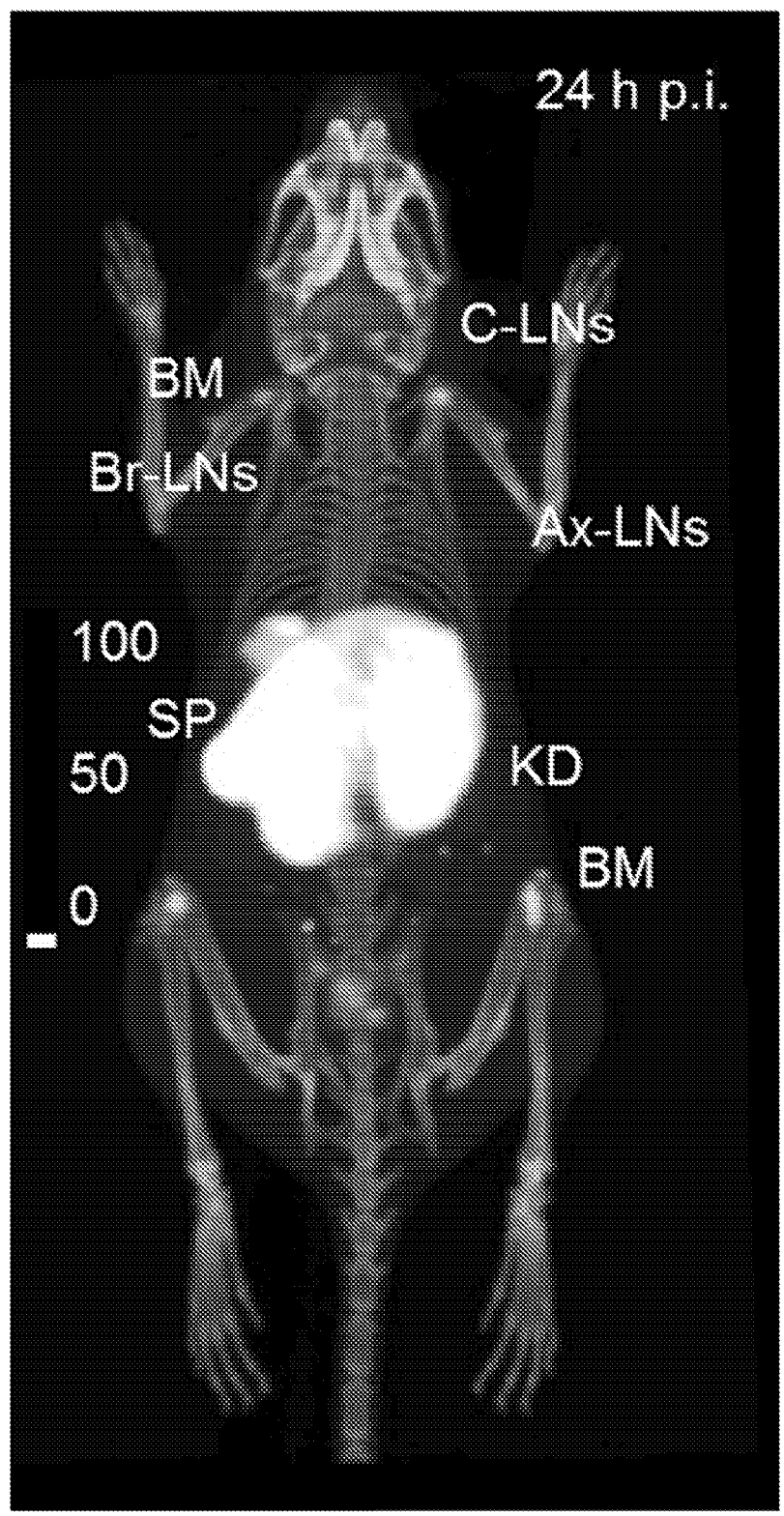

Immunotherapy using checkpoint-blocking antibodies against targets such as CTLA4 and PD-1 can be used to treat melanoma and non-small cell lung cancer in a subset of patients. The presence of T cells in a tumor correlates with improved survival. Immuno-positron emission tomography (immunoPET) was shown to visualize tumors by detecting infiltrating lymphocytes, which can be used to distinguish subjects that respond to checkpoint inhibitors from subjects that do not respond, or respond poorly, to checkpoint inhibitors. $^{89}$Zr-labeled PEGylated single domain antibody fragments (VHHs) specific for the T cell marker MHC II were used to track the presence of intratumoral T cells by immunoPET. Exemplary methods and compositions for generating such labels are shown in FIGS. 15A and 15B. Such $^{89}$Zr-labeled PEGylated single domain antibody fragments may be used to detect/assess tumor infiltrating lymphocytes, e.g., in response to checkpoint blockade in a subject (e.g., a patient), or a biological model of tumor progression (e.g., a B16 melanoma model). $^{89}$Zr-labeled PEGylated-anti-MHC II VHH (VHH7) detected thymus and secondary lymphoid structures as well as intratumoral MHC II positive T cells (FIGS. 16A and 16B). Wild-type B6 mice were injected with 0.5 million B16 melanoma cells (FIG. 16A) and injected with $^{89}$Zr-labeled PEGylated-anti-MHC II VHH 7 days following injection of the melanoma cells. PEG was 20 kDa in size. PET images were acquired 24 hours post injection with the $^{89}$Zr-labeled PEGylated-anti-MHC II VHH. The notation shown in FIG. 16A refers to the following: C-LNs: cervical lymph nodes; Ax: axillary, Br: brachial; KD: kidneys; SP: spleen; BM: bone marrow. As a control, wild-type B6 mice that were not injected with B6 cells were injected with $^{89}$Zr-labeled PEGylated-anti-MHC II VHH (FIG. 16B). PEG was 20 kDa in size. PET images were acquired 24 hours post injection with the $^{89}$Zr-labeled PEGylated-anti-MHC II VHH. The notation shown in FIG. 16B refers to the following: C-LNs: cervical lymph nodes; Ax: axillary, Br: brachial; KD: kidneys; SP: spleen; BM: bone marrow. The $^{89}$Zr-PEGylated-VHH7 was capable of detecting the B6 tumor cells in the mouse by detecting infiltrating lymphocytes into the tumor (FIG. 16A).

Immune responses occur in organized lymphoid structures, where professional antigen presenting cells interact with T and B lymphocytes to protect from infectious disease or cancer. Short of relying on survival, immune responses—whether harmful or protective—are commonly assessed by taking blood samples and measuring the levels of circulating lymphocytes and their products, such as cytokines and immunoglobulins. In humans, access to bone marrow, spleen and lymph nodes requires surgical interventions such as biopsies or sampling at autopsy, methods difficult to apply on a large scale. Similar limitations apply to the sampling of lymphoid organs in live animals, but at least animal models afford the possibility of euthanasia and examination at necropsy of any organ or tissue of interest. Most of mouse immunology thus relies on methods that do not provide longitudinal information for individual animals. The assessment of immune responses over time therefore remains a challenge. Intravital multi-photon microscopy can show migration of T. B cells and other immunocytes in real time and has clarified our understanding of, for example, the germinal center reaction. Nonetheless, such mapping of the movement of various lymphocyte and other cell subsets requires complicated invasive procedures. Tracking a cellular immune response in a living animal over time remains an unsolved challenge.

The field of tumor immunology has made great progress, in particular in the areas of antibodies used as checkpoint blockade and for cell-based therapies such as chimeric antigen receptor-expressing T cells (CAR-T cells). For certain cancers (melanoma, non-small cell lung cancer, acute lymphoblastic leukemia) immunotherapy has revolutionized clinical treatment and even produced cures, but the failure of a significant fraction of patients to respond—even in these treatable types of cancer—remains an issue. To follow and visualize immune responses longitudinally for prognosis would thus be highly desirable.

If it were possible to stratify patients into those who might benefit from certain forms of immunotherapy and separate them from those less likely to do so, expensive treatments with potentially severe side effects might be allocated to those individuals with a high probability of response. Positron emission tomography (PET) using labeled antibodies or antibody fragments (immuno-PET) may achieve this goal.

To achieve the goal of non-invasively monitoring the distribution of T cells, a small molecular weight antibody-derived format that retains antigen-binding capability, the variable region segment of camelid heavy chain-only antibodies, also referred to as VHHs or nanobodies, were used. These fragments are typically about 14 kDa in size and readily lend themselves to sortase-catalyzed enzymatic transformations for a variety of purposes, including the installation of radioisotopes for PET imaging.

Equivalents and Scope

In the claims articles such as "a." "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.)

What is claimed is:

1. A radiolabeled binding protein comprising:
   (i) a single domain antibody fragment VHH,
   (ii) a polyethylene glycol (PEG) of a molecular weight of at least 15 kDa,
   (iii) a radionuclide, wherein the radionuclide is rubidium-82, copper-61, copper-62, copper-64, yttrium-86, gallium-68 or zirconium-89, and
   (iv) a chelating moiety, wherein the chelating moiety is 1,4,7-triazacyclononane-triacetic acid (NOTA), 1,4,7,10-tetraazacyclododecane-tetraacetic acid (DOTA), tri-azacyclononane-phosphinate (TRAP), or desferrioxamine (DFO), wherein the radionuclide is bound by the chelating moiety;

the chelating moiety and the antibody fragment VHH are joined by a first linker, wherein the first linker comprises an amino acid sequence comprising a sortase recognition motif;

the PEG of a molecular weight of at least 15 kDa and the first linker are joined together by a second linker;

the first linker and the second linker together comprise the structure:

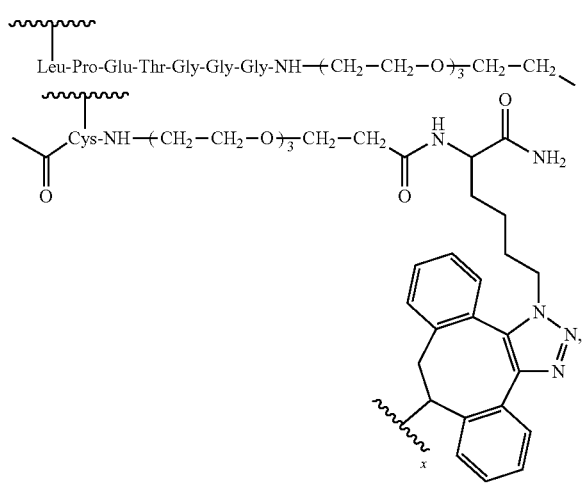

wherein the chelating moiety is attached at the cysteine (Cys), the PEG of a molecular weight of at least 15 kDa is attached through the position indicated by an x, and the leucine (Leu) is at the C-terminus of the antibody fragment VHH;
the ratio of the antibody fragment VHH to the chelating moiety is 1:1;
and the ratio of the antibody fragment VHH to the PEG of a molecular weight of at least 15 kDa is 1:1.

2. The radiolabeled binding protein of claim 1, wherein the antibody fragment VHH binds to a tumor cell, a tumor-associated cell, or a tumor antigen.

3. The radiolabeled binding protein of claim 1, wherein the antibody fragment VHH binds to an immune cell.

4. The radiolabeled binding protein of claim 1, wherein the antibody fragment VHH is from 10 kDa to 40 kDa in size.

5. The radiolabeled binding protein of claim 1, wherein the PEG of a molecular weight of at least 15 kDa further has a molecular weight 20 kDa.

6. The radiolabeled binding protein of claim 1, wherein the radionuclide is zirconium-89.

7. The radiolabeled binding protein of claim 1, wherein the radionuclide is copper-61.

8. The radiolabeled binding protein of claim 1, wherein the radionuclide is rubidium-82.

9. A method of diagnosing, monitoring, imaging, or treating a subject comprising: (a) administering the radiolabeled binding protein of claim 1 to the subject; and (b) detecting a radiolabel in the subject.

10. A method of obtaining a radiologic image of a subject comprising:
    (i) administering the radiolabeled binding protein of claim 1 to the subject; and
    (ii) obtaining a radiologic image of the subject by capturing the radiation emitted.

11. A method of treating a subject having a tumor, the method comprising:
    (i) administering the radiolabeled binding protein of claim 1 to the subject;
    (ii) obtaining a radiological image of the tumor;
    (iii) determining an intensity or a pattern of the radiologic image; and
    (iv) administering to the subject an agent intended to enhance or inhibit an immune response based on the intensity or the pattern of the radiologic image determined in step (iii).

12. A composition comprising the radiolabeled binding protein of claim 1, and an excipient.

13. A method of diagnosing, monitoring, imaging, or treating a subject comprising: (a) administering the composition of claim 12 to the subject; and (b) detecting a radiolabel in the subject.

14. The radiolabeled binding protein of claim 1, wherein the radionuclide is zirconium-89 which is bound by a desferrioxamine (DFO) chelating moiety.

15. The radiolabeled binding protein of claim 1, wherein the chelating moiety is 1,4,7-triazacyclononane-triacetic acid (NOTA).

16. The radiolabeled binding protein of claim 1, wherein the chelating moiety is desferrioxamine (DFO).

* * * * *